United States Patent
Chappie et al.

(10) Patent No.: US 11,161,844 B2
(45) Date of Patent: Nov. 2, 2021

(54) CYCLIC SUBSTITUTED IMIDAZO[4,5-C]QUINOLINE DERIVATIVES

(71) Applicant: Pfizer Inc., New York, NY (US)

(72) Inventors: Thomas Allen Chappie, Carlisle, MA (US); Paul Galatsis, Newton, MA (US); Michelle Renee Garnsey, Providence, RI (US); Christopher John Helal, Mystic, CT (US); Jaclyn Louise Henderson, Cambridge, MA (US); Bethany Lyn Kormos, Somerville, MA (US); Ravi G. Kurumbail, East Lyme, CT (US); Luis Angel Martinez-Alsina, Gales Ferry, CT (US); Martin Youngjin Pettersson, Littleton, MA (US); Antonia Friederike Stepan, Biberach an der Riss (DE); Travis T. Wager, Brookline, MA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 16/492,554

(22) PCT Filed: Mar. 1, 2018

(86) PCT No.: PCT/IB2018/051318
§ 371 (c)(1),
(2) Date: Sep. 9, 2019

(87) PCT Pub. No.: WO2018/163030
PCT Pub. Date: Sep. 13, 2018

(65) Prior Publication Data
US 2020/0039977 A1  Feb. 6, 2020

Related U.S. Application Data

(60) Provisional application No. 62/469,768, filed on Mar. 10, 2017.

(51) Int. Cl.
C07D 471/04 (2006.01)
C07D 471/14 (2006.01)

(52) U.S. Cl.
CPC ......... C07D 471/04 (2013.01); C07D 471/14 (2013.01)

(58) Field of Classification Search
CPC .................................................. C07D 471/04
USPC .......................................................... 549/82
See application file for complete search history.

(56) References Cited

U.S. PATENT DOCUMENTS

| 4,994,468 A | 2/1991 | Suzuki | |
|---|---|---|---|
| 2004/0054182 A1* | 3/2004 | Kato | A61P 11/06 546/82 |
| 2008/0213308 A1* | 9/2008 | Valiante | A61P 17/06 424/208.1 |
| 2015/0259340 A1 | 9/2015 | Almstetter | |

FOREIGN PATENT DOCUMENTS

WO  WO2017046675  3/2017

OTHER PUBLICATIONS

Venkatesh, J. Pharm. Sci. 89, 145-54 (2000).*
J. G. Cannon, Chapter Nineteen in Burger's Medicinal Chemistry and Drug Discovery, Fifth Edition, vol. I: Principles and Practice, Wiley-Interscience 1995, pp. 783-802.*
. . . Dorwald F. A. Side Reactions in Oroanic Synthesis 2005. Wiley: VCH. Weinheim No. IX of Preface No. 1-15.*
Goblyos, et al., "Structure-activity relationships of new 1H-imidazo[4,5-c]quinolin-4-amine derivatives as allosteric enhancers of the A3 adenosine receptor," Journal of Medicinal Chemistry, 49(11):3354-3361 (2006).
Kim, et al., "Novel 2- and 4-substituted 1H-imidazo[4,5-c]quinolin-4-amine derivatives as allosteric modulators of the A3 adenosine receptor," Journal of Medicinal Chemistry, 52(7):2098-2108 (2009).
Shiro, et al., "Synthesis and SAR study of imidazoquinolines as a novel structural class of microsomal prostaglandin $E_2$ synthase-1 inhibitors," Bioorganic and Medicinal Chemistry Letters, 22(1):285-288 (2011).

* cited by examiner

Primary Examiner — Nizal S Chandrakumar
(74) Attorney, Agent, or Firm — Haley Guiliano LLP; James F. Haley, Jr.

(57) ABSTRACT

The present invention provides novel cyclic substituted imidazo[4,5-c]quinoline derivatives of Formula (I), and the pharmaceutically acceptable salts thereof; wherein $R^1$, $R^2$, $R^4$, $R^5$, $R^6$, X and Z are as defined in the specification. The invention is also directed to pharmaceutical compositions comprising the compounds of Formula I and to use of the compounds in the treatment of diseases associated with LRRK2, such as neurodegenerative diseases including Parkinson's disease or Alzheimer's disease, cancer, Crohn's disease or leprosy.

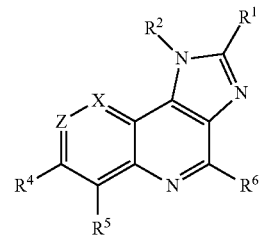

(I)

18 Claims, No Drawings

CYCLIC SUBSTITUTED IMIDAZO[4,5-C]QUINOLINE DERIVATIVES

CROSS-REFERENCE TO RELATED APPLICATIONS

This application is a United States National Phase Application filed under 35 U.S.C. § 371 from International Patent Application No. PCT/IB2018/051318, filed on Mar. 1, 2018, which claims the benefit of priority to US Provisional Patent Application Ser. No. 62/469,768 filed Mar. 10, 2017, the disclosures of which are hereby incorporated by reference in their entireties.

FIELD OF THE INVENTION

The present invention relates to small molecule inhibitors of leucine-rich repeat kinase 2 (LRRK2). This invention also relates to methods of inhibiting, in mammals, including humans, LRRK2 by administration of the small molecule LRRK2 inhibitors. The present invention also relates to the treatment of Parkinson's Disease (PD) and other neurodegenerative and/or neurological disorders in mammals, including humans with the LRRK2 inhibitors. More particularly, this invention relates to cyclic substituted imidazo[4,5-c]quinoline compounds useful for the treatment of neurodegenerative and/or neurological disorders, such as PD, Alzheimer's Disease (AD) and other LRRK2 associated disorders.

BACKGROUND OF THE INVENTION

LRRK2 is a 286 kDa protein in the ROCO protein family with a complex multidomain structure. Protein motifs that have been established for LRRK2 include an armadillo-like (ARM) domain, an ankyrin-like (ANK) domain, a leucine-rich repeat (LRR) domain, a Ras (renin-angiotensin system) of complex (ROC) domain, a C-terminal of ROC (COR) domain, a kinase domain, and a C-terminal WD40 domain. The ROC domain binds guanosine triphosphate (GTP) and the COR domain may be a regulator of the ROC domain's GTPase activity. The kinase domain has structural homology to the MAP kinase kinase kinases (MAPKKK) and has been shown to phosphorylate a number of cellular proteins in vitro, but the endogenous substrate has yet to be determined. LRRK2 has been found in various regions of the brain as well as in a number of peripheral tissues including heart, lung, spleen, and kidney.

LRRK2 has the ability to potentially play a complex role in multiple cellular processes as a consequence of its multidomain construct, each associated with putative protein-protein interactions, guanosine triphosphatase (GTPase) activity, and kinase activity. For example, LRRK2 has been associated with NFAT inhibition in the immune system and has been linked to vesicle trafficking, presynaptic homeostasis, mammalian target of rapamycin (mTOR) signaling, signaling through the receptor tyrosine kinase MET in papillary renal and thyroid carcinomas, cytoskeletal dynamics, the mitogen-activated protein kinase (MAPK) pathway, the tumor necrosis factor-α (TNF-α) pathway, the Wnt pathway and autophagy. Recent genome-wide association (GWA) genetic studies have implicated LRRK2 in the pathogenesis of various human diseases such as PD, inflammatory bowel disease (Crohn's disease), cancer and leprosy (Lewis, P. A. and Manzoni, C. Science Signaling 2012, 5(207), pe2).

Parkinson's disease (PD) is a relatively common age-related neurodegenerative disorder resulting from the progressive loss of dopamine-producing neurons and which affects up to 4% of the population over age 80. PD is characterized by both motor symptoms, such as tremor at rest, rigidity, akinesia and postural instability as well as non-motor symptoms such as impairment of cognition, sleep and sense of smell. GWA studies have linked LRRK2 to PD and many patients with point mutations in LRRK2 present symptoms that are indistinguishable from those with idiopathic PD. Over 20 LRRK2 mutations have been associated with autosomal-dominant Parkinsonism, and the R1441C, R1441G, R1441H, Y1699C, G2019S, I2020T and N1437H missense mutations are considered to be pathogenic. The LRRK2 R1441G mutation has been shown to increase the release of proinflammatory cytokines (higher levels of TNF-α, IL-1β, IL-12 and lower levels of IL-10) in microglial cells from transgenic mice and thus may result in direct toxicity to neurons (Gillardon, F. et al. Neuroscience 2012, 208, 41-48). In a murine model of neuroinflammation, induction of LRRK2 in microglia was observed and inhibition of LRRK2 kinase activity with small molecule LRRK2 inhibitors (LRRK2-IN-1 or sunitinib) or LRRK2 knockout resulted in attenuation of TNF-α secretion and nitric oxide synthase (iNOS) induction (Moehle, M. et al. J. Neurosci. 2012, 32(5), 1602-1611). The most common of the LRRK2 mutations, G2019S, is present in more than 85% of PD patients carrying LRRK2 mutations. This mutation, which is present in the LRRK2 kinase domain, leads to an enhancement of LRRK2 kinase activity. In the human brain LRRK2 expression is highest in the same regions of the brain that are impacted by PD, and LRRK2 is found in Lewy Bodies, a hallmark of PD. Recent studies indicate that a potent, selective, brain-penetrant kinase inhibitor for LRRK2 could be a therapeutic treatment for PD.

Dementia results from a wide variety of distinctive pathological processes. The most common pathological processes causing dementia are AD, cerebral amyloid angiopathy (CM) and prion-mediated diseases (see, e.g., Haan et al., Clin. Neurol. Neurosurg. 1990, 92(4):305-310; Glenner et al., J. Neurol. Sci. 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050. LRRK2 mutations have been associated with AD-like pathology, which suggests that there may be a partial overlap between the neurodegenerative pathways in both AD and PD (Zimprach, A. et al. Neuron 2004, 44, 601-607). In addition, the LRRK2 R1628P variant (COR domain) has been associated with an increased incidence of AD in a certain population, perhaps resulting from increased apoptosis and cell death (Zhao, Y. et al.; Neurobiology of Aging 2011, 32, 1990-1993).

An increased incidence of certain non-skin cancers such as renal, breast, lung and prostate cancers, as well as acute myelogenous leukemia (AML), has been reported in Parkinson's disease patients with the LRRK2 G2019S mutation (Saunders-Pullman, R. et al.; Movement Disorders, 2010, 25(15), 2536-2541). Since the G2019S mutation is associated with increased LRRK2 kinase activity, inhibition of this activity may be useful in the treatment of cancer, such as kidney, breast, lung, prostate and blood cancers.

Inflammatory bowel disease (IBD) or Crohn's disease (CD) is a complex disease and is believed to result from an inappropriate immune response to microbiota in the intestinal tract. GWA studies have recently identified LRRK2 as a major susceptibility gene for Crohn's disease, particularly the M2397T polymorphism in the WD40 domain (Liu, Z. et al. Nat. Immunol. 2011, 12, 1063-1070). In a recent study LRRK2 deficient mice were found to be more susceptible to dextran sodium sulfate induced colitis than their wild-type counterparts, indicating that LRRK2 may play a role in the pathogenesis of IBD (Liu, Z. and Lenardo, M.; Cell Research 2012, 1-3).

Both non-selective and selective small molecule compounds with LRRK2 inhibitory activity such as staurosporine, sunitinib, LRRK2-IN-1, CZC-25146, TAE684 and those in WO 2011/141756, WO 2012/028629 and WO 2012/058193 have been described. It is desirable to provide compounds which are potent and selective inhibitors of LRRK2 with a favorable pharmacokinetic profile and the ability to traverse the blood brain barrier. Accordingly, the present invention is directed to novel cyclic substituted imidazo[4,5-c]quinoline compounds with LRRK2 inhibitory activity and the use of these compounds in the treatment of diseases associated with LRRK2, such as neurodegenerative diseases, including PD.

SUMMARY OF THE INVENTION

A first embodiment of a first aspect of the present invention is a compound of Formula I

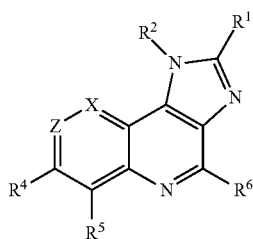

I or a pharmaceutically acceptable salt thereof; wherein X is $CR^7$ or N; Z is $CR^3$ or N; is a $C_3$-$C_7$cycloalkyl or a 4- to 7-membered heterocycloalkyl which contains 1 to 3 heteroatoms each independently selected from N, O and S, wherein the $C_3$-$C_7$cycloalkyl is substituted with 1 to 6 $R^8$, and the 4- to 7-membered heterocycloalkyl is optionally substituted with 1 to 6 $R^8$; $R^2$ is selected from the group consisting of $C_1$-$C_6$alkyl, $C_3$-$C_7$cycloalkyl and 4- to 7-membered heterocycloalkyl which contains 1 to 3 heteroatoms each independently selected from N, O and S, wherein the $C_1$-$C_6$alkyl, $C_3$-$C_7$cycloalkyl and 4- to 7-membered heterocycloalkyl are each optionally substituted with 1 to 6 $R^9$; $R^3$, $R^4$, $R^5$, $R^6$ and $R^7$ are each independently selected from the group consisting of hydrogen, amino, halo, hydroxy, cyano, $C_1$-$C_6$alkyl, $C_3$-$C_6$cycloalkyl and $C_1$-$C_6$alkoxy, wherein the $C_1$-$C_6$alkyl, $C_3$-$C_6$cycloalkyl and $C_1$-$C_6$alkoxy are each optionally substituted with 1 to 3 halo or $C_1$-$C_3$alkoxy; $R^8$ at each occurrence is independently selected from the group consisting of halo, —C(O)NH$_2$, —C(O)NH(C$_1$-C$_3$alkyl), —C(O)N(C$_1$-C$_3$alkyl)$_2$, $C_1$-$C_6$alkyl, $C_1$-$C_6$alkoxy and $C_3$-$C_6$cycloalkyl, wherein the $C_1$-$C_6$alkyl, $C_1$-$C_6$alkoxy and $C_3$-$C_6$cycloalkyl are each optionally substituted with 1 to 3 halo, cyano, hydroxy or $C_1$-$C_3$alkoxy; and $R^9$ at each occurrence is independently selected from the group consisting of halo, hydroxy, $C_1$-$C_6$alkyl, $C_1$-$C_6$alkoxy, and $C_1$-$C_6$alkoxyC$_1$-$C_6$alkyl, wherein the $C_1$-$C_6$alkyl, $C_1$-$C_6$alkoxy, and $C_1$-$C_6$alkoxyC$_1$-$C_6$alkyl are optionally substituted with one to three halo or a cyano.

A second embodiment of a first aspect of the present invention is a compound of the first embodiment of the first aspect of the Formula Ia

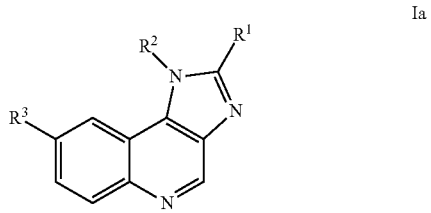

Ia or a pharmaceutically acceptable salt thereof; wherein $R^1$ is a $C_4$-$C_6$cycloalkyl or a 4- to 6-membered heterocycloalkyl which contains 1 to 2 heteroatoms each independently selected from N, O and S, wherein the $C_4$-$C_6$cycloalkyl is substituted with 1 to 4 $R^8$ and the 4- to 6-membered heterocycloalkyl is optionally substituted with 1 to 4 $R^8$; $R^2$ is selected from the group consisting of a $C_1$-$C_6$alkyl, $C_3$-$C_6$cycloalkyl and 5- to 6-membered heterocycloalkyl which contains 1 to 2 heteroatoms each independently selected from NR and O, wherein the $C_1$-$C_6$alkyl, $C_3$-$C_6$cycloalkyl and 5- to 6-membered heterocycloalkyl are each optionally substituted with 1 to 4 $R^9$; $R^3$ is selected from the group consisting of halo, cyano, $C_1$-$C_3$alkyl, $C_3$-$C_6$cycloalkyl and $C_1$-$C_3$alkoxy, wherein the $C_1$-$C_3$alkyl, $C_3$-$C_6$cycloalkyl and $C_1$-$C_3$alkoxy are each optionally substituted with 1 to 3 halo or $C_1$-$C_3$alkoxy; $R^8$ at each occurrence is independently selected from the group consisting of halo, $C_1$-$C_3$alkyl and $C_1$-$C_3$alkoxy, wherein the $C_1$-$C_3$alkyl and $C_1$-$C_3$alkoxy are each optionally substituted with 1 to 3 halo; and $R^9$ at each occurrence is independently selected from the group consisting of halo, $C_1$-$C_3$alkyl and $C_1$-$C_3$alkoxy, wherein the $C_1$-$C_3$alkyl and $C_1$-$C_3$alkoxy are optionally substituted with one to three halo or a cyano.

A third embodiment of a first aspect of the present invention is the compound of the second embodiment of the first aspect or a pharmaceutically acceptable salt thereof wherein $R^3$ is selected from the group consisting of chloro, fluoro, cyano, difluoromethyl and trifluoromethyl.

A fourth embodiment of a first aspect of the present invention is the compound of the third embodiment of the first aspect or a pharmaceutically acceptable salt thereof wherein $R^1$ is selected from the group consisting of cyclobutyl, cyclopentyl, cyclohexyl, oxetanyl, tetrahydrofuranyl and tetrahydropyranyl, wherein the cyclobutyl, cyclopentyl, and cyclohexyl are substituted with 1 to 3 $R^8$, and wherein the oxetanyl, tetrahydrofuranyl and tetrahydropyranyl are optionally substituted with 1 to 3 $R^8$; and $R^8$ at each occurrence is independently selected from the group consisting of halo, $C_1$-$C_3$alkyl and $C_1$-$C_3$alkoxy, wherein the $C_1$-$C_3$alkyl and $C_1$-$C_3$alkoxy are optionally substituted with 1 to 3 fluoro.

A fifth embodiment of the first aspect of the present invention is the compound of the third or fourth embodiment of the first aspect or a pharmaceutically acceptable salt thereof wherein $R^2$ is selected from the group consisting of 2,2-difluoropropyl, cyclobutyl, cyclopentyl, cyclohexyl, oxetanyl, tetrahydrofuranyl, tetrahydropyranyl and pyrrolidinyl wherein the cyclobutyl, cyclopentyl, cyclohexyl, oxetanyl, tetrahydrofuranyl, tetrahydropyranyl and pyrrolidinyl are optionally substituted with 1 to 3 $R^9$; and $R^9$ at each occurrence is independently selected from the group consisting of halo, $C_1$-$C_3$alkyl and $C_1$-$C_3$alkoxy, wherein the $C_1$-$C_3$alkyl and $C_1$-$C_3$alkoxy are optionally substituted with one to three fluoro or a cyano.

A sixth embodiment of a first aspect of the present invention is the compound of the third embodiment of the first aspect or a pharmaceutically acceptable salt thereof wherein $R^1$ is selected from the group consisting of oxetan-3-yl, tetrahydrofuran-2-yl, tetrahydrofuran-3-yl, 5-methyl-tetrahydrofuran-2-yl, tetrahydropyran-4-yl, 3-fluoro cyclobutyl, 3,3-difluorocyclobutyl, 3-methoxycyclobutyl, 3-fluoro-3-methylcyclobutyl, 3-fluorocyclopentyl, 3,3-difluorocyclopentyl, 4-fluorocyclohexyl, 2,2-difluorocyclohexyl and 4,4-difluorocyclohexyl.

A seventh embodiment of a first aspect of the present invention is the compound of the third or sixth embodiment of the first aspect or a pharmaceutically acceptable salt thereof wherein $R^2$ is selected from the group consisting of 2-methyltetrahydropyran-4-yl, 2,2-dimethyltetrahydropyran-4-yl, 2-(cyanomethyl)tetrahydropyran-4-yl, 3,3-difluorotetrahydropyran-4-yl, 1-methylpyrrolidin-3-yl and 4,4-difluoro-1-methylpyrrolidin-3-yl.

An eighth embodiment of a first aspect of the present invention is the compound of the second embodiment of the first aspect or a pharmaceutically acceptable salt thereof wherein $R^1$ is selected from the group consisting of oxetan-3-yl, tetrahydrofuran-2-yl, tetrahydrofuran-3-yl, 5-methyl-tetrahydrofuran-2-yl, tetrahydropyran-4-yl, 3-fluoro cyclobutyl, 3,3-difluorocyclobutyl, 3-methoxycyclobutyl, 3-fluoro-3-methylcyclobutyl, 3-fluorocyclopentyl, 3,3-difluorocyclopentyl, 4-fluorocyclohexyl, 2,2-difluorocyclohexyl and 4,4-difluorocyclohexyl; and $R^2$ is selected from the group consisting of 2-methyltetrahydropyran-4-yl, 2,2-dimethyltetrahydropyran-4-yl, 2-(cyanomethyl) tetrahydropyran-4-yl, 3,3-difluorotetrahydropyran-4-yl, 1-methylpyrrolidin-3-yl and 4,4-difluoro-1-methylpyrrolidin-3-yl.

A ninth embodiment of a first aspect of the present invention is the compound of the eighth embodiment of the first aspect or a pharmaceutically acceptable salt thereof wherein $R^1$ is selected from the group consisting of oxetan-3-yl, tetrahydrofuran-2-yl, tetrahydrofuran-3-yl, 5-methyl-tetrahydrofuran-2-yl and tetrahydropyran-4-yl.

A tenth embodiment of a first aspect of the present invention is the compound of the eighth embodiment of the first aspect or a pharmaceutically acceptable salt thereof wherein $R^1$ is selected from the group consisting of 3-fluoro cyclobutyl, 3,3-difluorocyclobutyl, 3-methoxycyclobutyl, 3-fluoro-3-methylcyclobutyl, 3-fluorocyclopentyl, 3,3-difluorocyclopentyl, 4-fluorocyclohexyl, 2,2-difluorocyclohexyl and 4,4-difluorocyclohexyl.

An eleventh embodiment of a first aspect of the present invention is the compound of the eighth embodiment of the first aspect or a pharmaceutically acceptable salt thereof wherein $R^2$ is selected from the group consisting of 2-methyltetrahydropyran-4-yl, 2,2-dimethyltetrahydropyran-4-yl, 2-(cyanomethyl)tetrahydropyran-4-yl and 3,3-difluorotetrahydropyran-4-yl.

A twelfth embodiment of a first aspect of the present invention is the compound of the eighth embodiment of the first aspect or a pharmaceutically acceptable salt thereof wherein $R^2$ is selected from the group consisting of 1-methylpyrrolidin-3-yl and 4,4-difluoro-1-methylpyrrolidin-3-yl.

A thirteenth embodiment of a first aspect of the present invention is the compound of the eighth embodiment of the first aspect or a pharmaceutically acceptable salt thereof wherein $R^3$ is fluoro or chloro.

A fourteenth embodiment of a first aspect of the present invention is the compound of the eighth embodiment of the first aspect or a pharmaceutically acceptable salt thereof wherein $R^3$ is cyano.

A fifteenth embodiment of a first aspect of the present invention is the compound of the eighth embodiment of the first aspect or a pharmaceutically acceptable salt thereof wherein $R^3$ is difluoromethyl or trifluoromethyl.

A sixteenth embodiment of a first aspect of the present invention is the compound of the second embodiment of the first aspect selected from the group consisting of 8-chloro-2-(cis-4-fluorocyclohexyl)-1-[(2R,4R)-2-methyl-tetrahydro-2H-pyran-4-yl]-1H-imidazo[4,5-c]quinoline;

8-chloro-2-(cis-3-fluorocyclobutyl)-1-[(2R,4R)-2-methyl-tetrahydro-2H-pyran-4-yl]-1H-imidazo[4,5-c]quinoline;

8-chloro-2-(cis-3-fluoro-3-methylcyclobutyl)-1-[(2R,4R)-2-methyltetrahydro-2H-pyran-4-yl]-1H-imidazo[4,5-c]quinoline;

8-chloro-1-[(2R,4R)-2-methyltetrahydro-2H-pyran-4-yl]-2-[(3R)-tetrahydrofuran-3-yl]-1H-imidazo[4,5-c]quinoline;

8-chloro-2-(3-fluoro-3-methylcyclobutyl)-1-[(2R,4R)-2-methyltetrahydro-2H-pyran-4-yl]-1H-imidazo[4,5-c]quinoline;

8-chloro-2-(cis-3-methoxycyclobutyl)-1-[(2R,4R)-2-methyltetrahydro-2H-pyran-4-yl]-1H-imidazo[4,5-c]quinoline;

8-chloro-1-[(2R,4R)-2-methyltetrahydro-2H-pyran-4-yl]-2-(tetrahydro-2H-pyran-4-yl)-1H-imidazo[4,5-c]quinoline;

8-chloro-2-(4,4-difluorocyclohexyl)-1-[(2R,4R)-2-methyl-tetrahydro-2H-pyran-4-yl]-1H-imidazo[4,5-c]quinoline;

8-chloro-1-[(2R,4R)-2-methyltetrahydro-2H-pyran-4-yl]-2-(tetrahydrofuran-2-yl)-1H-imidazo[4,5-c]quinoline, DIAST 1;

8-chloro-2-(5-methyltetrahydrofuran-3-yl)-1-[(2R,4R)-2-methyltetrahydro-2H-pyran-4-yl]-1H-imidazo[4,5-c]quinoline, DIAST 2;

8-chloro-2-(3,3-difluorocyclopentyl)-1-[(2R,4R)-2-methyl-tetrahydro-2H-pyran-4-yl]-1H-imidazo[4,5-c]quinoline;

8-chloro-1-[(2R,4R)-2-methyltetrahydro-2H-pyran-4-yl]-2-(oxetan-3-yl)-1H-imidazo[4,5-c]quinoline;

2-[(cis)-3-fluorocyclopentyl]-1-[(2R,4R)-2-methyltetrahydro-2H-pyran-4-yl]-1H-imidazo[4,5-c]quinoline-8-carbonitrile, ENT 1;

2-[(cis)-3-fluorocyclopentyl]-1-[(2R,4R)-2-methyltetrahydro-2H-pyran-4-yl]-1H-imidazo[4,5-c]quinoline-8-carbonitrile, ENT 2;

2-(cis-4-fluorocyclohexyl)-1-[(2R,4R)-2-methyltetrahydro-2H-pyran-4-yl]-1H-imidazo[4,5-c]quinoline-8-carbonitrile;

1-[(2R,4R)-2-methyltetrahydro-2H-pyran-4-yl]-2-[(3R)-tetrahydrofuran-3-yl]-1H-imidazo[4,5-c]quinoline-8-carbonitrile;

2-(4,4-difluorocyclohexyl)-1-[(2R,4R)-2-methyltetrahydro-2H-pyran-4-yl]-1H-imidazo[4,5-c]quinoline-8-carbonitrile;

2-(cis-3-fluoro-3-methylcyclobutyl)-1-[(2R,4R)-2-methyl-tetrahydro-2H-pyran-4-yl]-1H-imidazo[4,5-c]quinoline-8-carbonitrile;

2-(cis-3-fluorocyclobutyl)-1-[(2R,4R)-2-methyltetrahydro-2H-pyran-4-yl]-1H-imidazo[4,5-c]quinoline-8-carbonitrile;

2-(2,2-difluorocyclohexyl)-1-[(2R,4R)-2-methyltetrahydro-2H-pyran-4-yl]-1H-imidazo[4,5-c]quinoline-8-carbonitrile, DIAST 2;

8-(difluoromethyl)-1-[(2R,4R)-2-methyltetrahydro-2H-pyran-4-yl]-2-[(3R)-tetrahydrofuran-3-yl]-1H-imidazo[4,5-c]quinoline;

2-(cis-3-fluoro-3-methylcyclobutyl)-1-[(3R)-1-methylpyrrolidin-3-yl]-1H-imidazo[4,5-c]quinoline-8-carbonitrile;
2-(cis-4-fluorocyclohexyl)-1-[(3R)-1-methylpyrrolidin-3-yl]-1H-imidazo[4,5-c]quinoline-8-carbonitrile;
2-(cis-3-fluorocyclobutyl)-1-[(3R)-1-methylpyrrolidin-3-yl]-1H-imidazo[4,5-c]quinoline-8-carbonitrile;
1-[(3R)-1-methylpyrrolidin-3-yl]-2-[(3R)-tetrahydrofuran-3-yl]-1H-imidazo[4,5-c]quinoline-8-carbonitrile;
1-[(2R,4R)-2-methyltetrahydro-2H-pyran-4-yl]-2-[(3R)-tetrahydrofuran-3-yl]-8-(trifluoromethyl)-1H-imidazo[4,5-c]quinoline;
{cis-4-[8-chloro-2-(3,3-difluorocyclobutyl)-1H-imidazo[4,5-c]quinolin-1-yl]tetrahydro-2H-pyran-2-yl}acetonitrile, ENT 2;
{(2S,4R)-4-[8-chloro-2-(cis-4-fluorocyclohexyl)-1H-imidazo[4,5-c]quinolin-1-yl]tetrahydro-2H-pyran-2-yl}acetonitrile;
{(2S,4R)-4-[8-fluoro-2-(cis-4-fluorocyclohexyl)-1H-imidazo[4,5-c]quinolin-1-yl]tetrahydro-2H-pyran-2-yl}acetonitrile;
[cis-4-{8-chloro-2-[(3R)-tetrahydrofuran-3-yl]-1H-imidazo[4,5-c]quinolin-1-yl}tetrahydro-2H-pyran-2-yl]acetonitrile, DIAST 1;
8-fluoro-2-(cis-3-fluoro-3-methylcyclobutyl)-1-[(2R,4R)-2-methyltetrahydro-2H-pyran-4-yl]-1H-imidazo[4,5-c]quinoline;
2-[cis-3-fluorocyclopentyl]-1-[(3R)-1-methylpyrrolidin-3-yl]-1H-imidazo[4,5-c]quinoline-8-carbonitrile, DIAST 1;
2-[cis-3-fluorocyclopentyl]-1-[(3R)-1-methylpyrrolidin-3-yl]-1H-imidazo[4,5-c]quinoline-8-carbonitrile, DIAST 2;
8-fluoro-2-[cis-3-fluorocyclopentyl]-1-[(3R)-1-methylpyrrolidin-3-yl]-1H-imidazo[4,5-c]quinoline, DIAST 1;
8-fluoro-2-[trans-3-fluorocyclopentyl]-1-[(3R)-1-methylpyrrolidin-3-yl]-1H-imidazo[4,5-c]quinoline, DIAST 1;
8-fluoro-2-[trans-3-fluorocyclopentyl]-1-[(3R)-1-methylpyrrolidin-3-yl]-1H-imidazo[4,5-c]quinoline, DIAST 2;
8-fluoro-2-[trans-3-fluorocyclopentyl]-1-[(2R,4R)-2-methyltetrahydro-2H-pyran-4-yl]-1H-imidazo[4,5-c]quinoline, DIAST 1;
8-fluoro-2-[trans-3-fluorocyclopentyl]-1-[(2R,4R)-2-methyltetrahydro-2H-pyran-4-yl]-1H-imidazo[4,5-c]quinoline, DIAST 2;
1-(2,2-dimethyltetrahydro-2H-pyran-4-yl)-2-(3-fluorocyclopentyl)-1H-imidazo[4,5-c]quinoline-8-carbonitrile, DIAST A;
1-(2,2-dimethyltetrahydro-2H-pyran-4-yl)-2-(3-fluorocyclopentyl)-1H-imidazo[4,5-c]quinoline-8-carbonitrile, DIAST B;
1-(2,2-dimethyltetrahydro-2H-pyran-4-yl)-2-(3-fluorocyclopentyl)-1H-imidazo[4,5-c]quinoline-8-carbonitrile, DIAST C;
1-(2,2-dimethyltetrahydro-2H-pyran-4-yl)-2-(3-fluorocyclopentyl)-1H-imidazo[4,5-c]quinoline-8-carbonitrile, DIAST D;
8-fluoro-2-[cis-3-fluorocyclopentyl]-1-[(2R,4R)-2-methyltetrahydro-2H-pyran-4-yl]-1H-imidazo[4,5-c]quinoline, DIAST 1;
8-(difluoromethyl)-2-(3-fluorocyclopentyl)-1-[(2R,4R)-2-methyltetrahydro-2H-pyran-4-yl]-1H-imidazo[4,5-c]quinoline, mixture of 4 diasteromers;
1-(3,3-difluorotetrahydro-2H-pyran-4-yl)-2-(trans-3-fluorocyclobutyl)-1H-imidazo[4,5-c]quinoline-8-carbonitrile, DIAST 1;
1-(3,3-difluorotetrahydro-2H-pyran-4-yl)-2-(trans-3-fluorocyclobutyl)-1H-imidazo[4,5-c]quinoline-8-carbonitrile, DIAST 2;
1-(3,3-difluorotetrahydro-2H-pyran-4-yl)-2-(cis-3-fluorocyclobutyl)-1H-imidazo[4,5-c]quinoline-8-carbonitrile, DIAST 1;
1-(3,3-difluorotetrahydro-2H-pyran-4-yl)-2-(cis-3-fluorocyclobutyl)-1H-imidazo[4,5-c]quinoline-8-carbonitrile, DIAST 2;
1-(3,3-difluorotetrahydro-2H-pyran-4-yl)-2-(cis-3-methoxycyclobutyl)-1H-imidazo[4,5-c]quinoline-8-carbonitrile, DIAST 1;
1-(3,3-difluorotetrahydro-2H-pyran-4-yl)-2-(trans-3-methoxycyclobutyl)-1H-imidazo[4,5-c]quinoline-8-carbonitrile, DIAST 1;
1-(3,3-difluorotetrahydro-2H-pyran-4-yl)-2-(trans-3-methoxycyclobutyl)-1H-imidazo[4,5-c]quinoline-8-carbonitrile, DIAST 2;
1-(3,3-difluorotetrahydro-2H-pyran-4-yl)-2-(cis-3-methoxycyclobutyl)-1H-imidazo[4,5-c]quinoline-8-carbonitrile, DIAST 2;
1-[(4R)-2,2-dimethyltetrahydro-2H-pyran-4-yl]-2-[(1S,3S)-3-fluorocyclopentyl]-1H-imidazo[4,5-c]quinoline-8-carbonitrile, DIAST E;
1-[(4R)-2,2-dimethyltetrahydro-2H-pyran-4-yl]-2-[(1R,3S)-3-fluorocyclopentyl]-1H-imidazo[4,5-c]quinoline-8-carbonitrile, DIAST F;
1-[(4R)-2,2-dimethyltetrahydro-2H-pyran-4-yl]-2-[(1R,3R)-3-fluorocyclopentyl]-1H-imidazo[4,5-c]quinoline-8-carbonitrile, DIAST G;
1-[(4R)-2,2-dimethyltetrahydro-2H-pyran-4-yl]-2-[(1S,3R)-3-fluorocyclopentyl]-1H-imidazo[4,5-c]quinoline-8-carbonitrile, DIAST H;
1-(4,4-difluoro-1-methylpyrrolidin-3-yl)-2-(3-fluorocyclopentyl)-1H-imidazo[4,5-c]quinoline-8-carbonitrile, DIAST A;
1-(4,4-difluoro-1-methylpyrrolidin-3-yl)-2-(3-fluorocyclopentyl)-1H-imidazo[4,5-c]quinoline-8-carbonitrile, DIAST B;
1-(4,4-difluoro-1-methylpyrrolidin-3-yl)-2-(3-fluorocyclopentyl)-1H-imidazo[4,5-c]quinoline-8-carbonitrile, DIAST C;
1-(4,4-difluoro-1-methylpyrrolidin-3-yl)-2-(3-fluorocyclopentyl)-1H-imidazo[4,5-c]quinoline-8-carbonitrile, DIAST D;
1-(4,4-difluoro-1-methylpyrrolidin-3-yl)-2-(3-fluorocyclopentyl)-1H-imidazo[4,5-c]quinoline-8-carbonitrile, DIAST E;
1-(4,4-difluoro-1-methylpyrrolidin-3-yl)-2-(3-fluorocyclopentyl)-1H-imidazo[4,5-c]quinoline-8-carbonitrile, DIAST F;
1-(4,4-difluoro-1-methylpyrrolidin-3-yl)-2-(3-fluorocyclopentyl)-1H-imidazo[4,5-c]quinoline-8-carbonitrile, DIAST G; and
1-(4,4-difluoro-1-methylpyrrolidin-3-yl)-2-(3-fluorocyclopentyl)-1H-imidazo[4,5-c]quinoline-8-carbonitrile, DIAST H;
or a pharmaceutically acceptable salt thereof.

A seventeenth embodiment of a first aspect of the present invention is the compound of the sixteenth embodiment of the first aspect selected from the group consisting of
2-[(cis)-3-fluorocyclopentyl]-1-[(2R,4R)-2-methyltetrahydro-2H-pyran-4-yl]-1H-imidazo[4,5-c]quinoline-8-carbonitrile, ENT 1;
8-chloro-2-(cis-3-fluorocyclobutyl)-1-[(2R,4R)-2-methyltetrahydro-2H-pyran-4-yl]-1H-imidazo[4,5-c]quinoline;
2-(cis-4-fluorocyclohexyl)-1-[(2R,4R)-2-methyltetrahydro-2H-pyran-4-yl]-1H-imidazo[4,5-c]quinoline-8-carbonitrile;

8-chloro-2-(cis-3-fluoro-3-methylcyclobutyl)-1-[(2R,4R)-2-methyltetrahydro-2H-pyran-4-yl]-1H-imidazo[4,5-c]quinoline;

1-[(2R,4R)-2-methyltetrahydro-2H-pyran-4-yl]-2-[(3R)-tetrahydrofuran-3-yl]-1H-imidazo[4,5-c]quinoline-8-carbonitrile;

2-[cis-3-fluorocyclopentyl]-1-[(3R)-1-methylpyrrolidin-3-yl]-1H-imidazo[4,5-c]quinoline-8-carbonitrile, DIAST 2;

8-chloro-2-(cis-4-fluorocyclohexyl)-1-[(2R,4R)-2-methyltetrahydro-2H-pyran-4-yl]-1H-imidazo[4,5-c]quinoline;

8-fluoro-2-[cis-3-fluorocyclopentyl]-1-[(2R,4R)-2-methyltetrahydro-2H-pyran-4-yl]-1H-imidazo[4,5-c]quinoline, DIAST 1;

1-[(2R,4R)-2-methyltetrahydro-2H-pyran-4-yl]-2-[(3R)-tetrahydrofuran-3-yl]-8-(trifluoromethyl)-1H-imidazo[4,5-c]quinoline; and 2-[(cis)-3-fluorocyclopentyl]-1-[(2R,4R)-2-methyltetrahydro-2H-pyran-4-yl]-1H-imidazo[4,5-c]quinoline-8-carbonitrile, ENT 2;

or a pharmaceutically acceptable salt thereof.

An eighteenth embodiment of a first aspect of the present invention is the compound of the seventeenth embodiment of the first aspect selected from the group consisting of 2-[(cis)-3-fluorocyclopentyl]-1-[(2R,4R)-2-methyltetrahydro-2H-pyran-4-yl]-1H-imidazo[4,5-c]quinoline-8-carbonitrile, ENT 1;

8-chloro-2-(cis-3-fluorocyclobutyl)-1-[(2R,4R)-2-methyltetrahydro-2H-pyran-4-yl]-1H-imidazo[4,5-c]quinoline;

2-(cis-4-fluorocyclohexyl)-1-[(2R,4R)-2-methyltetrahydro-2H-pyran-4-yl]-1H-imidazo[4,5-c]quinoline-8-carbonitrile;

8-chloro-2-(cis-3-fluoro-3-methylcyclobutyl)-1-[(2R,4R)-2-methyltetrahydro-2H-pyran-4-yl]-1H-imidazo[4,5-c]quinoline; and 1-[(2R,4R)-2-methyltetrahydro-2H-pyran-4-yl]-2-[(3R)-tetrahydrofuran-3-yl]-1H-imidazo[4,5-c]quinoline-8-carbonitrile;

or a pharmaceutically acceptable salt thereof.

A first embodiment of a second aspect of the present invention is a pharmaceutical composition comprising a therapeutically effective amount of a compound according to any one of the first through eighteenth embodiments of the first aspect, or a pharmaceutically acceptable salt thereof together with a pharmaceutically acceptable carrier.

A first embodiment of a third aspect of the present invention is a method of treating a disease or disorder selected from the group consisting of Crohn's disease, Parkinson's disease, Lewy body dementia, frontotemporal dementia, corticobasal dementia, progressive supranuclear palsy, leprosy, Alzheimer's disease, tauopathy disease and Alpha-synucleinopathy in a patient, the method comprising administering to a patient in need thereof a therapeutically effective amount of a compound or pharmaceutically acceptable salt thereof according to any one of the first through eighteenth embodiments of the first aspect of the invention.

Another embodiment of the present invention is the compound or pharmaceutically acceptable salt thereof according to any one of the first through eighteenth embodiments of the first aspect of the present invention for use in the treatment of Crohn's disease or Parkinson's disease.

Another embodiment of the present invention is a method of inhibiting LRRK2 in a patient, the method comprising administering a LRRK2 inhibiting amount of a compound or a pharmaceutically acceptable salt thereof according to any one of the first through eighteenth embodiments of the first aspect.

Another embodiment of the present invention is a method of treating a neurodegenerative disease in a patient, the method comprising administering to a patient in need thereof a therapeutically effective amount of a compound or pharmaceutically acceptable salt thereof according to any one of the first through eighteenth embodiments of the first aspect.

Accordingly, the invention is also directed to methods of treating a patient (preferably a human) for diseases in which the LRRK2 kinase is involved, such as Parkinson's disease, by administering a therapeutically effective amount of a compound of any of the embodiments of Formula I, or a pharmaceutically acceptable salt thereof, and a pharmaceutically acceptable carrier.

The invention is also directed to methods of inhibiting LRRK2 kinase activity, by administering a therapeutically effective amount of a compound of Formula I or a pharmaceutically acceptable salt thereof, and a pharmaceutically acceptable carrier, to a mammal or a patient in need thereof.

The invention is also directed to methods of treating disorders responsive to the inhibition of LRRK2 kinase activity, such as neurological disorders (particularly Parkinson's disease), certain cancers, and certain immunological disorders (such as Crohn's disease and leprosy) by administering a therapeutically effective amount of a compound of Formula I or a pharmaceutically acceptable salt thereof, and a pharmaceutically acceptable carrier, to a mammal or a patient in need thereof.

The invention is also directed to methods for treating conditions or diseases of the central nervous system and neurological disorders in which the LRRK2 kinase is involved, particularly Parkinson's disease (but also including other neurological diseases which may include migraine; epilepsy; Alzheimer's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS) premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema) and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or a pharmaceutically acceptable salt thereof.

The present compounds of Formula I may be particularly suited to treatment of diseases or disorders such as Lewy body dementia, frontotemporal dementia, corticobasal dementia, progressive supranuclear palsy, leprosy, inflammatory bowel disease, inflammatory bowel syndrome, Alzheimer's disease, tauopathy diseases, Alpha-synucleinopathy, Parkinson's disease, Parkinson's disease with dementia, Parkinson's disease at risk syndrome, Lewy body variant of Alzheimer's disease, combined Parkinson's disease and Alzheimer's disease, multiple system atrophy, striatonigral degeneration, olivopontocerebellar atrophy, Shy-Drager syndrome, ulcerative colitis, juvenile parkinsonism, Steele-Richardson-Olszewski disease, Lytico-Bodig or parkinsonism-dementia-ALS complex of Guam, cortical basal ganglionic degeneration, progressive pallidal atrophy, Parkinsonism-dementia complex, pallidopyramidal disease, hereditary juvenile dystonia-parkinsonism, autosomal dominant Lewy body disease, Huntington disease, Wilson disease, hereditary ceruloplasmin deficiency, Hallervorden-Spatz disease, olivopontocerebellar and spinocerebellar degenerations, Machado-Joseph disease, familial amyotrophy-dementia-parkinsonism, disinhibition-dementia-parkinsonism-amyotrophycomplex, Gerstmann-Strausler-Scheinker disease, familial progressive subcortical gliosis, Lubag (x-linked dystonia parkinsonism), familial basal ganglia calcification, mitochondrial cytopathies with striatal necrosis, ceroid lipofuscinosis, familial Parkinsonism with peripheral neuropathy, Parkinsonism-pyramidal syndrome, neuroacanthocytosis and hereditary hemochromatosis.

The text revision of the fourth edition of the Diagnostic and Statistical Manual of Mental Disorders (DSM-IV-TR) (2000, American Psychiatric Association, Washington D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress.

Preferred methods are for treating a neurological disorder, most preferably Parkinson's disease, (but also other neurological disorders such as migraine; epilepsy; Alzheimer's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof. In addition, the compounds of Formula I and pharmaceutically acceptable salts thereof may also be employed in methods of treating other disorders associated with LRRK2 such as Crohn's disease, leprosy and certain cancers, such as kidney, breast, lung, prostate, lung and blood cancer.

Also provided herein are compositions comprising a pharmaceutically effective amount of one or more of the compounds described herein and a pharmaceutically acceptable vehicle, carrier or excipient.

The present invention is also directed to the use of a combination of a LRRK2 inhibitor compound of Formula I, and one or more additional pharmaceutically active agent(s).

Other features and advantages of this invention will be apparent from this specification and the appendent claims which describe the invention.

Definitions

The term "alkyl" refers to a linear or branched-chain saturated hydrocarbyl substituent (i.e., a substituent obtained from a hydrocarbon by removal of a hydrogen); in one embodiment from one to six carbon atoms (i.e., $C_1$-$C_6$alkyl); in another embodiment, from one to three carbon atoms (i.e., $C_1$-$C_3$alkyl). Examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent (i.e., a substituent obtained from a hydrocarbon by removal of a hydrogen) which is in turn attached to an oxygen atom; in one embodiment from one to six carbon atoms (i.e., $C_1$-$C_6$alkoxy); in another embodiment, from one to three carbon atoms (i.e., $C_1$-$C_3$alkoxy). Examples of such substituents include methoxy, ethoxy, propoxy (including n-propoxy and isopropoxy), butoxy (including n-butoxy, isobutoxy, sec-butoxy and tert-butoxy), pentoxy and the like.

The term "cycloalkyl" refers to a carbocyclic substituent obtained by removing a hydrogen from a saturated carbocyclic molecule and having the specified number of carbon atoms. In one embodiment, a cycloalkyl substituent has three to seven carbon atoms (i.e., $C_3$-$C_7$cycloalkyl). Examples of cycloalkyl include cyclopropyl, cyclobutyl, cyclopentyl, cyclohexyl and cycloheptyl. In another embodiment, a cycloalkyl substituent has three to six carbon atoms (i.e., $C_3$-$C_6$cycloalkyl). The term "cycloalkyl" includes mono-, bi- and tricyclic saturated carbocycles, as well as bridged and fused ring carbocycles, as well as spiro-fused ring systems.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. The term "heterocycloalkyl" refers to a substituent obtained by removing a hydrogen from a saturated or partially saturated ring structure containing the specified number of ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. If the heterocycloalkyl substituent is in turn substituted with a group or substituent, the group or substituent may be bound to a nitrogen heteroatom, or it may be bound to a ring carbon atom, as appropriate. As used herein, the term "heterocycloalkyl" as used herein refers to a monocyclic ring system containing the heteroatoms N, O or S as specified. Thus, for example, "four- to seven-membered heterocycloalkyl" refers to a heterocycloalkyl containing from 4 to 7 atoms, including one or more heteroatoms, in the cyclic moiety of the heterocycloalkyl. The number of heteroatoms present in a given heterocycle may be as specified. If the heterocycloalkyl group contains a nitrogen moiety N and is saturated then it is to be understood that the nitrogen is hydrogen or $C_1$-$C_6$alkyl. Examples of single-ring heterocycloalkyls include tetrahydropyranyl, azetidinyl, oxetanyl, thietanyl, dihydrofuranyl, tetrahydrofuranyl, dihydrothiophenyl, tetrahydrothiophenyl, pyrrolinyl, pyrrolidinyl, imidazolinyl, imidazolidinyl, pyrazolinyl, pyrazolidinyl, thiazolinyl, isothiazolinyl, thiazolidinyl, isothiazolidinyl, dihydropyranyl, piperidinyl, morpholinyl, piperazinyl, azepinyl, oxepinyl, thiepinyl, and diazepinyl.

The term "hydrogen" refers to a hydrogen substituent, and may be depicted as —H. The term "deutero" refers to a deuterium substituent, and may be depicted as -D.

The term "hydroxy" or "hydroxyl" refers to —OH. Compounds bearing a carbon to which one or more hydroxy substituents are attached include, for example, alcohols, enols and phenol.

The term "halo" or "halogen" refers to fluoro (which may be depicted as —F), chloro (which may be depicted as —Cl), bromo (which may be depicted as —Br), or iodo (which may be depicted as —I).

The foregoing groups, as derived from the groups listed above, may be C-attached or N-attached where such is possible. For instance, a group derived from pyrrolidine may be pyrrolidin-1-yl (N-attached) or pyrrolidin-3-yl (C-attached).

If substituents are described as being "independently selected" from a group, each instance of a substituent is selected independent of the other. Each substituent therefore may be identical to or different from the other substituent(s).

As used herein the terms "formula I", "Formula I", "formula (I)" or "Formula (I)" may be referred to as a "compound(s) of the invention." Such terms are also defined to include all forms of the compound of formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention may have asymmetric carbon atoms. The carbon-carbon bonds of the compounds of the invention may be depicted herein using a solid line ( ——— ), a solid wedge ( ◢◣ ) or a dotted wedge ( ·····||||| ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula (I) may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention comprises the tautomeric forms of compounds of the invention. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, p-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula (I) with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulfur, fluorine and chlorine, such as $^2$H, $^3$H, $^{13}$C, $^{11}$C, $^{14}$C, $^{15}$N, $^{18}$O, $^{17}$O, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

DETAILED DESCRIPTION OF THE INVENTION

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration;

and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, (hydroxypropyl)methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3$^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a LRRK2 inhibitor compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated. For example, a pharmaceutical composition for use in treating Parkinson's disease may comprise a compound of Formula I or a pharmaceutically acceptable salt thereof together with another agent such as a dopamine (levodopa, either alone or with a DOPA decarboxylase inhibitor), a monoamine oxidase (MAO) inhibitor, a catechol O-methyltransferase (COMT) inhibitor or an anticholinergic agent, or any combination thereof. Particularly preferred agents to combine with the compounds of Formula I for use in treating Parkinson's disease include levodopa, carbidopa, tolcapone, entacapone, selegiline, benztropine and trihexyphenidyl, or any combination thereof. Pharmaceutically active agents that may be used in combination with the compounds of Formula I and compositions thereof include, without limitation:

(i) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(ii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(iii) catechol O-methyltransferase (COMT) inhibitors, such as nitecapone, tolcapone (TASMAR), entacapone (COMTAN), and tropolone;

(iv) monoamine oxidase (MAO) inhibitors, such as selegiline (EMSAM), selegiline hydrochloride (I-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-ß (or fragments thereof), such as Aß$_{1-15}$ conjugated to pan HLA DR-binding epitope (PADRE®), ACC-001 (Elan/Wyeth), and Affitope;

(vii) antibodies to amyloid-ß (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate, celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the gingko biloba extract EGb-761 (ROKAN®, TEBONIN®), tramiprosate (CEREBRIL®, ALZHEMED®), KIACTA®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) phosphodiesterase (PDE) inhibitors, including (a) PDE1 inhibitors; (b) PDE2 inhibitors; (c) PDE3 inhibitors; (d) PDE4 inhibitors; (e) PDE5 inhibitors; (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)); and (g) PDE10 inhibitors such as 2-({4-[1-methyl-4-(pyridin-4-yl)-1H-pyrazol-3-yl]phenoxy}methyl)quinoline (PF-2545920);

(xiii) serotonin (5-hydroxytryptamine) 1A (5-HT$_{1A}$) receptor antagonists, such as spiperone, levo-pindolol, lecozotan;

(xiv) serotonin (5-hydroxytryptamine) 2C (5-HT$_{2C}$) receptor agonists, such as vabicaserin, and zicronapine; serotonin (5-hydroxytryptamine) 4 (5-HT$_4$) receptor agonists/antagonists, such as PRX-03140 (Epix) and PF-04995274;

(xv) serotonin (5-hydroxytryptamine) 3C (5-HT$_{3C}$) receptor antagonists, such as Ondansetron (Zofran);

(xvi) serotonin (5-hydroxytryptamine) 6 (5-HT$_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xviii) Glycine transporter-1 inhibitors such as paliflutine, ORG-25935, and ORG-26041; and mGluR modulators such as AFQ-059 and amantidine;

(xix) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xx) P450 inhibitors, such as ritonavir;

(xxi) tau therapy targets, such as davunetide;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the Reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in many cases, the compounds in Reaction Schemes 1 through 9 may be generated as a mixture of diastereomers and/or enantiomers; these may be separated at various stages of the synthetic schemes using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compounds of Formula I and intermediates thereof may be prepared according to the following reaction schemes and accompanying discussion. Unless otherwise indicated, $R^1$, $R^2$, $R^4$, $R^5$, $R^6$, X and Z in the reaction schemes and discussions that follow are as defined as the same as hereinabove. In general the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes may be described in the experimental section. The schemes and examples provided herein (including the corresponding description) are for illustration only, and not intended to limit the scope of the present invention.

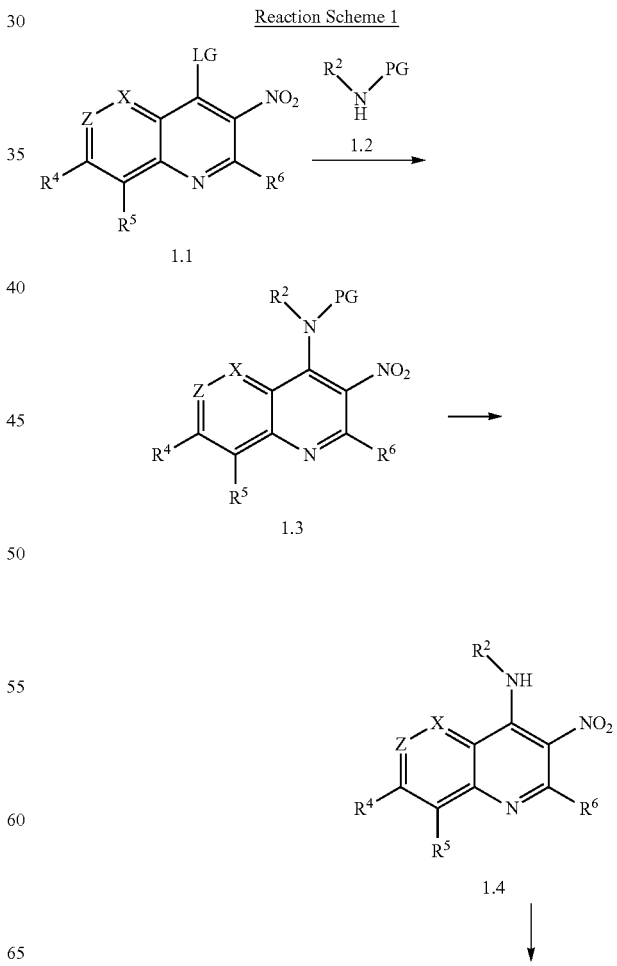

Reaction Scheme 1

-continued

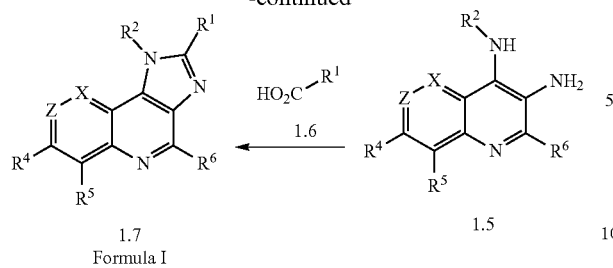

1.7
Formula I

Reaction Scheme 2

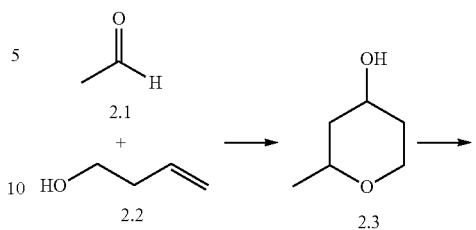

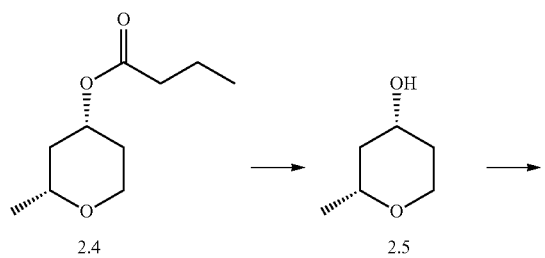

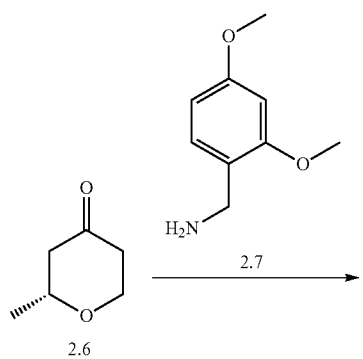

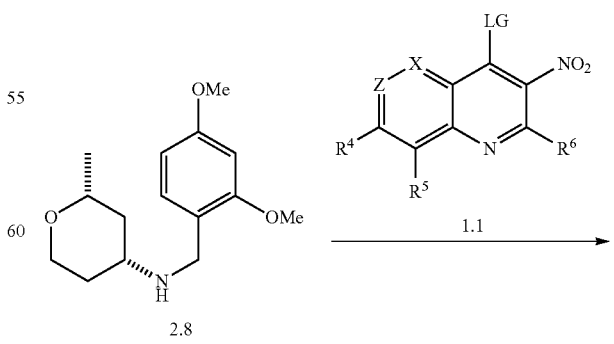

Reaction Scheme 1 depicts the preparation of compounds of Formula (I). Referring to Scheme 1, compounds 1.1 and 1.2 are either commercially available or can be made by methods described herein or other methods well known to those skilled in the art. In the compound of formula 1.1 the group designated LG represents an appropriate leaving group such as a halide (e.g., chloro or bromo) or triflate which is suitable to undergo nucleophilic displacement when reacted with the amine of formula 1.2. In the amine compound of formula 1.2, the group designated PG represents an appropriate amine protecting group such as an acid-labile protecting group selected from 2,4-dimethoxybenzyl (DMB), 4-methoxybenzyl (PMB) and t-butoxycarbonyl (Boc). The compounds of formulae 1.1 and 1.2 can be reacted, for example, in the presence of an appropriate base such as N,N-diisopropylethylamine (Hunig's base) or triethylamine in a suitable solvent such as acetonitrile or N,N-dimethylformamide (DMF) to afford the compound of formula 1.3. The reaction is typically carried out at an elevated temperature, such as 50 to 100° C. for a period of 1 to 48 hours. Removal of the protecting group, such as an acid-labile protecting group (PG) from the compound of formula 1.3 can typically be accomplished by treatment of 1.3 with an appropriate acid such as acetic acid, trifluoroacetic acid or hydrochloric acid to provide the compound of formula 1.4. Also, it is to be understood that in certain instances the compound of formula 1.1 can be reacted with an unprotected amine of formula $R^2$—$NH_2$ to arrive directly to a compound of formula 1.4. Reduction of the nitro group in the compound of formula 1.4 using conditions congruent with the functionality present affords the compound of formula 1.5. For example, the nitro group in the compound of formula 1.4 can be reduced to the corresponding amine of formula 1.5 by treatment of 1.4 with zinc dust and ammonium hydroxide in methanol or alternatively by hydrogenation of 1.4 using an appropriate catalyst such as platinum (IV) oxide in an appropriate solvent such as methanol, acetonitrile or a mixture thereof. Coupling the diamine compound 1.5 with the carboxylic acid of formula 1.6 then provides the desired compound of Formula I, also denoted as 1.7. The coupling reaction with the diamine of formula 1.5 and the carboxylic acid of formula 1.6 can be carried out in an appropriate solvent such as N,N-dimethylformamide or N-propylacetate in the presence of an appropriate base such as N,N-diisopropylethylamine and a coupling reagent such as 2,4,6-tripropyl-1,3,5,2,4,6-trioxatriphosphirane 2,4,6-trioxide or 1-ethyl-3-(3-dimethylaminopropyl)carbodiimide (EDCI). The coupling reaction is often heated between 60° C. and 110° C.

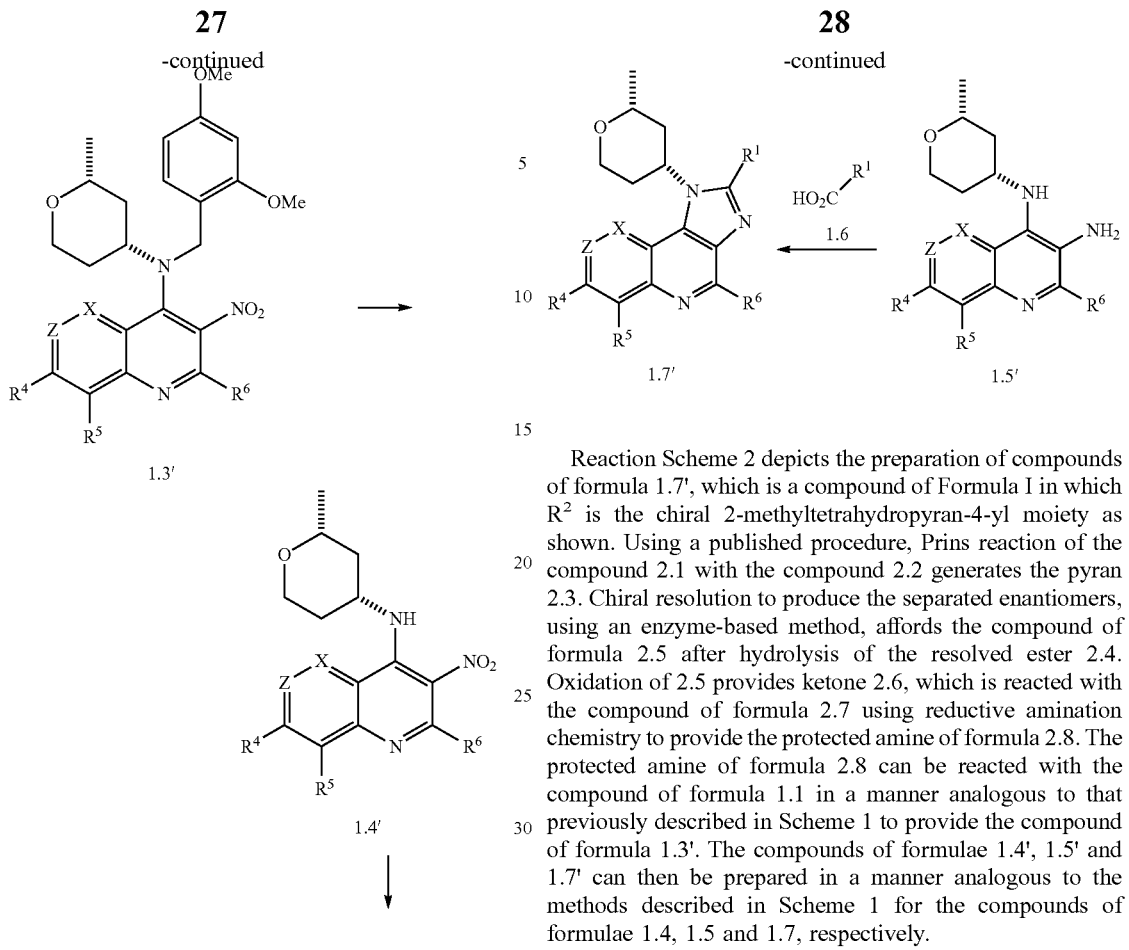

Reaction Scheme 2 depicts the preparation of compounds of formula 1.7', which is a compound of Formula I in which $R^2$ is the chiral 2-methyltetrahydropyran-4-yl moiety as shown. Using a published procedure, Prins reaction of the compound 2.1 with the compound 2.2 generates the pyran 2.3. Chiral resolution to produce the separated enantiomers, using an enzyme-based method, affords the compound of formula 2.5 after hydrolysis of the resolved ester 2.4. Oxidation of 2.5 provides ketone 2.6, which is reacted with the compound of formula 2.7 using reductive amination chemistry to provide the protected amine of formula 2.8. The protected amine of formula 2.8 can be reacted with the compound of formula 1.1 in a manner analogous to that previously described in Scheme 1 to provide the compound of formula 1.3'. The compounds of formulae 1.4', 1.5' and 1.7' can then be prepared in a manner analogous to the methods described in Scheme 1 for the compounds of formulae 1.4, 1.5 and 1.7, respectively.

Reaction Scheme 3

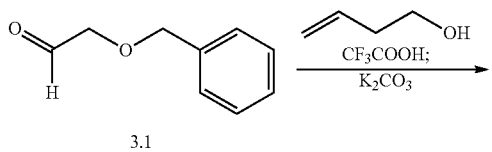

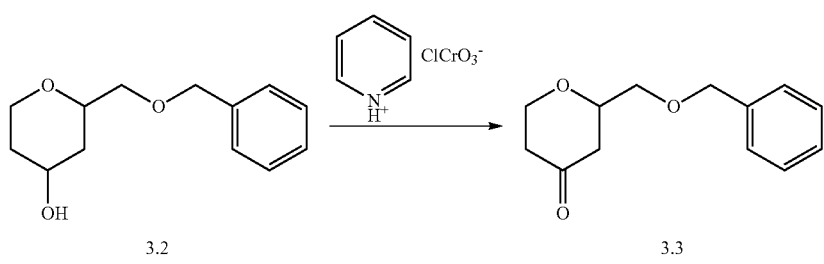

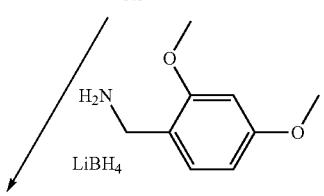

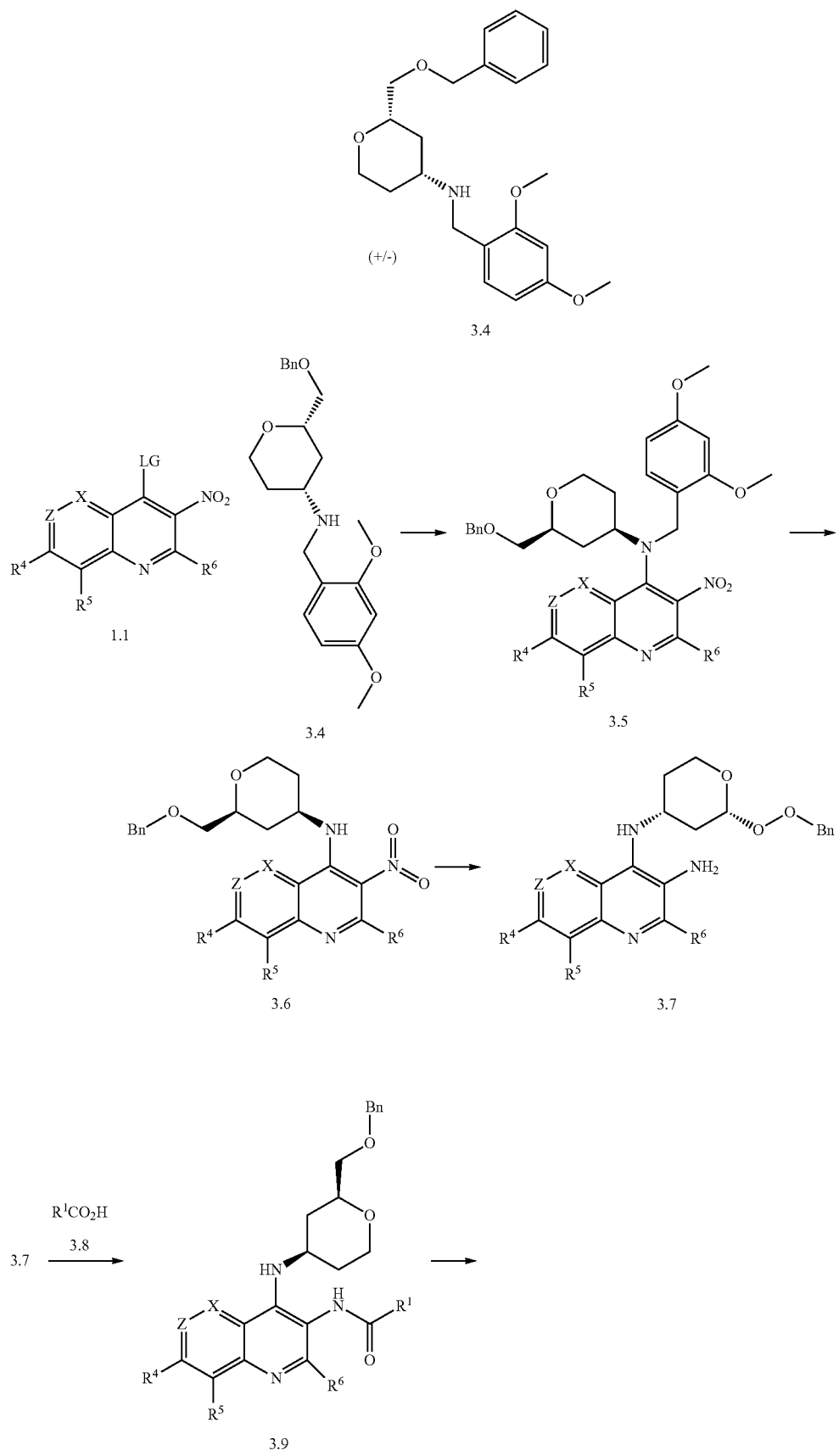

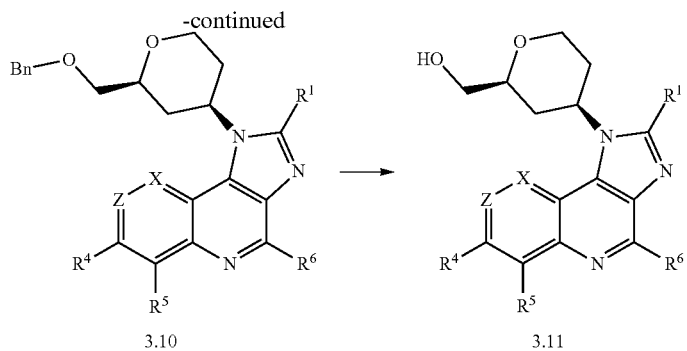

3.10 → 3.11

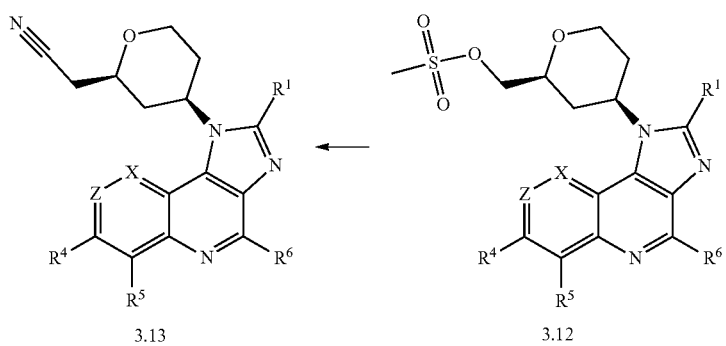

3.13 ← 3.12

Reaction Scheme 3 depicts the preparation of compounds of formula 3.13, which is a compound of Formula I in which $R^2$ is the chiral 2-cyanomethyltetrahydropyran-4-yl moiety as shown. Using a published procedure, Prins reaction of the compound 3.1 with but-3-en-1-ol generated the pyran 3.2. Oxidation of 3.2 gave ketone 3.3 which was reacted with dimethoxybenzylamine using reductive amination chemistry to provide the protected amine of formula 3.4. The protected amine of formula 3.4 can be reacted with the compound of formula 1.1 in a manner analogous to that previously described in Scheme 1 to provide the compound of formula 3.5. Removal of the protecting group under acidic conditions afforded 3.6. The nitro group of 3.6 is reduced by catalytic hydrogenation or by treatment with a metal such as zinc or iron to afford the diamine 3.7. Acylation of 3.7 with acid 3.8 under a variety of coupling conditions known to those skilled in the art affords 3.9. The amide 3.9 can be dehydrated under thermal conditions to afford 3.10. Deprotection of 3.10 with a Lewis acid such as $BCl_3$, TMSI, $AlCl_3$ or through palladium-catalyzed hydrogenolysis afford the alcohol 3.11. The alcohol 3.11 can be converted to an activated leaving group such as, but not limited to, a sulfonate such as the mesylate 3.12. The compounds of formulae 3.13 can then be prepared by nucleophilic displacement of the mesylate with cyanide anion.

Reaction Scheme 4

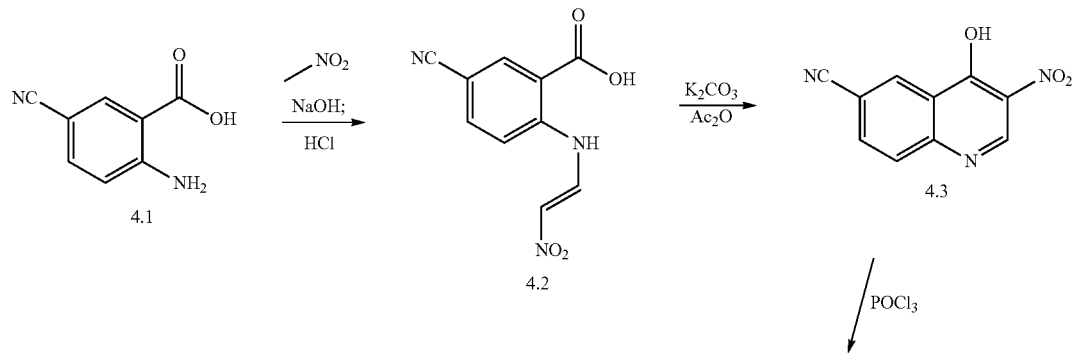

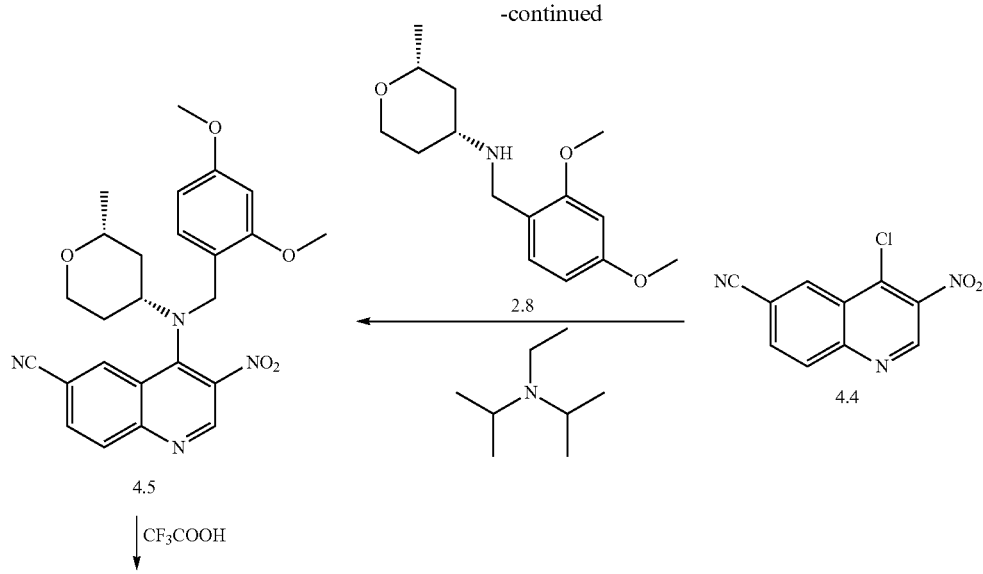

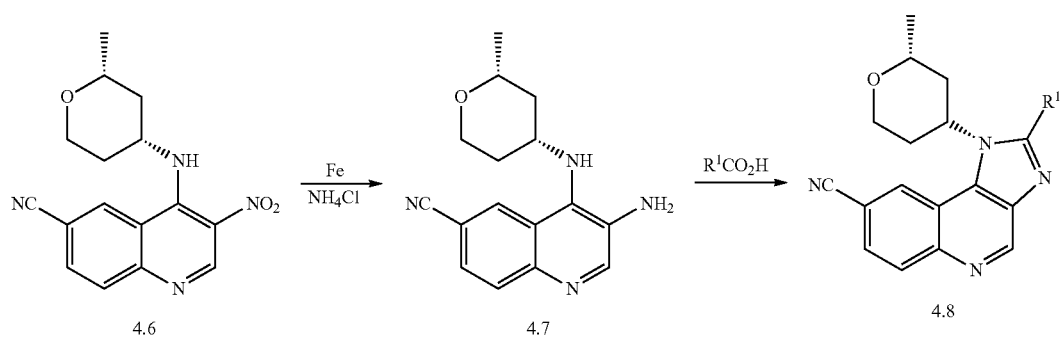

Reaction Scheme 4 depicts the preparation of compounds of formula 4.8, which is a compound of Formula I in which $R^2$ is the chiral 2-methyltetrahydropyran-4-yl moiety, Z is $CR^3$ and $R^3$ is cyano, X is CH and $R^4$, $R^5$ and $R^6$ are each hydrogen as shown. The reaction begins from known acid 4.1, which is reacted with N-hydroxy-2-nitroethenamine prepared in situ to afford 4.2. The nitroamine 4.2 was treated with an agent that activated the carboxylic acid followed by condensation to afford quinolone 4.3. The phenol of 4.3 can be converted to the activated chloride 4.4 with phosphorous oxychloride or thionyl chloride. Chloride 4.4 can undergo nucleophilic displacement with an appropriate amine such as 2.8 to afford 4.5. 4.5 can be deprotected to provide 4.6 which, in turn, is reduced to provide diamine 4.7. Compounds of formula 4.8 can be made from 4.7 by condensation with an appropriate acid $R^1CO_2H$ in a manner similar to that previously described.

Reaction Scheme 5

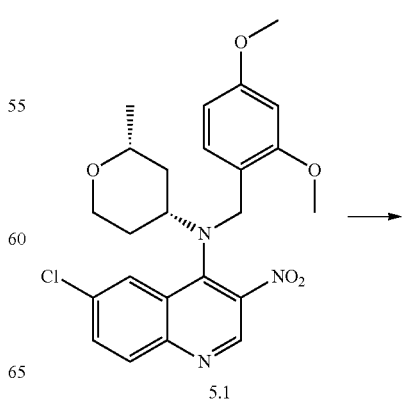

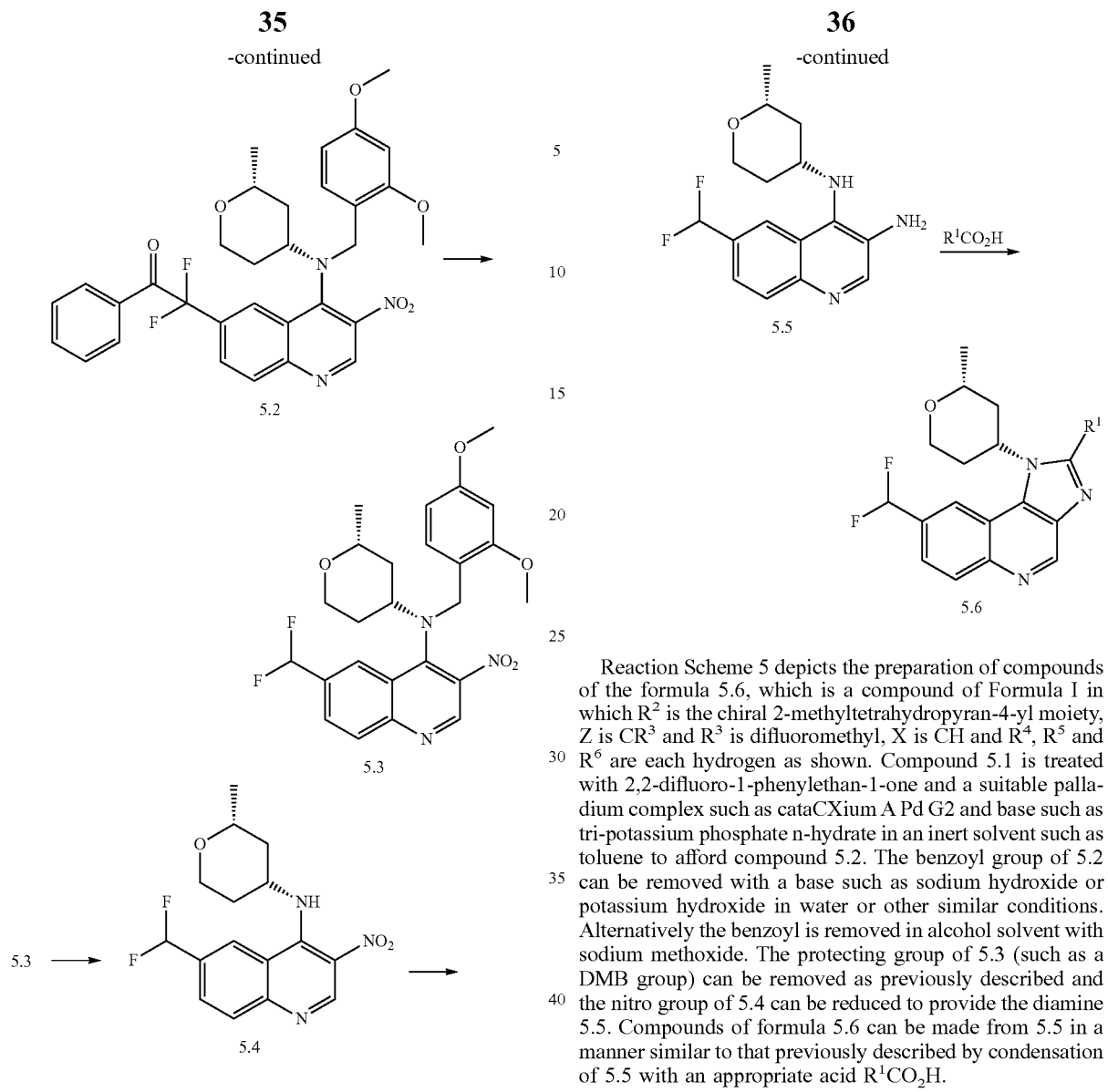

Reaction Scheme 5 depicts the preparation of compounds of the formula 5.6, which is a compound of Formula I in which $R^2$ is the chiral 2-methyltetrahydropyran-4-yl moiety, Z is $CR^3$ and $R^3$ is difluoromethyl, X is CH and $R^4$, $R^5$ and $R^6$ are each hydrogen as shown. Compound 5.1 is treated with 2,2-difluoro-1-phenylethan-1-one and a suitable palladium complex such as cataCXium A Pd G2 and base such as tri-potassium phosphate n-hydrate in an inert solvent such as toluene to afford compound 5.2. The benzoyl group of 5.2 can be removed with a base such as sodium hydroxide or potassium hydroxide in water or other similar conditions. Alternatively the benzoyl is removed in alcohol solvent with sodium methoxide. The protecting group of 5.3 (such as a DMB group) can be removed as previously described and the nitro group of 5.4 can be reduced to provide the diamine 5.5. Compounds of formula 5.6 can be made from 5.5 in a manner similar to that previously described by condensation of 5.5 with an appropriate acid $R^1CO_2H$.

Reaction Scheme 6

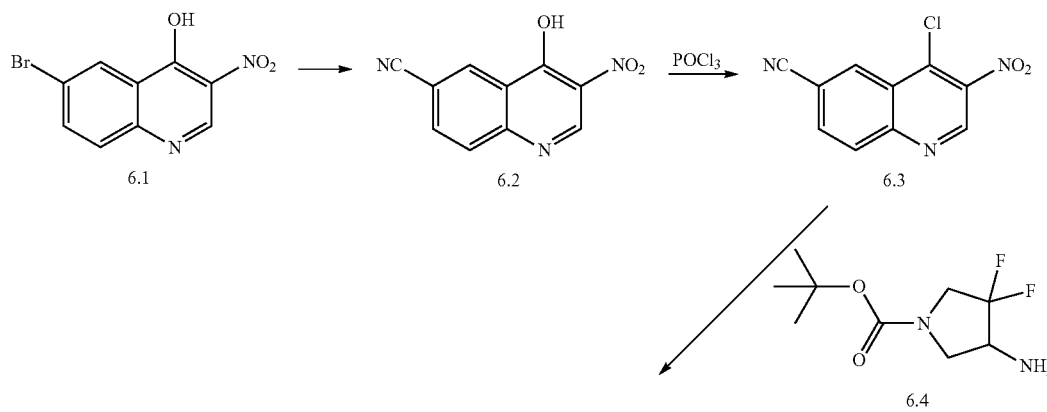

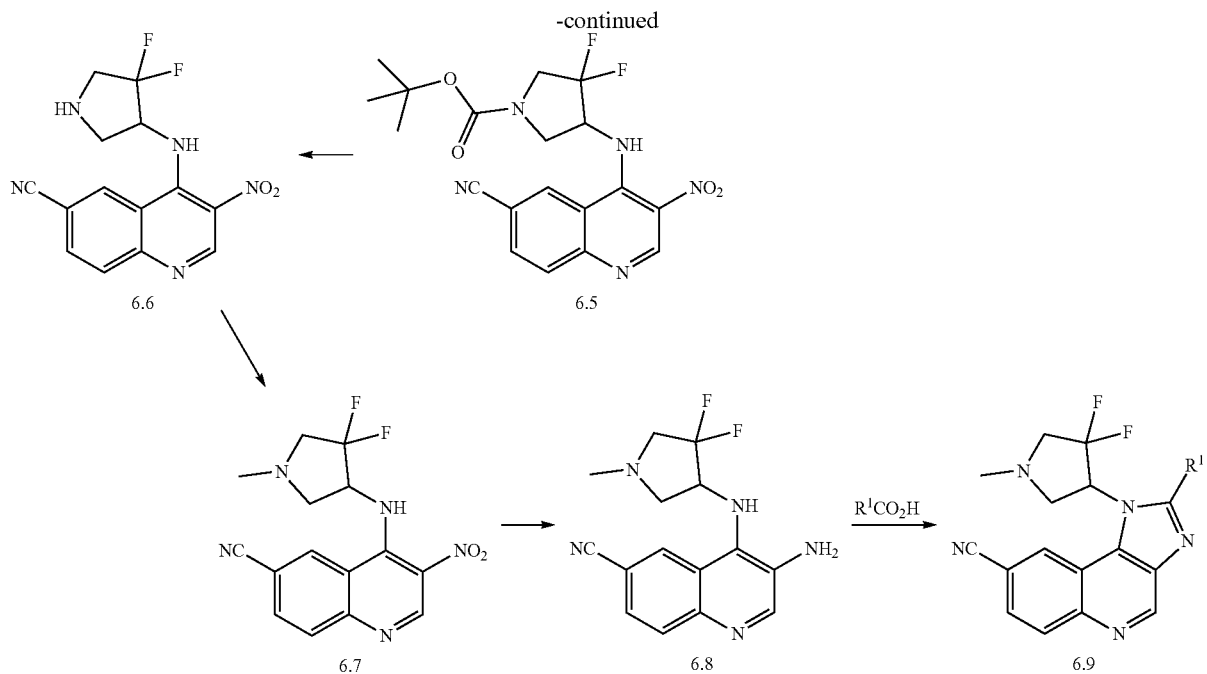

Reaction Scheme 6 depicts the preparation of compounds of the formula 6.9, which is a compound of Formula I in which $R^2$ is the chiral 4,4-difluoro-1-methylpyrrolidin-3-yl moiety, Z is $CR^3$ and $R^3$ is cyano, X is CH and $R^4$, $R^5$ and $R^6$ are each hydrogen as shown. This amine is available through a procedure described in US Published Patent Application 20150141402. This series of compounds may be prepared as in the examples above, through formation of the chloride 6.3 through reaction of 6.2 with phosphorous oxychloride or thionyl chloride in a suitable inert solvent. The chloride was treated with amine 6.4 in the presence of a suitable base such as Hunig's base (N,N-diisopropylethylamine) or triethylamine to afford 6.5. The protecting group is removed by treatment of 6.5 with an acid such as trifluoroacetic acid or hydrochloric acid. The secondary amine 6.6 can be methylated through a standard reductive amination using formaldehyde and a reducing agent such as sodium triacetoxyborohydride or sodium cyanoborohydride. The nitro group of compound 6.7 can be reduced through hydrogenation over a platinum catalyst or alternatively the nitro group can be reduced with a suitable metal such as iron or zinc. The claimed compounds 6.9 can be made from 6.8 through condensations with a suitable acid $R^1CO_2H$ under the conditions described previously.

Reaction Scheme 7

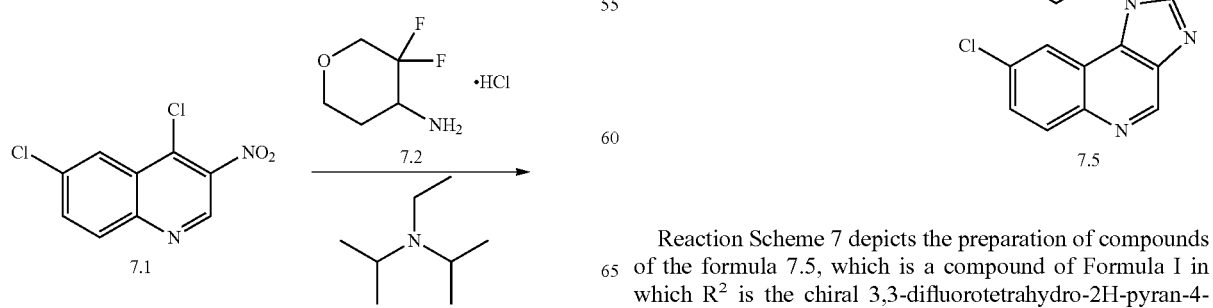

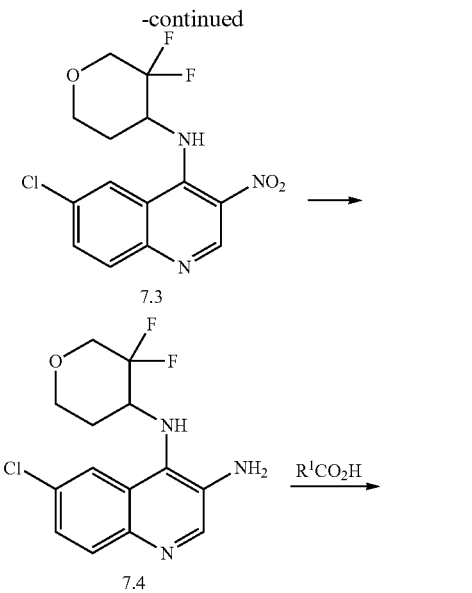

Reaction Scheme 7 depicts the preparation of compounds of the formula 7.5, which is a compound of Formula I in which $R^2$ is the chiral 3,3-difluorotetrahydro-2H-pyran-4-amine moiety, Z is $CR^3$ and $R^3$ is chloro, X is CH and $R^4$, $R^5$ and $R^6$ are each hydrogen as shown. The chloride 7.1 is treated with amine 7.2 in the presence of a suitable base such as Hunig's base or triethylamine to afford 7.3. The nitro group of compound 7.3 can be reduced through hydrogenation over a platinum catalyst or alternatively the nitro group can be reduced with a suitable metal such as iron or zinc. The compounds 7.5 can then be made from 7.4 through condensation with a suitable acid $R^1CO_2H$ under the conditions described previously.

Reaction Scheme 8

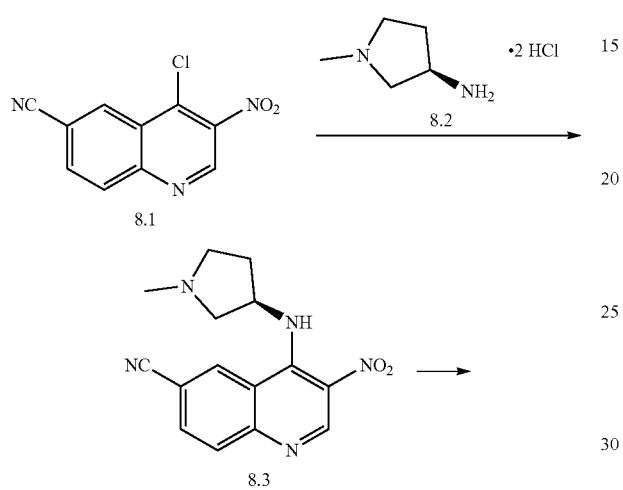

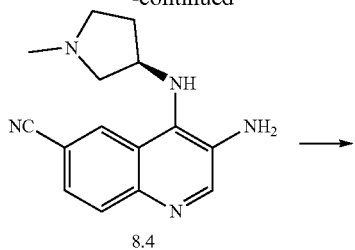

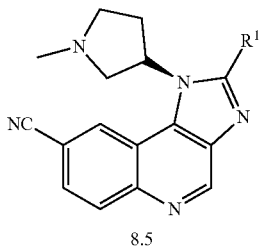

Reaction Scheme 8 depicts the preparation of compounds of the formula 8.5, which is a compound of Formula I in which $R^2$ is the chiral (R)-1-methylpyrrolidin-3-amine moiety, Z is $CR^3$ and $R^3$ is cyano, X is CH and $R^4$, $R^5$ and $R^6$ are each hydrogen as shown. The chloride was treated with chiral amine 8.2 in the presence of a suitable base such as Hunig's base or triethylamine to afford 8.3. The nitro group of compound 8.3 can be reduced through hydrogenation over a platinum catalyst or alternatively the nitro group can be reduced with a suitable metal such as iron or zinc. The compounds 8.5 can be made from 8.4 through condensation with a suitable acid $R^1CO_2H$ under the conditions described previously.

Reaction Scheme 9

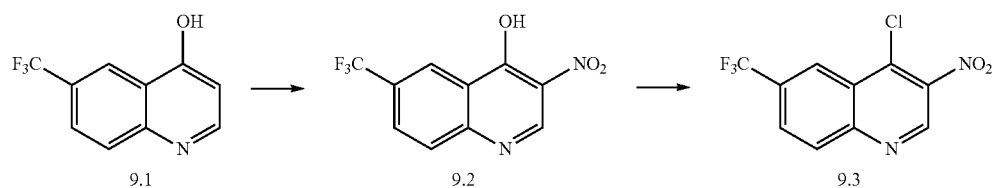

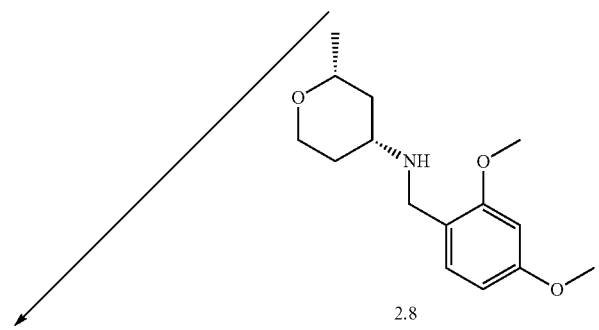

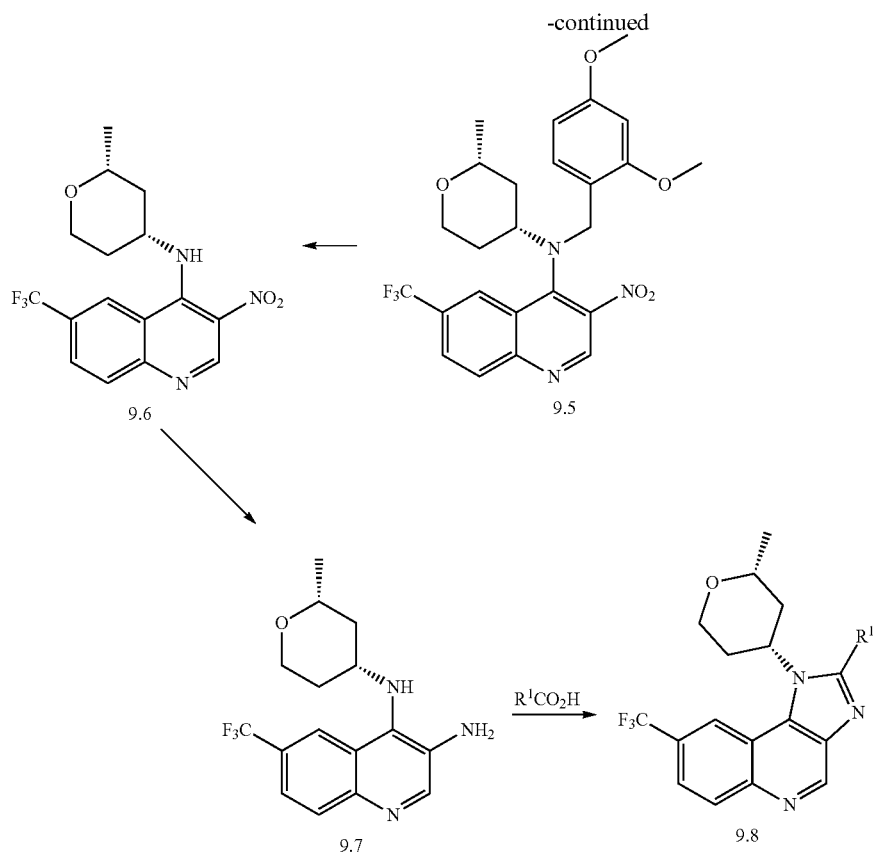

Reaction Scheme 9 depicts the preparation of compounds of the formula 9.8, which is a compound of Formula I in which $R^2$ is the chiral 2-methyltetrahydropyran-4-yl moiety, Z is $CR^3$ and $R^3$ is trifluoromethyl, X is CH and $R^4$, $R^5$ and $R^6$ are each hydrogen as shown. The chloride 9.3 was treated with amine 2.8 in the presence of a suitable base such as Hunig's base or triethylamine to afford 9.5. Removal of the protecting group under acidic conditions affords 9.6. The nitro group of compound 9.6 can be reduced through hydrogenation over a platinum catalyst or alternatively the nitro group can be reduced with a suitable metal such as iron or zinc. The claimed compounds 9.8 can be made from 9.7 through condensation with a suitable acid $R^1CO_2H$ under the conditions described previously.

The methods generically described in Schemes 1 through 9 are not to be construed in a limiting manner. It is to be understood by one skilled in the art that variation in the order of certain reaction steps and conditions may be employed to provide compounds of Formula I. The selection of which approach is best to utilize can be made by one skilled in the art of organic synthesis. More specific examples of the methods used to prepare compounds of Formula I are provided below in the Examples, and likewise these methods are also not to be construed by one skilled in the art in a limiting manner.

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

In the experimental sections that follow the following abbreviations may be used. ACN is acetonitrile; Ac$_2$O is acetic anhydride; br is broad; ° C. is degrees Celsius; CDCl$_3$ is deutero chloroform; CD$_3$OD is deutero methanol; CH$_3$NO$_2$ is nitromethane; d is doublet; DCM is dichloromethane; DEA is diethylamine; DIAST is diastereomer; DIEA is N,N-diisopropylethylamine; DMB is dimethoxybenzyl; DMSO is dimethyl sulfoxide, EDCI is 1-(3-dimethylaminopropyl)-3-ethylcarbodiimide hydrochloride; ENT is enantiomer; EtOAc is ethyl acetate; EtOH is ethanol; ES is electrospray; FA is formic acid; g is gram; h is hour; HCl is hydrochloric acid; H$_2$ is hydrogen; H$_2$O is water; HPLC is high performance liquid chromatography; Hz is hertz; K$_2$CO$_3$ is potassium carbonate; L is liter; LC is liquid chromatography; LCMS is liquid chromatography mass spectrometry; m is multiplet; M is molar; MeOH is methanol; MgSO$_4$ is magnesium sulfate; MHz is megahertz; min is minute; mL is milliliter, mM is millimole; μL is microliter; μM is micromole; MS is mass spectrometry; MsCl is methane sulfonyl chloride; MTBE is methyl tert-butyl ether; N$_2$ is nitrogen; NEt$_3$ is triethylamine; NaHCO$_3$ is sodium bicarbonate; Na$_2$SO$_4$ is sodium sulfate; NH$_4$Cl is ammonium chloride; NH$_4$HCO$_3$ is ammonium hydrogen carbonate; NH$_4$OH is ammonium hydroxide; NMR is nuclear magnetic resonance, PE is petroleum ether; PSI is pounds per square inch; Pt/C is platimun on carbon; RT is retention time or room temperature depending on context; s is singlet; SFC is super critical fluid chromatography; t is triplet; TFA is trifluoroacetic acid; THF is tetrahydrofuran; TLC is thin-layer chromatography; and T3P is propyl phosphonic anhydride.

PREPARATION OF INTERMEDIATES

Preparation P1 cis-N-(2,4-Dimethoxybenzyl)-2-methyltetrahydro-2H-pyran-4-amine (P1)

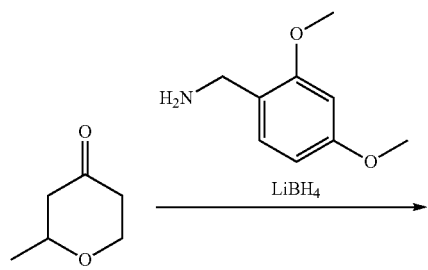

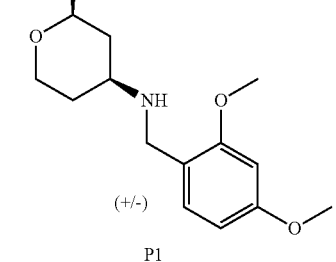

1-(2,4-Dimethoxyphenyl)methanamine (1.97 mL, 13.1 mmol) was added to a solution of 2-methyltetrahydro-4H-pyran-4-one (500 mg, 4.4 mmol) in methanol (10 mL). After stirring for 1 hour at room temperature, the reaction mixture was cooled to −78° C. and a solution of lithium borohydride (98%, 85 mg, 3.8 mmol) in tetrahydrofuran (1.5 mL) was added drop-wise. The reaction mixture was allowed to slowly warm to room temperature overnight, whereupon it was cooled to −20° C. and quenched via careful addition of saturated aqueous sodium bicarbonate solution. Ethyl acetate (25 mL) and sufficient water to solubilize the precipitate were added, and the aqueous layer was extracted with ethyl acetate. The combined organic layers were dried over magnesium sulfate, filtered, and concentrated in vacuo. Chromatography on silica gel [Gradient: 0% to 15% (10:1 methanol/concentrated ammonium hydroxide) in ethyl acetate] provided the product as a colorless oil. Yield: 936 mg, 3.53 mmol, 80%. $^1$H NMR (400 MHz, CDCl$_3$) δ 7.13 (d, J=8.0 Hz, 1H), 6.46 (d, half of AB quartet, J=2.2 Hz, 1H), 6.44 (dd, half of ABX pattern, J=8.1, 2.3 Hz, 1H), 4.00 (ddd, J=11.6, 4.6, 1.6 Hz, 1H), 3.82 (s, 3H), 3.81 (s, 3H), 3.76 (s, 2H), 3.37-3.46 (m, 2H), 2.63-2.72 (m, 1H), 1.85-1.92 (m, 1H), 1.78-1.85 (m, 1H), 1.37 (dddd, J=13, 12, 11, 4.6 Hz, 1H), 1.20 (d, J=6.2 Hz, 3H), 1.10 (ddd, J=12, 11, 11 Hz, 1H).

Alternate Preparation of P1 cis-N-(2,4-Dimethoxybenzyl)-2-methyltetrahydro-2H-pyran-4-amine (P1)

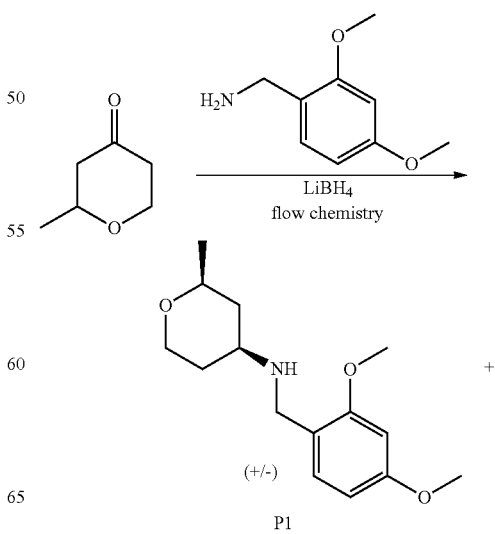

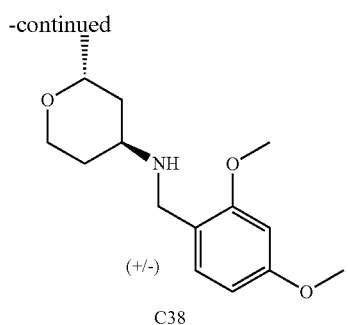

Using a syringe pump, 2-methyltetrahydro-4H-pyran-4-one (7.00 g, 61.3 mmol) was added over 3.5 hours (2 mL/hour) to a solution of 1-(2,4-dimethoxyphenyl)methanamine (9.21 mL, 61.3 mmol) in methanol (137 mL). After completion of the addition, the reaction mixture was allowed to stir at room temperature for 1 hour. This solution was then reacted with lithium borohydride (0.48 M solution in tetrahydrofuran, 153.2 mL, 73.5 mmol) using a flow reactor [25 mL reactor made up of a 1 mL glass chip with two feeding channels and perfluoroalkoxy tubing (24 mL volume); Temperature: −78° C.; Reaction concentration: 0.2 M; Residence time: 10 minutes; Flow rate: 1.25 mL/minute on both streams]. The collected reaction mixture was diluted with saturated aqueous sodium bicarbonate solution and extracted with ethyl acetate. The combined organic layers were dried over sodium sulfate, filtered, and concentrated in vacuo. $^1$H NMR analysis at this point revealed a cis: trans ratio of 10.7:1. Silica gel chromatography (Gradient: 0% to 20% methanol in ethyl acetate) afforded cis product P1. Yield: 11.59 g, 43.68 mmol, 71%. $^1$H NMR (400 MHz, CDCl$_3$) δ 7.16 (d, J=8.0 Hz, 1H), 6.41-6.48 (m, 2H), 4.00 (ddd, J=11.7, 4.7, 1.8 Hz, 1H), 3.82 (s, 3H), 3.80 (s, 3H), 3.78 (s, 2H), 3.36-3.46 (m, 2H), 2.70 (tt, J=11.2, 4.1 Hz, 1H), 1.87-1.94 (m, 1H), 1.79-1.87 (m, 1H), 1.35-1.47 (m, 1H), 1.20 (d, J=6.2 Hz, 3H), 1.08-1.19 (m, 1H).

Also isolated was the trans isomer C38. Yield: 1.24 g, 4.67 mmol, 7.6%. $^1$H NMR (400 MHz, CDCl$_3$) δ 7.14 (d, J=8.2 Hz, 1H), 6.42-6.48 (m, 2H), 3.84-3.94 (m, 2H), 3.82 (s, 3H), 3.81 (s, 3H), 3.69-3.77 (m, 3H), 2.97-3.02 (m, 1H), 1.72-1.82 (m, 1H), 1.44-1.66 (m, 3H), 1.14 (d, J=6.2 Hz, 3H).

Preparation P2

(2R,4R)—N-(2,4-Dimethoxybenzyl)-2-methyltetrahydro-2H-pyran-4-amine (P2)

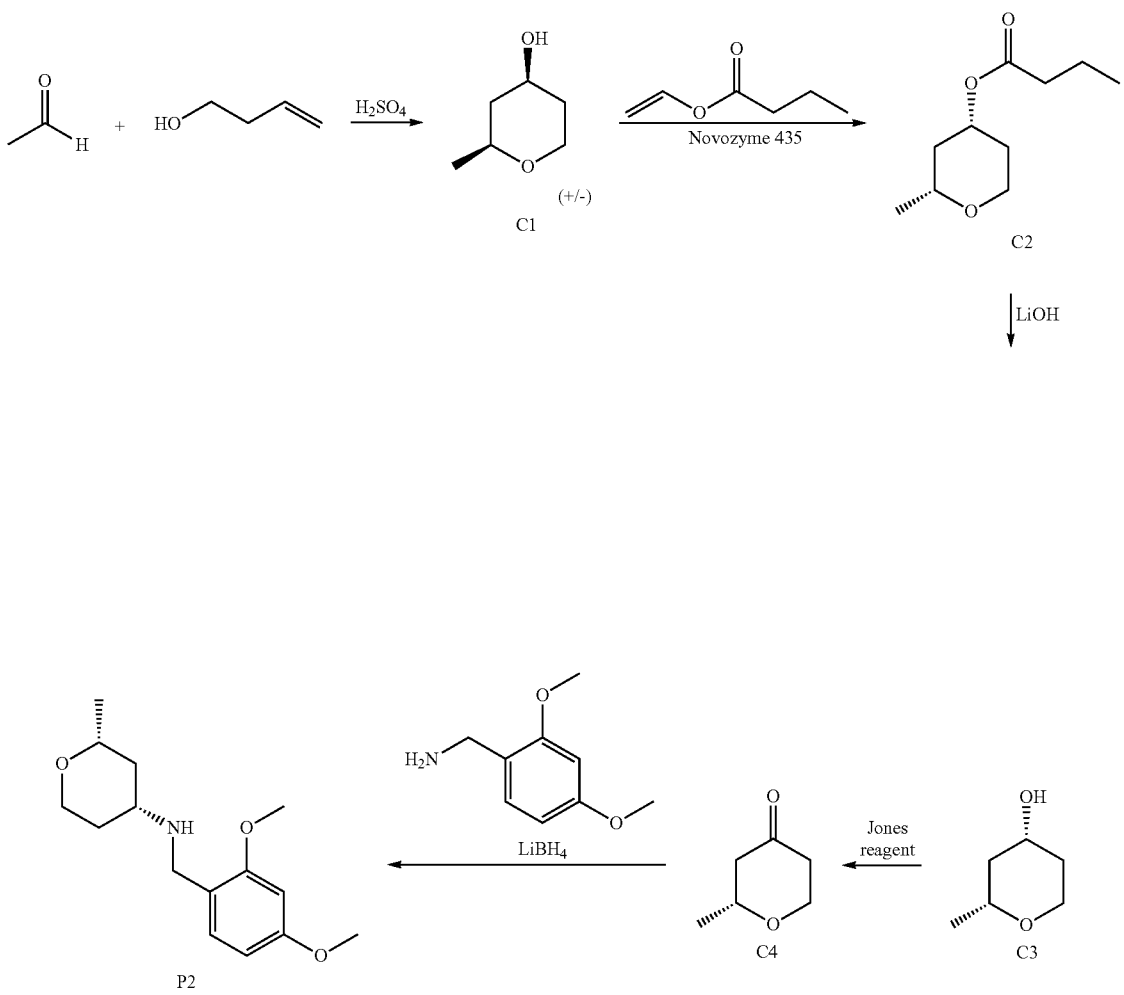

Step 1: Synthesis of cis-2-methyltetrahydro-2H-pyran-4-ol (C1)

But-3-en-1-ol (39.0 mL, 453 mmol) and acetaldehyde (25.5 mL, 454 mmol) were combined in aqueous sulfuric acid (20% w/w, 565 g) and stirred at 80° C. for 5 days. The reaction mixture was cooled to room temperature and extracted with diethyl ether, and then with dichloromethane; the combined organic layers were dried over magnesium sulfate, filtered, and concentrated in vacuo. Silica gel chromatography (Gradient: 0% to 25% ethyl acetate in heptane) afforded the product as a colorless oil. Yield: 11.2 g, 96.4 mmol, 21%. $^1$H NMR (400 MHz, CDCl$_3$) δ 3.99 (ddd, J=11.8, 4.9, 1.7 Hz, 1H), 3.71-3.80 (m, 1H), 3.35-3.46 (m, 2H), 1.82-1.98 (m, 3H), 1.48 (dddd, J=12.5, 12.4, 11.1, 4.9 Hz, 1H), 1.21 (d, J=6.2 Hz, 3H), 1.14-1.24 (m, 1H).

Step 2: Synthesis of (2R,4R)-2-methyltetrahydro-2H-pyran-4-ylbutanoate (C2)

Ethenyl butanoate (78.6 mL, 620 mmol) and Novozyme 435 (immobilized *Candida antarctica* lipase B, 25 g) were added to a solution of C1 (150 g, 1.29 mol) in tetrahydrofuran (1.3 L). The reaction mixture was stirred at room temperature for 2 hours, whereupon it was filtered through a pad of diatomaceous earth, which was then rinsed twice with dichloromethane. The combined filtrates were concentrated in vacuo and purified via silica gel chromatography (Gradient: 0% to 10% ethyl acetate in heptane), providing the product as an oil. Yield: 51.5 g, 276 mmol, 45%. The absolute configurations of C2 and subsequent intermediates were confirmed via an X-ray structural determination carried out on C14 (see Example 2). $^1$H NMR (400 MHz, CDCl$_3$) δ 4.82-4.92 (m, 1H), 3.99 (ddd, J=11.9, 4.9, 1.7 Hz, 1H), 3.42-3.52 (m, 2H), 2.25 (t, J=7.4 Hz, 2H), 1.92-2.00 (m, 1H), 1.84-1.91 (m, 1H), 1.52-1.69 (m, 3H), 1.28 (ddd, J=12, 11, 11 Hz, 1H), 1.20 (d, J=6.2 Hz, 3H), 0.94 (t, J=7.4 Hz, 3H).

Step 3: Synthesis of (2R,4R)-2-methyltetrahydro-2H-pyran-4-ol (C3)

A solution of C2 (51.5 g, 276 mmol) in methanol and tetrahydrofuran (1:1, 700 mL) was treated with a solution of lithium hydroxide (19.9 g, 831 mmol) in water (120 mL), and the reaction mixture was stirred overnight at room temperature. After removal of the organic solvents via concentration under reduced pressure, the aqueous residue was extracted 4 times with dichloromethane; the combined organic layers were dried over magnesium sulfate, filtered, and concentrated in vacuo to afford the product as a colorless oil. Yield: 27.3 g, 235 mmol, 85%. $^1$H NMR (400 MHz, CDCl$_3$) δ 3.99 (ddd, J=11.8, 4.8, 1.7 Hz, 1H), 3.71-3.80 (m, 1H), 3.35-3.47 (m, 2H), 1.82-1.98 (m, 3H), 1.48 (dddd, J=12.5, 12.4, 11.1, 4.8 Hz, 1H), 1.21 (d, J=6.2 Hz, 3H), 1.14-1.24 (m, 1H).

Step 4: Synthesis of (2R)-2-methyltetrahydro-4H-pyran-4-one (C4)

A solution of C3 (27.3 g, 235 mmol) in acetone (980 mL) was cooled in an ice bath and treated drop-wise with Jones reagent (2.5 M, 103 mL, 258 mmol). The reaction mixture was stirred for 10 minutes at 0° C., then warmed to room temperature, stirred for a further 30 minutes, and cooled to 0° C. 2-Propanol (18 mL, 240 mmol) was added, and stirring was continued for 30 minutes. After the mixture had been concentrated in vacuo, the residue was partitioned between water and dichloromethane; the aqueous layer was extracted 3 times with dichloromethane, and the combined organic layers were dried over magnesium sulfate, filtered, and concentrated under reduced pressure to provide the product as a light yellow oil. Yield: 23 g, 200 mmol, 85%. $^1$H NMR (400 MHz, CDCl$_3$) δ 4.25 (ddd, J=11.5, 7.4, 1.3 Hz, 1H), 3.70 (dqd, J=12.2, 6.1, 2.7 Hz, 1H), 3.64 (ddd, J=12.2, 11.6, 2.8 Hz, 1H), 2.55 (dddd, J=14.6, 12.4, 7.4, 1.0 Hz, 1H), 2.37 (ddd, J=14.4, 2.3, 2.3 Hz, 1H), 2.21-2.31 (m, 2H), 1.29 (d, J=6.2 Hz, 3H).

Step 5: Synthesis of (2R,4R)—N-(2,4-dimethoxybenzyl)-2-methyltetrahydro-2H-pyran-4-amine (P2)

1-(2,4-Dimethoxyphenyl)methanamine (20.3 mL, 135 mmol) was added to a solution of C4 (10.3 g, 90.2 mmol) in methanol (200 mL), and the reaction mixture was stirred for 1 hour at room temperature. It was then cooled to −78° C.; lithium borohydride solution (2 M in tetrahydrofuran, 45.1 mL, 90.2 mmol) was added drop-wise, and stirring was continued at −78° C. for 2 hours. After slowly warming to room temperature overnight, the reaction mixture was quenched via careful addition of saturated aqueous sodium bicarbonate solution. EtOAc (250 mL) and sufficient water to solubilize the precipitate were added, and the aqueous layer was extracted with EtOAc; the combined organic layers were dried over magnesium sulfate, filtered, and concentrated in vacuo. Silica gel chromatography (Gradient: 0% to 5% methanol in dichloromethane) provided the product as a colorless oil (10.4 g). Similar purification of mixed fractions afforded additional product (3.7 g). Combined yield: 14.1 g, 53.1 mmol, 59%. $^1$H NMR (400 MHz, CDCl$_3$) δ 7.13 (d, J=8.0 Hz, 1H), 6.42-6.47 (m, 2H), 3.99 (ddd, J=11.6, 4.6, 1.5 Hz, 1H), 3.82 (s, 3H), 3.80 (s, 3H), 3.76 (s, 2H), 3.36-3.45 (m, 2H), 2.63-2.73 (m, 1H), 1.85-1.92 (m, 1H), 1.78-1.85 (m, 1H), 1.38 (dddd, J=13, 12, 11, 4.7 Hz, 1H), 1.20 (d, J=6.2 Hz, 3H), 1.10 (ddd, J=11, 11, 11 Hz, 1H).

Alternate Preparation of P2

(2R,4R)—N-(2,4-Dimethoxybenzyl)-2-methyltetrahydro-2H-pyran-4-amine (P2)

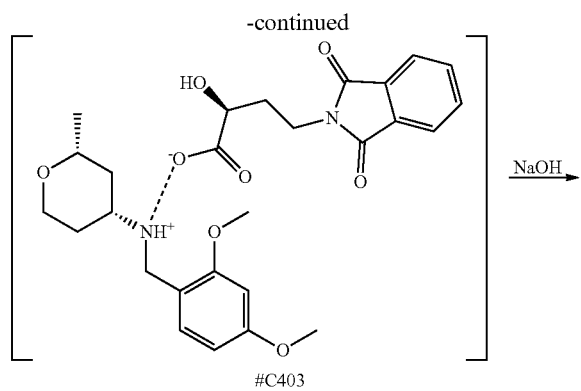

C403

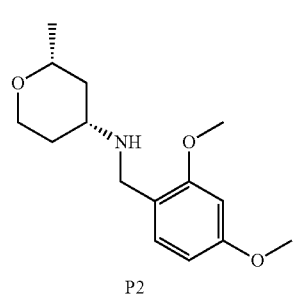

P2

A solution of P1 (200 mg, 0.754 mmol) in acetonitrile (0.05 M) was added to a slurry of (+)-(2S)-4-(1,3-dioxo-1,3-dihydro-2H-isoindol-2-yl)-2-hydroxybutanoic acid (93.9 mg, 0.377 mmol) in acetonitrile (0.15 M). The reaction mixture was heated to 75° C. to effect complete dissolution, and was then allowed to cool to room temperature and stir for an additional 18 hours. The resulting solid (C39) was collected via filtration, washed with acetonitrile, and dissolved in dichloromethane. This solution was washed three times with 1 M aqueous sodium hydroxide solution and once with saturated aqueous sodium chloride solution, dried over sodium sulfate, filtered, and concentrated in vacuo to afford the product as a colorless oil. The indicated absolute configuration was established via chiral HPLC comparison with a known sample of P2. The enantiomeric excess of this batch of P2 was determined to be 77.5% by supercritical fluid chromatography (Column: Chiral Technologies Chiralpak AS, 5 µm; Mobile phase A: carbon dioxide; Mobile phase B: ethanol containing 0.2% ammonium hydroxide; Gradient: 5% to 60% B). In this system, P2 was the second-eluting enantiomer. Yield: 68 mg, 0.26 mmol, 69%. ¹H NMR (400 MHz, CDCl₃) δ 7.13 (d, J=8.0 Hz, 1H), 6.46 (d, half of AB quartet, J=2.3 Hz, 1H), 6.44 (dd, half of ABX pattern, J=8.1, 2.4 Hz, 1H), 4.00 (ddd, J=11.7, 4.7, 1.8 Hz, 1H), 3.82 (s, 3H), 3.81 (s, 3H), 3.76 (s, 2H), 3.37-3.46 (m, 2H), 2.63-2.72 (m, 1H), 1.85-1.92 (m, 1H), 1.78-1.85 (m, 1H), 1.38 (dddd, J=12.7, 12.5, 11.3, 4.7 Hz, 1H), 1.20 (d, J=6.2 Hz, 3H), 1.10 (ddd, J=12.3, 11.3, 11.1 Hz, 1H).

Preparation P3

Synthesis of 6-chloro-N⁴-[(2R,4R)-2-methyltetrahydro-2H-pyran-4-yl]quinoline-3,4-diamine (C15)

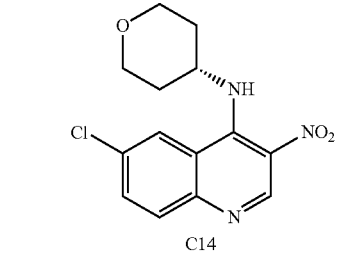

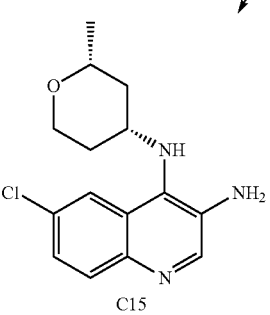

Step 1: Synthesis of 4,6-dichloro-3-nitroquinoline (C13)

N,N-Dimethylformamide (3.1 mL, 40 mmol) and thionyl chloride (97%, 6.9 mL, 93 mmol) were added to a suspension of 6-chloro-3-nitroquinolin-4-ol (15.38 g, 68.48 mmol) in dichloromethane (140 mL), and the reaction mixture was heated at reflux. After 5 hours, it was cooled to room temperature, diluted with additional dichloromethane (25 mL), and poured into saturated aqueous sodium bicarbonate solution (250 mL). The aqueous layer was extracted with dichloromethane (100 mL), then passed through a plug of diatomaceous earth, which was rinsed with dichloromethane (50 mL). The combined organic layers and organic filtrate were dried over magnesium sulfate, filtered, and concentrated in vacuo to afford the product as a pale tan solid. Yield: 16.8 g, quantitative. $^1$H NMR (400 MHz, CDCl$_3$) δ 9.25 (s, 1H), 8.42 (d, J=2.2 Hz, 1H), 8.17 (d, J=8.9 Hz, 1H), 7.89 (dd, J=9.0, 2.2 Hz, 1H).

Step 2: Synthesis of 6-chloro-N-[(2R,4R)-2-methyl-tetrahydro-2H-pyran-4-yl]-3-nitroquinolin-4-amine (C14)

Compound C13 (12.2 g, 50.2 mmol) was added to a solution of P2 (13.3 g, 50.1 mmol) and N,N-diisopropylethylamine (13.1 mL, 75.2 mmol) in acetonitrile (250 mL), and the reaction mixture was heated to 55° C. overnight. After concentration in vacuo, the residue was partitioned between aqueous sodium bicarbonate solution (100 mL) and dichloromethane (150 mL). The aqueous layer was extracted with dichloromethane (2×50 mL) and the combined organic layers were treated with trifluoroacetic acid (25 mL). {Caution: exotherm!}. After 20 minutes, saturated aqueous sodium carbonate solution (150 mL) was added portionwise, and the mixture was allowed to stir for 10 minutes. The aqueous layer was extracted twice with dichloromethane, and the combined organic layers were concentrated in vacuo, providing a reddish solid (17.3 g); this was triturated with diethyl ether (230 mL) to afford a yellow solid (14.0 g). A portion of this solid (10 g) was subjected to purification via supercritical fluid chromatography (Column: Lux Amylose-2, 5 μm; Mobile phase: 65:35 carbon dioxide/methanol), providing the product as a crystalline solid. The indicated absolute configuration was determined via single crystal X-ray structural determination on this material: see below. Yield: 7.1 g, 22 mmol, 62% (yield corrected for material omitted from purification). $^1$H NMR (400 MHz, CDCl$_3$) δ 9.36 (s, 1H), 9.11 (br d, J=9 Hz, 1H), 8.12 (d, J=2.0 Hz, 1H), 7.98 (d, J=8.9 Hz, 1H), 7.73 (dd, J=8.9, 2.2 Hz, 1H), 4.21-4.33 (m, 1H), 4.08-4.15 (m, 1H), 3.50-3.60 (m, 2H), 2.11-2.22 (m, 2H), 1.77 (dddd, J=12, 12, 12, 5 Hz, 1H), 1.49 (ddd, J=12, 12, 11 Hz, 1H), 1.28 (d, J=6.2 Hz, 3H).

Single-Crystal X-Ray Structural Determination of C14

Single Crystal X-Ray Analysis

Data collection was performed on a Bruker APEX diffractometer at room temperature. Data collection consisted of omega and phi scans.

The structure was solved by direct methods using SHELX software suite in the space group P2$_1$2$_1$2$_1$. The structure was subsequently refined by the full-matrix least squares method. All non-hydrogen atoms were found and refined using anisotropic displacement parameters.

The hydrogen atom located on nitrogen was found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek, 2003). The results indicate that the absolute structure has been correctly assigned. The method calculates that the probability that the structure is correct is 100.0. The Hooft parameter is reported as 0.017 with an esd of 0.09.

The final R-index was 4.8%. A final difference Fourier revealed no missing or misplaced electron density.

Pertinent crystal, data collection and refinement information is summarized in Table A. Atomic coordinates, bond lengths, bond angles, torsion angles and displacement parameters are listed in Tables B-E.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Strayer, and A. L. Spek, *J. Appl. Cryst.* 2008, 41, 96-103.
H. D. Flack, *Acta Cryst.* 1983, A39, 867-881.

TABLE A

Crystal data and structure refinement for C14.

| | |
|---|---|
| Empirical formula | C$_{15}$H$_{16}$ClN$_3$O$_3$ |
| Formula weight | 321.76 |
| Temperature | 273(2) K |
| Wavelength | 1.54178 Å |
| Crystal system | Orthorhombic |
| Space group | P2(1)2(1)2(1) |
| Unit cell dimensions | a = 6.7882(13) Å    α = 90° |
| | b = 10.0703(19) Å    β = 90° |
| | c = 21.883(4) Å    γ = 90° |
| Volume | 1495.9(5) Å$^3$ |
| Z | 4 |
| Density (calculated) | 1.429 Mg/m$^3$ |
| Absorption coefficient | 2.415 mm$^{-1}$ |
| F(000) | 672 |
| Crystal size | 0.22 × 0.16 × 0.10 mm$^3$ |
| Theta range for data collection | 4.04 to 70.57° |
| Index ranges | −8 <= h <= 7, −12 <= k <= 12, −26 <= l <= 24 |
| Reflections collected | 12473 |
| Independent reflections | 2784 [R(int) = 0.1613] |
| Completeness to theta = 70.57° | 97.3% |
| Absorption correction | Empirical |
| Max. and min. transmission | 0.7943 and 0.6187 |
| Refinement method | Full-matrix least-squares on F$^2$ |
| Data/restraints/parameters | 2784/1/204 |
| Goodness-of-fit on F$^2$ | 1.130 |
| Final R indices [I > 2sigma(I)] | R1 = 0.0481, wR2 = 0.1164 |
| R indices (all data) | R1 = 0.0514, wR2 = 0.1254 |
| Absolute structure parameter | −0.02(2) |
| Extinction coefficient | 0.0061(8) |
| Largest diff. peak and hole | 0.236 and −0.393 e · Å$^{-3}$ |

TABLE B

Atomic coordinates (×10$^4$) and equivalent isotropic displacement parameters (Å$^2$ × 10$^3$) for C14. U(eq) is defined as one-third of the trace of the orthogonalized U$^{ij}$ tensor.

| | x | y | z | U(eq) |
|---|---|---|---|---|
| C(1) | 1294(3) | −465(2) | 8392(1) | 41(1) |
| C(2) | 2045(4) | −1731(2) | 8096(1) | 47(1) |
| C(3) | 5002(3) | −692(3) | 7811(1) | 59(1) |
| C(4) | 4408(4) | 620(3) | 8086(1) | 50(1) |
| C(5) | 2992(3) | 394(2) | 8615(1) | 37(1) |
| C(6) | 2190(3) | 2218(2) | 9392(1) | 33(1) |

TABLE B-continued

Atomic coordinates (×10⁴) and equivalent isotropic displacement parameters ($Å^2 × 10^3$) for C14. U(eq) is defined as one-third of the trace of the orthogonalized $U^{ij}$ tensor.

|       | x       | y        | z        | U(eq)  |
|-------|---------|----------|----------|--------|
| C(7)  | 2088(3) | 3612(2)  | 9478(1)  | 36(1)  |
| C(8)  | 2116(3) | 4182(2)  | 10060(1) | 41(1)  |
| C(9)  | 2196(3) | 2165(2)  | 10525(1) | 36(1)  |
| C(10) | 2142(3) | 1467(2)  | 9960(1)  | 33(1)  |
| C(11) | 1948(3) | 75(2)    | 9985(1)  | 39(1)  |
| C(12) | 1914(4) | −574(2)  | 10537(1) | 47(1)  |
| C(13) | 2053(4) | 111(2)   | 11090(1) | 49(1)  |
| C(14) | 2179(3) | 1449(2)  | 11077(1) | 46(1)  |
| C(15) | 394(5)  | −2575(3) | 7835(1)  | 72(1)  |
| Cl(1) | 1654(2) | −2285(1) | 10550(1) | 79(1)  |
| N(1)  | 2317(3) | 1690(2)  | 8834(1)  | 44(1)  |
| N(2)  | 2029(3) | 4530(2)  | 8976(1)  | 46(1)  |
| N(3)  | 2205(3) | 3529(2)  | 10573(1) | 44(1)  |
| O(1)  | 3340(3) | −1422(2) | 7603(1)  | 56(1)  |
| O(2)  | 1960(3) | 4131(2)  | 8443(1)  | 59(1)  |
| O(3)  | 2016(4) | 5719(2)  | 9091(1)  | 78(1)  |

TABLE C

Bond lengths [Å] and angles [°] for C14.

| C(1)—C(2)   | 1.518(3) |
| C(1)—C(5)   | 1.521(3) |
| C(2)—O(1)   | 1.425(3) |
| C(2)—C(15)  | 1.517(3) |
| C(3)—O(1)   | 1.421(3) |
| C(3)—C(4)   | 1.507(4) |
| C(4)—C(5)   | 1.522(3) |
| C(5)—N(1)   | 1.464(3) |
| C(6)—N(1)   | 1.336(2) |
| C(6)—C(7)   | 1.418(3) |
| C(6)—C(10)  | 1.456(3) |
| C(7)—C(8)   | 1.396(3) |
| C(7)—N(2)   | 1.436(3) |
| C(8)—N(3)   | 1.304(3) |
| C(9)—N(3)   | 1.378(3) |
| C(9)—C(14)  | 1.406(3) |
| C(9)—C(10)  | 1.422(3) |
| C(10)—C(11) | 1.409(3) |
| C(11)—C(12) | 1.374(3) |
| C(12)—C(13) | 1.395(3) |
| C(12)—Cl(1) | 1.733(2) |
| C(13)—C(14) | 1.351(3) |
| N(2)—O(3)   | 1.223(2) |
| N(2)—O(2)   | 1.236(3) |
| C(2)—C(1)—C(5)    | 111.09(18) |
| O(1)—C(2)—C(15)   | 107.09(19) |
| O(1)—C(2)—C(1)    | 110.31(17) |
| C(15)—C(2)—C(1)   | 112.5(2)   |
| O(1)—C(3)—C(4)    | 111.7(2)   |
| C(3)—C(4)—C(5)    | 109.98(19) |
| N(1)—C(5)—C(1)    | 112.00(18) |
| N(1)—C(5)—C(4)    | 108.27(17) |
| C(1)—C(5)—C(4)    | 108.68(15) |
| N(1)—C(6)—C(7)    | 121.25(17) |
| N(1)—C(6)—C(10)   | 125.16(17) |
| C(7)—C(6)—C(10)   | 113.60(16) |
| C(8)—C(7)—C(6)    | 121.78(18) |
| C(8)—C(7)—N(2)    | 115.67(17) |
| C(6)—C(7)—N(2)    | 122.51(18) |
| N(3)—C(8)—C(7)    | 125.41(18) |
| N(3)—C(9)—C(14)   | 116.46(18) |
| N(3)—C(9)—C(10)   | 123.97(19) |
| C(14)—C(9)—C(10)  | 119.54(17) |
| C(11)—C(10)—C(9)  | 117.44(18) |
| C(11)—C(10)—C(6)  | 123.46(17) |
| C(9)—C(10)—C(6)   | 119.03(16) |
| C(12)—C(11)—C(10) | 120.51(18) |
| C(11)—C(12)—C(13) | 121.77(19) |
| C(11)—C(12)—Cl(1) | 119.23(16) |
| C(13)—C(12)—Cl(1) | 119.00(17) |
| C(14)—C(13)—C(12) | 118.66(19) |
| C(13)—C(14)—C(9)  | 121.96(19) |
| C(6)—N(1)—C(5)    | 132.47(17) |
| O(3)—N(2)—O(2)    | 120.82(18) |
| O(3)—N(2)—C(7)    | 118.24(18) |
| O(2)—N(2)—C(7)    | 120.93(17) |
| C(8)—N(3)—C(9)    | 115.92(17) |
| C(3)—O(1)—C(2)    | 111.14(16) |

Symmetry transformations used to generate equivalent atoms.

TABLE D

Anisotropic displacement parameters ($Å^2 × 10^3$) for C14. The anisotropic displacement factor exponent takes the form: $-2π^2[h^2 a^{*2}U^{11} + \ldots + 2 h k a^* b^* U^{12}]$.

|       | U11    | U22   | U33   | U23    | U13    | U12    |
|-------|--------|-------|-------|--------|--------|--------|
| C(1)  | 48(1)  | 44(1) | 31(1) | 0(1)   | −2(1)  | −4(1)  |
| C(2)  | 70(2)  | 38(1) | 33(1) | 0(1)   | −9(1)  | −3(1)  |
| C(3)  | 62(2)  | 71(2) | 45(1) | −12(1) | 15(1)  | 1(1)   |
| C(4)  | 61(1)  | 54(1) | 36(1) | −7(1)  | 12(1)  | −13(1) |
| C(5)  | 50(1)  | 38(1) | 24(1) | −5(1)  | 1(1)   | −2(1)  |
| C(6)  | 33(1)  | 38(1) | 30(1) | −4(1)  | 2(1)   | 0(1)   |
| C(7)  | 36(1)  | 36(1) | 38(1) | 0(1)   | 4(1)   | −1(1)  |
| C(8)  | 43(1)  | 35(1) | 44(1) | −9(1)  | 3(1)   | −1(1)  |
| C(9)  | 34(1)  | 44(1) | 31(1) | −8(1)  | 2(1)   | 6(1)   |
| C(10) | 30(1)  | 41(1) | 28(1) | −4(1)  | 4(1)   | 2(1)   |
| C(11) | 49(1)  | 40(1) | 28(1) | −4(1)  | 3(1)   | 2(1)   |
| C(12) | 60(1)  | 43(1) | 39(1) | 2(1)   | 6(1)   | 8(1)   |
| C(13) | 60(1)  | 57(1) | 29(1) | 6(1)   | 3(1)   | 15(1)  |
| C(14) | 53(1)  | 58(1) | 26(1) | −7(1)  | 2(1)   | 11(1)  |
| C(15) | 97(2)  | 53(2) | 65(2) | −7(1)  | −25(2) | −21(2) |
| Cl(1) | 138(1) | 40(1) | 60(1) | 9(1)   | 18(1)  | 5(1)   |
| N(1)  | 67(1)  | 36(1) | 29(1) | −3(1)  | 0(1)   | 3(1)   |
| N(2)  | 49(1)  | 40(1) | 47(1) | 5(1)   | 2(1)   | −1(1)  |
| N(3)  | 50(1)  | 44(1) | 37(1) | −12(1) | 0(1)   | 2(1)   |
| O(1)  | 82(1)  | 56(1) | 32(1) | −14(1) | 6(1)   | −2(1)  |
| O(2)  | 87(1)  | 53(1) | 38(1) | 8(1)   | 8(1)   | 3(1)   |
| O(3)  | 127(2) | 35(1) | 73(1) | 5(1)   | −4(1)  | −4(1)  |

TABLE E

Hydrogen coordinates ($\times 10^4$) and isotropic displacement parameters ($\text{Å}^2 \times 10^3$) for C14.

| | x | y | z | U(eq) |
|---|---|---|---|---|
| H(1A) | 451 | −690 | 8735 | 49 |
| H(1B) | 515 | 31 | 8099 | 49 |
| H(2A) | 2765 | −2251 | 8401 | 57 |
| H(3A) | 5887 | −535 | 7470 | 71 |
| H(3B) | 5704 | −1210 | 8114 | 71 |
| H(4A) | 3779 | 1166 | 7777 | 60 |
| H(4B) | 5569 | 1085 | 8231 | 60 |
| H(5) | 3684 | −67 | 8945 | 45 |
| H(8) | 2068 | 5104 | 10083 | 49 |
| H(11) | 1842 | −409 | 9624 | 47 |
| H(13) | 2060 | −345 | 11459 | 59 |
| H(14) | 2257 | 1911 | 11444 | 55 |
| H(15A) | −305 | −2077 | 7531 | 108 |
| H(15B) | −495 | −2820 | 8157 | 108 |
| H(15C) | 938 | −3361 | 7654 | 108 |
| H(111) | 2170(50) | 2330(30) | 8481(13) | 95 |

Step 3: Synthesis of 6-chloro-$N^4$-[(2R,4R)-2-methyltetrahydro-2H-pyran-4-yl]quinoline-3,4-diamine (C15)

Zinc dust (97.5%, 12.3 g, 183 mmol) was added in one portion to a suspension of C14 (7.40 g, 23.0 mmol) in methanol (100 mL) and concentrated ammonium hydroxide (100 mL). After 1 hour, the reaction mixture was filtered through diatomaceous earth; the filter pad was rinsed with dichloromethane (70 mL). The filtrate was diluted with water, and the aqueous layer was extracted with dichloromethane (2×60 mL). The combined organic layers were dried over sodium sulfate, filtered, concentrated in vacuo, and purified via silica gel chromatography (Gradient: 40% to 100% EtOAc in heptane) to provide the product. Yield: 3.68 g, 12.6 mmol, 55%. $^1$H NMR (400 MHz, CDCl$_3$) δ 8.48 (s, 1H), 7.91 (d, J=8.9 Hz, 1H), 7.74 (d, J=2.2 Hz, 1H), 7.40 (dd, J=8.9, 2.2 Hz, 1H), 4.02 (br dd, J=12, 5 Hz, 1H), 3.88 (br s, 2H), 3.29-3.56 (m, 4H), 1.82-1.96 (m, 2H), 1.56 (dddd, J=12, 12, 12, 5 Hz, 1H), 1.21-1.31 (m, 1H), 1.21 (d, J=6.2 Hz, 3H).

Preparation P4

Synthesis of 3-amino-4-{[(2R,4R)-2-methyltetrahydro-2H-pyran-4-yl]amino}quinoline-6-carbonitrile

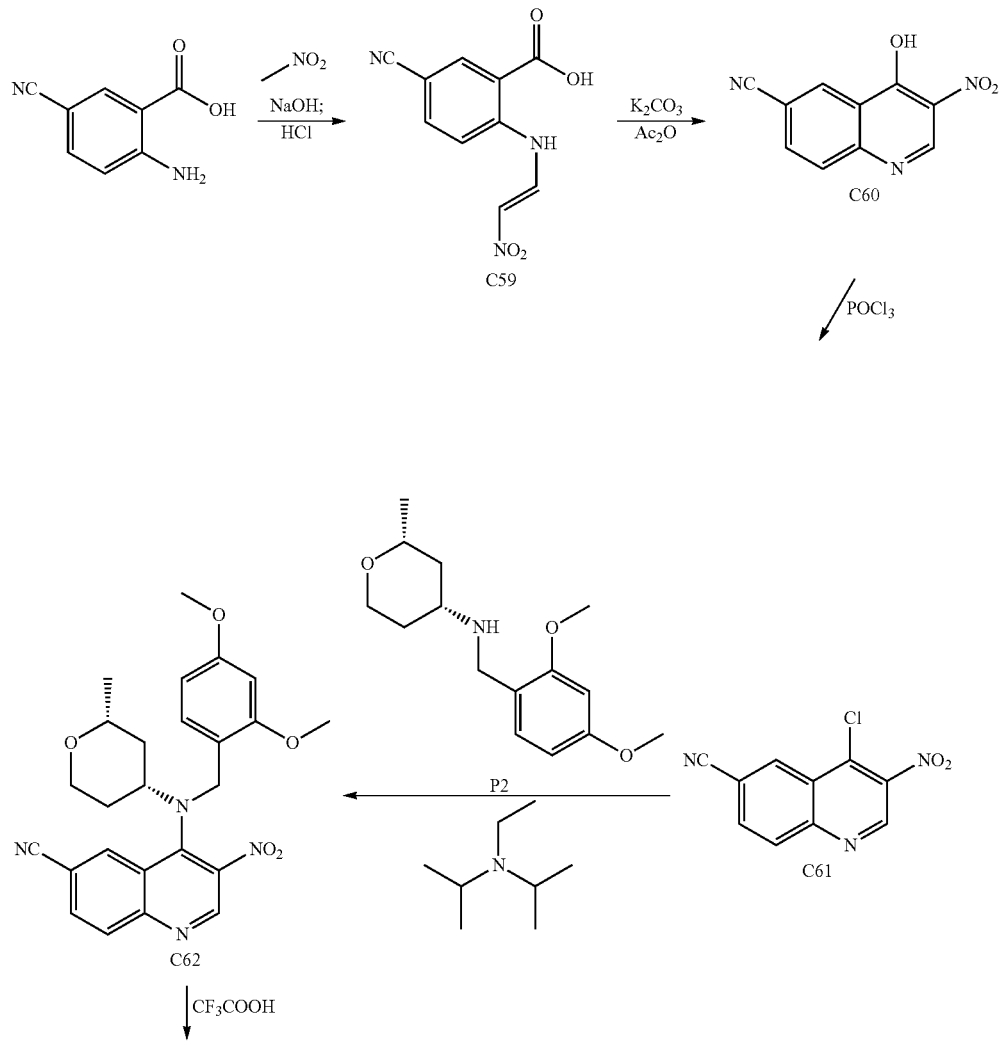

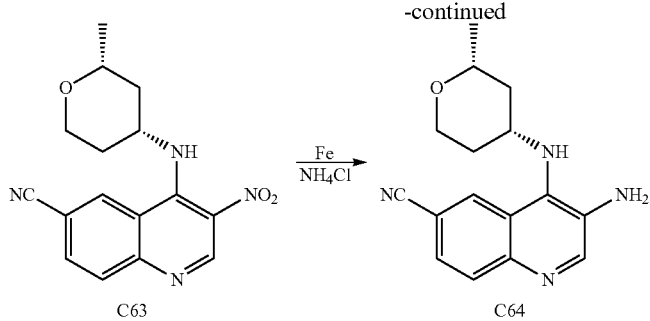

Step 1: Synthesis of 5-cyano-2-{[(E)-2-nitroethenyl]amino}benzoic acid (C59)

This experiment was run in two identical batches. {Caution!: this reaction should not be carried out on greater than a 1 gram scale, due to highly energetic reactants and intermediates. Use of proper safety precautions and a blast shield is essential.} Nitromethane (4.71 g, 77.2 mmol) was added in a drop-wise manner to a solution of sodium hydroxide (3.95 g, 98.8 mmol) in water (25 mL), and the resulting solution was allowed to heat to 45° C. over 5 minutes, whereupon it was cooled in a water bath and treated with concentrated hydrochloric acid (12 M, 10 mL) until the pH of the solution became acidic. This was then added to a suspension of 2-amino-5-cyanobenzoic acid (5.0 g, 31 mmol) in water (50 mL), acetone (10 mL) and concentrated hydrochloric acid (12 M, 50 mL) at 25° C., and the reaction mixture was allowed to stir at 25° C. for 15 hours. The two batches were combined at this point, and the resulting suspension was filtered; the collected solid was washed with water to provide the product as a yellow solid. From analysis of the $^1$H NMR, the product was presumed to exist as a mixture of rotamers. Yield: 13.8 g, 59.2 mmol, 95%. $^1$H NMR (400 MHz, DMSO-$d_6$) δ [13.15 (s) and 13.12 (s), total 1H], 8.37 (d, J=2.0 Hz, 1H), 8.07-8.15 (m, 2H), 7.92 (d, half of AB quartet, J=9.0 Hz, 1H), 6.86 (d, J=6.0 Hz, 1H).

Step 2: Synthesis of 4-hydroxy-3-nitroquinoline-6-carbonitrile (C60). Potassium carbonate (39.1 g, 283 mmol) was added to a suspension of C59 (22.0 g, 94.4 mmol) in acetic anhydride (200 mL). After the reaction mixture had been heated to 90° C. for 2 hours, it was filtered, and the collected material was washed with tert-butyl methyl ether (100 mL) and with water (400 mL), affording the product as a brown solid. Yield: 17.0 g, 79.0 mmol, 84%. LCMS m/z 215.9 [M+H]$^+$. $^1$H NMR (400 MHz, DMSO-$d_6$) δ 9.14 (s, 1H), 8.55 (dd, J=2.0, 0.5 Hz, 1H), 7.98 (dd, J=8.5, 2.0 Hz, 1H), 7.77 (dd, J=8.5, 0.5 Hz, 1H).

Step 3: Synthesis of 4-chloro-3-nitroquinoline-6-carbonitrile (C61)

Phosphorus oxychloride (11.7 g, 76.3 mmol) was added drop-wise to a solution of C60 (5.8 g, 26 mmol) in N,N-dimethylformamide and the reaction mixture was stirred at room temperature for 2 hours, whereupon it was poured into ice water (100 mL). The resulting mixture was filtered and the filter cake was washed with water (300 mL) to provide the product as a brown solid. Yield: 9.1 g, 39 mmol, 86%. $^1$H NMR (400 MHz, DMSO-$d_6$) δ 9.26 (s, 1H), 8.59 (d, J=1.8 Hz, 1H), 8.16 (dd, J=8.7, 1.9 Hz, 1H), 7.93 (d, J=8.8 Hz, 1H).

Step 4: Synthesis of 4-chloro-6-methoxy-3-nitroquinoline (C8)

Phosphorus oxychloride (11.7 g, 76.3 mmol) was added drop-wise to a solution of C7 (5.8 g, 26 mmol) in N,N-dimethylformamide (50 mL), and the reaction mixture was stirred at room temperature for 2 hours, whereupon it was poured into ice water (100 mL). The resulting mixture was filtered and the filter cake was washed with water (300 mL) to provide the product as a brown solid. Yield: 4.5 g, 19 mmol, 73%.

Step 5: Synthesis of 4-{(2,4-dimethoxybenzyl)[(2R,4R)-2-methyltetrahydro-2H-pyran-4-yl]amino}-3-nitroquinoline-6-carbonitrile (C62)

To a solution of C61 (8.81 g, 37.7 mmol) in acetonitrile (80 mL) was added P2 (11.0 g, 41.5 mmol), followed by N,N-diisopropylethylamine (5.85 g, 45.3 mmol). The reaction mixture was stirred for 2 hours at room temperature, whereupon it was concentrated in vacuo and purified via silica gel chromatography (Eluent: 4:1 petroleum ether/ethyl acetate), affording the product as a viscous orange oil that slowly solidified. Yield: 15.0 g, 32.4 mmol, 86%. LCMS m/z 313.0 [M-(2,4-dimethoxybenzyl)+H]$^+$. $^1$H NMR (400 MHz, DMSO-$d_6$) δ 9.18 (s, 1H), 8.55 (br dd, J=1.3, 1 Hz, 1H), 8.15 (d, J=1.0 Hz, 2H), 6.88 (d, J=8.0 Hz, 1H), 6.24-6.30 (m, 2H), 4.33 (br AB quartet, $J_{AB}$=14.5 Hz, $\Delta v_{AB}$=12 Hz, 2H), 3.76-3.92 (m, 2H), 3.62 (s, 3H), 3.42 (s, 3H), 3.3-3.4 (m, 2H, assumed; largely obscured by water peak), 1.83-2.00 (m, 2H), 1.70-1.83 (m, 1H), 1.42-1.54 (m, 1H), 1.09 (d, J=6.0 Hz, 3H).

Step 6: Synthesis of 4-{[(2R,4R)-2-methyltetrahydro-2H-pyran-4-yl]amino}-3-nitroquinoline-6-carbonitrile (C63)

A mixture of C62 (15.0 g, 32.4 mmol) and trifluoroacetic acid (18.5 g, 162 mmol) in dichloromethane (150 mL) was stirred at room temperature for 30 minutes, whereupon it was concentrated to a volume of 20 mL and treated with saturated aqueous sodium bicarbonate solution (200 mL). The aqueous layer was extracted with dichloromethane (3×150 mL), and the combined organic layers were dried over sodium sulfate, filtered, and concentrated in vacuo to provide the product as a yellow solid. Yield: 5.68 g, 18.2 mmol, 56%. LCMS m/z 313.0 [M+H]$^+$. $^1$H NMR (400 MHz, DMSO-$d_6$) δ 9.06-9.09 (m, 2H), 8.30 (br d, J=9.0 Hz, 1H), 8.14 (dd, half of ABX pattern, J=8.7, 1.6 Hz, 1H), 8.01 (d, half of AB quartet, J=8.8 Hz, 1H), 3.87-3.93 (m, 1H), 3.69-3.82 (m, 1H), 3.3-3.5 (m, 2H, assumed; largely obscured by water peak), 1.87-2.03 (m, 2H), 1.60-1.72 (m, 1H), 1.36-1.47 (m, 1H), 1.11 (d, J=6.0 Hz, 3H).

Step 7: Synthesis of 3-amino-4-{[(2R,4R)-2-methyltetrahydro-2H-pyran-4-yl]amino}quinoline-6-carbonitrile (C64)

Ethanol (60 mL) and water (15 mL) were added to a mixture of C63 (5.68 g, 18.2 mmol), iron (10.2 g, 183 mmol), and ammonium chloride (9.73 g, 182 mmol). The reaction mixture was heated to 80° C. for 1 hour, whereupon it was diluted with ethanol (100 mL) and filtered. The filtrate was concentrated in vacuo, and the resulting solid was partitioned between saturated aqueous sodium bicarbonate solution (100 mL) and dichloromethane (300 mL). The organic layer was dried over sodium sulfate, filtered, and concentrated under reduced pressure to afford the product as a brown solid. Yield: 4.73 g, 16.8 mmol, 92%. LCMS m/z 282.9 [M+H]$^+$. $^1$H NMR (400 MHz, CD$_3$OD) δ 8.55 (d, J=1.2 Hz, 1H), 8.51 (s, 1H), 7.90 (d, J=8.8 Hz, 1H), 7.60 (dd, J=8.5, 1.8 Hz, 1H), 3.92-4.00 (m, 1H), 3.58-3.69 (m, 1H), 3.39-3.50 (m, 2H), 1.78-1.94 (m, 2H), 1.56-1.69 (m, 1H), 1.29-1.40 (m, 1H), 1.17 (d, J=6.0 Hz, 3H).

Preparation P5

Synthesis of 6-(difluoromethyl)-N$^4$-((2R,4R)-2-methyltetrahydro-2H-pyran-4-yl) quinoline-3,4-diamine

Step 1: Synthesis of 2-(4-((2,4-dimethoxybenzyl)((2R,4R)-2-methyltetrahydro-2H-pyran-4-yl)amino)-3-nitroquinolin-6-yl)-2,2-difluoro-1-phenylethan-1-one An oven dried round bottomed flask (250 mL) was charged with cataCXium A Pd G2 (0.0850 g, 0.127 mmol), 6-chloro-N-(2,4-dimethoxybenzyl)-N-((2R,4R)-2-methyltetrahydro-2H-pyran-4-yl)-3-nitroquinolin-4-amine (3.00 g, 6.36 mmol), tri-potassium phosphate N-hydrate (5.86 g, 25.4 mmol), and magnetic stir bar. The vial was purge with N$_2$ and vacuum (3×). Then a toluene (36.7 mL, c=0.173 M) solution of 2,2-Difluoroacetophenone (1.98 g, 12.7 mmol, 1.68 mL) was added to the vial under N$_2$. The resulting solution was heated to 110° C. for 24 h. An aliquot of the reaction mixture was partitioned between NH$_4$Cl (aq., sat'd) and EtOAc. LC/MS analysis of the organic layer showed complete consumption of starting material and major product mass at 1.12 min. (ES+RT 1.12 min, m/z 592.5). The reaction mixture was cooled to RT, partitioned between NH$_4$Cl (aq., sat'd, 250 mL) and EtOAc (250 mL). Organic layer was isolated, dried over Na$_2$SO$_4$, filtered and concentrated under reduced pressure to yield an orange oily residue. This residue was re-dissolved in DCM (10 mL) and adsorbed on silica gel under reduced pressure to yield an orange solid. This solid was loaded on Combiflash 1 (220 g High Performance Gold Redisep column, 0 to 100% of EtOAc in heptane, 30CV) for purification purposes. Fractions containing the product spot were combined and concentrated under reduced pressure to yield 2.07 g of an orange solid. An NMR of that solid showed product along with some residual EtOAc. An LC/MS of the NMR sample showed major product mass at 1.12 min. (ES+1.12 min RT m/z 592.3). Material will be used as it is for next step reaction. $^1$H NMR (400 MHz, CDCl$_3$) δ 9.06 (s, 1H), 8.48 (s, 1H), 8.16 (d, J=8.8 Hz, 1H), 8.02 (m, 3H), 7.64 (m, 1H), 7.49 (m, 2H), 6.82 (d, J=8.2 Hz, 1H), 6.19 (d, J=8.5 Hz, 1H), 6.14 (s, 1H), 4.34 (s, 2H), 3.99 (d, J=11.6 Hz, 1H), 3.82-3.70

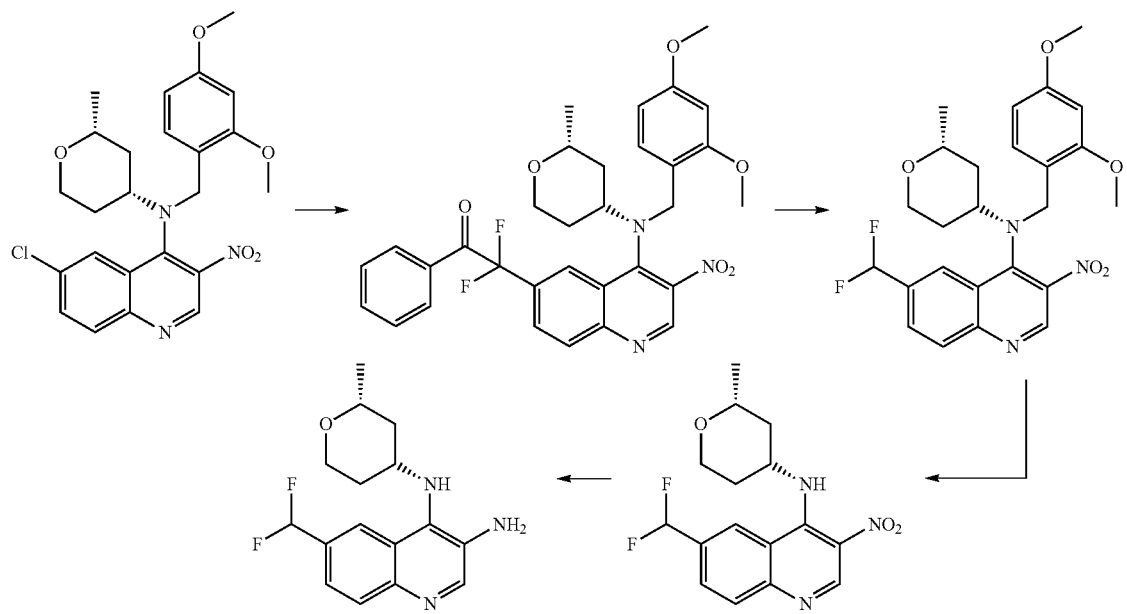

(m, 1H), 3.68 (s, 3H), 3.46 (s, 3H), 3.23 (m, 2H), 2.07-1.86 (m, 3H), 1.69 (q, J=11.9 Hz, 1H), 1.23-1.14 (d, 3H).

Step 2: Synthesis of 6-(difluoromethyl)-N-(2,4-dimethoxybenzyl)-N-((2R,4R)-2-methyltetrahydro-2H-pyran-4-yl)-3-nitroquinolin-4-amine

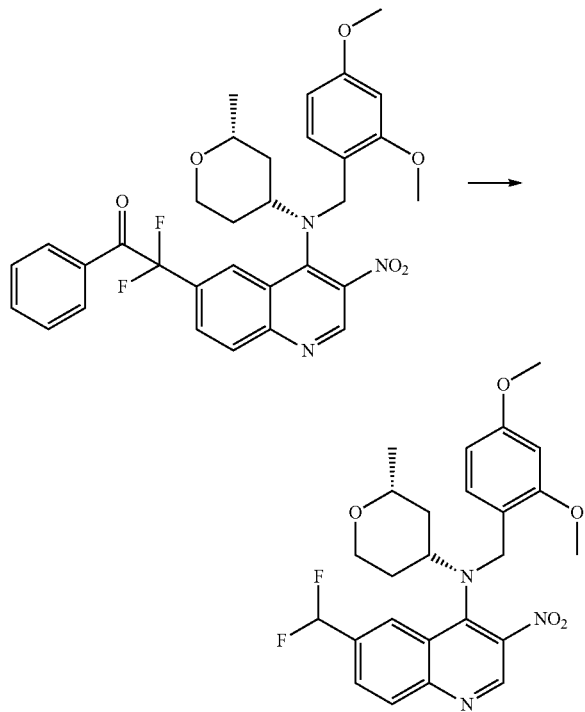

To a Toluene (4.67 mL, 0.16M) and water (0.28 mL) solution of 2-(4-((2,4-dimethoxybenzyl)((2R,4R)-2-methyl-tetrahydro-2H-pyran-4-yl)amino)-3-nitroquinolin-6-yl)-2,2-difluoro-1-phenylethan-1-one (0.470 g, 0.794 mmol) was added potassium hydroxide (0.267 g, 4.77 mmol, 6 eq.). The resulting solution was heated to 100° C. over 24 h. The reaction mixture was cooled down to RT, partitioned between water (150 mL) and dichloromethane (150 mL). Layers were isolated and resulting aq. layer was back extracted with dichloromethane (2×100 mL). Combined organic layers were dried over sodium sulfate, filtered and concentrated under reduced pressure to yield a yellow oily residue. Purification via silica gel regular column chromatography (0 to 80% of Ethyl acetate in heptane) yielded 0.337 g (0.691 mmol, 87%) of 6-(difluoromethyl)-N-(2,4-dimethoxybenzyl)-N-((2R,4R)-2-methyltetrahydro-2H-pyran-4-yl)-3-nitroquinolin-4-amine as an orange solid. $^1$H NMR (400 MHz, CDCl$_3$) δ 9.09 (s, 1H), 8.44 (s, 1H), 8.13 (d, J=8.6 Hz, 1H), 7.82 (d, J=8.5 Hz, 1H), 6.98-6.62 (m, 2H), 6.22 (dd, J=8.3, 2.4 Hz, 1H), 6.16 (d, J=2.4 Hz, 1H), 4.37 (m, 2H), 4.04 (d, J=11.5 Hz, 1H), 3.82 (m, 1H), 3.68 (s, 3H), 3.48 (s, 3H), 3.41 (m, 2H), 2.08-1.91 (m, 2H), 1.67 (q, J=11.8 Hz, 1H), 1.30-1.22 (m, 1H), 1.21 (d, J=6.2 Hz, 3H). LCMS: MS: M+H: 488.4; RT 1.00 min.

Step 3: Synthesis of 6-(difluoromethyl)-N-((2R,4R)-2-methyltetrahydro-2H-pyran-4-yl)-3-nitroquinolin-4-amine A dichloromethane (25.0 mL, c=0.152 M) solution of the product mixture from the previous step (1.85 g, 3.79 mmol) was chilled to 0° C. and treated with trifluoroacetic acid (1.73 g, 15.2 mmol, 1.16 mL). The resulting solution was allowed to warm to RT and left stirring at RT for 20 min. An aliquot of the reaction mixture, was diluted with MeOH and analyzed by LCMS which showed the reaction was complete and the minor presence of acetophenone DMB de-protected compound, The LCMS showed major presence of product mass at 0.84 min. (ES+RT 0.84 min, MS m/z 338.5). The reaction mixture was cooled to 0° C., diluted with DCM (20 mL) and basified to pH 8 with NaHCO$_3$ (aq., sat'd., 100 mL). Layers were isolated and resulting aq. layer was washed with DCM (2×50 mL). Combined organics were washed with brine (1×150 mL), dried over MgSO$_4$, filtered and concentrated under reduced pressure to yield 1.4 g of a yellow solid. The solid was re-dissolved in DCM:MeOH (20 mL; 8:1 ratio, respectively). This solution was adsorbed on silica gel under reduced pressure to yield a yellow solid. This solid was loaded on Combiflash (120 g high performance Gold Redisep column, 0 to 100% of EtOAc in heptane, 18CV) for purification purposes. The two products didn't separate (desired product and the benzoyl CF$_2$ product). Fractions containing both adduct were concentrated under reduced pressure to yield a yellow solid. Upon trituration with Et$_2$O (50 mL), a yellow precipitate formed. Solids were filtered and washed with Et$_2$O (2×50 mL). There was obtained 0.7 g of a yellow solid. The NMR of the solid showed the desired product with a negligible amount of an impurity. LCMS of the NMR sample (0.7 g, SOLID, 54.7%), showed product at 0.84 min. (ES+RT 0.84 min, m/z 338.5). Analysis of the filtrate didn't show any presence of desired product. Isolated product will be used as it is for next step reaction. The yield for the two step reaction (benzoyl deprotection and DMB de-protection is 61%).

Step 4: Synthesis of 6-(difluoromethyl)-N$^4$-((2R,4R)-2-methyltetrahydro-2H-pyran-4-yl)quinoline-3,4-diamine To a 250 mL Hastelloy parr reactor was added tetrahydrofuran (150 mL, c=0.0138 M) solution of 6-(difluoromethyl)-N-((2R,4R)-2-methyltetrahydro-2H-pyran-4-yl)-3-nitroquinolin-4-amine (0.700 g, 2.08 mmol). To this was added 5% Pt/C (0.600 g, 0.2 mmol) and the mixture was purged with N$_2$ (3×) then back filled with H$_2$ to 30 PSI and allowed to hydrogenate for 2 h. After that time, an aliquot of the reaction mixture was diluted with MeOH and analyzed by LCMS and it showed complete consumption of starting material and presence of a new more polar spot at 0.58 min. (ES+RT 0.58 min, MS m/z 308.4). The reaction mixture was diluted with THF (50 mL), filtered through a Celite pad, and the pad was washed with THF (3×50 mL). Combined filtrates were then dried under reduced pressure to yield an orange oily residue that was re-dissolved in DCM (15 mL). The resulting DCM heterogeneous solution (to remove Celite that was carried through) was filtered through an Acrodisc filter. The DCM solution was then concentrated under reduced pressure to yield 0.5474 g of a dark brown solid. An NMR of the solid showed major product peaks along with a small impurity. An LCMS of the NMR sample (0.5474 g, SOLID, 85.8%) showed the product mass at 0.58 min. (ES+RT 0.58 min, m/z 308.4). Material was used directly in the next step.

$^1$H NMR (400 MHz, CDCl$_3$) δ 8.55 (s, 1H), 8.05 (d, J=8.7 Hz, 1H), 7.92 (t, J=1.8 Hz, 1H), 7.56 (dd, J=8.7, 1.7 Hz, 1H), 6.82 (t, J=56.4 Hz, 1H), 4.02 (ddd, J=11.8, 4.7, 1.7 Hz, 1H), 3.86 (s, 2H), 3.80-3.71 (m, 1H), 3.53 (d, J=11.1 Hz, 1H), 3.48-3.36 (m, 2H), 1.99-1.89 (m, 1H), 1.85 (ddd, J=6.6, 4.9, 2.6 Hz, 2H), 1.61-1.50 (m, 1H), 1.20 (d, J=6.2 Hz, 3H). LCMS RT 0.58 min, (M+H: 308.4).

Preparation P6

3-amino-4-{[(3R)-1-methylpyrrolidin-3-yl]amino}quinoline-6-carbonitrile

Step 1: Synthesis of 4-{[(3R)-1-methylpyrrolidin-3-yl]amino}-3-nitroquinoline-6-carbonitrile (C95)

N,N-Diisopropylethylamine (251 mg, 1.94 mmol) was added to a 20° C. solution of C61 (210 mg, 0.899 mmol) and (3R)-1-methylpyrrolidin-3-amine (77.9 mg, 0.778 mmol) in acetonitrile (3 mL). The reaction mixture was stirred at 20° C. for 2 hours, whereupon it was concentrated in vacuo. Purification of the residue via silica gel chromatography (Gradient: 0% to 1% methanol in dichloromethane) afforded the product as a yellow solid. Yield: 210 mg, 0.706 mmol, 91%. LCMS m/z 297.9 [M+H]$^+$. $^1$H NMR (400 MHz, CDCl$_3$) δ 10.04-10.15 (br m, 1H), 9.45 (s, 1H), 8.55 (d, J=1.5 Hz, 1H), 8.07 (d, half of AB quartet, J=8.5 Hz, 1H), 7.92 (dd, half of ABX pattern, J=8.5, 1.8 Hz, 1H), 4.65-4.74 (m, 1H), 3.02-3.10 (m, 1H), 2.84-2.90 (m, 1H), 2.80 (dd, half of ABX pattern, J=9.9, 5.6 Hz, 1H), 2.61-2.71 (m, 1H) 2.46 (s, 3H), 2.41-2.50 (m, 1H), 2.06-2.16 (m, 1H).

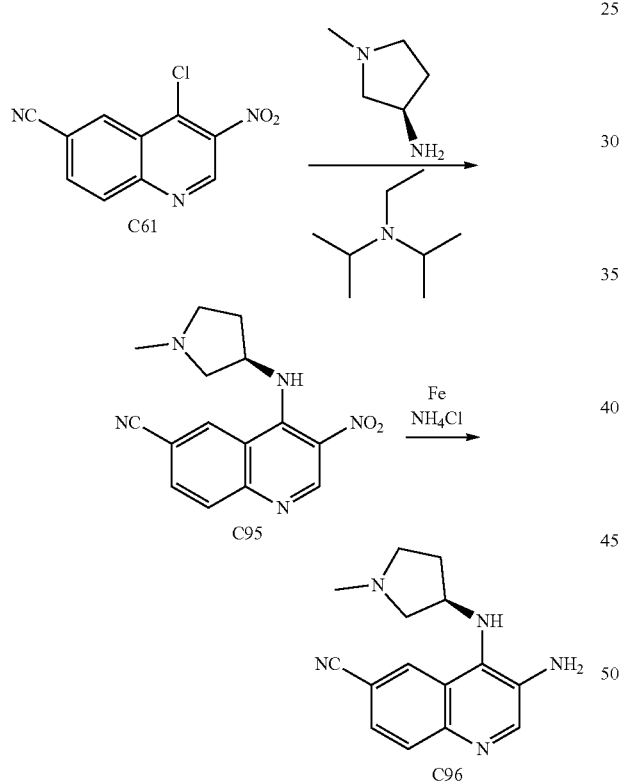

Step 2: Synthesis of 3-amino-4-{[(3R)-1-methylpyrrolidin-3-yl]amino}quinoline-6-carbonitrile (C96)

To a solution of C95 (100 mg, 0.336 mmol) in a mixture of ethanol (1 mL) and water (0.25 mL) were added ammonium chloride (36 mg, 0.673 mmol) and iron powder (75.1 mg, 1.34 mmol), and the reaction mixture was stirred at 80° C. for 1 hour. It was then filtered, and the filter cake was washed with methanol (30 mL). The organic layer from the combined filtrates was concentrated in vacuo and purified via silica gel chromatography (Gradient: 0% to 15% methanol in dichloromethane), affording the product as a yellow solid. Yield: 112 mg, assumed quantitative. $^1$H NMR (400 MHz, DMSO-d$_6$), characteristic peaks: δ 8.65-8.71 (br s, 1H), 8.58 (s, 1H), 7.89 (d, J=8.5 Hz, 1H), 7.62 (dd, J=8.5, 2.0 Hz, 1H), 5.56-5.70 (br s, 1H), 5.43 (d, J=10.5 Hz, 1H), 4.32-4.46 (br m, 1H), 2.81 (s, 3H), 1.84-1.95 (m, 1H).

Preparation P7

Synthesis of N$^4$-[(2R,4R)-2-methyltetrahydro-2H-pyran-4-yl]-6-(trifluoromethyl)quinoline-3,4-diamine (C101)

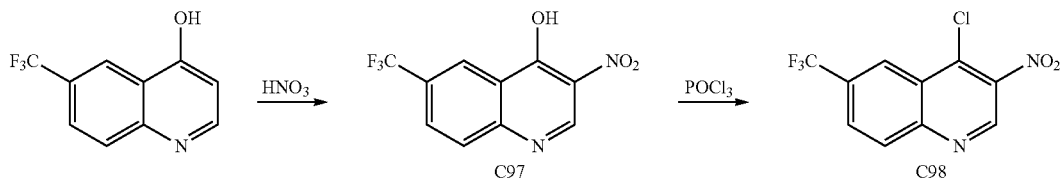

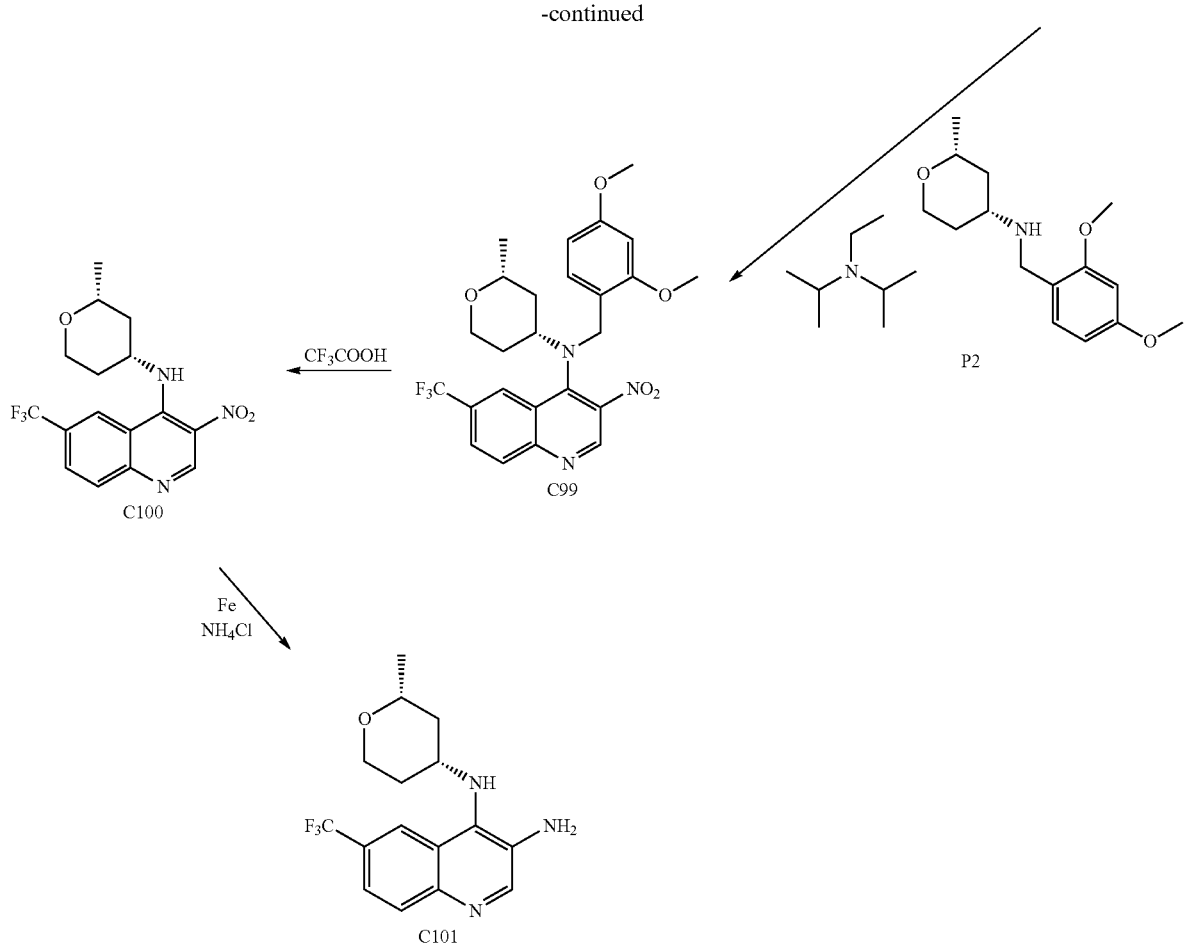

Step 1: Synthesis of 3-nitro-6-(trifluoromethyl)quinolin-4-ol (C97)

A solution of 6-(trifluoromethyl)quinolin-4-ol (2.00 g, 9.38 mmol) in concentrated nitric acid (10 mL) was stirred for 14 hours at 50° C., whereupon it was poured into water (50 mL). The resulting solid was isolated via filtration, providing the product as a pale yellow solid. Yield: 1.80 g, 6.97 mmol, 74%. $^1$H NMR (400 MHz, DMSO-$d_6$) δ 9.29 (s, 1H), 8.46 (s, 1H), 8.11 (d, J=9.0 Hz, 1H), 7.92 (d, J=8.5 Hz, 1H).

Step 2: Synthesis of 4-chloro-3-nitro-6-(trifluoromethyl)quinoline (C98)

Phosphorus oxychloride (3.25 mL, 34.9 mmol) was added to a 15° C. solution of compound C97 (3.00 g, 11.6 mmol) in N,N-dimethylformamide (10 mL), and the reaction mixture was stirred for 2 hours at 15° C. It was then poured into water (80 mL). Collection of the precipitate via filtration provided the product as a solid (2.40 g). This material was impure by $^1$H NMR analysis, and was taken directly into the following step. $^1$H NMR (400 MHz, DMSO-$d_6$), product peaks only: δ 9.22 (s, 1H), 8.40 (br s, 1H), 8.03 (br d, J=8.5 Hz, 1H), 7.92-7.97 (m, 1H).

Step 3: Synthesis of N-(2,4-dimethoxybenzyl)-N-[(2R,4R)-2-methyltetrahydro-2H-pyran-4-yl]-3-nitro-6-(trifluoromethyl)quinolin-4-amine (C99)

N,N-Diisopropylethylamine (3.36 g, 26.0 mmol) and P2 (2.43 g, 9.16 mmol) were slowly added to a 15° C. solution of C98 (from the previous step, 2.40 g, 8.68 mmol) in acetonitrile (30 mL), and the reaction mixture was stirred for 30 minutes at 80° C. Water (100 mL) was added, and the resulting mixture was extracted with ethyl acetate (3×100 mL). The combined organic layers were concentrated in vacuo, and the residue was purified via silica gel chromatography (Gradient: 9% to 25% ethyl acetate in petroleum ether) to provide the product as a yellow solid. Yield: 3.40 g, 6.73 mmol, 58% over 2 steps. $^1$H NMR (400 MHz, CDCl$_3$) δ 9.11 (s, 1H), 8.60 (br s, 1H), 8.15 (d, J=9.0 Hz, 1H), 7.92 (dd, J=8.8, 1.8 Hz, 1H), 6.84 (d, J=8.0 Hz, 1H), 6.22 (dd, J=8.3, 2.3 Hz, 1H), 6.16 (d, J=2.0 Hz, 1H), 4.33-4.44 (m, 2H), 4.02-4.10 (m, 1H), 3.77-3.87 (m, 1H), 3.68 (s, 3H), 3.50 (s, 3H), 3.36-3.46 (m, 2H), 1.95-2.10 (m, 3H), 1.67-1.78 (m, 1H), 1.23 (d, J=6.0 Hz, 3H).

Step 4: Synthesis of N-[(2R,4R)-2-methyltetrahydro-2H-pyran-4-yl]-3-nitro-6-(trifluoromethyl)quinolin-4-amine (C100)

Trifluoroacetic acid (7.67 g, 67.3 mmol) was added to a 15° C. solution of compound C99 (3.40 g, 6.73 mmol) in dichloromethane (30 mL), and the reaction mixture was stirred for 30 minutes at 15° C. Solvents were removed in vacuo, and the residue was diluted with water (100 mL) and extracted with ethyl acetate (3×100 mL). The combined organic layers were concentrated in vacuo to afford the product (2.50 g) as a pale yellow solid, a portion of which was used directly in the following step. LCMS m/z 355.8 [M+H]$^+$.

Step 5: Synthesis of $N^4$-[(2R,4R)-2-methyltetrahydro-2H-pyran-4-yl]-6-(trifluoromethyl)quinoline-3,4-diamine (C101)

Iron powder (314 mg, 5.62 mmol) and ammonium chloride (301 mg, 5.63 mmol) were added to a solution of C100 (from the previous step, 200 mg, ≤0.54 mmol) in ethanol (5 mL) and water (1 mL), and the reaction mixture was stirred for 1 hour at 80° C. It was then filtered through diatomaceous earth, and the filtrate was concentrated in vacuo. Silica gel chromatography (Gradient: 9% to 33% ethyl acetate in petroleum ether) afforded the product as a pale grey solid. Yield: 140 mg, 0.430 mmol, 80% over 2 steps. LCMS m/z 325.9 [M+H]$^+$.

Preparation P8 cis-2-[(Benzyloxy)methyl]-N-(2,4-dimethoxybenzyl)tetrahydro-2H-pyran-4-amine (#P510)

Step 1: Synthesis of 2-[(benzyloxy)methyl]tetrahydro-2H-pyran-4-ol (#C212).

A solution of (benzyloxy)acetaldehyde (25.0 g, 166 mmol) and but-3-en-1-ol (12.0 g, 166 mmol) in dichloromethane (550 mL) was added in a dropwise manner to a 0° C. solution of trifluoroacetic acid (57 g, 500 mmol) in dichloromethane (500 mL). The reaction mixture was stirred at room temperature (20° C.) for 18 hours, whereupon it was concentrated in vacuo. After the residue had been dissolved in methanol (450 mL), it was treated with potassium carbonate (80 g, 580 mmol), and the reaction mixture was stirred for 5 hours at 20° C. A reaction mixture from a similar reaction employing (benzyloxy)acetaldehyde (20.0 g, 133 mmol) was added, and the combined mixtures were filtered. The filtrate was concentrated under reduced pressure, and partitioned between water (500 mL) and ethyl acetate (200 mL). The aqueous layer was then extracted with ethyl acetate (2×150 mL), and the combined organic layers were concentrated in vacuo. Silica gel chromatography (Gradient: 20% to 25% ethyl acetate in petroleum ether) provided the product as a yellow oil. From examination of the $^1$H NMR spectrum this material was assumed to be a mixture of the cis and trans isomers. Combined yield: 42.9 g, 193 mmol, 64%. $^1$H NMR (400 MHz, CDCl$_3$) δ 7.39-7.26 (m, 5H), 4.64-4.53 (m, 2H), [4.29-4.25 (m), 4.11-3.76 (m), and 3.59-3.40 (m), total 6H], [1.96-1.83 (m), 1.71-1.48 (m), and 1.36-1.24 (m), total 4H, assumed; partially obscured by water peak].

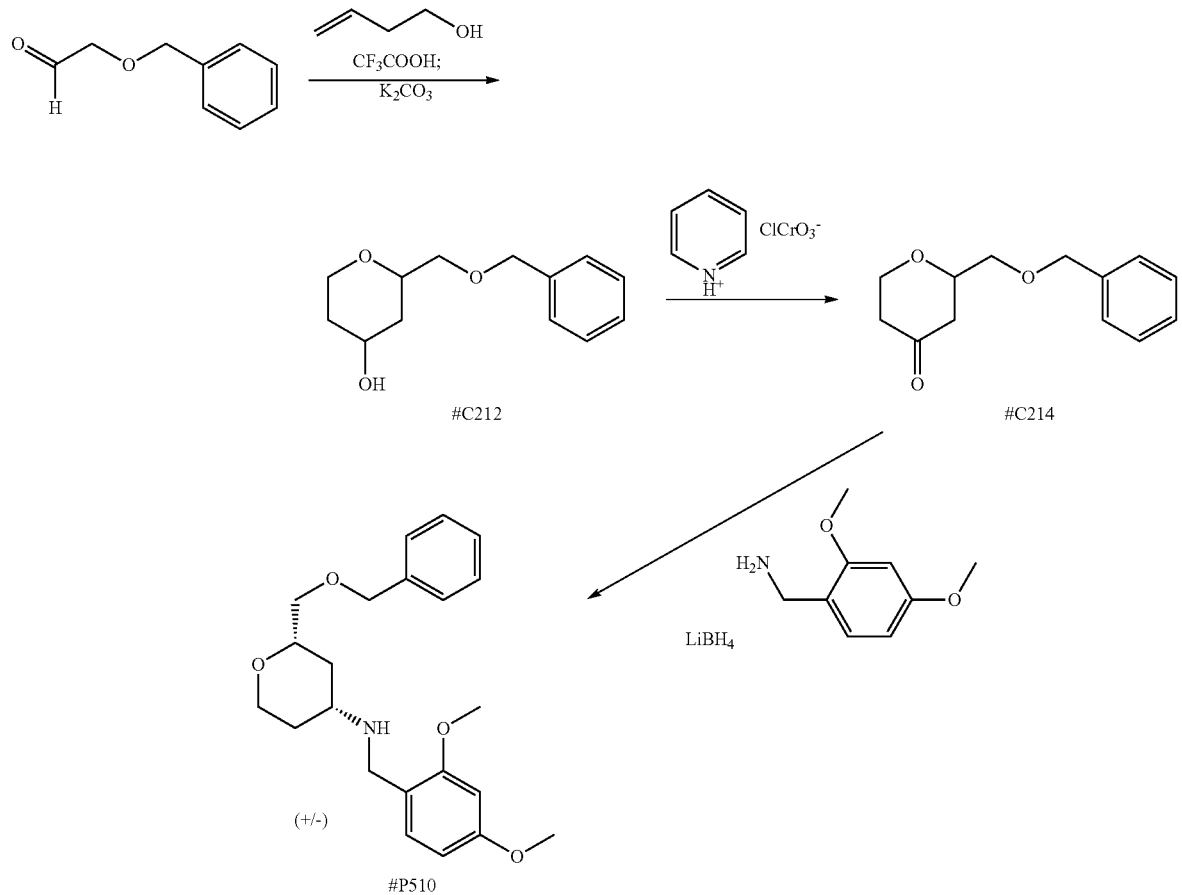

Step 2: Synthesis of 2-[(benzyloxy)methyl]tetrahydro-4H-pyran-4-one (#C214)

Pyridinium chlorochromate (48 g, 220 mmol) was added to a solution of #C212 (22.9 g, 103 mmol) in dichloromethane (350 mL), and the reaction mixture was stirred at room temperature (20° C.) for 18 hours. It was then combined with a similar reaction carried out using #C212 (20 g, 90 mmol), and the mixture was filtered and the concentrated in vacuo. The residue was purified via chromatography on silica gel (Eluent: 20% ethyl acetate in petroleum ether), affording the product as a colorless oil. Combined yield: 36.2 g, 164 mmol, 85%. $^1$H NMR (400 MHz, CDCl$_3$) δ 7.40-7.27 (m, 5H), 4.65-4.58 (m, 2H), 4.36 (ddd, J=11.5, 7.5, 1.5 Hz, 1H), 3.85 (dddd, J=11, 5, 4, 3 Hz, 1H), 3.72 (ddd, J=12.3, 11.5, 2.8 Hz, 1H), 3.58 (dd, half of ABX pattern, J=10.5, 4.0 Hz, 1H), 3.55 (dd, half of ABX pattern, J=10.3, 5.3 Hz, 1H), 2.63 (dddd, J=15, 12, 7.5, 1 Hz, 1H), 2.56-2.47 (m, 1H), 2.40-2.32 (m, 2H).

Step 3: Synthesis of cis-2-[(benzyloxy)methyl]-N-(2,4-dimethoxybenzyl) tetrahydro-2H-pyran-4-amine (#P510)

1-(2,4-Dimethoxyphenyl)methanamine (23 g, 140 mmol) was added to a solution of #C214 (20 g, 91 mmol) in methanol (275 mL). The reaction mixture was stirred at room temperature (20° C.) for 24 hours, whereupon it was cooled to −78° C. and treated in a drop-wise manner with lithium borohydride (2 M solution in tetrahydrofuran; 46.0 mL 92.0 mmol). The reaction mixture was allowed to slowly warm to room temperature, and was then stirred at room temperature overnight. This was combined with a similar reaction mixture that employed #C214 (16.18 g, 73.5 mmol) and concentrated in vacuo. The residue was mixed with saturated aqueous sodium bicarbonate solution (300 mL) and water (200 mL), and extracted with ethyl acetate (4×200 mL). The combined organic layers were dried over sodium sulfate, filtered, concentrated under reduced pressure, and purified via chromatography on silica gel (Gradient: 0% to 9% methanol in dichloromethane) to provide the product as a light yellow oil. Combined yield: 52.0 g, 140 mmol, 85%. LCMS m/z 371.9 [M+H]$^+$. $^1$H NMR (400 MHz, CDCl$_3$) δ 7.38-7.25 (m, 5H), 7.12 (d, J=8.0 Hz, 1H), 6.46 (d, half of AB quartet, J=2.5 Hz, 1H), 6.43 (dd, half of ABX pattern, J=8.0, 2.5 Hz, 1H), 4.58 (AB quartet, J$_{AB}$=12.0 Hz, Δv$_{AB}$=23.2 Hz, 2H), 4.07 (ddd, J=11.5, 4.5, 1.5 Hz, 1H), 3.81 (s, 3H), 3.80 (s, 3H), 3.75 (s, 2H), 3.59-3.39 (m, 4H), 2.75-2.65 (m, 1H), 1.91-1.80 (m, 2H), 1.48-1.35 (m, 1H), 1.23-1.12 (m, 1H).

Preparation P9

Synthesis of 6-fluoro-N$^4$-((2R,4R)-2-methyltetrahydro-2H-pyran-4-yl)quinoline-3,4-diamine

Step 1 Synthesis of (E)-5-fluoro-2-((2-nitrovinyl)amino)benzoic acid

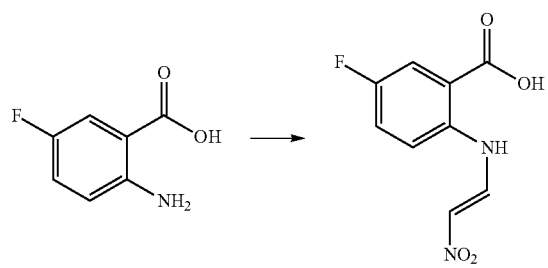 [SMILES: Nc1ccc(F)cc1C(=O)O ; O=C(O)c1cc(F)ccc1N/C=C/[N+](=O)[O-]]

Step 1: The following reaction should be run behind a blast shield. To a solution of NaOH (7.74 g, 193 mmol) in H$_2$O (50 mL) was carefully added CH$_3$NO$_2$ (9840 mg, 161 mmol) at 0° C., and the solution was stirred for 10 min at 15° C. The reaction mixture was adjusted to pH=2-3 by adding concentrated HCl (20 mL, 12.0 M) while the mixture was maintained at 15° C. The previous solution was added to a solution of 2-amino-5-fluorobenzoic acid (5.0 g, 32.23 mmol) in H$_2$O (50 mL), acetone (10 mL) and concentrated HCl (20.3 mL) maintained at 15° C. The resulting mixture was stirred for 1 h at 15° C. Soon thereafter, a yellow solid precipitated from the reaction mixture. The mixture was filtered and the product (E)-5-fluoro-2-((2-nitrovinyl)amino)benzoic acid was collected to provide 7.9 g, 93% yield. $^1$H NMR (400 MHz, DMSO-d$_6$) δ 12.92 (d, J=13.5 Hz, 1H), 8.05 (dd, J=13.6, 6.3 Hz, 1H), 7.81 (dd, J=9.3, 4.5 Hz, 1H), 7.72-7.67 (m, 1H), 7.60-7.52 (m, 1H), 6.73 (d, J=6.2 Hz, 1H)

Step 2: Synthesis of 6-fluoro-3-nitroquinolin-4-ol

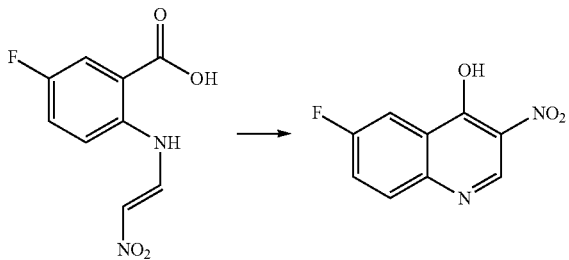 [SMILES: O=C(O)c1cc(F)ccc1N/C=C/[N+](=O)[O-] ; O=[N+]([O-])c1cnc2ccc(F)cc2c1O]

The following reaction should be run behind a blast shield. To a solution of E)-5-fluoro-2-((2-nitrovinyl)amino) benzoic acid (7.60 g, 33.6 mmol) in Ac$_2$O (50 mL) was added K$_2$CO$_3$ (13.9 g, 101 mmol) while at 15° C. The solution was then stirred for 1.5 h and heated to 90° C. After cooling to 15° C., the reaction mixture was poured into ice water (100 mL) and the mixture was filtered. The pale-grey solid 6-fluoro-3-nitroquinolin-4-ol was collected (6500 mg). The material was used directly in the next step. $^1$H NMR (400 MHz, DMSO-d6) δ 9.17 (s, 1H), 7.86 (dd, J=9.2, 3.0

Hz, 1H), 7.77 (dd, J=9.0, 4.7 Hz, 1H), 7.66 (td, J=8.6, 3.0 Hz, 1H), 1.90 (s, 1H). $^{19}$F NMR (376 MHz, DMSO-d6) δ −114.74

Step 3: Synthesis of 4-chloro-6-fluoro-3-nitroquinoline

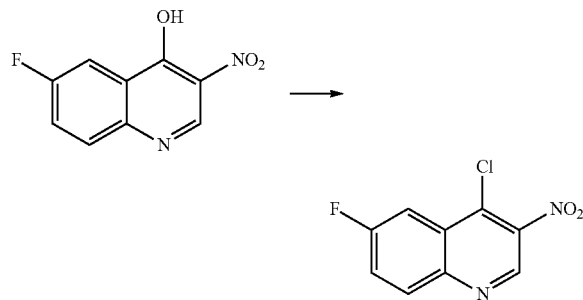

Phosphorus oxychloride (1470 mg, 9.61 mmol) was added drop-wise to a solution of 6-fluoro-3-nitroquinolin-4-ol (2 g, 9.6 mmol) in N,N-dimethylformamide (20 mL), and the reaction mixture was stirred at room temperature for 2 hours. At this point the reaction mixture was poured into ice water (100 mL). This mixture was filtered and the filter cake was washed with water (100 mL) to provide the product 4-chloro-6-fluoro-3-nitroquinoline as a brown solid. Yield: (1910 mg, 87.7%) The purity and structure were confirmed by $^1$H NMR (400 MHz, CDCl$_3$) δ 9.22 (d, J=0.7 Hz, 1H), 8.24 (dd, J=9.3, 5.2 Hz, 1H), 8.05 (dd, J=9.1, 2.8 Hz, 1H), 7.72 (ddd, J=9.3, 7.8, 2.8 Hz, 1H). $^{19}$F NMR (376 MHz, CDCl$_3$) δ −106.71; LCMS: M+H 226.6.

Step 4: Synthesis of N-(2,4-dimethoxybenzyl)-6-fluoro-N-((2S,4R)-2-methyltetrahydro-2H-pyran-4-yl)-3-nitroquinolin-4-amine

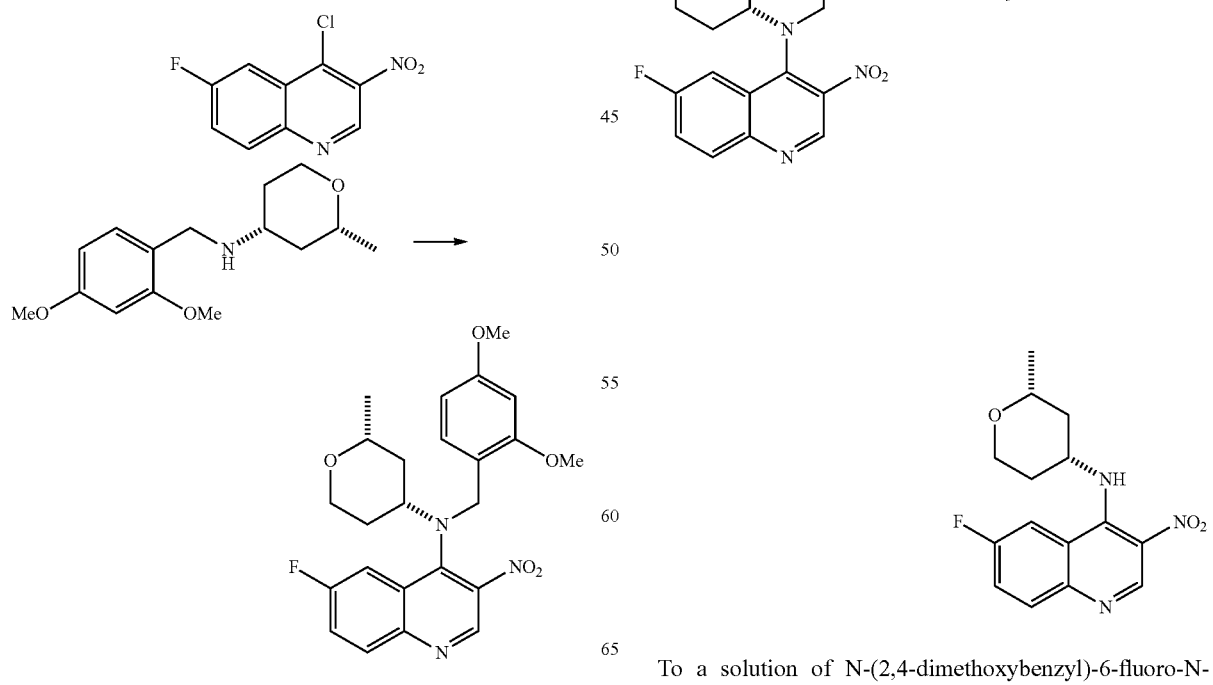

To a solution of 4-chloro-6-fluoro-3-nitroquinoline (1910 mg, 8.429 mmol), (2R,4R)—N-(2,4-dimethoxybenzyl)-2-methyltetrahydro-2H-pyran-4-amine (2240 mg, 8.43 mmol) in ACN (15 mL) was added DIEA (2400 mg, 18.5 mmol) drop-wise while the mixture was maintained at 20° C. and then it was stirred for 16 h. TLC (PE:EA, 5:1) showed the reaction was complete. LCMS RT 0.90 min) also showed the reaction was complete and the desired product mass was observed. The mixture was washed with water (50 mL) and extracted with EtOAc (100 mL×3), and concentrated under vacuo. The residue was purified by combiflash with EtOAc in PE (5% to 20%) and then was concentrated under vacuo to give the product N-(2,4-dimethoxybenzyl)-6-fluoro-N-((2S,4R)-2-methyltetrahydro-2H-pyran-4-yl)-3-nitroquinolin-4-amine as a yellow solid (3280 mg, 85.4%). The purity and structure was confirmed $^1$H NMR (400 MHz, CDCl$_3$) δ 9.00 (d, J=0.6 Hz, 1H), 8.05 (dd, J=9.2, 5.4 Hz, 1H), 7.86 (dd, J=10.2, 2.8 Hz, 1H), 7.52 (ddd, J=9.2, 7.7, 2.9 Hz, 1H), 6.85 (d, J=8.1 Hz, 1H), 6.28-6.14 (m, 2H), 4.32 (s, 2H), 4.02 (dt, J=11.6, 3.3 Hz, 1H), 3.85-3.71 (m, 1H), 3.68 (s, 3H), 3.51 (s, 3H), 3.47-3.31 (m, 2H), 2.01-1.81 (m, 3H), 1.61-1.49 (m, 1H), 1.19 (d, J=6.2 Hz, 3H). $^{19}$F NMR (376 MHz, CDCl$_3$) δ −111.16. LCMS: RT 0.81 min; MS 455.8 M+H.

Step 5: Synthesis of 6-fluoro-N-((2S,4R)-2-methyltetrahydro-2H-pyran-4-yl)-3-nitroquinolin-4-amine

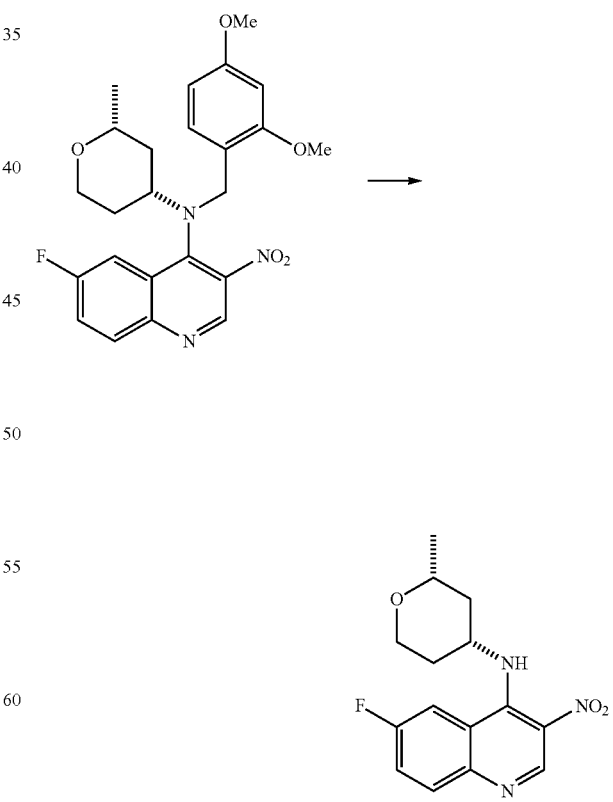

To a solution of N-(2,4-dimethoxybenzyl)-6-fluoro-N-((2S,4R)-2-methyltetrahydro-2H-pyran-4-yl)-3-nitroquinolin-4-amine (3270 mg, 7.179 mmol) in DCM (20 mL) was added TFA (2460 mg, 21.5 mmol) drop-wise while the reaction mixture was maintained at 25° C. The resulting solution was stirred at 25° C. for 1 h. LCMS, RT 0.58 min, MS 305.7 M+H, showed that the reaction was complete. The reaction solution was combined with a second reaction for workup and purification. The combined reaction solution was made basic with saturated NaHCO$_3$ solution (50 mL) and extracted with DCM (100 mL). The organic layer was dried over Na$_2$SO$_4$, filtered and concentrated. The residue was purified by combiflash (5%-10% MeOH in DCM) to give desired product 6-fluoro-N-((2S,4R)-2-methyltetrahydro-2H-pyran-4-yl)-3-nitroquinolin-4-amine (2000 mg, 88.6% combined yield) as a yellow solid. The purity and structure was confirmed by $^1$H NMR (400 MHz, CDCl$_3$) δ 9.34 (d, J=0.6 Hz, 1H), 9.03 (d, J=9.0 Hz, 1H), 8.04 (dd, J=9.2, 5.7 Hz, 1H), 7.77 (dd, J=10.2, 2.7 Hz, 1H), 7.56 (ddd, J=9.2, 7.5, 2.7 Hz, 1H), 4.26 (dddd, J=15.6, 11.3, 8.7, 4.3 Hz, 1H), 4.10 (ddd, J=12.1, 4.7, 1.8 Hz, 1H), 3.62-3.46 (m, 2H), 2.14 (tdd, J=15.1, 4.2, 2.1 Hz, 2H), 1.75 (qd, J=12.4, 4.7 Hz, 1H), 1.47 (dt, J=12.7, 11.1 Hz, 1H), 1.26 (d, J=6.1 Hz, 3H). $^{19}$F NMR (376 MHz, CDCl$_3$) δ −112.11. LCMS: MS 305.8 M+H.

Step 6: Synthesis of 6-fluoro-N$^4$-((2R,4R)-2-methyltetrahydro-2H-pyran-4-yl)quinoline-3,4-diamine

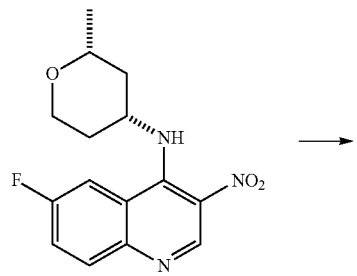

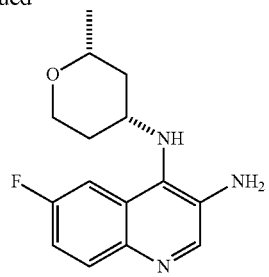

To a solution of 6-fluoro-N-((2S,4R)-2-methyltetrahydro-2H-pyran-4-yl)-3-nitroquinolin-4-amine (2000 mg, 6.551 mmol) in THF (30 mL) was added Pt/C (639 mg, 3.28 mmol) and stirred at 25° C. under atmospheric hydrogen for 3 h. LCMS (RT 0.53 min; MS 275.7 M+H) showed the reaction was complete as did TLC (DCM:MeOH, 50:1). The mixture was filtered and concentrated to give a residue. The residue was purified by combiflash (0-6% MeOH in DCM) to give the desired product 6-fluoro-N$^4$-((2R,4R)-2-methyltetrahydro-2H-pyran-4-yl)quinoline-3,4-diamine (1450 mg, 80.4%) as a yellow solid. The purity and structure was confirmed by LCMS RT 0.52 min, MS 275.7 M+H, Column: LCMS-E(4-302) Chromolith. Flash RP-18e 25-2 mm) HPLC RT 2.80 min, Mobile phase: 1.0% ACN in water (0.1% TFA) to 5% ACN in water (0.1% TFA) in 1 min; then from 5% ACN in water (0.1% TFA) to 100% ACN (0.1% TFA) in 5 minutes; hold at 100% ACN (0.1% TFA) for 2 minutes; Flow rate 1.2 mL/min). $^1$H NMR (400 MHz, DMSO-d6) δ 8.37 (s, 1H), 7.74 (ddd, J=20.6, 10.3, 4.3 Hz, 2H), 7.18 (ddd, J=9.1, 8.3, 2.8 Hz, 1H), 5.22 (s, 2H), 4.50 (d, J=10.5 Hz, 1H), 3.89-3.75 (m, 1H), 3.35-3.14 (m, 2H), 1.83-1.58 (m, 2H), 1.51 (qd, J=12.3, 4.7 Hz, 1H), 1.23 (q, J=12.8, 12.2 Hz, 2H), 1.04 (d, J=6.1 Hz, 3H). $^{19}$F NMR (377 MHz, DMSO-d6) δ −115.18.

Preparation P10

Synthesis of 3-Amino-4-[(4,4-difluoro-1-methylpyrrolidin-3-yl)amino]quinoline-6-carbonitrile (#P513)

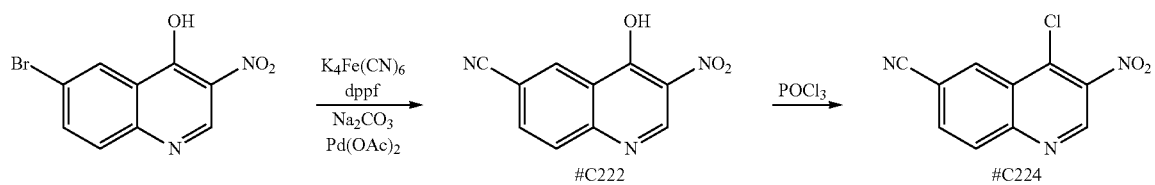

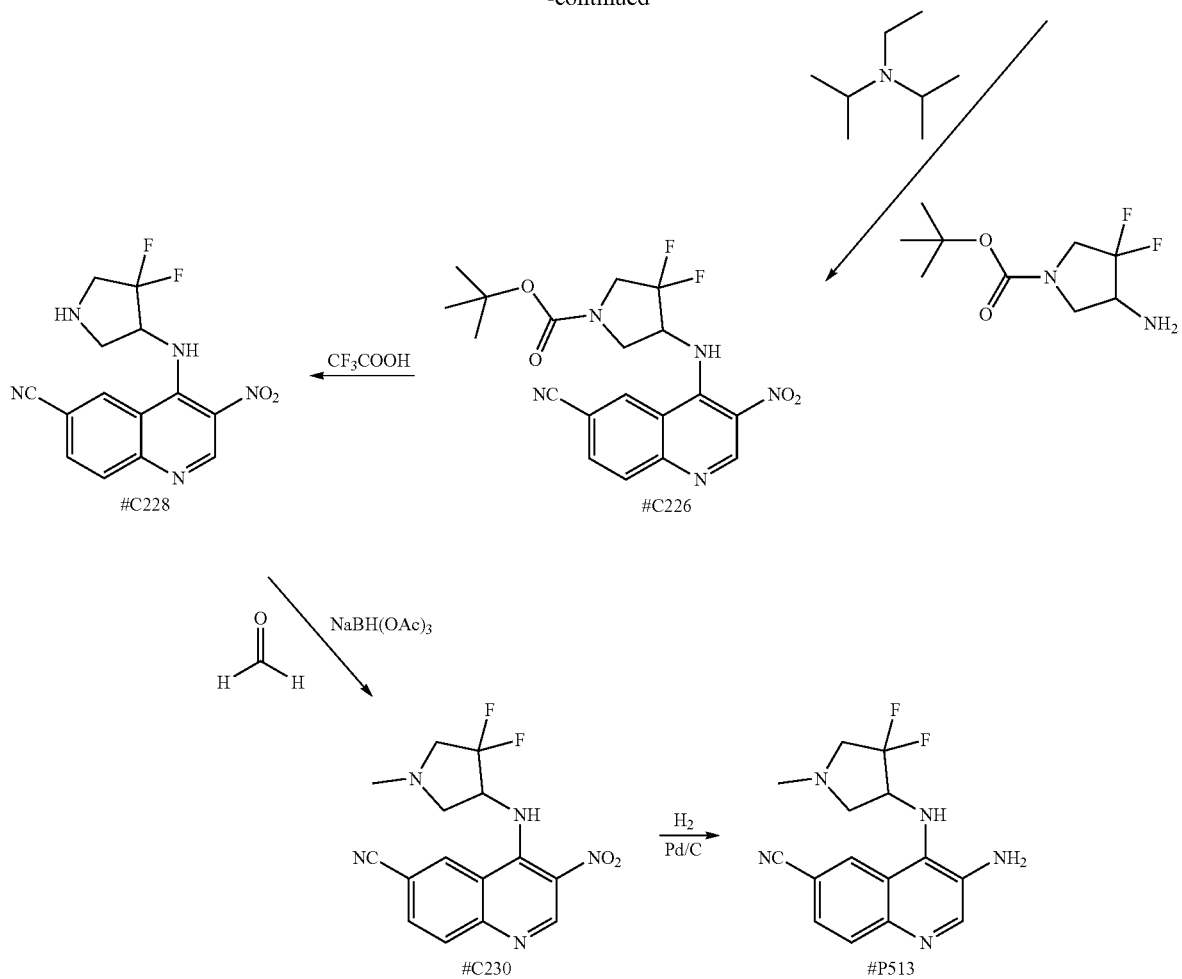

Step 1: Synthesis of
4-hydroxy-3-nitroquinoline-6-carbonitrile (#C222)

This reaction was run in two identical batches. A mixture of 6-bromo-3-nitroquinolin-4-ol (25.0 g, 92.9 mmol), potassium hexacyanoferrate(II) trihydrate (13.7 g, 32.4 mmol), 1,1'-bis(diphenylphosphino)ferrocene (5.15 g, 9.29 mmol), sodium carbonate (11.8 g, 111 mmol), and palladium(II) acetate (1.04 g, 4.63 mmol) in N,N-dimethylformamide (350 mL) was heated at 140° C. for 16 hours. The reaction mixture was cooled to room temperature, and the two batches were combined and filtered through diatomaceous earth. The filter cake was slowly rinsed with N,N-dimethylformamide (200 mL) and tert-butyl methyl ether (3.0 L) while the filtrate was stirred. A dark solid precipitated from the filtrate during the stirring, and the resulting mixture was stirred at 20° C. for 15 minutes, and then filtered. This second filtrate was concentrated in vacuo to a volume of approximately 40 mL; the residue was diluted with tert-butyl methyl ether (~200 mL), and the resulting yellow precipitate was collected by filtration, and then triturated with ethyl acetate (~200 mL). The product was obtained as a deep yellow solid. Combined yield: 20 g, 93 mmol, 50%. LCMS m/z 216.0 [M+H]$^+$. $^1$H NMR (400 MHz, DMSO-$d_6$) δ 9.00 (s, 1H), 8.51 (d, J=2.0 Hz, 1H), 7.83 (dd, J=8.5, 1.5 Hz, 1H), 7.69 (d, J=8.5 Hz, 1H).

Step 2: Synthesis of
4-chloro-3-nitroquinoline-6-carbonitrile (#C224)

To a 15° C. solution of #C222 (5.00 g, 23.2 mmol) in N,N-dimethylformamide (30 mL) was added phosphorus oxychloride (9.85 g, 64.2 mmol), and the reaction mixture was stirred at 15° C. for 1.5 hours. It was then poured into ice water (100 mL) and the resulting suspension was filtered. The collected solids were dissolved in tetrahydrofuran (100 mL) and filtered through a pad of silica gel. Concentration of the filtrate in vacuo afforded the product as a white solid. Yield: 3.10 g, 13.3 mmol, yield 57%. $^1$H NMR (400 MHz, CDCl$_3$) δ 9.39 (s, 1H), 8.83 (d, J=1.8 Hz, 1H), 8.35 (d, J=8.8 Hz, 1H), 8.10 (dd, J=8.8, 1.8 Hz, 1H).

Step 3: Synthesis of tert-butyl 4-[(6-cyano-3-nitro-quinolin-4-yl)amino]-3,3-difluoropyrrolidine-1-carboxylate (#C226)

tert-Butyl 4-amino-3,3-difluoropyrrolidine-1-carboxylate (prepared using the method described by D. C. Behenna et al., in U.S. Published Patent Application 2015 0141402 A1, May 21, 2015; 2.30 g, 10.3 mmol) was dissolved in acetonitrile (20 mL). N,N-Diisopropylethylamine (2.01 g, 15.5 mmol) and #C224 (3.04 g, 13.0 mmol) were added to this solution, and the reaction mixture was stirred for 14 hours at 20° C. After removal of volatiles in vacuo, purification via silica gel chromatography (Gradient: 9% to 17% tetrahydrofuran in petroleum ether) provided the product as a pale yellow solid. Yield: 3.20 g, 7.63 mmol, 74%. $^1$H NMR (400 MHz, CDCl$_3$) δ 9.52 (s, 1H), 9.21-9.04 (br m, 1H), 8.48 (br s, 1H), 8.20 (d, J=8.8 Hz, 1H), 8.00 (dd, J=8.6, 1.5 Hz, 1H), 4.88-4.74 (m, 1H), 4.23 (br dd, J=9.7, 8.8 Hz, 1H), 4.05-3.89 (br m, 1H), 3.89-3.75 (m, 1H), 3.60 (ddd, J=11.4, 8.4, 1.3 Hz, 1H), 1.51 (s, 9H).

Step 4: Synthesis of 4-[(4,4-difluoropyrrolidin-3-yl)amino]-3-nitroquinoline-6-carbonitrile (#C228)

Trifluoroacetic acid (1 mL) was added to a 15° C. solution of #C226 (1.10 g, 2.62 mmol) in dichloromethane (2 mL). After the reaction mixture had been stirred for 1 hour at 15° C., at which time LCMS analysis indicated conversion to the product: LCMS m/z 320.1 [M+H]$^+$, it was concentrated in vacuo and neutralized via addition of aqueous sodium bicarbonate solution (60 mL). The resulting mixture was extracted with ethyl acetate (3×50 mL), and the combined organic layers were concentrated under reduced pressure to afford the product as a pale yellow solid. Yield: 810 mg, 2.54 mmol, 97%. $^1$H NMR (400 MHz, DMSO-d$_6$) δ 9.19 (s, 1H), 9.00 (s, 1H), 8.68-8.57 (br m, 1H), 8.13 (br AB quartet, $J_{AB}$=8.5 Hz, $\Delta v_{AB}$=48.4 Hz, 2H), 4.61-4.43 (m, 1H), 3.58 (dd, J=12.0, 7.5 Hz, 1H), 3.41-3.28 (m, 1H), 3.26-3.12 (m, 1H), 3.12 (dd, J=11.8, 7.3 Hz, 1H).

Step 5: Synthesis of 4-[(4,4-difluoro-1-methylpyrrolidin-3-yl)amino]-3-nitroquinoline-6-carbonitrile (#C230)

Sodium triacetoxyborohydride (2.15 g, 10.1 mmol) was added to a 0° C. mixture of #C228 (810 mg, 2.54 mmol) in acetonitrile (5 mL). An aqueous solution of formaldehyde (37%, 824 mg, 10.2 mmol) was added to the 0° C. reaction mixture over 20 minutes, and stirring was then continued at room temperature for 1 hour, at which time LCMS analysis indicated conversion to the product: LCMS m/z 334.1 [M+H]$^+$. After solvents had been removed via concentration in vacuo, the residue was basified to pH 8 by addition of aqueous sodium bicarbonate solution, filtered, and concentrated under reduced pressure, providing the product as a red solid. Yield: 780 mg, 2.34 mmol, 92%. $^1$H NMR (400 MHz, CDCl$_3$), characteristic peaks: δ 9.59 (br d, J=8.8 Hz, 1H), 9.48 (s, 1H), 8.55 (br s, 1H), 8.14 (d, J=8.4 Hz, 1H), 7.96 (dd, J=8.8, 1.3 Hz, 1H), 3.29-3.03 (m, 3H), 2.86 (ddd, J=9.9, 5.1, 2.0 Hz, 1H), 2.47 (s, 3H).

Step 6: Synthesis of 3-amino-4-[(4,4-difluoro-1-methylpyrrolidin-3-yl)amino]quinoline-6-carbonitrile (#P513)

Palladium on carbon (10%; 1 g) was added to a solution of #C230 (3.00 g, 9.00 mmol) in methanol (30 mL), and the reaction mixture was hydrogenated under a balloon of hydrogen for 2 hours at 25° C. It was then filtered through diatomaceous earth, concentrated in vacuo, and purified via silica gel chromatography (Gradient: 17% to 33% tetrahydrofuran in petroleum ether), providing the product as a pale yellow solid. Yield: 1.30 g, 4.29 mmol, yield 48%. $^1$H NMR (400 MHz, CDCl$_3$) δ 8.59 (s, 1H), 8.24 (d, J=1.8 Hz, 1H), 8.03 (d, J=8.8 Hz, 1H), 7.60 (dd, J=8.8, 1.8 Hz, 1H), 4.32-4.19 (m, 1H), 4.09-3.96 (m, 3H), 3.18-2.97 (m, 3H), 2.64 (ddd, J=9.7, 6.6, 1.8 Hz, 1H), 2.41 (s, 3H).

Preparation P11

Synthesis of 3-amino-4-{[(2R,4R)-2-methyltetrahydro-2H-pyran-4-yl]amino}quinoline-6-carbonitrile

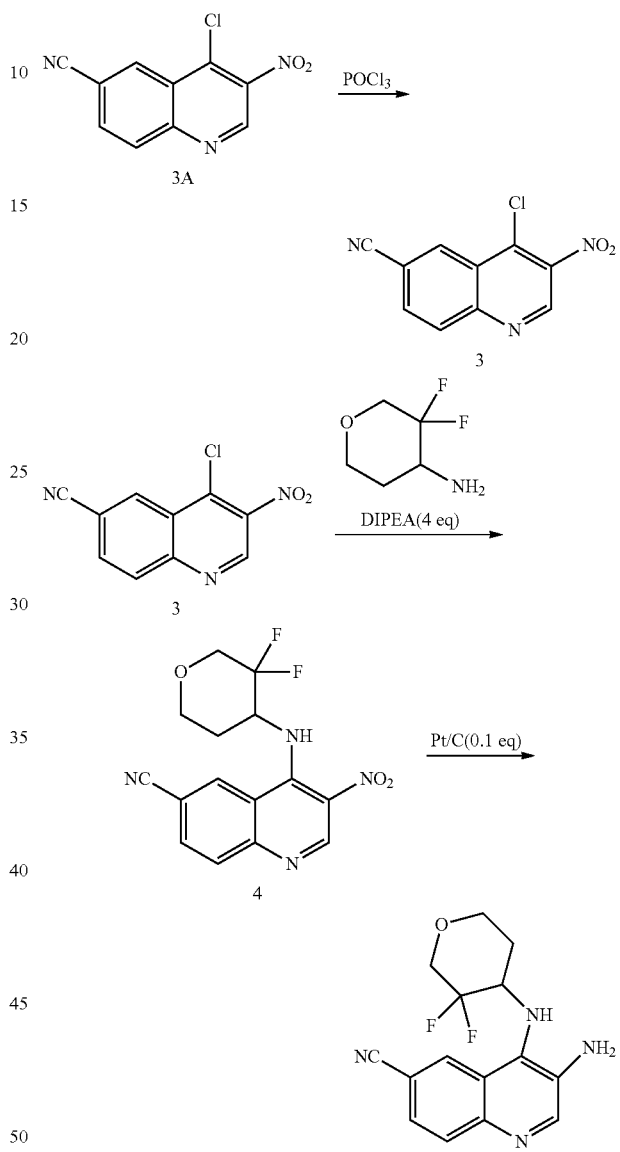

Step 1: Synthesis of 5-cyano-2-{[(E)-2-nitroethenyl]amino}benzoic acid (C59)

This experiment was run in two identical batches. {Caution: this reaction should not be carried out on greater than a 1 gram scale, due to highly energetic reactants and intermediates. Use of proper safety precautions and a blast shield is essential.} Nitromethane (4.71 g, 77.2 mmol) was added in a drop-wise manner to a solution of sodium hydroxide (3.95 g, 98.8 mmol) in water (25 mL), and the resulting solution was allowed to heat to 45° C. over 5 minutes, whereupon it was cooled in a water bath and treated with concentrated hydrochloric acid (12 M, 10 mL) until the pH of the solution became acidic. This was then added to a suspension of 2-amino-5-cyanobenzoic acid (5.0 g, 31 mmol) in water (50 mL), acetone (10 mL) and concentrated hydrochloric acid (12 M, 50 mL) at 25° C., and the reaction mixture was allowed to stir at 25° C. for 15 hours. The two batches were combined at this point, and the resulting suspension was filtered; the collected solid was washed with water to provide the product as a yellow solid. From analysis of the $^1$H NMR, the product was presumed to exist as a mixture of rotamers. Yield: 13.8 g, 59.2 mmol, 95%. $^1$H NMR (400 MHz, DMSO-$d_6$) δ [13.15 (s) and 13.12 (s), total 1H], 8.37 (d, J=2.0 Hz, 1H), 8.07-8.15 (m, 2H), 7.92 (d, half of AB quartet, J=9.0 Hz, 1H), 6.86 (d, J=6.0 Hz, 1H).

Step 2: Synthesis of 4-hydroxy-3-nitroquinoline-6-carbonitrile (C60)

Potassium carbonate (39.1 g, 283 mmol) was added to a suspension of C59 (22.0 g, 94.4 mmol) in acetic anhydride (200 mL). After the reaction mixture had been heated to 90° C. for 2 hours, it was filtered, and the collected material was washed with tert-butyl methyl ether (100 mL) and with water (400 mL), affording the product as a brown solid. Yield: 17.0 g, 79.0 mmol, 84%. LCMS m/z 215.9 [M+H]$^+$. $^1$H NMR (400 MHz, DMSO-$d_6$) δ 9.14 (s, 1H), 8.55 (dd, J=2.0, 0.5 Hz, 1H), 7.98 (dd, J=8.5, 2.0 Hz, 1H), 7.77 (dd, J=8.5, 0.5 Hz, 1H).

Step 3: Synthesis of 4-chloro-3-nitroquinoline-6-carbonitrile (C61)

Conversion of C60 to the product was carried out using the method described for synthesis of C8 from C7 in Example 1. The product was isolated as a brown solid. Yield: 9.1 g, 39 mmol, 86%. $^1$H NMR (400 MHz, DMSO-$d_6$) δ 9.26 (s, 1H), 8.59 (d, J=1.8 Hz, 1H), 8.16 (dd, J=8.7, 1.9 Hz, 1H), 7.93 (d, J=8.8 Hz, 1H).

Step 4: Synthesis of 4-chloro-6-methoxy-3-nitroquinoline (C8)

Phosphorus oxychloride (11.7 g, 76.3 mmol) was added drop-wise to a solution of C7 (5.8 g, 26 mmol) in N,N-dimethylformamide (50 mL), and the reaction mixture was stirred at room temperature for 2 hours, whereupon it was poured into ice water (100 mL). The resulting mixture was filtered and the filter cake was washed with water (300 mL) to provide the product as a brown solid. Yield: 4.5 g, 19 mmol, 73%.

Preparation P12

Synthesis of 3-amino-4-((3,3-difluorotetrahydro-2H-pyran-4-yl)amino)quinoline-6-carbonitrile

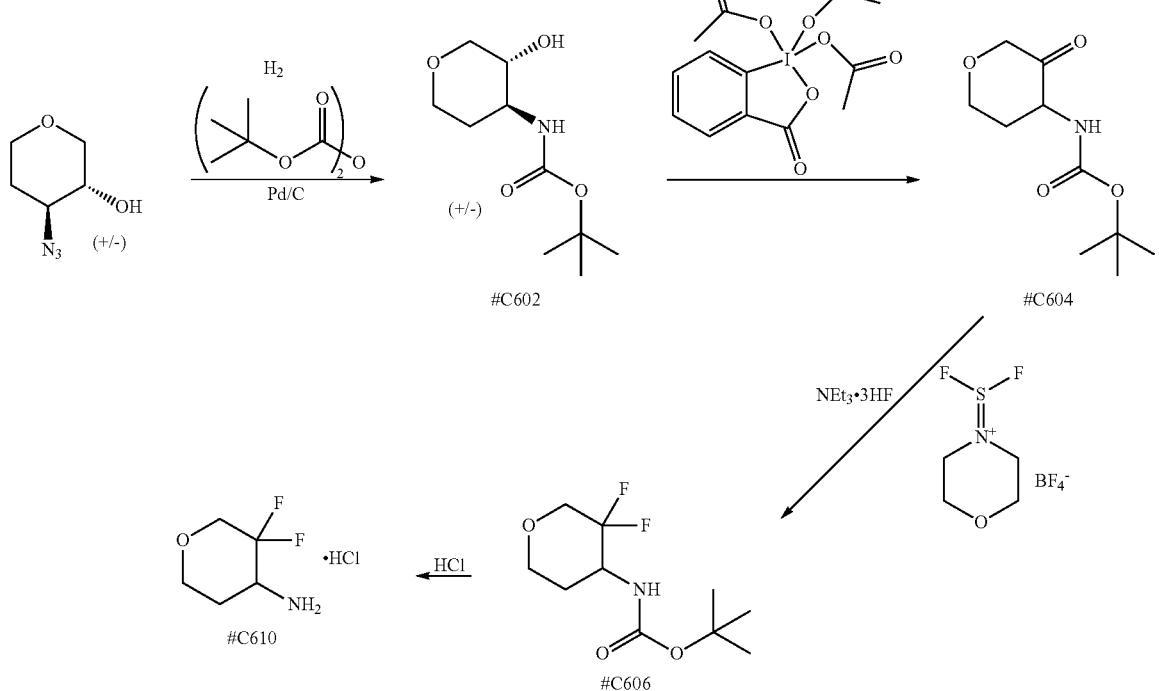

Step 1: Synthesis of tert-butyl (trans-3-hydroxytetrahydro-2H-pyran-4-yl)carbamate (#C602)

A solution of trans-4-azidotetrahydro-2H-pyran-3-ol (see M. Chini et al., Tetrahedron 1994, 50, 1261-1274) (14.8 g, 103 mmol) and di-tert-butyl dicarbonate (23.0 g, 105 mmol) in ethyl acetate (345 mL) was added to palladium on carbon (10%, 1.5 g) and the reaction mixture was stirred under 50 psi of hydrogen at 20° C. to 25° C. for 22 hours. It was then filtered through diatomaceous earth and the filter pad was rinsed with ethyl acetate and methanol. The combined filtrates were concentrated in vacuo and the residue was triturated once with a mixture of dichloromethane (10 mL) and [9:1 petroleum ether/tetrahydrofuran] (60 mL), affording the product as a white solid. Yield: 15.8 g, 72.7 mmol, 71%. $^1$H NMR (400 MHz, CDCl$_3$) δ 4.71-4.62 (br s, 1H), 4.01 (dd, J=11, 4 Hz, 1H), 3.98-3.87 (m, 2H), 3.57-3.42 (m, 2H), 3.40 (ddd, J=12, 12, 2 Hz, 1H), 3.13 (dd, J=11.0, 9.5 Hz, 1H), 1.96-1.88 (m, 1H), 1.59-1.47 (m, 1H, assumed; partially obscured by water peak), 1.47 (s, 9H).

Step 2: Synthesis of tert-butyl (3-oxotetrahydro-2H-pyran-4-yl)carbamate (#C604)

A solution of #C602 (35.1 g, 162 mmol) in dichloromethane (540 mL) was treated with [1,1,1-tris(acetyloxy)-1,1-dihydro-1,2-benziodoxol-3-(1H)-one] (Dess-Martin periodinane; 81.6 g, 192 mmol) and stirred at 25° C. for 18 hours. The reaction mixture was treated with saturated aqueous sodium bicarbonate solution and saturated aqueous sodium thiosulfate solution (250 mL); after stirring for 30 minutes, the layers were separated and the aqueous layer was extracted twice with dichloromethane (200 mL). The combined organic layers were dried over sodium sulfate, filtered, and concentrated in vacuo. Silica gel chromatography (Gradient: 10% to 30% ethyl acetate in petroleum ether) afforded the product as a yellow oil (27.95 g) that contained some aromatic material derived from the oxidizing reagent. This material was taken directly to the following step. $^1$H NMR (400 MHz, CDCl$_3$), product peaks only: δ 5.49-5.38 (br s, 1H), 4.55-4.42 (m, 1H), 4.08 (AB quartet, J$_{AB}$=14.8 Hz, Δν$_{AB}$=40.3 Hz, 2H), 4.07-3.99 (m, 1H), 3.89 (ddd, J=12.0, 11.5, 3.0 Hz, 1H), 2.75-2.63 (m, 1H), 1.96-1.81 (m, 1H), 1.44 (s, 9H).

Step 3: Synthesis of tert-butyl (3,3-difluorotetrahydro-2H-pyran-4-yl)carbamate (#C606)

A solution of #C604 (from the previous step; 27.95 g) in dichloromethane (124 mL) was slowly added to a 0° C. suspension of difluoro-4-morpholinylsulfonium tetrafluoroborate (XtalFluor-M®; 39.5 g, 163 mmol) and triethylamine trihydrofluoride (28.6 g, 177 mmol) in dichloromethane (384 mL), and the reaction mixture was allowed to slowly warm to 25° C. After three days, the reaction mixture was treated with saturated aqueous sodium bicarbonate solution (500 mL) and extracted with dichloromethane (500 mL). The organic layer was dried over sodium sulfate, filtered, and concentrated in vacuo. Chromatography on silica gel (Eluent: 10% ethyl acetate in petroleum ether) provided the product as a yellow solid. Yield: 8.93 g, 37.6 mmol, 23% over two steps. $^1$H NMR (400 MHz, CDCl$_3$) δ 4.91-4.75 (br m, 1H), 4.18-3.94 (m, 3H), 3.55-3.43 (m, 1H), 3.46 (dd, J=30.4, 12.8 Hz, 1H), 2.07-1.97 (m, 1H), 1.86-1.71 (m, 1H), 1.47 (s, 9H).

Step 4: Synthesis of 3,3-difluorotetrahydro-2H-pyran-4-amine, hydrochloride salt (#C610)

A solution of hydrogen chloride in methanol (4 M, 16.8 mL, 67.2 mmol) was added to a 10° C. solution of #C606 (3.18 g, 13.4 mmol) in methanol (35 mL). After the reaction mixture had stirred at 10° C. for 1 hour, it was concentrated in vacuo to afford the product as a white solid. Yield: 2.32 g, 13.4 mmol, quantitative. $^1$H NMR (400 MHz, DMSO-d$_6$) δ 9.03-8.89 (br s, 3H), 4.06-3.57 (m, 4H, assumed; partially obscured by water peak), 3.57-3.47 (m, 1H), 2.20-2.08 (m, 1H), 1.88-1.72 (m, 1H).

Step 5: Synthesis of 4-((3,3-difluorotetrahydro-2H-pyran-4-yl)amino)-3-nitroquinoline-6-carbonitrile

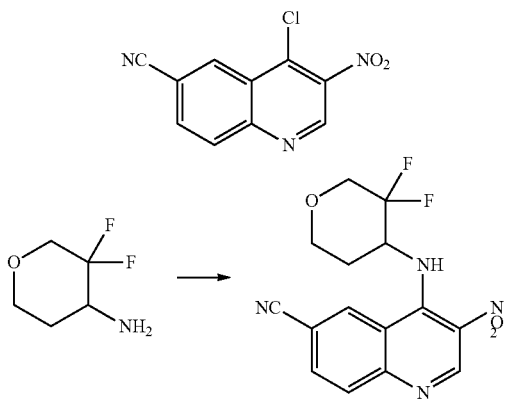

To a solution of 4-chloro-3-nitroquinoline-6-carbonitrile (1.77 g, 6.55 mmol) 3,3-difluorotetrahydro-2H-pyran-4-amine (1.16 g, 6.68 mmol) in MeCN (15 mL) was added DIEA (4.58 mL, 26.2 mmol) at 10° C. The mixture was stirred at 10° C. for 16 h. LCMS analysis showed the reaction was complete. Then the mixture was concentrated in vacuo and purified by combi flash (PE:EtOAc, 0% to 50%) to give (1 g, 45.7%) as a yellow solid. LCMS: RT=0.761, MS=335.2 M+H)$^1$H NMR (400 MHz, CDCl$_3$) δ 9.51 (s, 1H), 8.83 (d, J=10.3 Hz, 1H), 8.44-8.40 (m, 1H), 8.19 (dd, J=8.7, 0.6 Hz, 1H), 7.98 (dd, J=8.7, 1.7 Hz, 1H), 4.32 (ddd, J=22.7, 11.1, 5.3 Hz, 1H), 4.20-4.02 (m, 2H), 3.61 (t, J=11.4 Hz, 1H), 3.49 (dd, J=29.5, 12.8 Hz, 1H), 2.39 (m, 1H), 2.32-2.17 (m, 1H). $^{19}$F NMR (376 MHz, CDCl$_3$) δ −113.47 (d, J=251.4 Hz), −121.66 (d, J=249.1 Hz).

Step 6: Synthesis of 3-amino-4-((3,3-difluorotetrahydro-2H-pyran-4-yl)amino)quinoline-6-carbonitrile

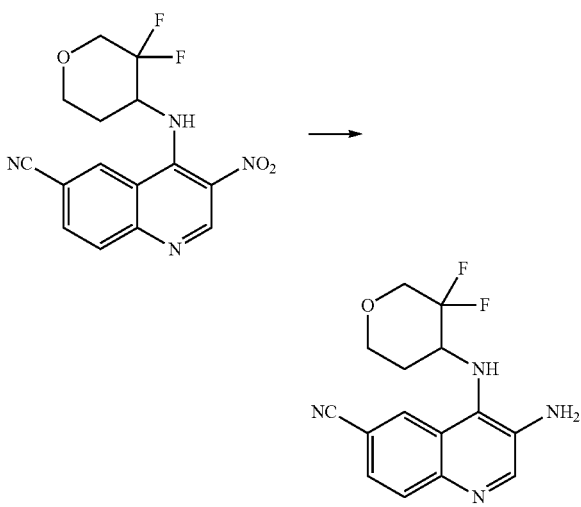

To a solution of 4-((3,3-difluorotetrahydro-2H-pyran-4-yl)amino)-3-nitroquinoline-6-carbonitrile (1000 mg, 2.992 mmol) and Pt/C (100 mg, 0.940 mmol) in THF (30 mL) was degassed with nitrogen at 20° C. The mixture was stirred under hydrogen atmosphere (50 PSI) at 20° C. for 2 h. LCMS analysis indicated the reaction was complete. The mixture was filtered and the filter cake was washed with THF (10 mL×3), The organic phases were concentrated at vacuo and combines with a similar batch and purified by combi flash (DCM:MeOH, 0% to 5%) to give the product (830 mg, 85.7%) as a yellow solid. LCMS RT 0.61 min; MS 305.1 M+H. $^1$H NMR (400 MHz, CDCl$_3$) δ 8.60 (s, 1H), 8.21 (d, J=1.7 Hz, 1H), 8.04 (d, J=8.7 Hz, 1H), 7.61 (dd, J=8.7, 1.7 Hz, 1H), 4.16-3.93 (m, 4H), 3.89-3.69 (m, 2H), 3.58-3.31 (m, 2H), 2.18-1.92 (m, 2H). $^{19}$F NMR (377 MHz, CDCl$_3$) δ −114.64 (d, J=245.9 Hz), −122.33 (d, J=246.0 Hz).

Preparation P13

Synthesis of 6-fluoro-N$^4$-((2R,4R)-2-methyltetra-hydro-2H-pyran-4-yl)quinoline-3,4-diamine Step 1: Synthesis of (E)-5-fluoro-2-((2-nitrovinyl)amino)benzoic acid

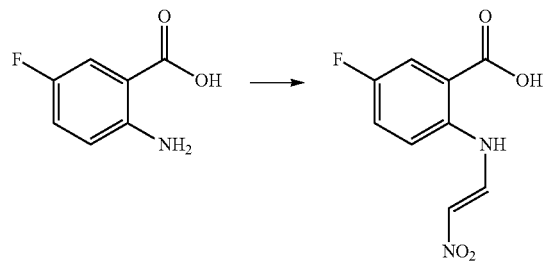 [SMILES: Nc1ccc(F)cc1C(=O)O ; O=C(O)c1cc(F)ccc1N/C=C/[N+](=O)[O-]]

The following reaction should be run behind a blast shield. To a solution of NaOH (7.74 g, 193 mmol) in H$_2$O (50 mL) was carefully added CH$_3$NO$_2$ (9840 mg, 161 mmol) at 0° C., and the solution was stirred for 10 min at 15° C. The reaction mixture was adjusted to pH 2-3 by adding concentrated HCl (20 mL, 12.0 M) while the mixture was maintained at 15° C. The previous solution was added to a solution of 2-amino-5-fluorobenzoic acid (5.0 g, 32.23 mmol) in H$_2$O (50 mL), acetone (10 mL) and concentrated HCl (20.3 mL) maintained at 15° C. The resulting mixture was stirred for 1 h at 15° C. Soon thereafter, a yellow solid precipitated from the reaction mixture. The mixture was filtered and the product (E)-5-fluoro-2-((2-nitrovinyl)amino)benzoic acid was collected. It was 7.9 g, and the isolated yield was 93%. $^1$H NMR (400 MHz, DMSO-d6) δ 12.92 (d, J=13.5 Hz, 1H), 8.05 (dd, J=13.6, 6.3 Hz, 1H), 7.81 (dd, J=9.3, 4.5 Hz, 1H), 7.72-7.67 (m, 1H), 7.60-7.52 (m, 1H), 6.73 (d, J=6.2 Hz, 1H).

Step 2: Synthesis of 6-fluoro-3-nitroquinolin-4-ol

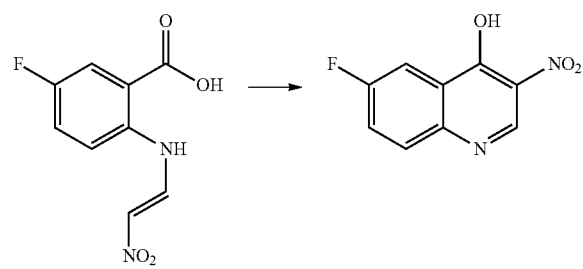 [SMILES: O=C(O)c1cc(F)ccc1N/C=C/[N+](=O)[O-] ; O=[N+]([O-])c1cnc2ccc(F)cc2c1O]

The following reaction should be run behind a blast shield. To a solution of (E)-5-fluoro-2-((2-nitrovinyl)amino)benzoic acid (7.60 g, 33.6 mmol) in Ac$_2$O (50 mL) was added K$_2$CO$_3$ (13.9 g, 101 mmol) while at 15° C. The solution was then stirred for 1.5 h and heated to 90° C. After cooling to 15° C., the reaction mixture was poured into ice water (100 mL) and the mixture was filtered. The resulting pale-grey solid, 6-fluoro-3-nitroquinolin-4-ol, was collected (6.50 g). The material was used directly in the next step. $^1$H NMR (400 MHz, DMSO-d6) δ 9.17 (s, 1H), 7.86 (dd, J=9.2, 3.0 Hz, 1H), 7.77 (dd, J=9.0, 4.7 Hz, 1H), 7.66 (td, J=8.6, 3.0 Hz, 1H), 1.90 (s, 1H). $^{19}$F NMR (376 MHz, DMSO-d6) δ−114.74.

Step 3: Synthesis of 4-chloro-6-fluoro-3-nitroquinoline

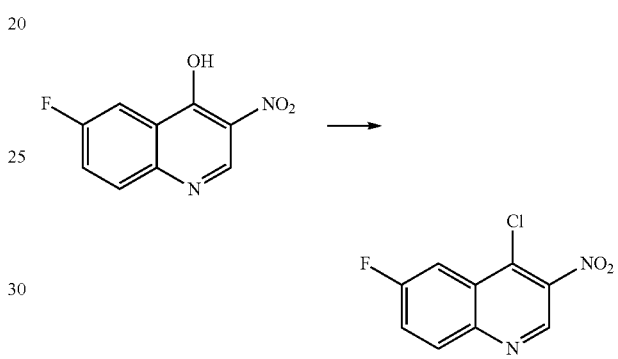

Phosphorus oxychloride (1470 mg, 9.61 mmol) was added drop-wise to a solution of 6-fluoro-3-nitroquinolin-4-ol (2 g, 9.6 mmol) in N,N-dimethylformamide (20 mL), and the reaction mixture was stirred at room temperature for 2 hours. The reaction mixture was then poured into ice water (100 mL). This mixture was filtered and the filter cake was washed with water (100 mL) to provide the product 4-chloro-6-fluoro-3-nitroquinoline as a brown solid. Yield: (1.91 g, 87.7%). The purity and structure were confirmed by $^1$H NMR (400 MHz, CDCl$_3$) δ 9.22 (d, J=0.7 Hz, 1H), 8.24 (dd, J=9.3, 5.2 Hz, 1H), 8.05 (dd, J=9.1, 2.8 Hz, 1H), 7.72 (ddd, J=9.3, 7.8, 2.8 Hz, 1H). $^{19}$F NMR (376 MHz, CDCl$_3$) δ −106.71; LCMS, M+H 226.6.

Step 4: Synthesis of (R)-6-fluoro-N-(1-methylpyrrolidin-3-yl)-3-nitroquinolin-4-amine

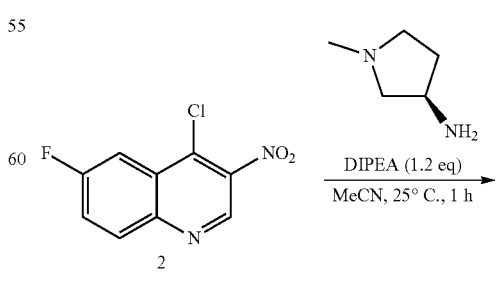

-continued

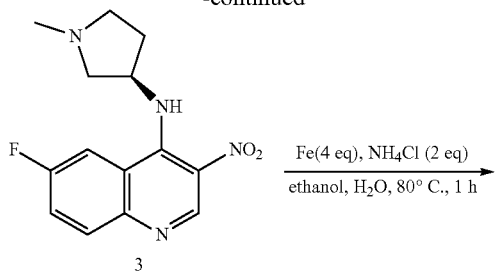

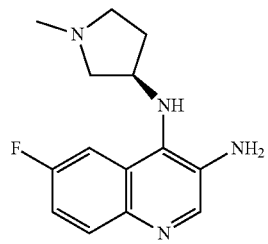

To a solution of 4-chloro-6-fluoro-3-nitroquinoline (5.56 g, 24.5 mmol) (R)-1-methylpyrrolidin-3-amine (5.10 g, 29.4 mmol) and in MeCN (50 mL) was added DIEA (12.7 g, 98.1 mmol) at 20° C. and the resulting solution was stirred at the 20° C. for 0.5 h. LCMS analysis showed the reaction was complete. The mixture was combined with one similar experiment. The mixture was concentrated in vacuo, after having added H$_2$O (200 mL). This was extracted with EtOAc (100 mL×4). The organic phase was concentrated in vacuo to a residue containing EtOAc (70 mL) which was then crystallized with MTBE (200 mL) to give the product (10.3 g, 72.5%) as a yellow solid. LCMS: RT 0.29 min; MS 290.7); $^1$H NMR (400 MHz, CDCl$_3$) δ 9.77 (s, 1H), 9.31 (s, 1H), 8.00 (dd, J=9.2, 5.7 Hz, 1H), 7.87 (dd, J=10.5, 2.7 Hz, 1H), 7.53 (ddd, J=9.2, 7.4, 2.7 Hz, 1H), 4.72 (tp, J=8.1, 3.7 Hz, 1H), 3.08-2.95 (m, 1H), 2.84 (d, J=5.2 Hz, 2H), 2.68-2.55 (m, 1H), 2.52-2.40 (m, 4H), 2.18-2.01 (m, 1H). $^{19}$F NMR (377 MHz, CDCl$_3$) δ −112.87.

Step 5: Synthesis of (R)-6-fluoro-N$^4$-(1-methylpyrrolidin-3-yl)quinoline-3,4-diamine To a solution of (R)-6-fluoro-N-(1-methylpyrrolidin-3-yl)-3-nitroquinolin-4-amine (9.2 g, 31.7 mmol), Fe (7.08 g, 127 mmol), NH$_4$Cl (3.39 g, 63.4 mmol) in EtOH/H$_2$O (80 mL/20 mL) at 20° C. The mixture was stirred at 80° C. for 1 h. LCMS indicated the reaction was complete. (LCMS: RT 2.40 min; MS 261.2). The mixture was filtered and the filter cake was washed with MeOH (100 mL×5), The organic phases were concentrated in vacuo and purified by combi flash (THF:MeOH, 0% to 30%, 0.5% TEA) to give (3.08 g, 33.3%) as a brown oil and (1.83 g, 19.8%) as a brown oil. LCMS: RT 2.36 min, MS 261.2. $^1$H NMR (400 MHz, DMSO-d$_6$) δ 8.39 (s, 1H), 7.79 (dd, J=9.1, 5.9 Hz, 1H), 7.72 (dd, J=11.5, 2.8 Hz, 1H), 7.21 (ddd, J=9.2, 8.3, 2.8 Hz, 1H), 5.29 (s, 2H), 4.78 (d, J=10.5 Hz, 1H), 4.13-4.00 (m, 1H), 2.85 (d, J=8.6 Hz, 1H), 2.72-2.62 (m, 1H), 2.55 (m, 1H), 2.36 (m, 4H), 2.08 (dtd, J=13.8, 8.3, 5.7 Hz, 1H), 1.81-1.68 (m, 1H). $^{19}$F NMR (376 MHz, DMSO-d$_6$) δ −115.16. LCMS (RT 2.37 min, MS 261.2) Instrument & Column: LCMS-T (4-302); Waters XBridge C18 30×2.0 mm, 3.5 um; Mobile phase: A) 0.05% NH$_4$OH in Water; B) ACN. Gradient: 0% B increase to 95% B within 5.8 min; hold at 95% B for 1.1 min. Flow rate 1.0 mL/min.

Preparation P14

Synthesis of 3-amino-4-((2,2-dimethyltetrahydro-2H-pyran-4-yl)amino)quinoline-6-carbonitrile

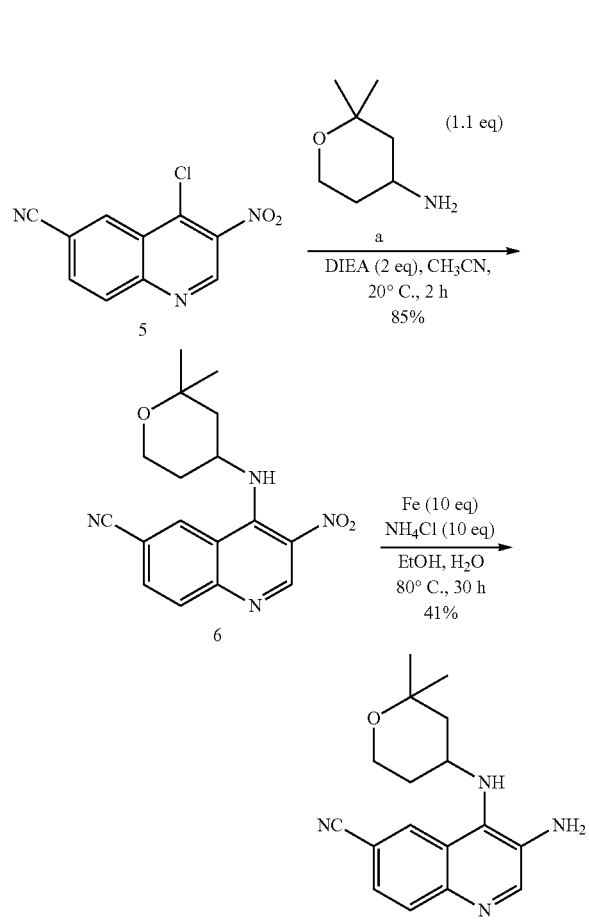

Step 1: Synthesis of 4-((2,2-dimethyltetrahydro-2H-pyran-4-yl)amino)-3-nitroquinoline-6-carbonitrile The 4-chloro-3-nitroquinoline-6-carbonitrile (4.74 g, 17.55 mmol) was suspended in MeCN (50 mL) then 2,2-dimethyltetrahydro-2H-pyran-4-amine (2.49 g, 19.3 mmol) was added, after the DIEA (4.54 g, 35.1 mmol) was added the mixture was stirred at 20° C. for 2 h, turning brown to tan. LCMS indicated complete conversion to the desired product. The mixture was concentrated under vacuum, the residue was purified by silica gel column chromatography (PE/EtOAc=1/1) to give the desired product (4.88 g, 85% yield) as yellow solid. The purity and structure of the product were confirmed by LCMS and $^1$HNMR. LCMS: RT 0.73 min, MS 327.0)$^1$H NMR (400 MHz, DMSO-d$_6$) δ 9.09 (s, 1H), 9.02 (s, 1H), 8.42 (d, J=8.4 Hz, 1H), 8.15 (dd, J=8.6, 1.6 Hz, 1H), 8.01 (d, J=8.6 Hz, 1H), 3.98 (m, 1H), 3.76-3.66 (m, 1H), 3.60 (td, J=12.2, 2.3 Hz, 1H), 2.01 (ddd, J=12.6, 4.6, 2.6 Hz, 1H), 1.93-1.82 (m, 1H), 1.67 (m, 1H), 1.56 (t, J=12.3 Hz, 1H), 1.19 (d, J=7.7 Hz, 6H).

Step 2: Synthesis of 3-amino-4-((2,2-dimethyltetrahydro-2H-pyran-4-yl)amino)quinoline-6-carbonitrile 4-((2,2-dimethyltetrahydro-2H-pyran-4-yl)amino)-3-nitroquinoline-6-carbonitrile (4.88 g, 14.95 mmol) was added to a flask along with the iron (8.35 g, 150 mmol) and the ammonium chloride (8 g, 150 mmol). The ethanol (50 mL) and water (10 mL) was added and the reaction was heated to 80° C. LCMS after 6 hours showed partial conversion. The reaction was stirred at room temperature overnight. At this juncture iron (4.2 g) and ammonium chloride (4 g) were added and stirred at 80° C. for another 2 h. LCMS after 2 hour indicated starting material still remained. Additional iron (4.2 g) and ammonium chloride (4 g) were added and stirred at 80° C. for another 2 h. LCMS after 6 hour showed complete conversion. The reaction mixture was combined with a second batch and then filtered. The yellow solution was concentrated to dryness to give a brown solid. This was separated between sat aqueous NaHCO$_3$ (100 mL) and DCM (100 mL). The organic layer was dried with Na$_2$SO$_4$, filtered, and concentrated to give the crude product. The crude product was purified by silica gel column chromatography (pure EtOAc) to give the desired product (2.35 g for two batches, 41% yield in total) as yellow solid. The purity and structure of the product were confirmed by LCMS and $^1$HNMR. LCMS: (RT 0.61 min, MS 297.1) $^1$H NMR (400 MHz, DMSO-d$_6$) δ 8.63 (dd, J=1.8, 0.6 Hz, 1H), 8.53 (s, 1H), 7.85 (d, J=8.6 Hz, 1H), 7.58 (dd, J=8.6, 1.7 Hz, 1H), 5.31 (s, 2H), 4.88 (d, J=10.3 Hz, 1H), 3.72-3.57 (m, 2H), 3.49 (td, J=12.3, 2.2 Hz, 1H), 1.69 (ddt, J=8.6, 6.6, 3.1 Hz, 1H), 1.49 (qd, J=12.4, 5.2 Hz, 1H), 1.39 (dd, J=13.2, 11.3 Hz, 1H), 1.10 (d, J=16.2 Hz, 6H).

EXAMPLES

Example 1

8-chloro-2-(cis-4-fluorocyclohexyl)-1-[(2R,4R)-2-methyltetrahydro-2H-pyran-4-yl]-1H-imidazo[4,5-c]quinoline

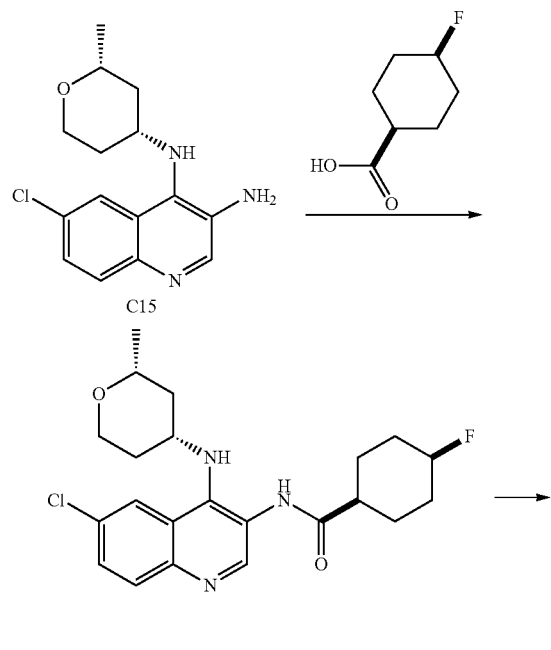

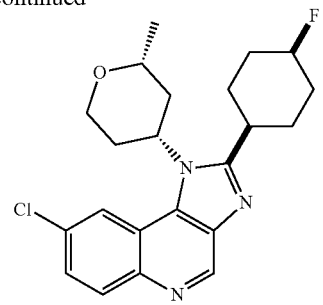

To a solution of 6-chloro-N$^4$-[(2R,4R)-2-methyltetrahydro-2H-pyran-4-yl]quinoline-3,4-diamine (50 mg, 0.171 mmol) was added cis-4-fluorocyclohexane-1-carboxylic acid (27.6 mg, 0.189 mmol) and EDCI (65.7 mg, 0.343 mmol) in pyridine (0.3 mL) at 20° C. The mixture was stirred at 25° C. for 2 h. LCMS showed the reaction was complete. The mixture was treated with H$_2$O (2 mL) and extracted with EtOAc (3×3 mL), and then was concentrated in vacuo to give the amide intermediate (72 mg, 100%, crude) as yellow oil. The crude product was used in the next step without further purification. LCMS: RT 0.66 min, MS 420.2 M+H.

To a solution of amide from the previous step (72 mg, 0.171 mmol) in n-propyl acetate (0.5 mL) was added T3P (218 mg, 0.343 mmol) at 110° C. The mixture was stirred at 110° C. for 16 h. LCMS showed the reaction was completed. (MS=402.2 M+H) The mixture was purified, and the product was obtained (34.1 mg, 49.5%), via HPLC purification (Column: Agela Durashell, 5 μm; Mobile phase A: 0.05% ammonium hydroxide in water; Mobile phase B: acetonitrile; Gradient: 46% to 56% B).

$^1$H NMR (400 MHz, CD$_3$OD) δ 1.36 (d, J=6.1 Hz, 3H), 1.74-2.07 (m, 5H), 2.21 (t, J=12.1 Hz, 2H), 2.43 (b, 1H), 2.76 (b, 1H), 3.32 (d, J=1.7 Hz, 2H), 3.84 (td, J=12.1, 2.7 Hz, 2H), 4.32 (dd, J=12.1, 5.4 Hz, 1H), 4.62 (m, 1H), 4.93-5.08 (m, 2H), 5.27 (b, 1H), 7.72 (dd, J=9.0, 2.2 Hz, 1H), 8.18 (d, J=8.9 Hz, 1H), 8.86 (b, 1H), 9.14 (s, 1H). LCMS: RT 3.01 min, MS 402.3 M+H; Column: Waters XBridge C18 50×2.0 mm, 5 um; Mobile phase: C) 10 mM NH$_4$HCO$_3$ in Water; D) ACN. Gradient: 1% D increase to 5% D within 0.6 min; 5% DB increase to 100% D within 3.4 min. Flow rate 0.8 mL/min MS Ionization: ESI.

Example 2

8-chloro-2-(cis-3-fluorocyclobutyl)-1-[(2R,4R)-2-methyltetrahydro-2H-pyran-4-yl]-1H-imidazo[4,5-c]quinoline

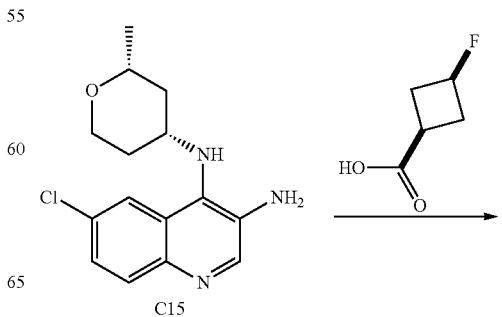

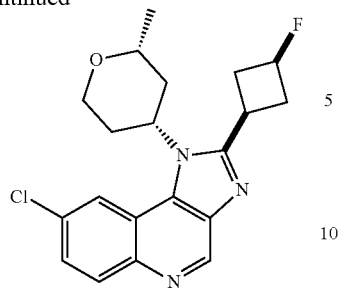

To a solution of 6-chloro-N⁴-[(2R,4R)-2-methyltetrahydro-2H-pyran-4-yl]quinoline-3,4-diamine (50 mg, 0.171 mmol) and cis-3-fluorocyclobutane-1-carboxylic acid (22.3 mg, 0.189 mmol) in n-propyl acetate (0.3 mL) was added DIEA (44.3 mg, 0.343 mmol) and T3P (164 mg, 0.257 mmol) at 60° C. The mixture was stirred at 60° C. for 1 h. and was stirred at 90° C. for 16 h. LCMS showed the reaction was complete. The mixture was concentrated in vacuo and purified by reversed-phase HPLC (Column: Agela Durashell, 5 µm; Mobile phase A: 0.05% ammonium hydroxide in water; Mobile phase B: acetonitrile; Gradient: 42% to 62% B) to provide the product (14.66 mg, 22.9%). ¹H NMR (400 MHz, CD₃OD) δ 1.34 (d, J=6.2 Hz, 3H), 1.79-2.13 (m, 2H), 2.31 (b, 1H), 2.47-2.87 (m, 3H), 2.88-3.09 (m, 2H), 3.58 (tt, J=9.8, 7.5 Hz, 1H), 3.69-3.91 (m, 2H), 4.28 (dd, J=11.9, 5.2 Hz, 1H), 5.11 (q, J=7.1 Hz, 1H), 5.25 (p, J=7.1 Hz, 1H), 7.67 (dd, J=8.9, 2.1 Hz, 1H), 8.12 (d, J=8.9 Hz, 1H), 8.64 (b, 1H), 9.11 (s, 1H). LCMS: 374.3 M+H.

Example 3

8-chloro-2-(cis-3-fluoro-3-methylcyclobutyl)-1-[(2R,4R)-2-methyl tetrahydro-2H-pyran-4-yl]-1H-imidazo[4,5-c]quinoline

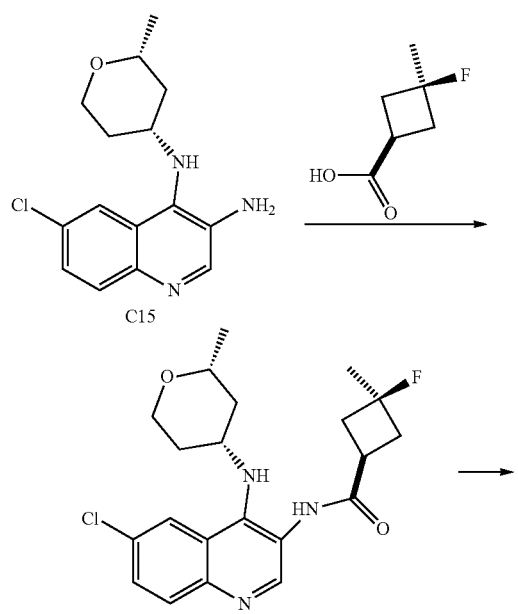

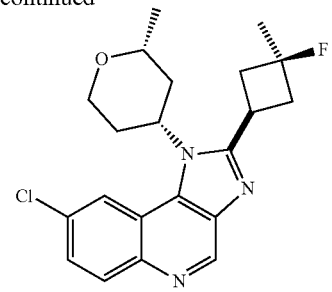

To a mixture of 6-chloro-N⁴-[(2R,4R)-2-methyltetrahydro-2H-pyran-4-yl]quinoline-3,4-diamine (50 mg, 0.17 mmol) and (1r,3r)-3-fluoro-3-methylcyclobutane-1-carboxylic acid (24.9 mg, 0.189 mmol) in pyridine (0.3 mL) was added EDCI (65.7 mg, 0.343 mmol). The mixture was stirred at 25° C. for 16 h. LCMS (RT 0.56 min, MS 406.0 M+H) showed that the reaction was complete. The mixture was treated with water (1 mL) and extracted with EtOAc (2 mL×3), the solvent was removed in vacuo to give the crude product (red oil, about 70 mg). The crude product was directly used in the next step without further purification.

To a mixture of the intermediate amide (70 mg, 0.17 mmol) in propyl acetate (0.5 mL) was added T3P (219 mg, 0.375 mmol). The mixture was heated at 110° C. and stirred for 16 h. LCMS (MS 388.0 M+H) showed the reaction was complete. The mixture was concentrated in vacuo to give the residue (crude, about 85 mg). The crude residue was purified on prep-HPLC to afford a mixture of two products due to isomerization. This mixture was separated via thin-layer chromatography on silica gel (Eluent: 1:1 THF/petroleum ether) to give the first-eluting diastereomer (14.12 mg, 21% yield) as a white solid. The second-eluting diastereomer was further purified by combiflash (DCM:MeOH, 10:1) to give the product designated as Example 3 (15.18 mg, 23% yield) as a white solid.

Example 3: ¹H NMR (400 MHz, CD₃OD) δ 1.35 (d, J=6.1 Hz, 3H), 1.68 (d, J=21.9 Hz, 3H), 2.03 (d, J=45.4 Hz, 2H), 2.37 (b, 1H), 2.58-2.77 (m, 3H), 2.90 (dd, J=20.9, 10.0 Hz, 2H), 3.54-3.67 (m, 1H), 3.71-3.92 (m, 2H), 4.30 (dd, J=11.9, 5.3 Hz, 1H), 5.07 (b, 1H), 7.73 (dd, J=9.0, 2.2 Hz, 1H), 8.18 (d, J=8.9 Hz, 1H), 8.75 (b, 1H), 9.16 (s, 1H). The stereochemistry of Example 3 was confirmed by 2-D NOE spectroscopy. LCMS RT 2.70 min, MS 388.0 M+H, Mobile phase: A) 0.1% FA in Water; B) 0.1% FA in ACN. Gradient: 1% B increase to 5% B within 0.6 min; 5% B increase to 100% B within 3.4 min. Flow rate 0.8 mL/min; HPLC RT 3.61 min, Mobile phase: 1.0% ACN in water (0.1% TFA) to 5% ACN in water (0.1% TFA) in 1 min; then from 5% ACN in water (0.1% TFA) to 100% ACN (0.1% TFA) in 5 minutes; hold at 100% ACN (0.1% TFA) for 2 minutes; Flow rate 1.2 mL/min.

The following examples were made in a similar fashion to Examples 1-3 above.

Example 4

8-chloro-1-[(2R,4R)-2-methyltetrahydro-2H-pyran-4-yl]-2-[(3R)-tetrahydrofuran-3-yl]-1H-imidazo[4,5-c]quinoline

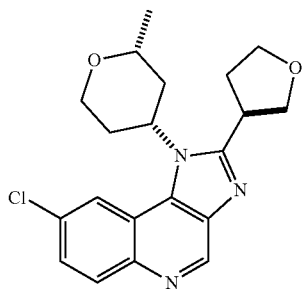

¹H NMR (400 MHz, CDCl₃) δ 1.39 (d, J=6.1 Hz, 3H), 2.02 (m, 2H), 2.40-2.61 (m, 3H), 2.82 (b, 1H), 3.65-3.94 (m, 3H), 4.07 (dt, J=8.4, 7.1 Hz, 1H), 4.17 (t, J=7.9 Hz, 2H), 4.24-4.46 (m, 2H), 4.97 (b, 1H), 7.63 (dd, J=8.9, 2.2 Hz, 1H), 8.22 (d, J=8.9 Hz, 1H), 8.65 (b, 1H), 9.28 (s, 1H). LCMS: MS: 372.1 (M+H); RT 2.33 min; Column: Waters XBridge C18, 50×2.0 mm, 5 um; Mobile Phase A: 0.1% FA in Water; Mobile Phase B: 0.1% FA in ACN. Gradient: 1% B increase to 5% B within 0.6 min; 5% B increase to 100% B within 3.4 min. Flow rate 0.8 mL/min.

Example 5

8-chloro-2-(3-fluoro-3-methylcyclobutyl)-1-[(2R,4R)-2-methyltetrahydro-2H-pyran-4-yl]-1H-imidazo[4,5-c]quinoline

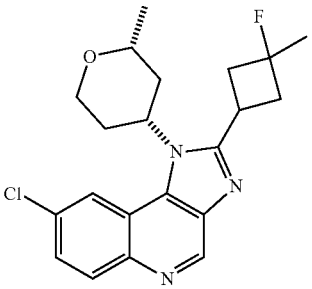

MS 388.054 M+H; RT 2.95 min; Method: Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% B for 1 minute, then linear from 5.0% to 95% B over 3.0 minutes, then 95% B for 1 minute. Flow rate: 2 mL/minute.

Example 6

8-chloro-2-(cis-3-methoxycyclobutyl)-1-[(2R,4R)-2-methyltetrahydro-2H-pyran-4-yl]-1H-imidazo[4,5-c]quinoline

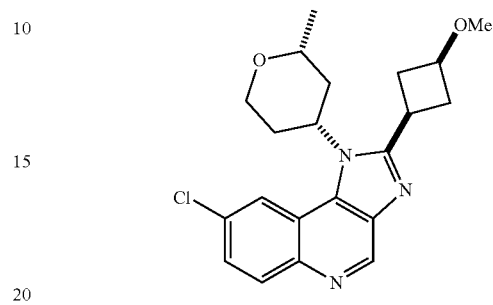

MS 386.358 M+H; RT 2.75 min; Method: Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% B for 1 minute, then linear from 5.0% to 95% B over 3.0 minutes, then 95% B for 1 minute. Flow rate: 2 mL/minute.

Example 7

8-chloro-1-[(2R,4R)-2-methyltetrahydro-2H-pyran-4-yl]-2-(tetrahydro-2H-pyran-4-yl)-1H-imidazo[4,5-c]quinoline

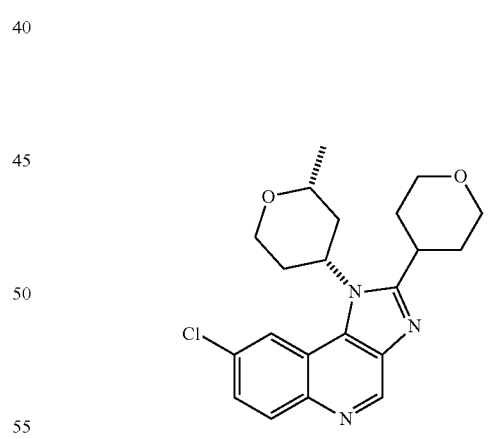

MS 386; RT 2.45 min; Column XBridge C18 2.1×50 mm; 5 μm; Temperature 40° C.; Mobile Phase A: 0.0375% TFA in water; Mobile Phase B: 0.01875% TFA in acetonitrile. Gradient: Initial 1% B, Time 0.00 min; 1% B, Time 0.60 min; 5% B, Time 4.00 min; 100% B, Time 4.30 min; 1% B, Time 4.70 min 1% B; Flow rate 0.8 mL/min.

Example 8

8-chloro-2-(4,4-difluorocyclohexyl)-1-[(2R,4R)-2-methyltetrahydro-2H-pyran-4-yl]-1H-imidazo[4,5-c]quinoline

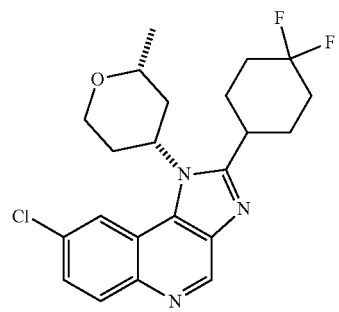

MS 420 M+H (RT 2.63 min; Column XBridge C18 2.1 mm×50 mm, 5 µm Temperature 40° C.; Mobile Phase A: 0.0375% TFA in water; Mobile Phase B: 0.01875% TFA in acetonitrile; Gradient: Initial 10% B; Time 0.00 min 10% B; Time 0.50 min 10% B; Time 4.00 min 100% B; Time 4.30 min 0% B; Time 4.70 min 10% B; Flow rate 0.8 mL/min.

Example 9

8-chloro-1-[(2R,4R)-2-methyltetrahydro-2H-pyran-4-yl]-2-(tetrahydrofuran-2-yl)-1H-imidazo[4,5-c]quinoline, DIAST 1

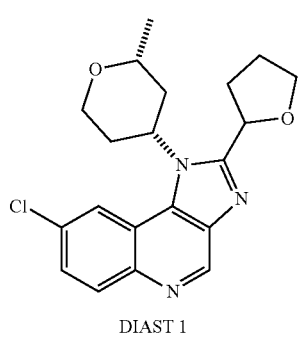

DIAST 1

The diastereomeric mixture containing Example 9 was separated into its component diastereomers via supercritical fluid chromatography [Column: Chiral Technologies ChiralCel OD-H, 5 µm; Mobile phase: 93:7 carbon dioxide/(methanol containing 0.2% ammonium hydroxide)]. The first-eluting diastereomer was designated as Example 9. MS 372.5 M+H (RT 3.32 minutes; Column: Phenomenex Lux Cellulose-1, 4.6×100 mm, 5 µm; Mobile phase: 90:10 carbon dioxide/(methanol containing 0.2% ammonium hydroxide); Back pressure: 120 bar; Flow rate: 3.0 mL/minute)

Example 10

8-chloro-2-(5-methyltetrahydrofuran-3-yl)-1-[(2R,4R)-2-methyltetrahydro-2H-pyran-4-yl]-1H-imidazo[4,5-c]quinoline, DIAST 2

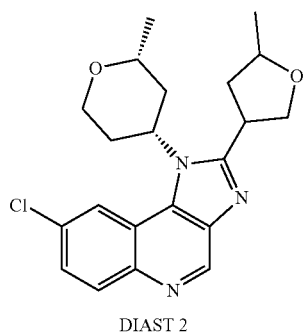 [SMILES: CC1CC(c2nc3cnc4ccc(Cl)cc4c3n2[C@@H]2CCO[C@H](C)C2)CO1]

DIAST 2

Example 10 was synthesized from 5-methyltetrahydrofuran-3-carboxylic acid. The resulting diastereomeric mixture was separated into its component diastereomers via supercritical fluid chromatography [Column: Phenomenex Lux Cellulose-1, 5 µm; Mobile phase: 75:25 carbon dioxide:(2-propanol containing 0.2% 1-am inopropan-2-ol)]. The second-eluting diastereomer was designated as Example 10. MS 388.4 M+H;

Example 11

8-chloro-2-(3,3-difluorocyclopentyl)-1-[(2R,4R)-2-methyltetrahydro-2H-pyran-4-yl]-1H-imidazo[4,5-c]quinoline

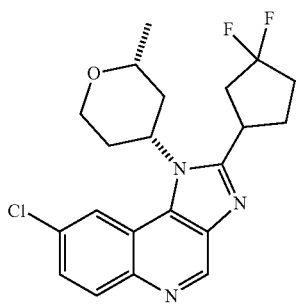

MS 406; RT 2.61 min; Column: XBridge C18, 2.1×50 mm; 5 µm; Mobile phase A: 0.0375% TFA in water; Mobile phase B: 0.01875% TFA in acetonitrile; Gradient: 10% B for 0.50 min; 10% to 100% B over 3.5 minutes; Flow rate: 0.8 mL/min.

Example 12

8-chloro-1-[(2R,4R)-2-methyltetrahydro-2H-pyran-4-yl]-2-(oxetan-3-yl)-1H-imidazo[4,5-c]quinoline

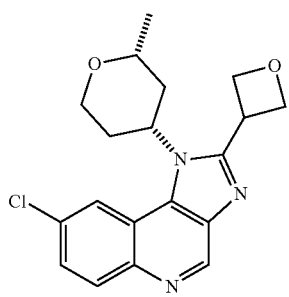

MS 358.0; RT 2.58 min; Column: Waters XBridge C18, 50×2.0 mm, 5 um; Mobile phase A: 10 mM NH$_4$HCO$_3$ in water; Mobile phase B: ACN. Gradient: 1% to 5% B over 0.6 min; 5% to 100% B over 3.4 min; Flow rate 0.8 mL/min.

Example 13

2-[(cis)-3-fluorocyclopentyl]-1-[(2R,4R)-2-methyltetrahydro-2H-pyran-4-yl]-1H-imidazo[4,5-c]quinoline-8-carbonitrile, ENT 1

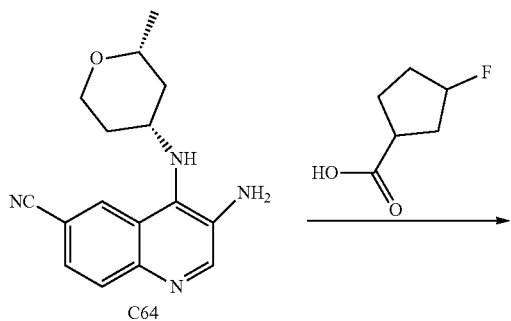

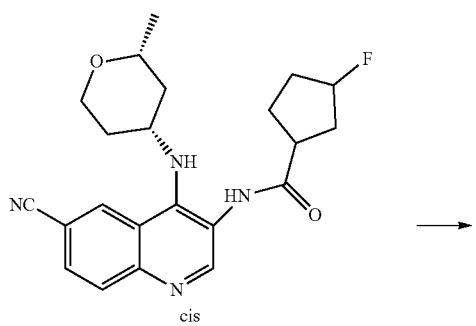

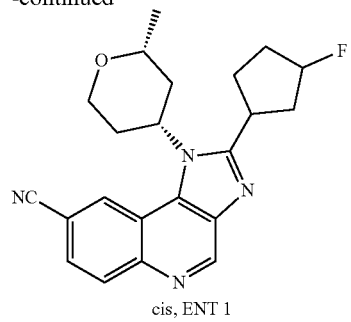

cis, ENT 1

To a mixture of 3-amino-4-(((2R,4R)-2-methyltetrahydro-2H-pyran-4-yl)amino) quinoline-6-carbonitrile (500 mg, 1.77 mmol) and 3-fluorocyclopentanecarboxylic acid (281 mg, 2.13 mmol) in pyridine (3 mL) was added EDCI (679 mg, 3.54 mmol). The mixture was maintained at 25° C. and stirred for 2 h. LCMS indicated that the reaction that there were two products. The mixture was treated with water (5 mL) and extracted with EtOAc (10 mL×3), the solvent was removed in vacuo to give the crude residue, which was purified by CombiFlash eluting with PE:THF (100% to 10% of PE) to give two isomers. The less polar spot (220 mg, 31.3% yield) was a yellow solid. The more polar spot (250 mg, 35.6% yield) was also a yellow solid. The structures were confirmed by spectral analysis. Less polar material. LCMS: RT 0.62 min, MS 397.2 M+H, purity 91.52%. HPLC: RT 2.91 min, purity 92.95%. $^1$H NMR (400 MHz, CDCl$_3$) δ ppm 1.23 (dd, J=6.11, 2.20 Hz, 4H) 1.78-2.06 (m, 4H) 2.21-2.55 (m, 6H) 3.08-3.20 (m, 1H) 3.36-3.50 (m, 2H) 3.65 (br d, J=9.78 Hz, 1H) 3.73-3.80 (m, 1H) 3.79 (br s, 1H) 3.99-4.18 (m, 2H) 5.28-5.48 (m, 1H) 7.02 (s, 1H) 7.55 (br d, J=4.89 Hz, 1H) 7.80 (dd, J=8.80, 1.47 Hz, 1H) 8.12 (d, J=8.80 Hz, 1H) 8.36 (d, J=1.47 Hz, 1H) 8.96 (s, 1H). $^{19}$F NMR (377 MHz, CDCl$_3$) δ ppm −167.85 (br d, J=11.44 Hz, 1 F).

More polar material. LCMS: RT 0.62 min, MS 397.2 M+H, purity 95.14%. HPLC: RT 2.85 min, purity 91.5%. $^1$H NMR 400 MHz, CDCl$_3$) δ ppm 1.24 (dd, J=6.11, 1.71 Hz, 4H) 1.90-2.44 (m, 10H) 3.12-3.23 (m, 1H) 3.38-3.49 (m, 2H) 3.57-3.68 (m, 1H) 4.01-4.09 (m, 1H) 4.15 (br d, J=9.78 Hz, 1H) 5.18-5.49 (m, 1H) 7.41 (s, 1H) 7.81 (dd, J=8.80, 1.47 Hz, 1H) 8.12 (d, J=8.80 Hz, 1H) 8.35 (d, J=1.47 Hz, 1H) 8.98 (s, 1H). $^{19}$F NMR (377 MHz, CDCl$_3$) δ ppm −172.42 to −169.11 (m, 1 F).

To a mixture of the more polar isomer (250 mg, 0.631 mmol) in propyl acetate (2 mL) was added T3P (803) and the mixture was heated at 100° C. and stirred for 16 h. LCMS showed the reaction was completed. Both isomers were produced in the same reaction. In a second experiment, the less polar isomer (220 mg, 0.555 mmol) in propyl acetate was added T3P and the mixture was heated at 100° C. and stirred for 16 h. The two reaction mixtures were combined for one workup and purification. The mixture was treated with NaHCO$_3$ (5 mL) and extracted with EtOAc (10 mL×3), the solvent was removed under vacuo to give the crude, which was purified by CombiFlash eluting with PE:THF (100% to 10% of PE) to give two isomers. The less polar spot (150 mg, 31.5% yield) was a yellow solid. The more polar spot (1000 mg, 21% yield) was a yellow solid, which possessed a cis configuration around the cyclopentane ring, as established by Heteronuclear Overhauser Effect Spectroscopy. Less polar material: LCMS RT 0.72 min; MS 379.2 M+H; purity 98.11%. HPLC RT 3.69 min, purity 86.58%)$^1$H NMR (400 MHz, CDCl₃) δ ppm 1.40 (d, J=6.02 Hz, 3H) 1.90-2.85 (m, 11H) 3.70-3.91 (m, 3H) 4.38 (br d, J=8.03 Hz, 1H) 5.33-5.52 (m, 1H) 7.85 (dd, J=8.53, 1.51 Hz, 1H) 8.37 (d, J=8.53 Hz, 1H) 8.97 (br s, 1H) 9.38 (s, 1H). ¹⁹F NMR (376 MHz, CDCl₃) δ ppm −172.02 to −169.02 (m, 1 F). More polar material: LCMS: RT 0.70 min, MS 379.2 M+H, purity 99.6%. HPLC: RT 3.53 min, purity 79.1%. ¹H NMR (400 MHz, CDCl₃) δ ppm 1.40 (dd, J=6.02, 1.51 Hz, 4H) 1.87-2.81 (m, 15H) 3.47-3.88 (m, 5H) 4.36 (br s, 1H) 5.22-5.45 (m, 1H) 6.98 (s, 2H) 7.81-7.88 (m, 1H) 8.37 (d, J=9.04 Hz, 1H) 9.01 (br s, 1H) 9.43 (s, 1H). ¹⁹F NMR (376 MHz, CDCl₃) δ ppm −168.17 (br s, 1 F).

The more polar material from the previous experiment was purified by chiral SFC. Column: Chiral Technologies Chiralpak IC, 10 μm; Mobile phase: 60:40 carbon dioxide/(ethanol containing 0.1% ammonium hydroxide). Example 13 was the first-eluting isomer (Peak 1) (23.3 mg, 23.3% yield, white solid).

¹H NMR 400 MHz, CDCl₃) δ ppm 1.39 (d, J=6.02 Hz, 3H) 1.75 (br s, 2H) 1.77-2.14 (m, 3H) 2.27 (td, J=12.92, 6.78 Hz, 1H) 2.21-2.83 (m, 1H) 2.34-2.42 (m, 1H) 2.45-2.83 (m, 4H) 3.57 (quin, J=8.66 Hz, 1H) 3.75 (br d, J=9.03 Hz, 2H) 4.35 (br s, 1H) 5.01 (br s, 1H) 5.23-5.45 (m, 1H) 7.84 (dd, J=8.53, 1.51 Hz, 1H) 8.36 (d, J=8.53 Hz, 1H) 9.01 (br s, 1H) 9.42 (s, 1H). ¹⁹F NMR 376 MHz, CDCl₃) δ ppm −168.14 (br s, 1 F). LCMS RT 2.95 min; MS 379.2 M+H; Column: Waters XBridge C18, 30×2.0 mm, 3.5 um; Mobile phase: A) 0.05% NH₄OH in Water; B) ACN. Gradient: 0% B increase to 95% B within 5.8 min; hold at 95% B for 1.1 min; Flow rate 1.0 mL/min. HPLC RT 3.55 min; Column: HPLC-BC Ultimate XB-C18, 3 um, 3.0×50 mm; Mobile phase: 1.0% ACN in water (0.1% TFA) to 5% ACN in water (0.1% TFA) in 1 min; then from 5% ACN in water (0.1% TFA) to 100% ACN (0.1% TFA) in 5 minutes; hold at 100% ACN (0.1% TFA) for 2 minutes; Flow rate 1.2 mL/min.

Example 14

2-[(cis)-3-fluorocyclopentyl]-1-[(2R,4R)-2-methyltetrahydro-2H-pyran-4-yl]-1H-imidazo[4,5-c]quinoline-8-carbonitrile, ENT 2

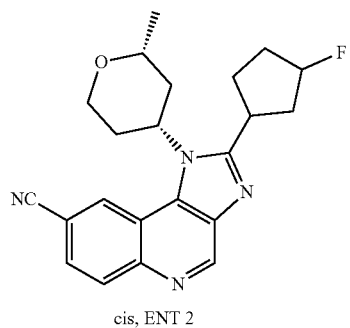 [SMILES: C[C@@H]1C[C@H](n2c(C3CCC(F)C3)nc3cnc4ccc(C#N)cc4c32)CCO1]

cis, ENT 2

Peak 2 (16.3 mg, 16.3% yield, white solid)¹H NMR 400 MHz, CDCl₃) δ ppm 1.39 (d, J=6.53 Hz, 3H) 1.79-2.90 (m, 11H) 3.56 (quin, J=8.66 Hz, 1H) 3.76 (br s, 2H) 4.38 (br s, 1H) 5.02 (br s, 1H) 5.23-5.47 (m, 1H) 7.83 (dd, J=8.78, 1.25 Hz, 1H) 8.36 (d, J=9.03 Hz, 1H) 8.83-9.18 (m, 1H) 9.42 (s, 1H); ¹⁹F NMR 376 MHz, CDCl₃) δ ppm −168.13 (br s, 1 F); LCMS RT 2.95 min; MS 379.2 M+H; Method: Instrument & Column: LCMS-T(4-302); Waters XBridge C18 30×2.0 mm, 3.5 um; Mobile phase: A) 0.05% NH₄OH in Water; B) ACN. Gradient: 0% B increase to 95% B within 5.8 min; hold at 95% B for 1.1 min; Flow rate 1.0 mL/min; MS Ionization: ESI.

HPLC RT 3.55 min, Conditions: Instrument & Column: HPLC-BC Ultimate XB-C18, 3 um, 3.0×50 mm, Mobile phase: 1.0% ACN in water (0.1% TFA) to 5% ACN in water (0.1% TFA) in 1 min; then from 5% ACN in water (0.1% TFA) to 100% ACN (0.1% TFA) in 5 minutes; hold at 100% ACN (0.1% TFA) for 2 minutes; Flow rate: 1.2 mL/min);

ee value: RT 3.90 min, ee value: 99.1%. Instrument: SFC-D (12-102) Method: Column: Chiralpak IC-3 150×4.6 mm I.D., 3 um; Mobile phase: 40% of ethanol (0.05% DEA) in CO₂; Flow rate: 2.5 mL/min; Column temperature: 40° C.

Example 15

2-(cis-4-fluorocyclohexyl)-1-[(2R,4R)-2-methyltetrahydro-2H-pyran-4-yl]-1H-imidazo[4,5-c]quinoline-8-carbonitrile

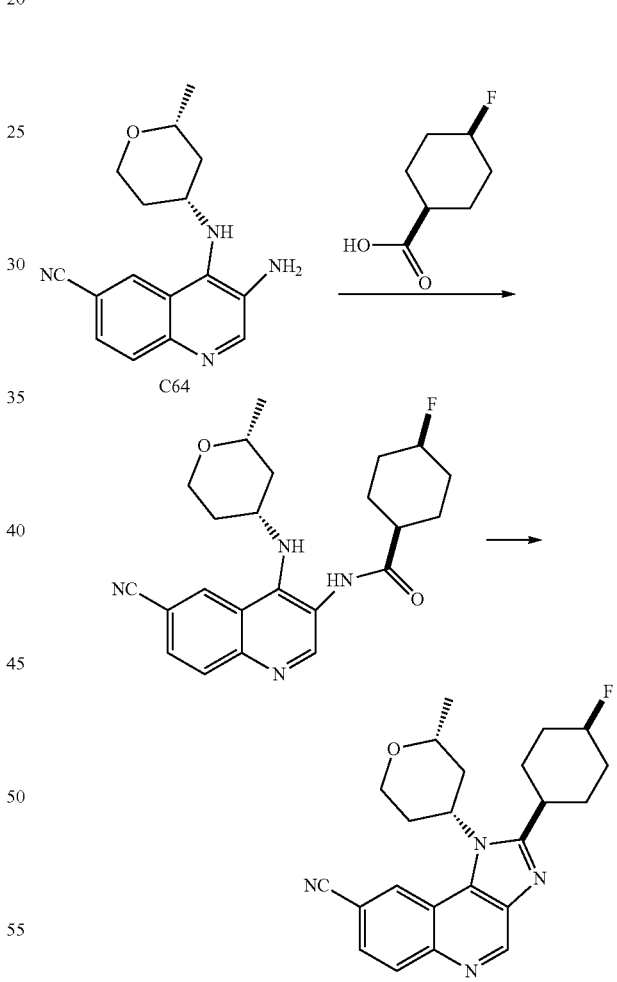

A solution of 3-amino-4-{[(2R,4R)-2-methyltetrahydro-2H-pyran-4-yl]amino}quinoline-6-carbonitrile (50 mg, 0.177 mmol) (1S,4S))-4-fluorocyclohexane-1-carboxylic acid (28.5 mg, 0.195 mmol) and EDCI (67.9 mg, 0.354 mmol) was stirred in pyridine (0.3 mL) at 20° C. The mixture was stirred at 25° C. for 2 h. LCMS showed the reaction was complete. The mixture was treated with H₂O (2 mL) and extracted with EtOAc (3×3 mL), then was concentrated under vacuo to give the intermediate amide (70.7 mg, 100%, crude) as yellow oil. The crude product was used in the next step without further purification. LCMS RT 0.64 min, MS 411.2 M+H.

To a solution of the previous product (72.7 mg, 0.177 mmol) in n-propyl acetate (0.5 mL) was added T3P (225 mg, 0.354 mmol). The mixture was stirred at 110° C. for 16 h. LCMS showed the reaction was complete. LCMS RT 0.72 min, MS 393.2 M+H. The mixture was purified by preparative HPLC. The product containing fractions were lyophilized to afford 9.6 mg, 14% yield. Column: Waters XBridge C18 50×2.0 mm, 5 um Mobile phase: C) 10 mM $NH_4HCO_3$ in Water; D) ACN. Gradient: 1% D increase to 5% D within 0.6 min; 5% D increase to 100% D within 3.4 min; Flow rate 0.8 mL/min; MS Ionization: ESI.

$^1$H NMR (400 MHz, $CD_3OD$) δ 1.38 (d, J=6.1 Hz, 3H), 1.75-1.89 (m, 1H), 1.93 (d, J=12.7 Hz, 3H), 2.05 (m, 1H), 2.40 (b, 1H), 2.23 (t, J=12.8 Hz, 5H), 2.72 (b, 1H), 3.41 (q, J=11.6 Hz, 1H), 3.89 (q, J=12.7, 11.1 Hz, 2H), 4.34 (m, 1H), 4.62 (s, 1H), 4.99 (d, J=31.3 Hz, 1H), 5.36 (b, 1H), 7.98 (dd, J=8.7, 1.6 Hz, 1H), 8.35 (d, J=8.7 Hz, 1H), 9.09-9.44 (m, 1H). LCMS RT 2.79 min, MS 393.3 M+H; Column: Waters XBridge C18, 50×2.0 mm, 5 um; Mobile phase A: 10 mM $NH_4HCO_3$ in water; Mobile phase B: ACN. Gradient: 1% to 5% B over 0.6 min, then 5% to 100% B over 3.4 min; Flow rate 0.8 mL/min.

Example 16

1-[(2R,4R)-2-methyltetrahydro-2H-pyran-4-yl]-2-[(3R)-tetrahydrofuran-3-yl]-1H-imidazo[4,5-c]quinoline-8-carbonitrile

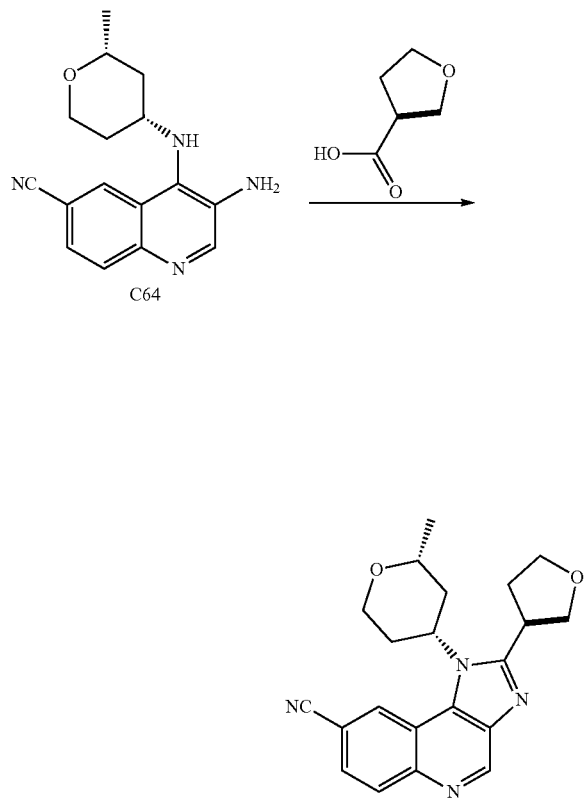

3-amino-4-{[(2R,4R)-2-methyltetrahydro-2H-pyran-4-yl]amino}quinoline-6-carbonitrile (50 mg, 0.18 mmol) and (S)-tetrahydrofuran-3-carboxylic acid (30.8 mg, 0.266 mmol) were added into DMF (2 mL), followed by T3P in DMF (0.277 mL, 0.44 mmol, 1.6 M) and finally DIEA (68 mg, 0.531 mmol). The mixture was then heated to 110° C. for 15 hours. LCMS showed the reaction was complete. The mixture was poured into water (10 mL) and extracted with EtOAc (10 mL×3), the organic layer was dried over anhydrous $Na_2SO_4$ and concentrated under reduced pressure to give the crude product, then purified by preparative HPLC (Waters XBridge Prep OBD C18 150×30 mm, 5 u; water (0.05% ammonia hydroxide v/v) ACN 25 mL/min). Concentrated and then lyophilized to afford the desired product as white solid (12.2 mg, 19% yield).

$^1$H NMR (400 MHz, DMSO-$d_6$) δ 1.25 (d, J=6.1 Hz, 3H), 1.90-2.27 (m, 3H), 2.29-2.41 (m, 1H), 2.41-2.49 (m, 2H), 3.78 (dd, J=25.7, 13.5 Hz, 2H), 3.91 (q, J=7.4 Hz, 1H), 4.00 (t, J=7.5 Hz, 2H), 4.10 (t, J=7.5 Hz, 1H), 4.18 (m, 1H), 4.25 (t, J=7.7 Hz, 1H), 5.31 (b, 1H), 8.03 (dt, J=8.8, 2.0 Hz, 1H), 8.31 (dd, J=8.7, 2.9 Hz, 1H), 9.02 (5, 1H), 9.34 (d, J=2.1 Hz, 1H). LCMS Column: Waters XBridge C18 50×2.0 mm, 5 um; Mobile phase: A) 0.1% FA in Water; B) 0.1% FA in ACN. Gradient: 1% B increase to 5% B within 0.6 min; 5% B increase to 100% B within 3.4 min; Flow rate 0.8 mL/min MS Ionization: ESI. HPLC: HPLC-AE Ultimate XB-C18, 3 um, 3.0×50 mm; Mobile phase: 1.0% ACN in water (0.1% TFA) to 5% ACN in water (0.1% TFA) in 1 min, then from 5% ACN in water (0.1% TFA) to 100% ACN (0.1% TFA) in 5 minutes; hold at 100% ACN (0.1% TFA) for 2 minutes; Flow rate: 1.2 mL/min.

The following examples were made in a similar fashion to the examples above.

Example 17

2-(4,4-difluorocyclohexyl)-1-[(2R,4R)-2-methyltetrahydro-2H-pyran-4-yl]-1H-imidazo[4,5-c]quinoline-8-carbonitrile

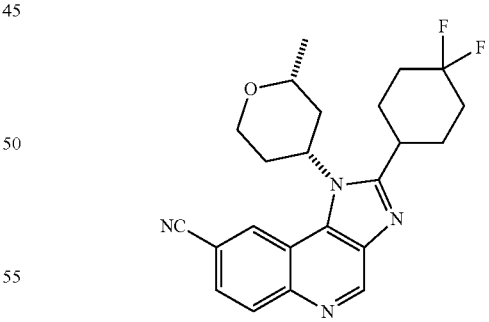

$^1$H NMR (400 MHz, $CDCl_3$) δ 1.40 (d, J=5.9 Hz, 3H), 1.81-2.16 (m, 6H), 2.33 (m, 4H), 2.62 (m, 1H), 3.17 (b, 1H), 3.78 (q, J=13.1, 10.7 Hz, 3H), 4.38 (b, 1H), 4.96 (b, 1H), 7.84 (dd, J=8.6, 1.7 Hz, 1H), 8.37 (d, J=8.7 Hz, 1H), 8.78 (b, 1H), 9.39 (s, 1H). LCMS: RT 2.84 min; MS 411.1 M+H; Column: Waters XBridge C18 50×2.0 mm, 5 um; Mobile phase: A) 0.1% FA in Water; B) 0.1% FA in ACN. Gradient: 1% B increase to 5% B within 0.6 min; 5% B increase to 100% B within 3.4 min; Flow rate 0.8 mL/min.

Example 18

2-(cis-3-fluoro-3-methylcyclobutyl)-1-[(2R,4R)-2-methyltetrahydro-2H-pyran-4-yl]-1H-imidazo[4,5-c]quinoline-8-carbonitrile

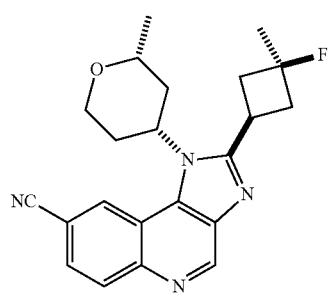

$^1$HNMR 400 MHz, CD$_3$OD) δ ppm 9.30 (s, 1H) 9.10 (br s, 1H) 8.34 (d, J=8.66 Hz, 1H) 7.98 (dd, J=8.75, 1.69 Hz, 1H) 5.13 (br s, 1H) 4.34-4.22 (m, 2H) 3.89-3.81 (m, 2H) 3.01-2.90 (m, 2H) 2.87-2.76 (m, 2H) 2.64 (br s, 1H) 2.32 (br s, 1H) 2.14 (br s, 1H) 2.07 (br s, 1H) 1.56 (d, J=21.9 Hz, 3H) 1.37 (d, J=6.11 Hz, 3H). LCMS RT 2.74 min; MS 379.0 M+H; purity: 100%. Instrument: Agilent LCMS1200-6140A(4-302LCMS-AL); Column: Waters XBridge C18 50×2.0 mm, 5 um; Mobile phase: A) 0.1% FA in Water; B) 0.1% FA in ACN. Gradient: 1% B increase to 5% B within 0.6 min; 5% B increase to 100% B within 3.4 min; Flow rate 0.8 mL/min.

Example 19

2-(cis-3-fluorocyclobutyl)-1-[(2R,4R)-2-methyltetrahydro-2H-pyran-4-yl]-1H-imidazo[4,5-c]quinoline-8-carbonitrile

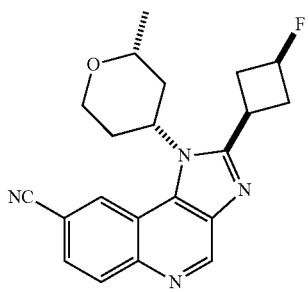

$^1$HNMR (400 MHz, CD$_3$OD) δ ppm 9.30 (s, 1H) 9.08 (br s, 1H) 8.34 (d, J=8.66 Hz, 1H) 7.98 (dd, J=8.69, 1.66 Hz, 1H) 5.20 (dq, J=55.8, 7.14 Hz, 1H) 4.61 (s, 1H) 4.32 (dd, J=11.8, 5.19 Hz, 1H) 3.89-3.81 (m, 2H) 3.63 (tt, J=9.76, 7.53 Hz, 1H) 3.03-2.97 (m, 2H) 2.86-2.76 (m, 2H) 2.64 (br s, 1H) 2.31 (br s, 1H) 2.14 (br s, 1H) 2.02 (br s, 1H) 1.37 (d, J=6.14 Hz, 3H). LCMS: 2.68 min; MS 365.3 M+H; Column: Waters XBridge C18 50×2.0 mm, 5 um; Mobile phase A: 10 mM NH$_4$HCO$_3$ in Water; Mobile phase B: ACN. Gradient: 1% to 5% B over 0.6 min, then 5% to 100% B over 3.4 min; Flow rate 0.8 mL/min.

Example 20

2-(2,2-difluorocyclohexyl)-1-[(2R,4R)-2-methyltetrahydro-2H-pyran-4-yl]-1H-imidazo[4,5-c]quinoline-8-carbonitrile, DIAST 2

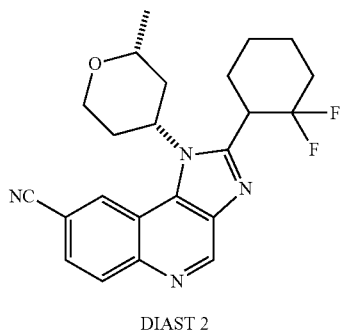

DIAST 2

The diastereomeric mixture containing Example 20 was separated into its component diastereomers via supercritical fluid chromatography [Column: Phenomenex Lux Cellulose-2, 10 µm; Mobile phase: 60:40 carbon dioxide/(methanol containing 0.1% ammonium hydroxide)]. The second-eluting diastereomer was designated as Example 20. MS 411.1 M+H; RT 2.86 min; Instrument: Agilent LCMS(4-302LCMS-AL); Column: Waters XBridge C18 50×2.0 mm, 5 um; Mobile phase: A) 0.1% FA in Water; B) 0.1% FA in ACN. Gradient: 1% B increase to 5% B within 0.6 min; 5% B increase to 100% B within 3.4 min; Flow rate 0.8 mL/min.

Example 21

8-(difluoromethyl)-1-((2R,4R)-2-methyltetrahydro-2H-pyran-4-yl)-2-((R)-tetrahydrofuran-3-yl)-1H-imidazo[4,5-c]quinoline

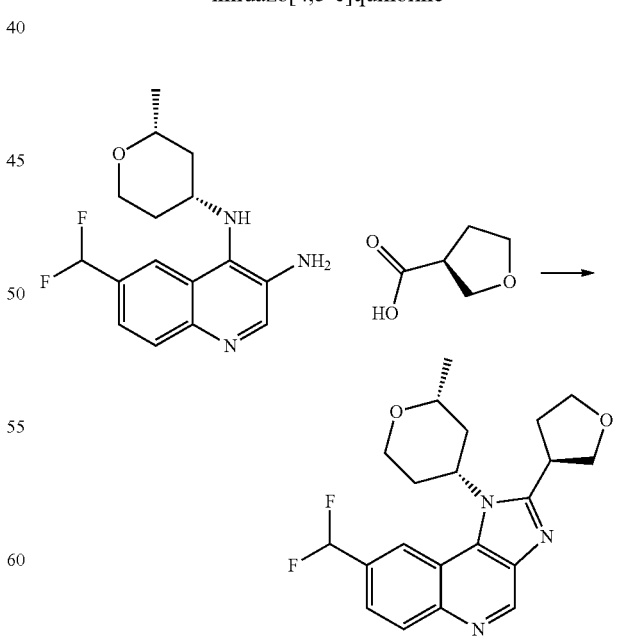

To a Toluene (3.00 mL, c=0.108 M) solution 6-(difluoromethyl)-N$^4$-((2R,4R)-2-methyltetrahydro-2H-pyran-4-yl)quinoline-3,4-diamine (0.100 g, 0.325 mmol) was added (S)-tetrahydrofuran-3-carboxylic acid (0.039 g, 0.342 mmol, 1.05 eq.), N-ethyl-N-isopropylpropan-2-amine (0.046 g, 0.358 mmol, 1.10 eq.), and lastly 2,4,6-tripropyl-1,3,5,2,4,6-trioxatriphosphorinane-2,4,6-trioxide (0.228 g, 0.358 mmol, 1.10 eq.). The resulting solution was heated to 60° C. for 90 min. Then the temperature of the reaction was increased to 100° C. and the reaction mixture was stirred at that temperature over 4 h. The reaction mixture was partitioned between EtOAc (10 mL) and NaHCO₃ (aq., sat'd., 10 mL). The organic layer was separated, dried over Na₂SO₄, filtered and concentrated under reduced pressure to yield a dark orange oily residue. Purification via regular silica column chromatography (0 to 15% of MeOH in DCM) yielded 8-(difluoromethyl)-1-((2R,4R)-2-methyltetrahydro-2H-pyran-4-yl)-2-((R)-tetrahydrofuran-3-yl)-1H-imidazo[4,5-c]quinoline as an off-white solid (0.065 g, 0.168 mmol, 52% yield). HNMR 400 MHz, CD₃OD) δ ppm 1.36 (d, J=6.53 Hz, 3H) 1.97-2.23 (m, 2H) 2.38-2.53 (m, 2H) 2.40-2.66 (m, 3H) 2.80 (br s, 1H) 3.81-3.93 (m, 2H) 4.00-4.09 (m, 1H) 4.11-4.25 (m, 3H) 4.29-4.39 (m, 2H) 5.33 (br s, 1H) 6.94-7.26 (m, 1H) 7.92 (d, J=8.53 Hz, 1H) 8.34 (d, J=8.53 Hz, 1H) 8.84-9.10 (m, 1H) 8.99 (br s, 1H) 9.24 (s, 1H)); ¹⁹F NMR 376 MHz, CD₃OD) δ ppm −113.72 to −108.29 (m, 1 F); LCMS MS 388.0 M+H.

General procedure for the following Examples 22-25: N,N-Diisopropylethylamine (25.4 mg, 0.196 mmol) and 2,4,6-tripropyl-1,3,5,2,4,6-trioxatriphosphinane 2,4,6-trioxide (50% solution in ethyl acetate, 238 mg, 0.374 mmol) were added to a solution of the diamine (0.19 mmol) and acid (0.191 mmol) in toluene (1 mL), and the reaction mixture was stirred at 70° C. for 1 hour. LCMS at this point indicated conversion to the intermediate amide and the reaction mixture was then stirred at 105° C. for 16 hours, whereupon it was concentrated in vacuo and purified by reversed phase HPLC (Column: Agela Durashell, 5 μm; Mobile phase A: 0.05% ammonium hydroxide in water; Mobile phase B: acetonitrile), affording the product.

Example 22

2-(cis-3-fluoro-3-methylcyclobutyl)-1-[(3R)-1-methylpyrrolidin-3-yl]-1H-imidazo[4,5-c]quinoline-8-carbonitrile

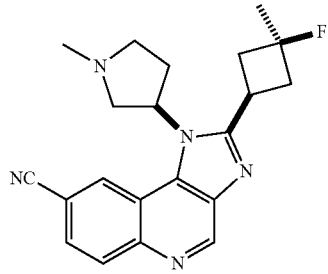

MS 364.2 M+H; RT 2.97; Instrument: Agilent LCMS (4-302LCMS-AL); Column: Waters XBridge C18, 50×2.0 mm; 5 um; Mobile phase A: 10 mM NH₄HCO₃ in Water; Mobile phase B: ACN. Gradient: 1% to 5% B over 0.6 min; 5% to 100% B over 3.4 min. Flow rate 0.8 mL/min.

Example 23

2-(cis-4-fluorocyclohexyl)-1-[(3R)-1-methylpyrrolidin-3-yl]-1H-imidazo[4,5-c]quinoline-8-carbonitrile

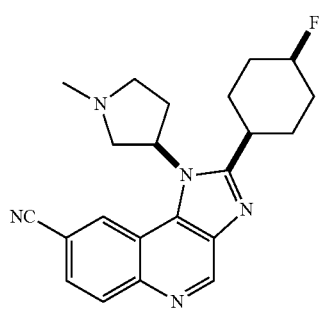

MS 378.2 M+H; RT 2.94 min; Instrument: Agilent LCMS (4-302LCMS-AL); Column: Waters XBridge C18 50×2.0 mm, 5 um; Mobile phase A: 10 mM NH₄HCO₃ in Water; Mobile phase B: ACN. Gradient: 1% to 5% B over 0.6 min; 5% to 100% B over 3.4 min; Flow rate: 0.8 mL/min.

Example 24

2-(cis-3-fluorocyclobutyl)-1-[(3R)-1-methylpyrrolidin-3-yl]-1H-imidazo[4,5-c]quinoline-8-carbonitrile

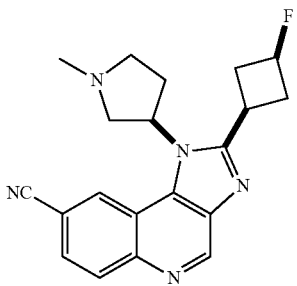

MS 350.2 M+H; RT 2.83 min; Instrument: Agilent LCMS (4-302LCMS-AL); Column: Waters XBridge C18, 50×2.0 mm, 5 um; Mobile phase A: 10 mM NH₄HCO₃ in water; Mobile phase B: ACN. Gradient: 1% to 5% B over 0.6 min; 5% to 100% B over 3.4 min; Flow rate: 0.8 mL/min.

Example 25

1-[(3R)-1-methylpyrrolidin-3-yl]-2-[(3R)-tetrahydrofuran-3-yl]-1H-imidazo[4,5-c]quinoline-8-carbonitrile

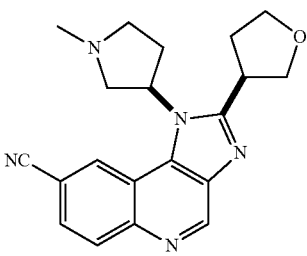

MS 348.1 M+H; RT 1.68 min; Instrument: Agilent LCMS (4-302LCMS-AL); Column: Waters XBridge C18 50×2.0 mm, 5 um Mobile phase: A) 0.1% FA in Water; B) 0.1% FA in ACN. Gradient: 1% B increase to 5% B within 0.6 min; 5% B increase to 100% B within 3.4 min; Flow rate 0.8 mL/min).

Example 26

1-[(2R,4R)-2-methyltetrahydro-2H-pyran-4-yl]-2-[(3R)-tetrahydrofuran-3-yl]-8-(trifluoromethyl)-1H-imidazo[4,5-c]quinoline

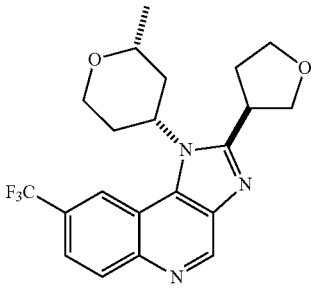

General synthesis used for Example 26:

To a solution of an appropriate acid (i.e. $R^1CO_2H$, 0.422 mmol) in N,N-dimethylformamide (2 mL) was added diamine (137 mg, 0.421 mmol), N,N-diisopropylethylamine (161 mg, 1.25 mmol), and 2,4,6-tripropyl-1,3,5,2,4,6-trioxatriphosphinane 2,4,6-trioxide (50% solution in ethyl acetate, 0.39 mL, 0.655 mmol). The reaction mixture was stirred for 2 hours at 110° C., whereupon it was diluted with water (80 mL) and extracted with EtOAc (3×80 mL). The combined organic layers were concentrated in vacuo and purified by reversed phase HPLC (Column: Agela Durashell, 5 μm; Mobile phase A: 0.05% ammonium hydroxide in water; Mobile phase B: acetonitrile), providing the product as a pale grey or white solid.

$^1$H NMR (400 MHz, CDCl$_3$) δ 1.37 (d, J=6.1 Hz, 3H), 1.81-2.19 (m, 2H), 2.39-2.65 (m, 3H), 2.80 (b, 1H), 3.65-3.81 (m, 2H), 3.85 (b, 1H), 4.07 (dt, J=8.5, 7.1 Hz, 1H), 4.18 (q, J=7.4 Hz, 2H), 4.26-4.47 (m, 2H), 5.02 (b, 1H), 7.87 (dd, J=8.8, 1.9 Hz, 1H), 8.40 (d, J=8.7 Hz, 1H), 8.99 (b, 1H), 9.39 (s, 1H). LCMS: MS 406.0 M+H. Mobile phase: A) 0.1% FA in Water; B) 0.1% FA in ACN. Gradient: 1% B increase to 5% B within 0.6 min; 5% B increase to 100% B within 3.4 min; Flow rate 0.8 mL/min. HPLC: 3.87/10 min, 95.87% purity. HPLC-AE Ultimate XB-C18, 3 um, 3.0×50 mm. Mobile phase: 1.0% ACN in water (0.1% TFA) to 5% ACN in water (0.1% TFA) in 1 min; then from 5% ACN in water (0.1% TFA) to 100% ACN (0.1% TFA) in 5 minutes; hold at 100% ACN (0.1% TFA) for 2 minutes; Flow rate 1.2 mL/min.

Example 27

2-(cis-4-(8-chloro-2-(3,3-difluorocyclobutyl)-1H-imidazo[4,5-c]quinolin-1-yl)tetrahydro-2H-pyran-2-yl)acetonitrile, ENT 1, and 2-(cis-4-(8-chloro-2-(3,3-difluorocyclobutyl)-1H-imidazo[4,5-c]quinolin-1-yl)tetrahydro-2H-pyran-2-yl)acetonitrile], ENT 2 (Example 27)

Step 1: Synthesis of N-(cis-2-((benzyloxy)methyl)tetrahydro-2H-pyran-4-yl)-6-chloro-N-(2,4-dimethoxybenzyl)-3-nitroquinolin-4-amine

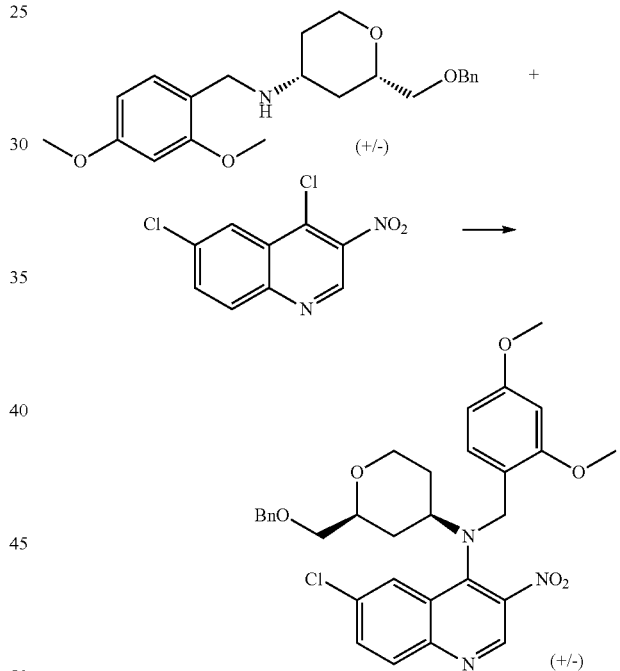

cis-2-((Benzyloxy)methyl)-N-(2,4-dimethoxybenzyl)tetrahydro-2H-pyran-4-amine (20.8 g, 56.0 mmol) was placed in a flask and then taken up in acetonitrile (300 mL) and DIEA (21.7 g, 168 mmol). Then 4,6-dichloro-3-nitroquinoline (17.2 g, 61.6 mmol) was added to the mixture portion wise. The reaction mixture was stirred for 16 h at room temperature (25° C.). LCMS indicated that the reaction was complete. The mixture was concentrated to half volume, diluted with water (400 mL) and extracted with EtOAc (300 mL×2). The combined organic layer was dried over anhydrous Na$_2$SO$_4$, filtered and concentrated to give the residue (41 g). The crude product was purified with ISCO Combiflash (330 g column, EtOAc in PE from 0 to 25%) to give N-(cis-2-((benzyloxy)methyl)tetrahydro-2H-pyran-4-yl)-6-chloro-N-(2,4-dimethoxybenzyl)-3-nitroquinolin-4-amine as a yellow solid (26.1 g, 80.6% yield). $^1$H NMR (400 MHz, CDCl₃) δ 9.01 (s, 1H), 8.21 (d, J=2.4 Hz, 1H), 7.97 (d, J=8.9 Hz, 1H), 7.68 (dd, J=8.9, 2.3 Hz, 1H), 7.38-7.21 (m, 5H), 6.89-6.73 (m, 1H), 6.27-6.13 (m, 2H), 4.64-4.46 (m, 2H), 4.42-4.23 (m, 2H), 4.15-4.05 (m, 1H), 3.85-3.71 (m, 1H), 3.68 (s, 3H), 3.57-3.53 (m, 1H), 3.53 (s, 3H), 3.48-3.37 (m, 3H), 1.95 (m, 3H), 1.71 (q, J=11.8 Hz, 1H). LC-MS: MS 578.0 M+H; RT 0.92 min.

Step 2: Synthesis of N-(cis-2-((benzyloxy)methyl) tetrahydro-2H-pyran-4-yl)-6-chloro-3-nitroquinolin-4-amine

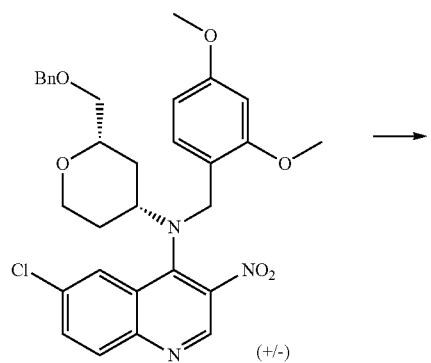

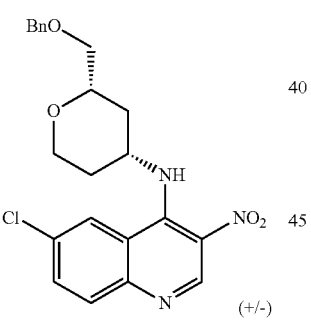

N-(cis-2-((Benzyloxy)methyl)tetrahydro-2H-pyran-4-yl)-6-chloro-N-(2,4-dimethoxy benzyl)-3-nitroquinolin-4-amine (26.00 g, 10.4 mmol) was dissolved in DCM (300 mL), then TFA trifluoroacetic acid (30 mL) was slowly added drop-wise to the reaction mixture at 20° C. The reaction mixture was stirred for 1.0 h. LCMS indicated that the reaction was complete and showed the desired product mass. The reaction mixture was concentrated under reduced pressure. The residue was taken up with EtOAc and poured into saturated aqueous NaHCO₃ (200 mL) in portions. The mixture was extracted with EtOAc (500 mL×3). The combined organic phases were dried over anhydrous Na₂SO₄, filtered and concentrated in vacuo to give N-(cis-2-((benzyloxy)methyl)tetrahydro-2H-pyran-4-yl)-6-chloro-3-nitroquinolin-4-amine (17.8 g, 92% yield) as the yellow solid. LCMS: MS 427.9 M+H; RT 0.83 min; purity 97.283%.

Step 3: Synthesis of N⁴-(cis-2-((benzyloxy)methyl) tetrahydro-2H-pyran-4-yl)-6-chloroquinoline-3,4-diamine

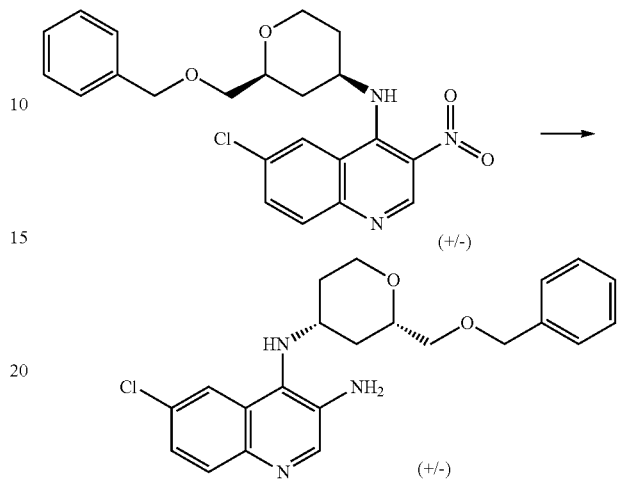

To a solution of N-(cis-2-((benzyloxy)methyl)tetrahydro-2H-pyran-4-yl)-6-chloro-3-nitroquinolin-4-amine (6.0 g, 14.02 mmol) in THF (200 mL) was added Pt/C (1370 mg) in one portion under argon at 20° C. After the flask was purged with argon, the mixture was saturated with hydrogen and stirred under 50 psi of hydrogen at 20° C. for 3 h. LCMS indicated the formation of the desired product. The mixture was filtered and the filtrate was concentrated to give the desired product N⁴-(cis-2-((benzyloxy)methyl)tetrahydro-2H-pyran-4-yl)-6-chloroquinoline-3,4-diamine as a brown solid (5750 mg, 103% yield). ¹H NMR (400 MHz, CDCl₃) δ 8.46 (s, 1H), 7.89 (d, J=8.9 Hz, 1H), 7.72 (d, J=2.2 Hz, 1H), 7.38 (dd, J=8.9, 2.2 Hz, 1H), 7.31 (d, J=5.4 Hz, 4H), 7.30-7.23 (m, 1H), 4.62-4.49 (m, 2H), 4.08 (ddd, J=11.7, 4.7, 1.6 Hz, 1H), 3.89 (s, 2H), 3.74 (dddd, J=6.7, 4.2, 2.5, 1.2 Hz, 1H), 3.59-3.39 (m, 4H), 3.34 (d, J=9.5 Hz, 1H), 1.92-1.80 (m, 3H), 1.59 (qd, J=12.4, 4.7 Hz, 1H). LCMS: MS 397.8.

Step 4: Synthesis of N-(4-((cis-2-((benzyloxy) methyl)tetrahydro-2H-pyran-4-yl)amino)-6-chloro-quinolin-3-yl)-3,3-difluorocyclobutane-1-carboxamide

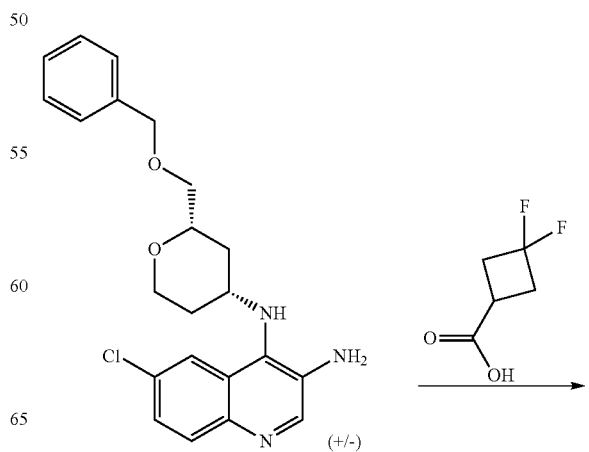

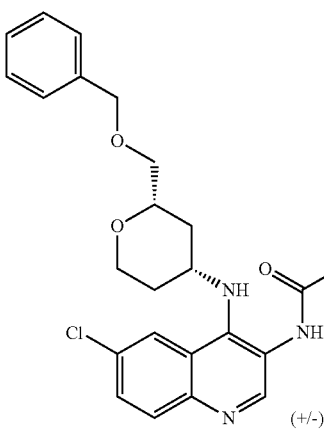

N⁴-(cis-2-((Benzyloxy)methyl)tetrahydro-2H-pyran-4-yl)-6-chloroquinoline-3,4-diamine (600 mg, 0.251 mmol) was dissolved in pyridine (12.0 mL) and 3,3-difluoro cyclobutane-1-carboxylic acid (226 mg, 1.66 mmol) was then added followed by EDCI (578 mg, 3.02 mmol). The resultant mixture was stirred at 25° C. for 16 hours. LCMS showed the formation of the desired product as the main product. The dark red mixture was concentrated and the residue was poured to water (50 mL) and extracted with EtOAc (50 mL×3). The combined organic layer was dried over anhydrous Na₂SO₄, filtered and concentrated to give the crude product N-(4-((cis-2-((benzyloxy)methyl) tetrahydro-2H-pyran-4-yl)amino)-6-chloroquinolin-3-yl)-3,3-difluorocyclobutane-1-carboxamide as red oil (0.83 g, 107% yield). LCMS: MS 516.1 M+H.

Step 5: Synthesis of 1-(cis-2-((benzyloxy)methyl)tetrahydro-2H-pyran-4-yl)-8-chloro-2-(3,3-difluorocyclobutyl)-1H-imidazo[4,5-c]quinoline

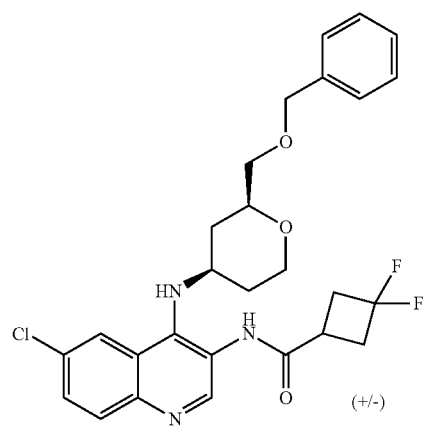

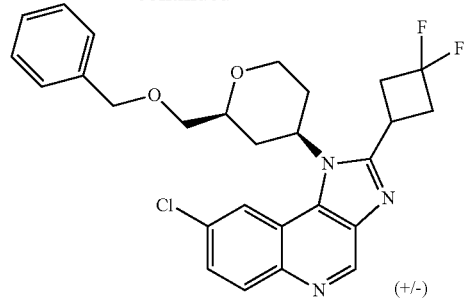

Step 6: Synthesis of N-(4-((cis-2-((benzyloxy)methyl)tetrahydro-2H-pyran-4-yl)amino)-6-chloroquinolin-3-yl)-3,3-difluorocyclobutane-1-carboxamide (830 mg, 1.61 mmol) was dissolved in HOAc (15.0 mL) and stirred at 105° C. for 16 h. LCMS showed the formation of the desired product as the main product. The reaction was combined with another experiment and worked up. HOAc was removed in vacuo. The residue was taken up with NaHCO₃ (100 mL, half saturated) and extracted with EtOAc (100 mL). The combined organic layer was dried over anhydrous Na₂SO₄, filtered and concentrated to give the crude product 1-(cis-2-((benzyloxy)methyl)tetrahydro-2H-pyran-4-yl)-8-chloro-2-(3,3-difluorocyclobutyl)-1H-imidazo[4,5-c]quinoline as yellow solid (880 mg, 93.6% yield based on the combined yield from two reactions. LCMS: MS 498.2 M+H.

Step 7: Synthesis of (cis-4-(8-chloro-2-(3,3-difluorocyclobutyl)-1H-imidazo[4,5-c]quinolin-1-yl)tetrahydro-2H-pyran-2-yl)methanol

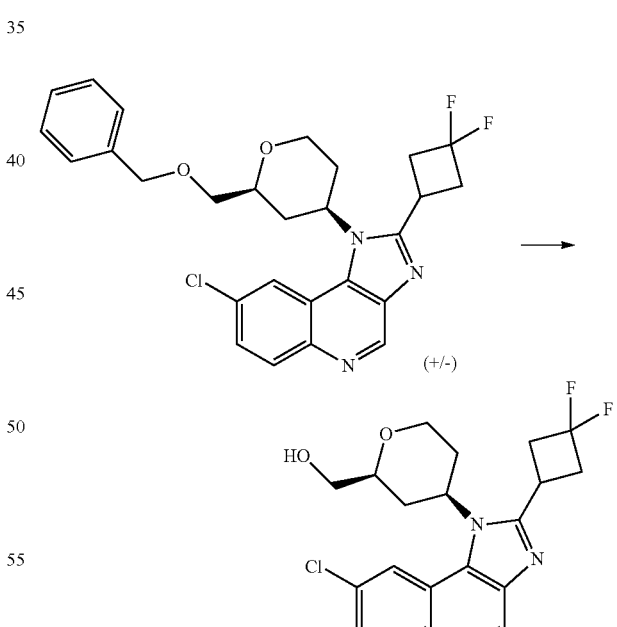

To the solution of 1-(cis-2-((benzyloxy)methyl)tetrahydro-2H-pyran-4-yl)-8-chloro-2-(3,3-difluorocyclobutyl)-1H-imidazo[4,5-c]quinoline (880 mg, 1.77 mmol) in DCM (30 mL) was treated with BCl₃ (5.30 mL, 5.30 mmol) in portions at 10° C. The resultant mixture was then stirred at 25° C. for 1 hour. LCMS indicated the formation of the desired product. The mixture was poured into NaHCO₃ (80 mL, saturated, aq.) and extracted with DCM (50 mL×2). The combined organic layer was dried over anhydrous Na$_2$SO$_4$, filtered and concentrated to give the crude product as brown solid (1.08 g). The crude was purified with ISCO Combi-flash (MeOH in DCM from 0 to 2.0%, 12 g column) to give the desired product (cis-4-(8-chloro-2-(3,3-difluorocyclobutyl)-1H-imidazo[4,5-c]quinolin-1-yl)tetrahydro-2H-pyran-2-yl)methanol as an off-white solid (737 mg, quantitative). LCMS: MS 408.1 M+H.

Step 8: Synthesis of (cis-4-(8-chloro-2-(3,3-difluorocyclobutyl)-1H-imidazo[4,5-c]quinolin-1-yl)tetrahydro-2H-pyran-2-yl)methyl methanesulfonate

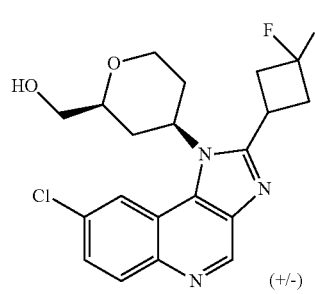

(+/-)

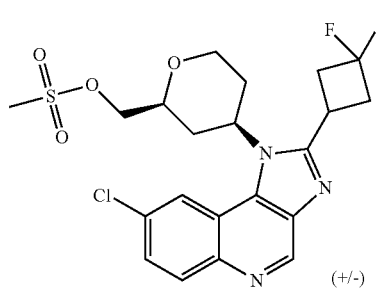

(+/-)

(cis-4-(8-Chloro-2-(3,3-difluorocyclobutyl)-1H-imidazo [4,5-c]quinolin-1-yl) tetrahydro-2H-pyran-2-yl)methanol (737 mg, 1.81 mmol) was dissolved in DCM (25 mL) and treated with NEt$_3$ (549 mg, 5.42 mmol) and MsCl (248 mg, 0.177 mL, 2.17 mmol). The resultant mixture was stirred at 25° C. for 1 hour. LCMS showed the formation of the desired product. The mixture was poured to water (50 mL) and extracted with EtOAc (50 mL×2). The combined organic layer was dried over anhydrous Na$_2$SO$_4$, filtered and concentrated to give the desired product (cis-4-(8-chloro-2-(3,3-difluorocyclobutyl)-1H-imidazo[4,5-c]quinolin-1-yl) tetrahydro-2H-pyran-2-yl)methyl methanesulfonate as light yellow foaming solid (733 mg, 83.5% yield). LCMS: MS 486.0 M+H; RT 0.71 min; purity 99.068%.

Step 9: Synthesis of {cis-4-[8-chloro-2-(3,3-difluorocyclobutyl)-1H-imidazo[4,5-c]quinolin-1-yl]tetrahydro-2H-pyran-2-yl}acetonitrile

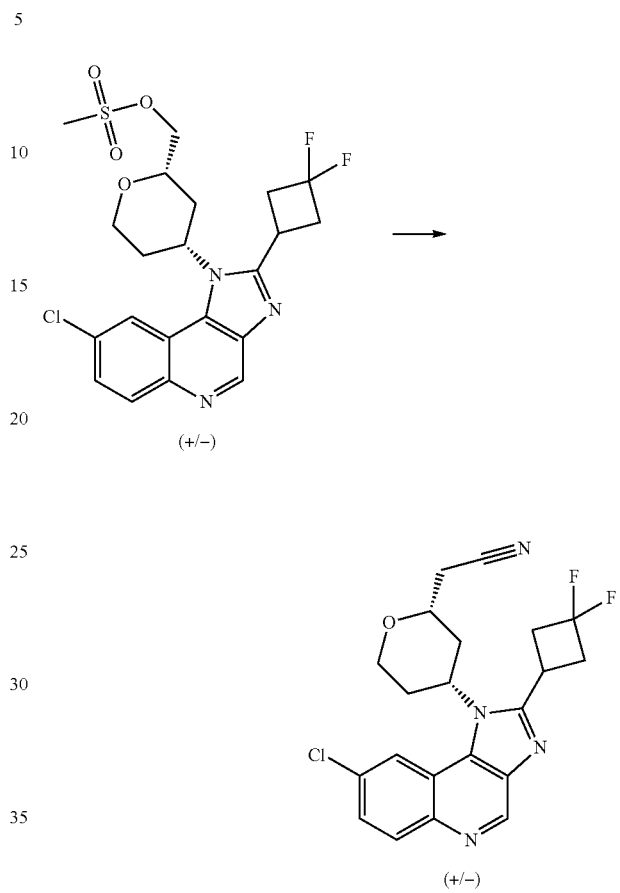

To a solution of (cis-4-(8-chloro-2-(3,3-difluorocyclobutyl)-1H-imidazo[4,5-c]quinolin-1-yl)tetrahydro-2H-pyran-2-yl)methyl methanesulfonate (733 mg, 1.51 mmol) in DMSO (15 mL) was added tetrabutyl ammonium cyanide, (n-Bu)$_4$N$^+$CN$^-$, (1210 mg, 4.53 mmol). Then the solution was heated at 80° C. for 16 h. LCMS indicated the formation of the desired product as the main product. The mixture was diluted with MTBE (100 mL), washed with water (100 mL×2) and brine (50 mL). The combined aqueous layer was extracted with MTBE (50 mL). The combined MTBE layer was dried over anhydrous Na$_2$SO$_4$, filtered and concentrated to give the crude product as yellow oil (1.0 g). The crude product was purified with ISCO Combi-flash (MeOH in DCM from 0 to 2%, 20 g column) to give the desired product as light yellow foaming solid (430 mg). A sample of the product was sent to chiral HPLC analysis. The solid was added to ACN (50 mL) and H$_2$O (120 mL) and lyophilized for 48 h. LCMS: MS 417.0.

The lyophilization gave the desired product {cis-4-[8-chloro-2-(3,3-difluorocyclobutyl)-1H-imidazo[4,5-c]quinolin-1-yl]tetrahydro-2H-pyran-2-yl}acetonitrile as light yellow solid (395 mg, 62.8% yield). $^1$H NMR (400 MHz, CD$_3$OD) δ 9.16 (s, 1H), 8.67 (b, 1H), 8.18 (d, J=9.0 Hz, 1H), 7.73 (dd, J=9.0, 2.2 Hz, 1H), 5.14 (b, 1H), 4.37 (dd, J=12.0, 5.4 Hz, 1H), 4.10-3.94 (m, 2H), 3.88 (td, J=12.2, 2.7 Hz, 1H), 3.30-3.13 (m, 4H), 2.96-2.66 (m, 3H), 2.54 (b, 1H), 2.11 (b, 2H).

Step 10: Separation to provide {cis-4-[8-chloro-2-(3,3-difluorocyclobutyl)-1H-imidazo[4,5-c]quinolin-1-yl]tetrahydro-2H-pyran-2-yl}acetonitrile, ENT 1 and {cis-4-[8-chloro-2-(3,3-difluorocyclobutyl)-1H-imidazo[4,5-c]quinolin-1-yl]tetrahydro-2H-pyran-2-yl}acetonitrile, ENT 2 (Example 27)

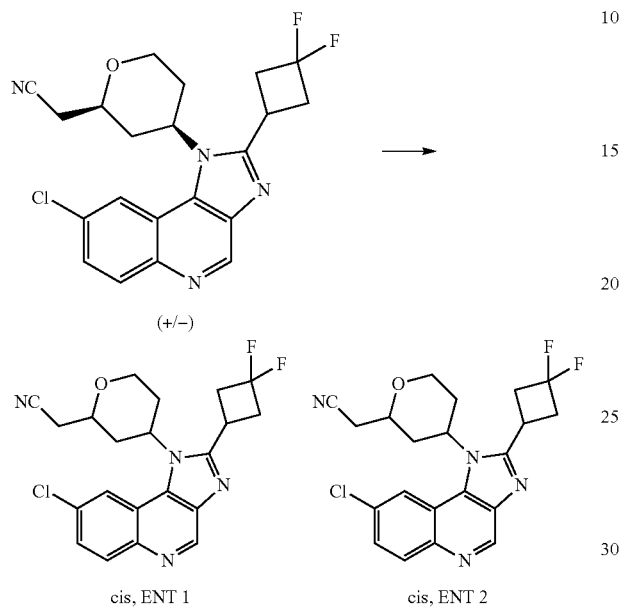

{cis-4-[8-Chloro-2-(3,3-difluorocyclobutyl)-1H-imidazo[4,5-c]quinolin-1-yl]tetrahydro-2H-pyran-2-yl}acetonitrile (395 mg, 0.948 mmol) was separated into its component enantiomers using SFC separation [Column: Phenomenex Lux Cellulose-2, 10 μm; Mobile phase: 60:40 carbon dioxide/(ethanol containing 0.1% ammonium hydroxide)]. The fractions from SFC group were concentrated to give these desired products as light yellow foaming solid Peak 1 (185.4 mg) and Peak 2 (202.8 mg). These solids were purified with ISCO Combi-flash (MeOH in DCM from 0 to 2%, 4 g column) to give the desired product as light yellow foaming solid Peak 1 (180 mg) and Peak 2 (202 mg) and submitted to lyophilization. Peak 2, the second-eluting enantiomer, was designated as Example 27.

Peak 1: LCMS: MS 417.0 M+H. Peak 2: LCMS: MS 417.0 M+H.

Peak 1 and Peak 2 HPLC: Instrument and Column: HPLC-AE Ultimate XB-C18, 3 um, 3.0×50 mm; Mobile phase: 1.0% ACN in water (0.1% TFA) to 5% ACN in water (0.1% TFA) in 1 min; then from 5% ACN in water (0.1% TFA) to 100% ACN (0.1% TFA) in 5 minutes; hold at 100% ACN (0.1% TFA) for 2 minutes; Flow rate: 1.2 mL/min. Peak 1: RT 3.66 min; Peak 2: RT 3.66 min.

Peak 1 and Peak 2 $^1$HNMR and $^{19}$FNMR run on Bruker_L_400 MHz.

Peak 1: $^1$H NMR (400 MHz, CD$_3$OD) δ 9.16 (s, 1H), 8.67 (b, 1H), 8.18 (d, J=9.0 Hz, 1H), 7.73 (dd, J=9.0, 2.2 Hz, 1H), 5.14 (b, 1H), 4.37 (dd, J=12.0, 5.4 Hz, 1H), 4.10-3.94 (m, 2H), 3.88 (td, J=12.2, 2.7 Hz, 1H), 3.30-3.13 (m, 4H), 2.96-2.66 (m, 3H), 2.54 (b, 1H), 2.11 (b, 2H). $^{19}$F NMR (376 MHz, CD$_3$OD) δ −98.82 (d, J=194.6 Hz).

Peak 2: $^1$H NMR (400 MHz, CD$_3$OD) δ 9.16 (s, 1H), 8.67 (b, 1H), 8.18 (d, J=8.9 Hz, 1H), 7.73 (dd, J=8.9, 2.2 Hz, 1H), 5.13 (b, 1H), 4.38 (dd, J=12.1, 5.3 Hz, 1H), 4.11-3.93 (m, 2H), 3.88 (td, J=12.2, 2.7 Hz, 1H), 3.29-3.13 (m, 4H), 2.96-2.66 (m, 3H), 2.54 (b, 1H), 2.04 (b, 2H). $^{19}$F NMR (376 MHz, CD$_3$OD) δ −98.83 (d, J=194.9 Hz)

Peak 1 and Peak 2 chiral HPLC: Instrument: SFC-G (12-102); Method: Column: Lux Cellulose-2 150×4.6 mm I.D., 3 um, Mobile phase: A: CO$_2$ B: Ethanol (0.05% DEA) Gradient: from 5% to 40% of B in 5.5 min and hold 40% B for 3 min, then 5% of B for 1.5 min; Flow rate: 2.5 mL/min; Column temperature: 40° C.

Peak 1: RT 5.84 min, purity 99.261%; Peak 2: RT 6.29 min, purity 99.809%. The two peaks were isolated from the eluent by evaporation. Peak 1: 168.73 mg, 42.7% yield and Peak 2: 166.73 mg, 42.2% yield.

The following examples were made in a similar manner to the compound of Example 27.

Example 28

{(2S,4R)-4-[8-chloro-2-(cis-4-fluorocyclohexyl)-1H-imidazo[4,5-c]quinolin-1-yl]tetrahydro-2H-pyran-2-yl}acetonitrile

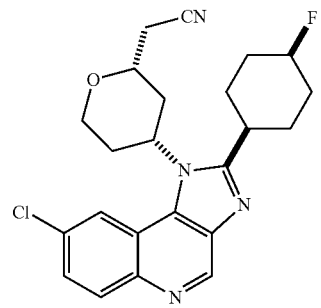

MS 427.1 M+H; RT 2.80 min; Instrument: Agilent LCMS (4-302LCMS-AL); Column: Waters XBridge C18 50×2.0 mm, 5 um; Mobile phase A: 10 mM NH$_4$HCO$_3$ in water; Mobile phase B: ACN. Gradient: 1% to 5% B over 0.6 min; 5% to 100% B over 3.4 min; Flow rate 0.8 mL/min.

Example 29

{(2S,4R)-4-[8-fluoro-2-(cis-4-fluorocyclohexyl)-1H-imidazo[4,5-c]quinolin-1-yl]tetrahydro-2H-pyran-2-yl}acetonitrile

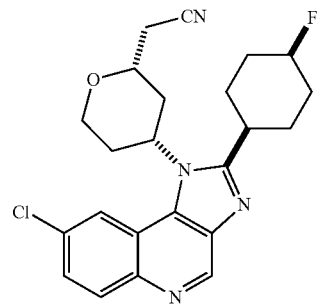

MS 411.3; RT 2.65 min; Column: Waters XBridge C18 50×2.0 mm, 5 um; Mobile phase A: 10 mM NH$_4$HCO$_3$ in water; Mobile phase B: ACN. Gradient: 1% to 5% B over 0.6 min; 5% to 100% B over 3.4 min; Flow rate 0.8 mL/min.

Example 30

[cis-4-{8-chloro-2-[(3R)-tetrahydrofuran-3-yl]-1H-imidazo[4,5-c]quinolin-1-yl}tetrahydro-2H-pyran-2-yl]acetonitrile, DIAST 1

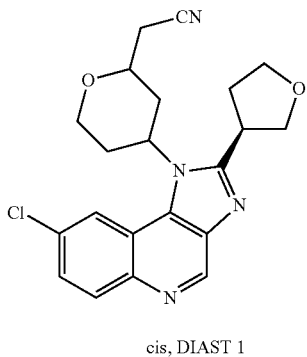 [SMILES: N#CCC1CC(n2c([C@H]3CCOC3)nc3cnc4ccc(Cl)cc4c32)CCO1]

cis, DIAST 1

The diastereomeric mixture containing Example 30 was separated into its component diastereomers via supercritical fluid chromatography [Column: Chiral Technologies Chiralpak AD, 10 μm; Mobile phase: 7:3, carbon dioxide:(2-propanol containing 0.1% ammonium hydroxide)]. The first-eluting diastereomer was designated as Example 30. MS 397.1 M+H; RT 0.65 min; Instrument & Column: LCMS-AH(4-302) Chromolith. Flash RP-18e 25×2 mm; Method: MS Ionization: ESI. Chiral Column: RT 5.30 min; SFC-G (12-102) Method: Column: ChiralPak AD-3 150×4.6 mm I.D., 3 um Mobile phase: A: $CO_2$ B: IPA (0.05% DEA); Gradient: from 5% to 40% of B in 5.5 min and hold 40% for 3 min, then 5% of B for 1.5 min; Flow rate: 2.5 mL/min; Column temperature: 40° C.

Example 31

8-fluoro-2-(cis-3-fluoro-3-methylcyclobutyl)-1-[(2R,4R)-2-methyltetrahydro-2H-pyran-4-yl]-1H-imidazo[4,5-c]quinoline Step 1: Synthesis of cis-3-fluoro-N-(6-fluoro-4-{[(2R,4R)-2-methyltetrahydro-2H-pyran-4-yl]amino}quinolin-3-yl)-3-methylcyclobutanecarboxamide

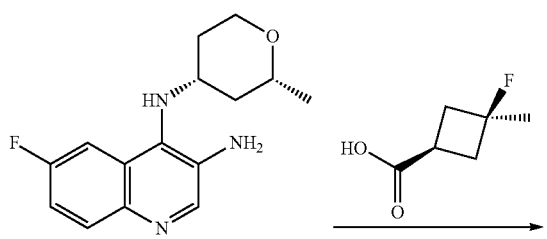

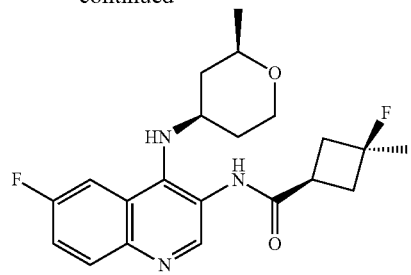

To a solution of 6-fluoro-$N^4$-((2R,4R)-2-methyltetrahydro-2H-pyran-4-yl)quinoline-3,4-diamine (50 mg, 0.182 mmol) was added cis-3-fluoro-3-methylcyclobutane-1-carboxylic acid (26.4 mg, 0.20 mmol) and EDCI (69.6 mg, 0.363 mmol) in pyridine (0.3 mL) and the mixture was stirred at 20° C. for 2 h. LCMS showed the reaction was complete. The mixture was treated with $H_2O$ (2 mL) and extracted with EtOAc (3×3 mL), and then was concentrated in vacuo to give cis-3-fluoro-N-(6-fluoro-4-(((2R,4R)-2-methyltetrahydro-2H-pyran-4-yl)amino)quinolin-3-yl)-3-methyl cyclobutane-1-carboxamide (70.7 mg, 100%, crude) as a yellow oil. The crude product was used in the next step without further purification. LCMS: MS 390.1 M+H.

Step 2: Synthesis of 8-fluoro-2-(cis-3-fluoro-3-methylcyclobutyl)-1-[(2R,4R)-2-methyltetrahydro-2H-pyran-4-yl]-1H-imidazo[4,5-c]quinoline

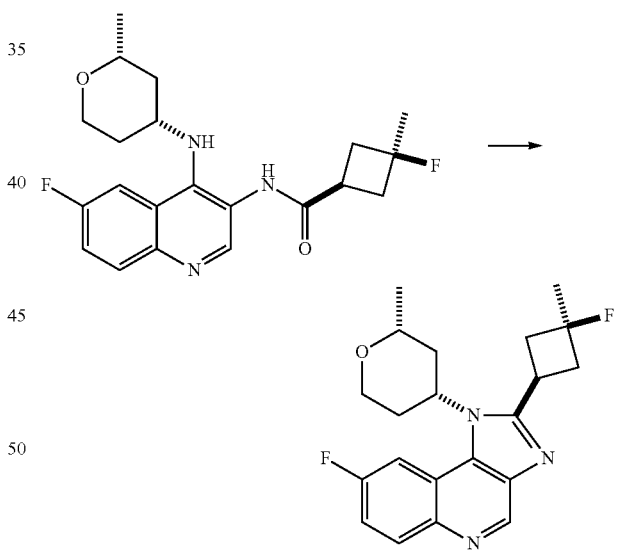

To a solution of cis-3-fluoro-N-(6-fluoro-4-{[(2R,4R)-2-methyltetrahydro-2H-pyran-4-yl]amino}quinolin-3-yl)-3-methylcyclobutanecarboxamide (70.7 mg, 0.182 mmol) in n-propyl acetate (0.5 mL) was added T3P (231 mg, 0.363 mmol) and then the reaction mixture was heated to 110° C. and maintained at that temperature for 16 h. LCMS showed the reaction was complete. The mixture was purified by preparative HPLC*. LCMS: MS 372.2 M+H; RT 0.69 min. The product was lyophilized to afford 32.68 mg, (48.5%). $^1$H NMR (400 MHz, $CD_3OD$) δ 9.12 (s, 1H), 8.34 (b, 1H), 8.24-8.17 (m, 1H), 7.57 (ddd, J=9.3, 7.8, 2.7 Hz, 1H), 5.15 (b, 1H), 4.28 (dd, J=11.9, 5.3 Hz, 1H), 3.94-3.72 (m, 2H), 3.64 (p, J=8.7 Hz, 1H), 2.90 (dd, J=20.7, 10.2 Hz, 2H), 2.79-2.63 (m, 3H), 2.25 (b, 1H), 1.96 (b, 2H), 1.67 (d, J=21.9 Hz, 3H), 1.33 (d, J=6.1 Hz, 3H); $^{19}$F NMR (376 MHz, CD$_3$OD) δ −113.49.

*Column: Waters XBridge C18 50×2.0 mm; 5 um; Mobile phase: C) 10 mM NH$_4$HCO$_3$ in Water; D) ACN. Gradient: 1% D increase to 5% D within 0.6 min; 5% DB increase to 100% D within 3.4 min; Flow rate 0.8 mL/min MS Ionization: ESI HPLC: Mobile phase: 1.0% ACN in water (0.1% TFA) to 5% ACN in water (0.1% TFA) in 1 min; then from 5% ACN in water (0.1% TFA) to 100% ACN (0.1% TFA) in 5 minutes; hold at 100% ACN (0.1% TFA) for 2 minutes; Flow rate 1.2 mL/min.

Examples 32-64

The following examples were made by procedures previously described in this section. The following procedure is representative:

Synthesis of a Mixture of Examples 57-60

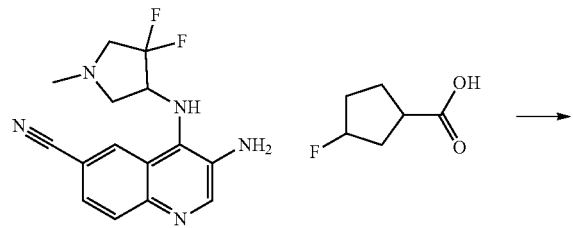

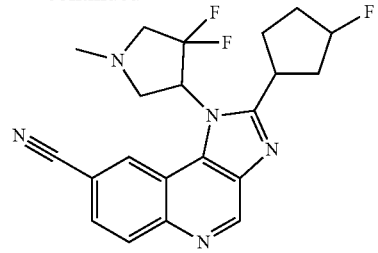

Step 1: To a mixture of one enantiomer of 1-(4,4-difluoro-1-methylpyrrolidin-3-yl)-2-(3-fluorocyclopentyl)-1H-imidazo[4,5-c]quinoline-8-carbonitrile (see footnote 11 in Table 1 below) (150 mg, 0.495 mmol) and 3-fluorocyclopentane-1-carboxylic acid (68.8 mg, 0.495 mmol) in EtOAc (2.91 mL, c=0.17 M) was added N,N-diisopropylethylamine (192 mg, 1.48 mmol, 0.258 mL) and 1-propylphosphonic acid cyclic anhydride (944 mg, 1.48 mmol, 0.883 mL). The mixture was heated at 80° C. overnight. LCMS showed mostly uncyclized amide but some ring closure observed. The reaction mixture was heated for 48 hrs. LCMS indicated some amide was still present. The reaction mixture was concentrated to dryness and then taken up in 3 mL of toluene and to it was added propylphosphonic acid cyclic anhydride (944 mg, 1.48 mmol, 0.883 mL) and the mixture was heated at 110° C. overnight. LCMS showed complete product formation. The reaction mixture was diluted with EtOAc and washed with water. The aqueous phase was washed with EtOAc. The combined EtOAc extracts were washed with brine, dried over Na$_2$SO$_4$, filtered and concentrated. The residue was chromatographed (SIM) on a 4 g gold column eluting with a 0-100% EtOAc/Heptane gradient which resulted in a mixture of the four diastereomeric products as an off white solid. The separation of these isomers is described in footnote 12 of Table 1 below.

TABLE 1

Structure, IUPAC Name and LCMS for Examples

| Example Number | Structure | IUPAC Name | Mass Spectrum |
|---|---|---|---|
| 32 | cis, DIAST 1 | 2-[cis-3-fluorocyclopentyl]-1-[(3R)-1-methylpyrrolidin-3-yl]-1H-imidazo[4,5-c]quinoline-8-carbonitrile, DIAST 1[1] | LCMS MS 364.2 M + H; ee value: 100%, |

TABLE 1-continued

Structure, IUPAC Name and LCMS for Examples

| Example Number | Structure | IUPAC Name | Mass Spectrum |
|---|---|---|---|
| 33 | cis, DIAST 2 | 2-[cis-3-fluorocyclopentyl]-1-[(3R)-1-methylpyrrolidin-3-yl]-1H-imidazo[4,5-c]quinoline-8-carbonitrile, DIAST 2[1] | LCMS MS 364.2 M + H; ee value 96.3% |
| 34 | cis, DIAST 1 | 8-fluoro-2-[cis-3-fluorocyclopentyl]-1-[(3R)-1-methylpyrrolidin-3-yl]-1H-imidazo[4,5-c]quuinoline, DIAST 1[2] | LCMS MS 357.3 M + H; ee value 96.9% |
| 35 | trans, DIAST 1 | 8-fluoro-2-[trans-3-fluorocyclopentyl]-1-[(3R)-1-methylpyrrolidin-3-yl]-1H-imidazo[4,5-c]quinoline, DIAST 1[2] | LCMS MS 357.8 M + H; ee value 71.9% |
| 36 | trans, DIAST 2 | 8-fluoro-2-[trans-3-fluorocyclopentyl]-1-[(3R)-1-methylpyrrolidin-3-yl]-1H-imidazo[4,5-c]quinoline, DIAST 2[2] | LCMS MS 357.8 M + H; ee value 99.0% |

TABLE 1-continued

Structure, IUPAC Name and LCMS for Examples

| Example Number | Structure | IUPAC Name | Mass Spectrum |
|---|---|---|---|
| 37 | trans, DIAST 1 | 8-fluoro-2-[trans-3-fluroocyclopentyl]-1-[(2R,4R)-2-methyl-tetrahydro-2H-pyran-4-yl]-1H-imidazo[4,5-c]quinoline, DIAST 1[3] | LCMS MS 372.2 M + H; ee value 99.7% |
| 38 | trans, DIAST 2 | 8-fluoro-2-[trans-3-fluorocyclopentyl]-1-[(2R,4R)-2-methyltetrahydro-2H-pyran-4-yl]-1H-imidazo[4,5-c]quinoline, DIAST 2[3] | LCMS MS 372.3 M + H; ee value 93.3% |
| 39 | DIAST A | 1-(2,2-dimethyltetrahydro-2H-pyran-4-yl)-2-(3-fluorocyclopentyl)-1H-imidazo[4,5-c]quinoline-8-carbonitrile, DIAST A[4,5] | LCMS MS 393.2 M + H |
| 40 | DIAST B | 1-(2,2-dimethyltetrahydro-2H-pyran-4-yl)-2-(3-fluorocyclopentyl)-1H-imidazo[4,5-c]quinoline-8-carbonitrile, DIAST B[4,5] | LCMS MS 393.2 M + H |

TABLE 1-continued

Structure, IUPAC Name and LCMS for Examples

| Example Number | Structure | IUPAC Name | Mass Spectrum |
|---|---|---|---|
| 41 | 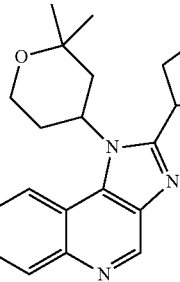<br>DIAST C | 1-(2,2-dimethyltetrahydro-2H-pyran-4-yl)-2-(3-fluorocyclopentyl)-1H-imidazo[4,5-c]quinoline-8-carbonitrile, DIAST C[4,5] | LCMS MS 393.2 M + H |
| 42 | 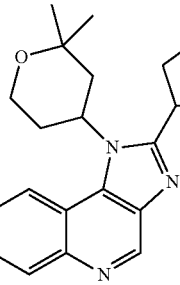<br>DIAST D | 1-(2,2-dimethyltetrahydro-2H-pyran-4-yl)-2-(3-fluorocyclopentyl)-1H-imidazo[4,5-c]quinoline-8-carbonitrile, DIAST D[4,5] | LCMS MS 393.2 M + H |
| 43 | 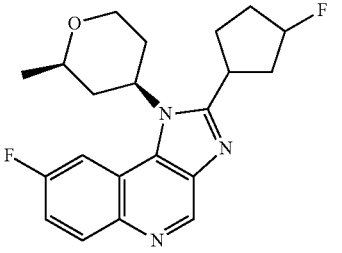<br>cis, DIAST 1 | 8-fluoro-2-[cis-3-fluorocyclopentyl]-1-[(2R,4R)-2-methyltetrahydro-2H-pyran-4-yl]-1H-imidazo[4,5-c]quinoline, DIAST 1[3] | LCMS MS 373.3 M + H; ee value 100% |
| 44 | 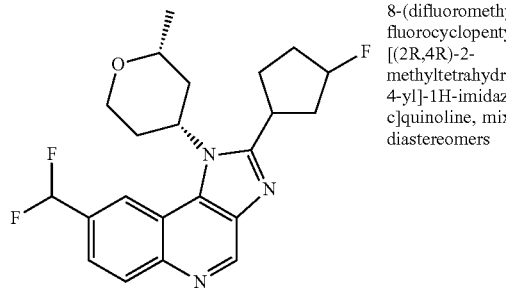 | 8-(difluoromethyl)-2-(3-fluorocyclopentyl)-1-[(2R,4R)-2-methyltetrahydro-2H-pyran-4-yl]-1H-imidazo[4,5-c]quinoline, mixture of 4 diastereomers | LCMS MS 404.5 M + H |

TABLE 1-continued

Structure, IUPAC Name and LCMS for Examples

| Example Number | Structure | IUPAC Name | Mass Spectrum |
|---|---|---|---|
| 45 | DIAST 1 | 1-(3,3-difluorotetrahydro-2H-pyran-4-yl)-2-(trans-3-fluorocyclobutyl)-1H-imidazo[4,5-c]quinoline-8-carbonitrile, DIAST 1[6] | LCMS MS 387.4 M + H |
| 46 | DIAST 2 | 1-(3,3-difluorotetrahydro-2H-pyran-4-yl)-2-(trans-3-fluorocyclobutyl)-1H-imidazo[4,5-c]quinoline-8-carbonitrile, DIAST 2[6] | LCMS MS 387.4 M + H |
| 47 | DIAST 1 | 1-(3,3-difluorotetrahydro-2H-pyran-4-yl)-2-(cis-3-fluorocyclobutyl)-1H-imidazo[4,5-c]quinoline-8-carbonitrile, DIAST 1[7] | LCMS MS 387.4 M + H |
| 48 | DIAST 2 | 1-(3,3-difluorotetrahydro-2H-pyran-4-yl)-2-(cis-3-fluorocyclobutyl)-1H-imidazo[4,5-c]quinoline-8-carbonitrile, DIAST 2[7] | LCMS MS 387.4 M + H |

TABLE 1-continued

Structure, IUPAC Name and LCMS for Examples

| Example Number | Structure | IUPAC Name | Mass Spectrum |
|---|---|---|---|
| 49 | DIAST 1 | 1-(3,3-difluorotetrahydro-2H-pyran-4-yl)-2-(cis-3-methoxycyclobutyl)-1H-imidazo[4,5-c]quinoline-8-carbonitrile, DIAST 1[8] | LCMS MS 399.2 M + H; |
| 50 | DIAST 1 | 1-(3,3-difluorotetrahydro-2H-pyran-4-yl)-2-(trans-3-methoxycyclobutyl)-1H-imidazo[4,5-c]quinoline-8-carbonitrile, DIAST 1[9] | LCMS MS 399.2 M + H; |
| 51 | DIAST 2 | 1-(3,3-difluorotetrahydro-2H-pyran-4-yl)-2-(trans-3-methoxycyclobutyl)-1H-imidazo[4,5-c]quinoline-8-carbonitrile, DIAST 2[9] | LCMS MS 399.2 M + H; |
| 52 | DIAST 2 | 1-(3,3-difluorotetrahydro-2H-pyran-4-yl)-2-(cis-3-methoxycyclobutyl)-1H-imidazo[4,5-c]quinoline-8-carbonitrile, DIAST 2[8] | LCMS MS 399.2 M + H |

TABLE 1-continued

Structure, IUPAC Name and LCMS for Examples

| Example Number | Structure | IUPAC Name | Mass Spectrum |
|---|---|---|---|
| 53 | DIAST E | 1-[(4R)-2,2-dimethyltetrahydro-2H-pyran-4-yl]-2-[(1S,3S)-3-fluorocyclopentyl]-1H-imidazo[4,5-c]quinoline-8-carbonitrile, DIAST E[4,10] | LCMS MS 393.3 M + H |
| 54 | DIAST F | 1-[(4R)-2,2-dimethyltetrahydro-2H-pyran-4-yl]-2-[(1R,3S)-3-fluorocyclopentyl]-1H-imidazo[4,5-c]quinoline-8-carbonitrile, DIAST F[4,10] | LCMS MS 393.3 M + H |
| 55 | DIAST G | 1-[(4R)-2,2-dimethyltetrahydro-2H-pyran-4-yl]-2-[(1R,3R)-3-fluorocyclopentyl]-1H-imidazo[4,5-c]quinoline-8-carbonitrile, DIAST G[4,10] | LCMS MS 393.3 M + H |
| 56 | DIAST H | 1-[(4R)-2,2-dimethyltetrahydro-2H-pyran-4-yl]-2-[(1S,3R)-3-fluorocyclopentyl]-1H-imidazo[4,5-c]quinoline-8-carbonitrile, DIAST H[4,10] | LCMS MS 393.3 M + H |

TABLE 1-continued

Structure, IUPAC Name and LCMS for Examples

| Example Number | Structure | IUPAC Name | Mass Spectrum |
|---|---|---|---|
| 57 | DIAST A | 1-(4,4-difluoro-1-methylpyrrolidin-3-yl)-2-(3-fluorocyclopentyl)-1H-imidazo[4,5-c]quinolin-8-carbonitrile, DIAST A[11,12] | LCMS MS 400.4 M + H |
| 58 | DIAST B | 1-(4,4-difluoro-1-methylpyrrolidin-3-yl)-2-(3-fluorocyclopentyl)-1H-imidazo[4,5-c]quinoline-8-carbonitrile, DIAST B[11,12] | LCMS MS 400.4 M + H |
| 59 | DIAST C | 1-(4,4-difluoro-1-methylpyrrolidin-3-yl)-2-(3-fluorocyclopentyl)-1H-imidazo[4,5-c]quinoline-8-carbonitrile, DIAST C[11,12] | LCMS MS 400.4 M + H |
| 60 | DIAST D | 1-(4,4-difluoro-1-methylpyrrolidin-3-yl)-2-(3-fluorocyclopentyl)-1H-imidazo[4,5-c]quinoline-8-carbonitrile, DIAST D[11,12] | LCMS MS 400.4 M + H |

TABLE 1-continued

Structure, IUPAC Name and LCMS for Examples

| Example Number | Structure | IUPAC Name | Mass Spectrum |
|---|---|---|---|
| 61 | DIAST E | 1-(4,4-difluoro-1-methylpyrrolidin-3-yl)-2-(3-fluorocyclopentyl)-1H-imidazo[4,5-c]quinoline-8-carbonitrile, DIAST E[11,13] | LCMS MS 400.4 M + H |
| 62 | DIAST F | 1-(4,4-difluoro-1-methylpyrrolidin-3-yl)-2-(3-fluorocyclopentyl)-1H-imidazo[4,5-c]quinoline-8-carbonitrile, DIAST F[11,13] | LCMS MS 400.4 M + H |
| 63 | DIAST G | 1-(4,4-difluoro-1-methylpyrrolidin-3-yl)-2-(3-fluorocyclopentyl)-1H-imidazo[4,5-c]quinoline-8-carbonitrile, DIAST G[11,13] | LCMS MS 400.4 M + H |
| 64 | DIAST H | 1-(4,4-difluoro-1-methyl-pyrrolidin-3-yl)-2-(3-fluorocyclopentyl)-1H-imidazo[4,5-c]quinoline-8-carbonitrile, DIAST H[11,13] | LCMS MS 400.4 M + H |

1. Examples 32 and 33 were derived from a synthesis using 3-fluorocyclopentanecarboxylic acid. The diastereomeric mixture of 4 products was separated using reversed-phase HPLC (Column: Xtimate™ C18, 5 μm; Mobile phase A: 10 mM ammonium bicarbonate in water; Mobile phase B: acetonitrile; Gradient: 33% to 63% B); the first-eluting material consisted of the cis-cyclopentyl isomers, according to 2D NMR analysis. This mixture was separated into its component diastereomers via supercritical fluid chromatography [Column: Chiral Technologies Chiralpak AD, 10 μm; Mobile phase: 70:30 carbon dioxide/(2-propanol containing 0.1% ammonium hydroxide)]. The first-eluting diastereomer was designated as Example 32, and the second-eluting as Example 33.

2. Examples 34, 35, and 36 were derived from a synthesis using 3-fluorocyclopentanecarboxylic acid. The diastereomeric mixture of 4 products was separated using reversed-phase HPLC (Column: Waters XBridge C18 OBD, 5 μm; Mobile phase A: water containing 0.05% ammonium hydroxide; Mobile phase B: acetonitrile; Gradient: 35% to 65% B). The first-eluting peak consisted of the cis isomers, and the second-eluting peak consisted of the trans isomers, via Heteronuclear Overhauser Effect Spectroscopy.

Separation of the two cis isomers was effected using supercritical fluid chromatography [Column: Phenomenex Lux Cellulose-2, 10 μm; Mobile phase: 60:40 carbon dioxide/(methanol containing 0.1% ammonium hydroxide)]; Example 34 was the first-eluting diastereomer.

Separation of the two trans isomers was carried out using supercritical fluid chromatography [Column: Chiral Technologies Chiralcel OJ, 5 μm; Mobile phase: 80:20 carbon dioxide/(ethanol containing 0.1% ammonium hydroxide)]. Example 35 was the first-eluting diastereomer, and Example 36 the second-eluting diastereomer.

3. Examples 37, 38, and 43 were derived from a synthesis using 3-fluorocyclopentanecarboxylic acid. The diastereomeric mixture of 4 products was separated using reversed-phase HPLC (Column: Waters XBridge C18 OBD, 5 μm; Mobile phase A: water containing 0.05% ammonium hydroxide; Mobile phase B: acetonitrile; Gradient: 30% to 60% B). The first-eluting peak consisted of the cis isomers, and the second-eluting peak consisted of the trans isomers, via Heteronuclear Overhauser Effect Spectroscopy.

Separation of the cis isomers was effected using supercritical fluid chromatography [Column: Phenomenex Lux Cellulose-2, 10 μm; Mobile phase: 60:40 carbon dioxide/ (methanol containing 0.1% ammonium hydroxide)]; Example 43 was the first-eluting diastereomer.

Separation of the two trans isomers was carried out using supercritical fluid chromatography [Column: Phenomenex Lux Cellulose-2, 10 μm; Mobile phase: 60:40 carbon dioxide/(methanol containing 0.1% ammonium hydroxide)]; Example 37 was the first-eluting diastereomer, and Example 38 the second-eluting diastereomer.

4. The compound of Preparation P14, 3-amino-4-((2,2-dimethyltetrahydro-2H-pyran-4-yl)amino)quinoline-6-carbonitrile, was separated into its component enantiomers via supercritical fluid chromatography {Column: Chiral Technologies Chiralpak AD-H, 5 μm; Mobile phase: 80:20 carbon dioxide/[2-propanol containing 0.2% (7 M ammonia in methanol)]}. The first-eluting enantiomer, ENT 1, was used in Examples 39, 40, 41, and 42, and the second-eluting enantiomer, ENT 2, was used in Examples 53, 54, 55, and 56.

5. Examples 39, 40, 41, and 42 were synthesized as a mixture of diastereomers, from 3-fluorocyclopentanecarboxylic acid and ENT 1 from footnote 4. The resulting mixture was separated into its component diastereomers in the following manner. The mixture of four products was subjected to supercritical fluid chromatography: {[Column: Phenomenex Lux Cellulose-3, 5 μm; Mobile phase: 92.5:7.5 carbon dioxide/[ethanol containing 0.2% (7 M ammonia in methanol)]}. From this column were obtained the following:

The first-eluting diastereomer was designated as Example 42 (DIAST D).

The second-eluting diastereomer was designated as Example 41 (DIAST C).

The third-eluting material was a mixture of two diastereomers; this was subjected to supercritical fluid chromatography {Column: Chiral Technologies Chiralpak IC, 5 μm; Mobile phase: 70:30 carbon dioxide/[ethanol containing 0.2% (7 M ammonia in methanol)]}. The first-eluting diastereomer from this separation was designated as Example 39 (DIAST A), and the second-eluting diastereomer as Example 40 (DIAST B).

Using an analytical SFC system {[Column: Phenomenex Lux Cellulose-3, 4.6×250 mm, 5 μm; Mobile phase A: carbon dioxide; Mobile phase B: [ethanol containing 0.2% (7 M ammonia in methanol)]; Gradient: 5% B for 1.0 minute, then 5% to 60% B over 8.0 minutes; Back pressure: 120 bar; Flow rate: 3.0 mL/minute}, Example 42 exhibited a retention time of 3.12 minutes, and Example 41 exhibited a retention time of 3.28 minutes.

Using a different analytical SFC system {Column: Chiral Technologies Chiralpak IC, 4.6×250 mm, 5 μm; Mobile phase A: carbon dioxide; Mobile phase B: [ethanol containing 0.2% (7 M ammonia in methanol)]}.; Gradient: 5% B for 1.0 minute, then 5% to 60% B over 8.0 minutes; Back pressure: 120 bar; Flow rate: 3.0 mL/minute}, Example 39 exhibited a retention time of 7.57 minutes, and Example 40 exhibited a retention time of 7.92 minutes.

6. The diastereomeric mixture of Examples 45 and 46 was separated via supercritical fluid chromatography [Column: Chiral Technologies Chiralpak AS, 5 μm; Mobile phase: 60:40 carbon dioxide/(ethanol containing 0.1% ammonium hydroxide)]. Example 45 was the first-eluting diastereomer, and Example 46 was the second-eluting diastereomer.

7. The diastereomeric mixture of Examples 47 and 48 was separated via supercritical fluid chromatography [Column: Chiral Technologies Chiralpak AS, 5 μm; Mobile phase: 60:40 carbon dioxide/(ethanol containing 0.1% ammonium hydroxide)]. Example 47 was the first-eluting diastereomer, and Example 48 was the second-eluting diastereomer.

8. The diastereomeric mixture of Examples 49 and 52 was separated via supercritical fluid chromatography [Column: Chiral Technologies Chiralpak AS, 5 μm; Mobile phase: 70:30 carbon dioxide/(ethanol containing 0.1% ammonium hydroxide)]. Example 49 was the first-eluting diastereomer, and Example 52 was the second-eluting diastereomer.

9. The diastereomeric mixture of Examples 50 and 51 was separated via supercritical fluid chromatography [Column: Chiral Technologies Chiralpak AS, 5 μm; Mobile phase: 70:30 carbon dioxide/(ethanol containing 0.1% ammonium hydroxide)]. Example 50 was the first-eluting diastereomer, and Example 51 was the second-eluting diastereomer.

10. Examples 53, 54, 55, and 56 were synthesized as a mixture of diastereomers, from 3-fluorocyclopentanecarboxylic acid and ENT 2 from footnote 4. The resulting mixture was separated into its component diastereomers in the following manner. The mixture of four products was subjected to supercritical fluid chromatography: {[Column: Chiral Technologies Chiralpak IC, 5 μm; Mobile phase: 60:40 carbon dioxide/[2-propanol containing 0.2% (7 M ammonia in methanol)]}. From this column were obtained the following:

The first-eluting material was a mixture of two diastereomers, which was separated as described below.

The second-eluting material was a single diastereomer, designated as Example 53 (DIAST E).

The third-eluting material was a single diastereomer, designated as Example 55 (DIAST G).

The mixture of the two diastereomers that eluted first was separated via supercritical fluid chromatography {Column: Chiral Technologies Chiralpak AS-H, 5 μm; Mobile phase: 92.5:7.5 carbon dioxide/[methanol containing 0.2% (7 M ammonia in methanol)]}. The first-eluting diastereomer from this separation was designated as Example 56 (DIAST H), and the second-eluting diastereomer as Example 54 (DIAST F).

Using an analytical SFC system, {[Column: Chiral Technologies Chiralpak IC, 4.6×250 mm, 5 μm; Mobile phase A: carbon dioxide; Mobile phase B: [2-propanol containing 0.2% (7 M ammonia in methanol)]}.; Gradient: 5% B for 1.0 minute, then 5% to 60% B over 8.0 minutes, then 60% B for 0.5 minutes; Back pressure: 120 bar; Flow rate: 3.0 mL/minute}, Example 53 exhibited a retention time of 8.74 minutes, and Example 55 exhibited a retention time of 9.24 minutes.

Using a different analytical SFC system {Column: Chiral Technologies Chiralpak AS-H, 4.6×250 mm, 5 µm; Mobile phase A: carbon dioxide; Mobile phase B: [methanol containing 0.2% (7 M ammonia in methanol)]; Gradient: 5% B for 1.0 minute, then 5% to 60% B over 8.0 minutes; Back pressure: 120 bar; Flow rate: 3.0 mL/minute}, Example 56 exhibited a retention time of 3.60 minutes, and Example 54 exhibited a retention time of 3.82 minutes.

11. The compound of Preparation P10, 3-amino-4-[(4,4-difluoro-1-methylpyrrolidin-3-yl)amino]quinoline-6-carbonitrile, was separated into its component enantiomers via supercritical fluid chromatography {Column: Chiral Technologies Chiralpak AS, 5 µm; Mobile phase: 80:20 carbon dioxide/[2-propanol containing 0.2% (7 M ammonia in methanol)]}. The first-eluting enantiomer, ENT 1 was used in synthesis of Examples 57, 58, 59, and 60, and the second-eluting enantiomer, ENT 2, was used in synthesis of Examples 61, 62, 63, and 64.

12. Examples 57, 58, 59, and 60 were synthesized as a mixture of diastereomers, from 3-fluorocyclopentanecarboxylic acid and ENT 1 from footnote 11. The resulting mixture was separated into its component diastereomers in the following manner. The mixture of four products was subjected to supercritical fluid chromatography: {[Column: Chiral Technologies Chiralpak IC, 5 µm; Mobile phase: 80:20 carbon dioxide/[methanol containing 0.2% (7 M ammonia in methanol)]}. From this column were obtained the following:

The first-eluting material was a mixture of two diastereomers, which was separated as described below.

The second-eluting material was a single diastereomer, designated as Example 57 (DIAST A).

The third-eluting material was a single diastereomer, designated as Example 58 (DIAST B).

The mixture of the two diastereomers that eluted first was separated via supercritical fluid chromatography {Column: Chiral Technologies Chiralpak AS-H, 5 µm; Mobile phase: 87.5:12.5 carbon dioxide/[ethanol containing 0.2% (7 M ammonia in methanol)]}. The first-eluting diastereomer from this separation was designated as Example 60 (DIAST D), and the second-eluting diastereomer as Example 59 (DIAST C).

Using an analytical SFC system, {[Column: Chiral Technologies Chiralpak IC, 4.6×250 mm, 5 µm; Mobile phase A: carbon dioxide; Mobile phase B: [methanol containing 0.2% (7 M ammonia in methanol)]}; Gradient: 5% B for 1.0 minute, then 5% to 60% B over 8.0 minutes; Back pressure: 120 bar; Flow rate: 3.0 mL/minute}, Example 57 exhibited a retention time of 6.39 minutes, and Example 58 exhibited a retention time of 6.64 minutes.

Using a different analytical SFC system {Column: Chiral Technologies Chiralpak AS-H, 4.6×250 mm, 5 µm; Mobile phase A: carbon dioxide; Mobile phase B: [ethanol containing 0.2% (7 M ammonia in methanol)]; Gradient: 5% B for 1.0 minute, then 5% to 60% B over 8.0 minutes; Back pressure: 120 bar; Flow rate: 3.0 mL/minute}, Example 60 exhibited a retention time of 4.72 minutes, and Example 59 exhibited a retention time of 4.93 minutes.

13. Examples 61, 62, 63, and 64 were synthesized as a mixture of diastereomers, from 3-fluorocyclopentanecarboxylic acid and ENT 2 from footnote 11. The resulting mixture was separated into its component diastereomers in the following manner. The mixture of four products was subjected to supercritical fluid chromatography {[Column: Chiral Technologies Chiralcel OJ-H, 5 µm; Mobile phase: 90:10 carbon dioxide/[ethanol containing 0.2% (7 M ammonia in methanol)]}. From this column were obtained the following: The first-eluting material was a single diastereomer, designated as Example 62 (DIAST F).

The second-eluting material was a mixture of two diastereomers, which was separated as described below.

The third-eluting material was a single diastereomer, designated as Example 64 (DIAST H).

The mixture of the two diastereomers that eluted second was separated via supercritical fluid chromatography {Column: Phenomenex Lux Amylose-1, 5 µm; Mobile phase: 80:20 carbon dioxide/[ethanol containing 0.2% (7 M ammonia in methanol)]}. The first-eluting diastereomer from this separation was designated as Example 63 (DIAST G), and the second-eluting diastereomer as Example 61 (DIAST E).

Using an analytical SFC system, {[Column: Chiral Technologies Chiralcel OJ-H, 4.6×250 mm, 5 µm; Mobile phase A: carbon dioxide; Mobile phase B:/[ethanol containing 0.2% (7 M ammonia in methanol)]}; Gradient: 5% B for 1.0 minute, then 5% to 60% B over 8.0 minutes; Back pressure: 120 bar; Flow rate: 3.0 mL/minute}, Example 62 exhibited a retention time of 3.70 minutes, and Example 64 exhibited a retention time of 4.36 minutes.

Using a different analytical SFC system {Column: Phenomenex Lux Amylose-1, 4.6×250 mm, 5 µm; Mobile phase A: carbon dioxide; Mobile phase B: [ethanol containing 0.2% (7 M ammonia in methanol)]; Gradient: 5% B for 1.0 minute, then 5% to 60% B over 8.0 minutes; Back pressure: 120 bar; Flow rate: 3.0 mL/minute}, Example 63 exhibited a retention time of 4.30 minutes, and Example 61 exhibited a retention time of 5.29 minutes.

Biological Assays

LRRK2 Assay

LRRK2 kinase activity was measured using Lantha Screen technology from Invitrogen. GST-tagged truncated LRRK2 from Invitrogen (Cat #PV4874) was incubated with a fluorescein-labeled peptide substrate based upon ezrin/radixin/moesin (ERM), also known as LRRKtide (Invitrogen cat #PR8976A), in the presence of a dose response of compound. Upon completion, the assay was stopped and detected with a terbium labeled anti-phospho-ERM antibody (Invitrogen, cat #PR8975A). The assay was carried out under the following protocol: The compound dose response was prepared by diluting compound to a top concentration of 0.3 mM in 100% DMSO and serial diluted by half-log in DMSO to give an 11 point curve, 100× final assay concentration. Using Echo acoustic dispensing, 60 nL of compound was transferred to a low volume Corning 384-well assay plate. 3 µL of a working solution of substrate (200 nM LRRKtide, 2 mM ATP) prepared in assay buffer (50 mM HEPES, pH 7.5, 3 mM $MgCl_2$, with 2 mM DTT and 0.01% Brij35 added fresh) was added to the 60 nL compound assay plate. The kinase reaction was started with 3 µL of a working solution of LRRK2 enzyme at a concentration of 4 µg/mL. The final reaction concentrations were 100 nM LRRKtide, 1 mM ATP, 2 µg/mL LRRK2 enzyme and a compound dose response with a top dose of 3 µM. The reaction was allowed to progress at room temperature for 30 minutes and then stopped with the addition of 6 µL of detection buffer (20 mM Tris pH 7.6, 0.01% NP-40, 6 mM EDTA with 2 nM terbium labeled anti-phospho-ERM). After an incubation of 1 hour at room temperature, the plate was read on an Envision with an excitation wavelength of 340 nm and a reading emission at both 520 nm and 495 nm. The ratio of the 520 nm and 495 nm emission was used to analyze the data. Inhibition of mutant G2019S LRRK2 (Invitrogen cat #PV4881) was measured in the exact same method. All final concentrations of substrate ATP and enzyme were the same.

Table 2, below, provides the LRRK2 IC$_{50}$ data for the compounds of the invention.

TABLE 2

| Example Number | IUPAC Name | LRRK2, WT IC$_{50}$ (nM)[a] | LRRK2, G2019S IC$_{50}$ (nM)[b] |
|---|---|---|---|
| 1 | 8-chloro-2-(cis-4-fluorocyclohexyl)-1-[(2R,4R)-2-methyltetrahydro-2H-pyran-4-yl]-1H-imidazo[4,5-c]quinoline | 7.32 | 4.75 |
| 2 | 8-chloro-2-(cis-3-fluorocyclobutyl)-1-[(2R,4R)-2-methyltetrahydro-2H-pyran-4-yl]-1H-imidazo[4,5-c]quinoline | 8.99 | 5.49 |
| 3 | 8-chloro-2-(cis-3-fluoro-3-methylcyclobutyl)-1-[(2R,4R)-2-methyltetrahydro-2H-pyran-4-yl]-1H-imidazo[4,5-c]quinoline | 6.81 | 5.44 |
| 4 | 8-chloro-1-[(2R,4R)-2-methyltetrahydro-2H-pyran-4-yl]-2-[(3R)-tetrahydrofuran-3-yl]-1H-imidazo[4,5-c]quinoline | 12.3[e] | 7.40[f] |
| 5 | 8-chloro-2-(3-fluoro-3-methylcyclobutyl)-1-[(2R,4R)-2-methyltetrahydro-2H-pyran-4-yl]-1H-imidazo[4,5-c]quinoline | 16.4 | 17.2 |
| 6 | 8-chloro-2-(cis-3-methoxycyclobutyl)-1-[(2R,4R)-2-methyltetrahydro-2H-pyran-4-yl]-1H-imidazo[4,5-c]quinoline | 19.1 | 11.9 |
| 7 | 8-chloro-1-[(2R,4R)-2-methyltetrahydro-2H-pyran-4-yl]-2-(tetrahydro-2H-pyran-4-yl)-1H-imidazo[4,5-c]quinoline | 16.3 | 18.2[f] |
| 8 | 8-chloro-2-(4,4-difluorocyclohexyl)-1-[(2R,4R)-2-methyltetrahydro-2H-pyran-4-yl]-1H-imidazo[4,5-c]quinoline | 15.9 | 12.1 |
| 9 | 8-chloro-1-[(2R,4R)-2-methyltetrahydro-2H-pyran-4-yl]-2-(tetrahydrofuran-2-yl)-1H-imidazo[4,5-c]quinoline, DIAST 1 | 18.5 | 11.3 |
| 10 | 8-chloro-2-(5-methyltetrahydrofuran-3-yl)-1-[(2R,4R)-2-methyltetrahydro-2H-pyran-4-yl]-1H-imidazo[4,5-c]quinoline, DIAST 2 | 23.1 | 23.3 |
| 11 | 8-chloro-2-(3,3-difluorocyclopentyl)-1-[(2R,4R)-2-methyltetrahydro-2H-pyran-4-yl]-1H-imidazo[4,5-c]quinoline | 20.3 | 13.8 |
| 12 | 8-chloro-1-[(2R,4R)-2-methyltetrahydro-2H-pyran-4-yl]-2-(oxetan-3-yl)-1H-imidazo[4,5-c]quinoline | 23.0 | 21.2[f] |
| 13 | 2-[(cis)-3-fluorocyclopentyl]-1-[(2R,4R)-2-methyltetrahydro-2H-pyran-4-yl]-1H-imidazo[4,5-c]quinoline-8-carbonitrile, ENT 1 | 6.29 | 3.84 |
| 14 | 2-[(cis)-3-fluorocyclopentyl]-1-[(2R,4R)-2-methyltetrahydro-2H-pyran-4-yl]-1H-imidazo[4,5-c]quinoline-8-carbonitrile, ENT 2 | 15.2 | 10.8 |
| 15 | 2-(cis-4-fluorocyclohexyl)-1-[(2R,4R)-2-methyltetrahydro-2H-pyran-4-yl]-1H-imidazo[4,5-c]quinoline-8-carbonitrile | 6.75 | 8.30 |
| 16 | 1-[(2R,4R)-2-methyltetrahydro-2H-pyran-4-yl]-2-[(3R)-tetrahydrofuran-3-yl]-1H-imidazo[4,5-c]quinoline-8-carbonitrile | 16.2 | 10.6 |
| 17 | 2-(4,4-difluorocyclohexyl)-1-[(2R,4R)-2-methyltetrahydro-2H-pyran-4-yl]-1H-imidazo[4,5-c]quinoline-8-carbonitrile | 15.6 | 11.2 |
| 18 | 2-(cis-3-fluoro-3-methylcyclobutyl)-1-[(2R,4R)-2-methyltetrahydro-2H-pyran-4-yl]-1H-imidazo[4,5-c]quinoline-8-carbonitrile | 10.4 | 8.40 |
| 19 | 2-(cis-3-fluorocyclobutyl)-1-[(2R,4R)-2-methyltetrahydro-2H-pyran-4-yl]-1H-imidazo[4,5-c]quinoline-8-carbonitrile | 16.1 | 12.4 |
| 20 | 2-(2,2-difluorocyclohexyl)-1-[(2R,4R)-2-methyltetrahydro-2H-pyran-4-yl]-1H-imidazo[4,5-c]quinoline-8-carbonitrile, DIAST 2 | 17.7 | 10.4 |
| 21 | 8-(difluoromethyl)-1-[(2R,4R)-2-methyltetrahydro-2H-pyran-4-yl]-2-[(3R)-tetrahydrofuran-3-yl]-1H-imidazo[4,5-c]quinoline | 16.6[c] | N.D.[d] |
| 22 | 2-(cis-3-fluoro-3-methylcyclobutyl)-1-[(3R)-1-methylpyrrolidin-3-yl]-1H-imidazo[4,5-c]quinoline-8-carbonitrile | 14.2 | 36.5 |
| 23 | 2-(cis-4-fluorocyclohexyl)-1-[(3R)-1-methylpyrrolidin-3-yl]-1H-imidazo[4,5-c]quinoline-8-carbonitrile | 10.9 | 33.0 |
| 24 | 2-(cis-3-fluorocyclobutyl)-1-[(3R)-1-methylpyrrolidin-3-yl]-1H-imidazo[4,5-c]quinoline-8-carbonitrile | 5.27 | 22.4 |

TABLE 2-continued

IUPAC Name and Biological Data for Examples 1-64

| Example Number | IUPAC Name | LRRK2, WT IC$_{50}$ (nM)$^a$ | LRRK2, G2019S IC$_{50}$ (nM)$^b$ |
|---|---|---|---|
| 25 | 1-[(3R)-1-methylpyrrolidin-3-yl]-2-[(3R)-tetrahydrofuran-3-yl]-1H-imidazo[4,5-c]quinoline-8-carbonitrile | 32.5 | 80.0 |
| 26 | 1-[(2R,4R)-2-methyltetrahydro-2H-pyran-4-yl]-2-[(3R)-tetrahydrofuran-3-yl]-8-(trifluoromethyl)-1H-imidazo[4,5-c]quinoline | 9.79 | 5.71 |
| 27 | {cis-4-[8-chloro-2-(3,3-difluorocyclobutyl)-1H-imidazo[4,5-c]quinolin-1-yl]tetrahydro-2H-pyran-2-yl}acetonitrile, ENT 2 | 12.0 | 12.2 |
| 28 | {(2S,4R)-4-[8-chloro-2-(cis-4-fluorocyclohexyl)-1H-imidazo[4,5-c]quinolin-1-yl]tetrahydro-2H-pyran-2-yl}acetonitrile | 9.71 | 5.12 |
| 29 | {(2S,4R)-4-[8-fluoro-2-(cis-4-fluorocyclohexyl)-1H-imidazo[4,5-c]quinolin-1-yl]tetrahydro-2H-pyran-2-yl}acetonitrile | 6.53 | 4.63 |
| 30 | [cis-4-{8-chloro-2-[(3R)-tetrahydrofuran-3-yl]-1H-imidazo[4,5-c]quinolin-1-yl}tetrahydro-2H-pyran-2-yl]acetonitrile, DIAST 1 | 6.06 | 3.02 |
| 31 | 8-fluoro-2-(cis-3-fluoro-3-methylcyclobutyl)-1-[(2R,4R)-2-methyltetrahydro-2H-pyran-4-yl]-1H-imidazo[4,5-c]quinoline | 22.0 | 15.8 |
| 32 | 2-[cis-3-fluorocyclopentyl]-1-[(3R)-1-methyl pyrrolidin-3-yl]-1H-imidazo[4,5-c]quinoline-8-carbonitrile, DIAST 1 | 19.6 | 37.9 |
| 33 | 2-[cis-3-fluorocyclopentyl]-1-[(3R)-1-methylpyrrolidin-3-yl]-1H-imidazo[4,5-c]quinoline-8-carbonitrile, DIAST 2 | 6.56 | 4.30 |
| 34 | 8-fluoro-2-[cis-3-fluorocyclopentyl]-1-[(3R)-1-methylpyrrolidin-3-yl]-1H-imidazo[4,5-c]quinoline, DIAST 1 | 59.6 | 77.0 |
| 35 | 8-fluoro-2-[trans-3-fluorocyclopentyl]-1-[(3R)-1-methylpyrrolidin-3-yl]-1H-imidazo[4,5-c]quinoline, DIAST 1 | >2910 | N.D. |
| 36 | 8-fluoro-2-[trans-3-fluorocyclopentyl]-1-[(3R)-1-methylpyrrolidin-3-yl]-1H-imidazo[4,5-c]quinoline, DIAST 2 | >2840 | N.D. |
| 37 | 8-fluoro-2-[trans-3-fluorocyclopentyl]-1-[(2R,4R)-2-methyltetrahydro-2H-pyran-4-yl]-1H-imidazo[4,5-c]quinoline, DIAST 1 | 200 | N.D. |
| 38 | 8-fluoro-2-[trans-3-fluorocyclopentyl]-1-[(2R,4R)-2-methyltetrahydro-2H-pyran-4-yl]-1H-imidazo[4,5-c]quinoline, DIAST 2 | 202 | N.D. |
| 39 | 1-(2,2-dimethyltetrahydro-2H-pyran-4-yl)-2-(3-fluorocyclopentyl)-1H-imidazo[4,5-c]quinoline-8-carbonitrile, DIAST A | 4.65 | 4.41 |
| 40 | 1-(2,2-dimethyltetrahydro-2H-pyran-4-yl)-2-(3-fluorocyclopentyl)-1H-imidazo[4,5-c]quinoline-8-carbonitrile, DIAST B | 7.14 | 4.33 |
| 41 | 1-(2,2-dimethyltetrahydro-2H-pyran-4-yl)-2-(3-fluorocyclopentyl)-1H-imidazo[4,5-c]quinoline-8-carbonitrile, DIAST C | 64.1 | 49.6 |
| 42 | 1-(2,2-dimethyltetrahydro-2H-pyran-4-yl)-2-(3-fluorocyclopentyl)-1H-imidazo[4,5-c]quinoline-8-carbonitrile, DIAST D | 46.1 | 46.0 |
| 43 | 8-fluoro-2-[cis-3-fluorocyclopentyl]-1-[(2R,4R)-2-methyltetrahydro-2H-pyran-4-yl]-1H-imidazo[4,5-c]quinoline, DIAST 1 | 5.68$^c$ | N.D. |
| 44 | 8-(difluoromethyl)-2-(3-fluorocyclopentyl)-1-[(2R,4R)-2-methyltetrahydro-2H-pyran-4-yl]-1H-imidazo[4,5-c]quinoline, mixture of 4 diastereomers | N.D. | N.D. |
| 45 | 1-(3,3-difluorotetrahydro-2H-pyran-4-yl)-2-(trans-3-fluorocyclobutyl)-1H-imidazo[4,5-c]quinoline-8-carbonitrile, DIAST 1 | 2140$^c$ | N.D. |
| 46 | 1-(3,3-difluorotetrahydro-2H-pyran-4-yl)-2-(trans-3-fluorocyclobutyl)-1H-imidazo[4,5-c]quinoline-8-carbonitrile, DIAST 2 | N.D. | N.D. |
| 47 | 1-(3,3-difluorotetrahydro-2H-pyran-4-yl)-2-(cis-3-fluorocyclobutyl)-1H-imidazo[4,5-c]quinoline-8-carbonitrile, DIAST 1 | N.D. | N.D. |
| 48 | 1-(3,3-difluorotetrahydro-2H-pyran-4-yl)-2-(cis-3-fluorocyclobutyl)-1H-imidazo[4,5-c]quinoline-8-carbonitrile, DIAST 2 | N.D. | N.D. |

TABLE 2-continued

IUPAC Name and Biological Data for Examples 1-64

| Example Number | IUPAC Name | LRRK2, WT IC$_{50}$ (nM)$^a$ | LRRK2, G2019S IC$_{50}$ (nM)$^b$ |
|---|---|---|---|
| 49 | 1-(3,3-difluorotetrahydro-2H-pyran-4-yl)-2-(cis-3-methoxycyclobutyl)-1H-imidazo[4,5-c]quinoline-8-carbonitrile, DIAST 1 | N.D. | N.D. |
| 50 | 1-(3,3-difluorotetrahydro-2H-pyran-4-yl)-2-(trans-3-methoxycyclobutyl)-1H-imidazo[4,5-c]quinoline-8-carbonitrile, DIAST 1 | >3000$^c$ | N.D. |
| 51 | 1-(3,3-difluorotetrahydro-2H-pyran-4-yl)-2-(trans-3-methoxycyclobutyl)-1H-imidazo[4,5-c]quinoline-8-carbonitrile, DIAST 2 | 272$^c$ | N.D. |
| 52 | 1-(3,3-difluorotetrahydro-2H-pyran-4-yl)-2-(cis-3-methoxycyclobutyl)-1H-imidazo[4,5-c]quinoline-8-carbonitrile, DIAST 2 | N.D. | N.D. |
| 53 | 1-[(4R)-2,2-dimethyltetrahydro-2H-pyran-4-yl]-2-[(1S,3S)-3-fluorocyclopentyl]-1H-imidazo[4,5-c]quinoline-8-carbonitrile, DIAST E | 413 | N.D. |
| 54 | 1-[(4R)-2,2-dimethyltetrahydro-2H-pyran-4-yl]-2-[(1R,3S)-3-fluorocyclopentyl]-1H-imidazo[4,5-c]quinoline-8-carbonitrile, DIAST F | >3000 | N.D. |
| 55 | 1-[(4R)-2,2-dimethyltetrahydro-2H-pyran-4-yl]-2-[(1R,3R)-3-fluorocyclopentyl]-1H-imidazo[4,5-c]quinoline-8-carbonitrile, DIAST G | 2520 | N.D. |
| 56 | 1-[(4R)-2,2-dimethyltetrahydro-2H-pyran-4-yl]-2-[(1S,3R)-3-fluorocyclopentyl]-1H-imidazo[4,5-c]quinoline-8-carbonitrile, DIAST H | >3000 | N.D. |
| 57 | 1-(4,4-difluoro-1-methylpyrrolidin-3-yl)-2-(3-fluorocyclopentyl)-1H-imidazo[4,5-c]quinoline-8-carbonitrile, DIAST A | 4.54 | 5.94 |
| 58 | 1-(4,4-difluoro-1-methylpyrrolidin-3-yl)-2-(3-fluorocyclopentyl)-1H-imidazo[4,5-c]quinoline-8-carbonitrile, DIAST B | 12.2 | 21.2 |
| 59 | 1-(4,4-difluoro-1-methylpyrrolidin-3-yl)-2-(3-fluorocyclopentyl)-1H-imidazo[4,5-c]quinoline-8-carbonitrile, DIAST C | 30.5 | 141 |
| 60 | 1-(4,4-difluoro-1-methylpyrrolidin-3-yl)-2-(3-fluorocyclopentyl)-1H-imidazo[4,5-c]quinoline-8-carbonitrile, DIAST D | 57.1 | 97.4 |
| 61 | 1-(4,4-difluoro-1-methylpyrrolidin-3-yl)-2-(3-fluorocyclopentyl)-1H-imidazo[4,5-c]quinoline-8-carbonitrile, DIAST E | 464 | N.D. |
| 62 | 1-(4,4-difluoro-1-methylpyrrolidin-3-yl)-2-(3-fluorocyclopentyl)-1H-imidazo[4,5-c]quinoline-8-carbonitrile, DIAST F | >3000 | N.D. |
| 63 | 1-(4,4-difluoro-1-methylpyrrolidin-3-yl)-2-(3-fluorocyclopentyl)-1H-imidazo[4,5-c]quinoline-8-carbonitrile, DIAST G | >1840 | N.D. |
| 64 | 1-(4,4-difluoro-1-methylpyrrolidin-3-yl)-2-(3-fluorocyclopentyl)-1H-imidazo[4,5-c]quinoline-8-carbonitrile, DIAST H | 2300 | N.D. |

$^a$Geometric mean of 2-4 determinations, unless otherwise indicated
$^b$IC$_{50}$ value from a single determination, unless otherwise indicated
$^c$IC$_{50}$ value represents a single determination
$^d$Not determined
$^e$IC$_{50}$ value represents the geometric mean of ≥5 determinations
$^f$IC$_{50}$ value represents the geometric mean of 2-4 determinations

We claim:

1. A compound of Formula Ia

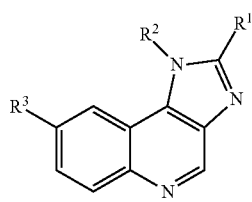

Ia or a pharmaceutically acceptable salt thereof; wherein $R^1$ is a $C_4$-$C_6$cycloalkyl or a 4- to 6-membered heterocycloalkyl which contains 1 to 2 heteroatoms each independently selected from N, O and S, wherein the $C_4$-$C_6$cycloalkyl is substituted with 1 to 4 $R^8$ and the 4- to 6-membered heterocycloalkyl is optionally substituted with 1 to 4 $R^8$;

$R^2$ is a 5- to 6-membered heterocycloalkyl which contains 1 to 2 heteroatoms each independently selected from N and O, wherein the 5- to 6-membered heterocycloalkyl is optionally substituted with 1 to 4 $R^9$;

$R^3$ is selected from the group consisting of halo, cyano, C1-$C_3$alkyl, $C_3$-$C_6$cycloalkyl and $C_1$-$C_3$alkoxy, wherein the $C_1$-$C_3$alkyl, $C_3$-$C_6$cycloalkyl and $C_1$-$C_3$alkoxy are each optionally substituted with 1 to 3 halo or $C_1$-$C_3$alkoxy;

R⁸ at each occurrence is independently selected from the group consisting of halo, $C_1$-$C_3$alkyl and $C_1$-$C_3$alkoxy, wherein the $C_1$-$C_3$alkyl and $C_1$-$C_3$alkoxy are each optionally substituted with 1 to 3 halo; and R⁹ at each occurrence is independently selected from the group consisting of halo, $C_1$-$C_3$alkyl and $C_1$-$C_3$alkoxy, wherein the $C_1$-$C_3$alkyl and $C_1$-$C_3$alkoxy are optionally substituted with 1 to 3 halo or a cyano.

2. The compound of claim 1 or a pharmaceutically acceptable salt thereof
wherein
R³ is selected from the group consisting of chloro, fluoro, cyano, difluoromethyl and trifluoromethyl.

3. The compound of claim 2 or a pharmaceutically acceptable salt thereof
wherein
R¹ is selected from the group consisting of cyclobutyl, cyclopentyl, cyclohexyl, oxetanyl, tetrahydrofuranyl and tetrahydropyranyl, wherein the cyclobutyl, cyclopentyl, and cyclohexyl are substituted with 1 to 3 R⁸, and wherein the oxetanyl, tetrahydrofuranyl and tetrahydropyranyl are optionally substituted with 1 to 3 R⁸; and R⁸ at each occurrence is independently selected from the group consisting of halo, $C_1$-$C_3$alkyl and $C_1$-$C_3$alkoxy, wherein the $C_1$-$C_3$alkyl and $C_1$-$C_3$alkoxy are optionally substituted with 1 to 3 fluoro.

4. The compound of claim 1 or a pharmaceutically acceptable salt
thereof wherein
R² is selected from the group consisting of cyclobutyl, cyclopentyl, cyclohexyl, oxetanyl, tetrahydrofuranyl, tetrahydropyranyl and pyrrolidinyl wherein the cyclobutyl, cyclopentyl, cyclohexyl, oxetanyl, tetrahydrofuranyl, tetrahydropyranyl and pyrrolidinyl are optionally substituted with 1 to 3 R⁹; and R⁹ at each occurrence is independently selected from the group consisting of halo, $C_1$-$C_3$alkyl and $C_1$-$C_3$alkoxy, wherein the $C_1$-$C_3$alkyl and $C_1$-$C_3$alkoxy are optionally substituted with one to three fluoro or a cyano.

5. The compound of claim 1 or a pharmaceutically acceptable salt
thereof wherein
R¹ is selected from the group consisting of oxetan-3-yl, tetrahydrofuran-2-yl, tetrahydrofuran-3-yl, 5-methyl-tetrahydrofuran-2-yl, tetrahydropyran-4-yl, 3-fluorocyclobutyl, 3,3-difluorocyclobutyl, 3-methoxycyclobutyl, 3-fluoro-3-methylcyclobutyl, 3-fluorocyclopentyl, 3,3-difluorocyclopentyl, 4-fluorocyclohexyl, 2,2-difluorocyclohexyl and 4,4-difluorocyclohexyl.

6. The compound of claim 1 or a pharmaceutically acceptable salt thereof wherein
R² is selected from the group consisting of 2-methyltetrahydropyran-4-yl, 2,2-dimethyltetrahydropyran-4-yl, 2-(cyanomethyl)tetrahydropyran-4-yl, 3,3-difluorotetrahydropyran-4-yl, 1-methylpyrrolidin-3-yl and 4,4-difluoro-1-methylpyrrolidin-3-yl.

7. The compound of claim 1 or a pharmaceutically acceptable salt thereof wherein
R¹ is selected from the group consisting of oxetan-3-yl, tetrahydrofuran-2-yl, tetrahydrofuran-3-yl, 5-methyl-tetrahydrofuran-2-yl, tetrahydropyran-4-yl, 3-fluoro cyclobutyl, 3,3-difluorocyclobutyl, 3-methoxycyclobutyl, 3-fluoro-3-methylcyclobutyl, 3-fluorocyclopentyl, 3,3-difluorocyclopentyl, 4-fluorocyclohexyl, 2,2-difluorocyclohexyl and 4,4-difluorocyclohexyl; and R² is selected from the group consisting of 2-methyltetrahydropyran-4-yl, 2,2-dimethyltetrahydropyran-4-yl, 2-(cyanomethyl)tetrahydropyran-4-yl, 3,3-difluorotetrahydropyran-4-yl, 1-methylpyrrolidin-3-yl and 4,4-difluoro-1-methylpyrrolidin-3-yl.

8. The compound of claim 7 or a pharmaceutically acceptable salt thereof wherein
R¹ is selected from the group consisting of oxetan-3-yl, tetrahydrofuran-2-yl, tetrahydrofuran-3-yl, 5-methyl-tetrahydrofuran-2-yl and tetrahydropyran-4-yl.

9. The compound of claim 7 or a pharmaceutically acceptable salt thereof wherein
R¹ is selected from the group consisting of 3-fluorocyclobutyl, 3,3-difluorocyclobutyl, 3-methoxycyclobutyl, 3-fluoro-3-methylcyclobutyl, 3-fluorocyclopentyl, 3,3-difluorocyclopentyl, 4-fluorocyclohexyl, 2,2-difluorocyclohexyl and 4,4-difluorocyclohexyl.

10. The compound of claim 7 or a pharmaceutically acceptable salt thereof wherein
R² is selected from the group consisting of 2-methyltetrahydropyran-4-yl, 2,2-dimethyltetrahydropyran-4-yl, 2-(cyanomethyl)tetrahydropyran-4-yl and 3,3-difluorotetrahydropyran-4-yl.

11. The compound of claim 7 or a pharmaceutically acceptable salt thereof wherein
R² is selected from the group consisting of 1-methylpyrrolidin-3-yl and 4,4-difluoro-1-methylpyrrolidin-3-yl.

12. The compound of claim 7 for a pharmaceutically acceptable salt thereof wherein
R³ is fluoro or chloro.

13. The compound of claim 7 or a pharmaceutically acceptable salt thereof wherein
R³ is cyano.

14. The compound of claim 7 or a pharmaceutically acceptable salt thereof wherein
R³ is difluoromethyl or trifluoromethyl.

15. A compound of claim 1 selected from the group consisting of
8-chloro-2-(cis-4-fluorocyclohexyl)-1-[(2R,4R)-2-methyltetrahydro-2H-pyran-4-yl]-1H-imidazo[4,5-c]quinoline;
8-chloro-2-(cis-3-fluorocyclobutyl)-1-[(2R,4R)-2-methyltetrahydro-2H-pyran-4-yl]-1H-imidazo[4,5-c]quinoline;
8-chloro-2-(cis-3-fluoro-3-methylcyclobutyl)-1-[(2R,4R)-2-methyltetrahydro-2H-pyran-4-yl]-1H-imidazo[4,5-c]quinoline;
8-chloro-1-[(2R,4R)-2-methyltetrahydro-2H-pyran-4-yl]-2-[(3R)-tetrahydrofuran-3-yl]-1H-imidazo[4,5-c]quinoline;
8-chloro-2-(3-fluoro-3-methylcyclobutyl)-1-[(2R,4R)-2-methyltetrahydro-2H-pyran-4-yl]-1H-imidazo[4,5-c]quinoline;
8-chloro-2-(cis-3-methoxycyclobutyl)-1-[(2R,4R)-2-methyltetrahydro-2H-pyran-4-yl]-1H-imidazo[4,5-c]quinoline;
8-chloro-1-[(2R,4R)-2-methyltetrahydro-2H-pyran-4-yl]-2-(tetrahydro-2H-pyran-4-yl)-1H-imidazo[4,5-c]quinoline;
8-chloro-2-(4,4-difluorocyclohexyl)-1-[(2R,4R)-2-methyltetrahydro-2H-pyran-4-yl]-1H-imidazo[4,5-c]quinoline;
8-chloro-1-[(2R,4R)-2-methyltetrahydro-2H-pyran-4-yl]-2-(tetrahydrofuran-2-yl)-1H-imidazo[4,5-c]quinoline, DIAST 1;

8-chloro-2-(5-methyltetrahydrofuran-3-yl)-1-[(2R,4R)-2-methyltetrahydro-2H-pyran-4-yl]-1H-imidazo[4,5-c]quinoline, DIAST 2;

8-chloro-2-(3,3-difluorocyclopentyl)-1-[(2R,4R)-2-methyltetrahydro-2H-pyran-4-yl]-1H-imidazo[4,5-c]quinoline;

8-chloro-1-[(2R,4R)-2-methyltetrahydro-2H-pyran-4-yl]-2-(oxetan-3-yl)-1H-imidazo[4,5-c]quinoline;

2-[(cis)-3-fluorocyclopentyl]-1-[(2R,4R)-2-methyltetrahydro-2H-pyran-4-yl]-1H-imidazo[4,5-c]quinoline-8-carbonitrile, ENT 1;

2-[(cis)-3-fluorocyclopentyl]-1-[(2R,4R)-2-methyltetrahydro-2H-pyran-4-yl]-1H-imidazo[4,5-c]quinoline-8-carbonitrile, ENT 2;

2-(cis-4-fluorocyclohexyl)-1-[(2R,4R)-2-methyltetrahydro-2H-pyran-4-yl]-1H-imidazo[4,5-c]quinoline-8-carbonitrile;

1-[(2R,4R)-2-methyltetrahydro-2H-pyran-4-yl]-2-[(3R)-tetrahydrofuran-3-yl]-1H-imidazo[4,5-c]quinoline-8-carbonitrile;

2-(4,4-difluorocyclohexyl)-1-[(2R,4R)-2-methyltetrahydro-2H-pyran-4-yl]-1H-imidazo[4,5-c]quinoline-8-carbonitrile;

2-(cis-3-fluoro-3-methylcyclobutyl)-1-[(2R,4R)-2-methyltetrahydro-2H-pyran-4-yl]-1H-imidazo[4,5-c]quinoline-8-carbonitrile;

2-(cis-3-fluorocyclobutyl)-1-[(2R,4R)-2-methyltetrahydro-2H-pyran-4-yl]-1H-imidazo[4,5-c]quinoline-8-carbonitrile;

2-(2,2-difluorocyclohexyl)-1-[(2R,4R)-2-methyltetrahydro-2H-pyran-4-yl]-1H-imidazo[4,5-c]quinoline-8-carbonitrile, DIAST 2;

8-(difluoromethyl)-1-[(2R,4R)-2-methyltetrahydro-2H-pyran-4-yl]-2-[(3R)-tetrahydrofuran-3-yl]-1H-imidazo[4,5-c]quinoline;

2-(cis-3-fluoro-3-methylcyclobutyl)-1-[(3R)-1-methylpyrrolidin-3-yl]-1H-imidazo[4,5-c]quinoline-8-carbonitrile;

2-(cis-4-fluorocyclohexyl)-1-[(3R)-1-methylpyrrolidin-3-yl]-1H-imidazo[4,5-c]quinoline-8-carbonitrile;

2-(cis-3-fluorocyclobutyl)-1-[(3R)-1-methylpyrrolidin-3-yl]-1H-imidazo[4,5-c]quinoline-8-carbonitrile;

1-[(3R)-1-methylpyrrolidin-3-yl]-2-[(3R)-tetrahydrofuran-3-yl]-1H-imidazo[4,5-c]quinoline-8-carbonitrile;

1-[(2R,4R)-2-methyltetrahydro-2H-pyran-4-yl]-2-[(3R)-tetrahydrofuran-3-yl]-8-(trifluoromethyl)-1H-imidazo[4,5-c]quinoline;

{cis-4-[8-chloro-2-(3,3-difluorocyclobutyl)-1H-imidazo[4,5-c]quinolin-1-yl]tetrahydro-2H-pyran-2-yl}acetonitrile, ENT 2;

{(2S,4R)-4-[8-chloro-2-(cis-4-fluorocyclohexyl)-1H-imidazo[4,5-c]quinolin-1-yl]tetrahydro-2H-pyran-2-yl}acetonitrile;

{(2S,4R)-4-[8-fluoro-2-(cis-4-fluorocyclohexyl)-1H-imidazo[4,5-c]quinolin-1-yl]tetrahydro-2H-pyran-2-yl}acetonitrile;

[cis-4-{8-chloro-2-[(3R)-tetrahydrofuran-3-yl]-1H-imidazo[4,5-c]quinolin-1-yl}tetrahydro-2H-pyran-2-yl]acetonitrile, DIAST 1;

8-fluoro-2-(cis-3-fluoro-3-methylcyclobutyl)-1-[(2R,4R)-2-methyltetrahydro-2H-pyran-4-yl]-1H-imidazo[4,5-c]quinoline;

2-[cis-3-fluorocyclopentyl]-1-[(3R)-1-methylpyrrolidin-3-yl]-1H-imidazo[4,5-c]quinoline-8-carbonitrile, DIAST 1;

2-[cis-3-fluorocyclopentyl]-1-[(3R)-1-methylpyrrolidin-3-yl]-1H-imidazo[4,5-c]quinoline-8-carbonitrile, DIAST 2;

8-fluoro-2-[cis-3-fluorocyclopentyl]-1-[(3R)-1-methylpyrrolidin-3-yl]-1H-imidazo[4,5-c]quinoline, DIAST 1;

8-fluoro-2-[trans-3-fluorocyclopentyl]-1-[(3R)-1-methylpyrrolidin-3-yl]-1H-imidazo[4,5-c]quinoline, DIAST 1;

8-fluoro-2-[trans-3-fluorocyclopentyl]-1-[(3R)-1-methylpyrrolidin-3-yl]-1H-imidazo[4,5-c]quinoline, DIAST 2;

8-fluoro-2-[trans-3-fluorocyclopentyl]-1-[(2R,4R)-2-methyltetrahydro-2H-pyran-4-yl]-1H-imidazo[4,5-c]quinoline, DIAST 1;

8-fluoro-2-[trans-3-fluorocyclopentyl]-1-[(2R,4R)-2-methyltetrahydro-2H-pyran-4-yl]-1H-imidazo[4,5-c]quinoline, DIAST 2;

1-(2,2-dimethyltetrahydro-2H-pyran-4-yl)-2-(3-fluorocyclopentyl)-1H-imidazo[4,5-c]quinoline-8-carbonitrile, DIAST A;

1-(2,2-dimethyltetrahydro-2H-pyran-4-yl)-2-(3-fluorocyclopentyl)-1H-imidazo[4,5-c]quinoline-8-carbonitrile, DIAST B;

1-(2,2-dimethyltetrahydro-2H-pyran-4-yl)-2-(3-fluorocyclopentyl)-1H-imidazo[4,5-c]quinoline-8-carbonitrile, DIAST C;

1-(2,2-dimethyltetrahydro-2H-pyran-4-yl)-2-(3-fluorocyclopentyl)-1H-imidazo[4,5-c]quinoline-8-carbonitrile, DIAST D;

8-fluoro-2-[cis-3-fluorocyclopentyl]-1-[(2R,4R)-2-methyltetrahydro-2H-pyran-4-yl]-1H-imidazo[4,5-c]quinoline, DIAST 1;

8-(difluoromethyl)-2-(3-fluorocyclopentyl)-1-[(2R,4R)-2-methyltetrahydro-2H-pyran-4-yl]-1H-imidazo[4,5-c]quinoline, mixture of 4 diasteromers;

1-(3,3-difluorotetrahydro-2H-pyran-4-yl)-2-(trans-3-fluorocyclobutyl)-1H-imidazo[4,5-c]quinoline-8-carbonitrile, DIAST 1;

1-(3,3-difluorotetrahydro-2H-pyran-4-yl)-2-(trans-3-fluorocyclobutyl)-1H-imidazo[4,5-c]quinoline-8-carbonitrile, DIAST 2;

1-(3,3-difluorotetrahydro-2H-pyran-4-yl)-2-(cis-3-fluorocyclobutyl)-1H-imidazo[4,5-c]quinoline-8-carbonitrile, DIAST 1;

1-(3,3-difluorotetrahydro-2H-pyran-4-yl)-2-(cis-3-fluorocyclobutyl)-1H-imidazo[4,5-c]quinoline-8-carbonitrile, DIAST 2;

1-(3,3-difluorotetrahydro-2H-pyran-4-yl)-2-(cis-3-methoxycyclobutyl)-1H-imidazo[4, c]quinoline-8-carbonitrile, DIAST 1;

1-(3,3-difluorotetrahydro-2H-pyran-4-yl)-2-(trans-3-methoxycyclobutyl)-1H-imidazo[4,5-c]quinoline-8-carbonitrile, DIAST 1;

1-(3,3-difluorotetrahydro-2H-pyran-4-yl)-2-(trans-3-methoxycyclobutyl)-1H-imidazo[4,5-c]quinoline-8-carbonitrile, DIAST 2;

1-(3,3-difluorotetrahydro-2H-pyran-4-yl)-2-(cis-3-methoxycyclobutyl)-1H-imidazo[4, c]quinoline-8-carbonitrile, DIAST 2;

1-[(4R)-2,2-dimethyltetrahydro-2H-pyran-4-yl]-2-[(1S,3S)-3-fluorocyclopentyl]-1H-imidazo[4,5-c]quinoline-8-carbonitrile, DIAST E;

1-[(4R)-2,2-dimethyltetrahydro-2H-pyran-4-yl]-2-[(1R,3S)-3-fluorocyclopentyl]-1H-imidazo[4,5-c]quinoline-8-carbonitrile, DIAST F;

1-[(4R)-2,2-dimethyltetrahydro-2H-pyran-4-yl]-2-[(1R,3R)-3-fluorocyclopentyl]-1H-imidazo[4,5-c]quinoline-8-carbonitrile, DIAST G;

1-[(4R)-2,2-dimethyltetrahydro-2H-pyran-4-yl]-2-[(1S,3R)-3-fluorocyclopentyl]-1H-imidazo[4,5-c]quinoline-8-carbonitrile, DIAST H;

1-(4,4-difluoro-1-methylpyrrolidin-3-yl)-2-(3-fluorocyclopentyl)-1H-imidazo[4,5-c]quinoline-8-carbonitrile, DIAST A;

1-(4,4-difluoro-1-methylpyrrolidin-3-yl)-2-(3-fluorocyclopentyl)-1H-imidazo[4,5-c]quinoline-8-carbonitrile, DIAST B;

1-(4,4-difluoro-1-methylpyrrolidin-3-yl)-2-(3-fluorocyclopentyl)-1H-imidazo[4,5-c]quinoline-8-carbonitrile, DIAST C;

1-(4,4-difluoro-1-methylpyrrolidin-3-yl)-2-(3-fluorocyclopentyl)-1H-imidazo[4,5-c]quinoline-8-carbonitrile, DIAST D;

1-(4,4-difluoro-1-methylpyrrolidin-3-yl)-2-(3-fluorocyclopentyl)-1H-imidazo[4,5-c]quinoline-8-carbonitrile, DIAST E;

1-(4,4-difluoro-1-methylpyrrolidin-3-yl)-2-(3-fluorocyclopentyl)-1H-imidazo[4,5-c]quinoline-8-carbonitrile, DIAST F;

1-(4,4-difluoro-1-methylpyrrolidin-3-yl)-2-(3-fluorocyclopentyl)-1H-imidazo[4,5-c]quinoline-8-carbonitrile, DIAST G; and 1-(4,4-difluoro-1-methylpyrrolidin-3-yl)-2-(3-fluorocyclopentyl)-1H-imidazo[4,5-c]quinoline-8-carbonitrile, DIAST H;

or a pharmaceutically acceptable salt thereof.

16. A compound of claim 15 selected from the group consisting of

2-[(cis)-3-fluorocyclopentyl]-1-[(2R,4R)-2-methyltetrahydro-2H-pyran-4-yl]-1H-imidazo[4,5-c]quinoline-8-carbonitrile, ENT 1;

8-chloro-2-(cis-3-fluorocyclobutyl)-1-[(2R,4R)-2-methyltetrahydro-2H-pyran-4-yl]-1H-imidazo[4,5-c]quinoline;

2-(cis-4-fluorocyclohexyl)-1-[(2R,4R)-2-methyltetrahydro-2H-pyran-4-yl]-1H-imidazo[4,5-c]quinoline-8-carbonitrile;

8-chloro-2-(cis-3-fluoro-3-methylcyclobutyl)-1-[(2R,4R)-2-methyltetrahydro-2H-pyran-4-yl]-1H-imidazo[4,5-c]quinoline;

1-[(2R,4R)-2-methyltetrahydro-2H-pyran-4-yl]-2-[(3R)-tetrahydrofuran-3-yl]-1H-imidazo[4,5-c]quinoline-8-carbonitrile;

2-[cis-3-fluorocyclopentyl]-1-[(3R)-1-methylpyrrolidin-3-yl]-1H-imidazo[4,5-c]quinoline-8-carbonitrile, DIAST 2;

8-chloro-2-(cis-4-fluorocyclohexyl)-1-[(2R,4R)-2-methyltetrahydro-2H-pyran-4-yl]-1H-imidazo[4,5-c]quinoline;

8-fluoro-2-[cis-3-fluorocyclopentyl]-1-[(2R,4R)-2-methyltetrahydro-2H-pyran-4-yl]-1H-imidazo[4,5-c]quinoline, DIAST 1;

1-[(2R,4R)-2-methyltetrahydro-2H-pyran-4-yl]-2-[(3R)-tetrahydrofuran-3-yl]-8-(trifluoromethyl)-1H-imidazo[4,5-c]quinoline; and 2-[(cis)-3-fluorocyclopentyl]-1-[(2R,4R)-2-methyltetrahydro-2H-pyran-4-yl]-1H-imidazo[4,5-c]quinoline-8-carbonitrile, ENT 2;

or a pharmaceutically acceptable salt thereof.

17. A compound of claim 15 selected from the group consisting of

2-[(cis)-3-fluorocyclopentyl]-1-[(2R,4R)-2-methyltetrahydro-2H-pyran-4-yl]-1H-imidazo[4,5-c]quinoline-8-carbonitrile, ENT 1;

8-chloro-2-(cis-3-fluorocyclobutyl)-1-[(2R,4R)-2-methyltetrahydro-2H-pyran-4-yl]-1H-imidazo[4,5-c]quinoline;

2-(cis-4-fluorocyclohexyl)-1-[(2R,4R)-2-methyltetrahydro-2H-pyran-4-yl]-1H-imidazo[4,5-c]quinoline-8-carbonitrile;

8-chloro-2-(cis-3-fluoro-3-methylcyclobutyl)-1-[(2R,4R)-2-methyltetrahydro-2H-pyran-4-yl]-1H-imidazo[4,5-c]quinoline; and 1-[(2R,4R)-2-methyltetrahydro-2H-pyran-4-yl]-2-[(3R)-tetrahydrofuran-3-yl]-1H-imidazo[4,5-c]quinoline-8-carbonitrile;

or a pharmaceutically acceptable salt thereof.

18. A pharmaceutical composition comprising a therapeutically effective amount of a compound according to claim 1, or a pharmaceutically acceptable salt thereof, together with a pharmaceutically acceptable carrier.

* * * * *